US012410437B2

(12) United States Patent
Djuranovic et al.

(10) Patent No.: US 12,410,437 B2
(45) Date of Patent: *Sep. 9, 2025

(54) INCORPORATION OF INTERNAL POLYA-ENCODED POLY-LYSINE SEQUENCE TAGS AND THEIR VARIATIONS FOR THE TUNABLE CONTROL OF PROTEIN SYNTHESIS IN BACTERIAL AND EUKARYOTIC CELLS

(71) Applicants: Washington University, St. Louis, MO (US); The Johns Hopkins University, Baltimore, MD (US)

(72) Inventors: Sergej Djuranovic, St. Louis, MO (US); Rachel Green, Baltimore, MD (US)

(73) Assignees: Washington University, St. Louis, MO (US); The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/182,948

(22) Filed: Mar. 13, 2023

(65) Prior Publication Data

US 2023/0265442 A1 Aug. 24, 2023

Related U.S. Application Data

(63) Continuation of application No. 16/317,761, filed as application No. PCT/US2017/041766 on Jul. 12, 2017, now Pat. No. 11,603,533.

(60) Provisional application No. 62/361,307, filed on Jul. 12, 2016, provisional application No. 62/427,518, filed on Nov. 29, 2016, provisional application No. 62/437,464, filed on Dec. 21, 2016, provisional application No. 62/438,017, filed on Dec. 22, 2016.

(51) Int. Cl.
*C12N 15/64* (2006.01)
*C12N 9/22* (2006.01)
*C12N 15/11* (2006.01)

(52) U.S. Cl.
CPC ............... *C12N 15/64* (2013.01); *C12N 9/22* (2013.01); *C12N 15/11* (2013.01); *C12N 2310/20* (2017.05); *C12N 2800/80* (2013.01)

(58) Field of Classification Search
CPC .................................................. C12N 15/64
See application file for complete search history.

(56) References Cited

U.S. PATENT DOCUMENTS

| 4,873,316 | A | 10/1989 | Meade et al. | |
|---|---|---|---|---|
| 8,697,359 | B1* | 4/2014 | Zhang | C12Q 1/68 |
| | | | | 435/6.13 |
| 2009/0311753 | A1 | 12/2009 | Imai et al. | |
| 2016/0017366 | A1 | 1/2016 | Chen et al. | |

FOREIGN PATENT DOCUMENTS

| EP | 0264166 A1 | 4/1988 |
|---|---|---|
| EP | 3009511 A2 | 4/2016 |
| EP | 3009511 B1 | 5/2017 |
| WO | 2016086988 A1 | 6/2016 |
| WO | 2018013720 A1 | 1/2018 |

OTHER PUBLICATIONS

User Manual Entitled: "Flp-In(TM) System For Generating Stable Mammalian Expression Cell Lines by Flp Recombinase-Mediated Integration," Invitrogen Corporation, Nov. 9, 2010, 40 pages, Catalog Nos. K6010-01, K6010-02, Version E, No. 25-0306, Retrieved from URL: https://tools.thermofisher.com/content/sfs/manuals/flpinsystem_man.pdf.
Voinnet O., et al., "An Enhanced Transient Expression System In Plants Based On Suppression Of Gene Silencing By the P19 Protein Of Tomato Bushy Stunt Virus," The Plant Journal, Blackwell Publishing Ltd., 2003, vol. 33, pp. 949-956.
Winoto A., et al., "A Novel, Inducible And T Cell-Specific Enhancer Located At The 3' End Of The T Cell Receptor a Focus," The EMBO Journal, 1989, vol. 8, No. 3, pp. 729-733.
Wolpowitz D., et al., "Cysteine-Rich Domain Isoforms of the Neuregulin-1 Gene Are Required for Maintenance of Peripheral Synapses," Neuron, Jan. 2000, vol. 25, pp. 79-91.
Yan S., et al., "Ribosome Excursions During mRNA Translocation Mediate Broad Branching of Frameshift Pathways," Cell, Feb. 26, 2015, vol. 160, pp. 870-881, 13 Pages.
Yonashiro R., et al., "The Rqc2/Tae2 Subunit of the Ribosome-Associated Quality Control (RQC) Complex Marks Ribosome-Stalled Nascent Polypeptide Chains for Aggregation," Elife, 2016, vol. 5, Article e11794, pp. 1-16.
Amann E., et al., "Tightly Regulated tac Promoter Vectors Useful for the Expression of Unfused and Fused Proteins in *Escherichia coli*," Gene, 1988, vol. 69, No. 2, pp. 301-315.
Arthur L.L., et al., "Rapid Generation Of Hypomorphic Mutations," Nature Communications, 2016, vol. 8, No. 14112, pp. 1-15.
Arthur L.L., et al., "Translational Control by Lysine-encoding A-rich Sequences", Science Advances, Jul. 24, 2015, vol. 1, No. 6, p. e1500154, 12 pages, XP055452293.
Baldari C., et al., "A Novel Leader Peptide which allows Efficient Secretion of a Fragment of Human Interleukin 1 beta in *Saccharomyces cerevisiae*," EMBO Journal, Jan. 1987, vol. 6(1), pp. 229-234.
Banerji J., et al., "A Lymphocyte-Specific Cellular Enhancer Is Located Downstream of the Joining Region in Immunoglobulin Heavy Chain Genes," Cell, Jul. 1983, vol. 33, No. 3, pp. 729-740.
Belew A.T., et al., "Endogenous Ribosomal Frameshift Signals Operate As mRNA Destabilizing Elements Through At Least Two Molecular Pathways In Yeast," Nucleic Acids Research, Apr. 2011, vol. 39, No. 7, pp. 2799-2808.
Belew A.T., et al., "Ribosomal Frameshifting In The CCR5 mRNA Is Regulated By miRNAs And The NMD Pathway," Nature, Aug. 21, 2014, vol. 512, No. 7514, pp. 265-269, 29 Pages.

(Continued)

*Primary Examiner* — Suzanne M Noakes
(74) *Attorney, Agent, or Firm* — Polsinelli PC

(57) ABSTRACT

The present disclosure relates to modulation of protein expression.

8 Claims, 74 Drawing Sheets
(33 of 74 Drawing Sheet(s) Filed in Color)
Specification includes a Sequence Listing.

(56) References Cited

OTHER PUBLICATIONS

Belfield E.J., et al., "The gateway pDEST17 expression vector encodes a-1 ribosomal frameshifting sequence," Nucleic Acids Research, Jan. 31, 2007, vol. 35, No. 4, pp. 1322-1332.
Bonde M.T., et al., "Predictable Tuning Of Protein Expression In Bacteria," Nature Methods, Mar. 2016, vol. 13, No. 3, pp. 233-236, 8 Pages.
Boshart M., et al., "A Very Strong Enhancer Is Locate Upstream of an Immediate Early Gene of Human Cytomegalovirus," Cell, Jun. 1985, vol. 41, pp. 521-530.
Brandman O., et al., "A Ribosome-Bound Quality Control Complex Triggers Degradation of Nascent Peptides and Signals Translation Stress," Cell, Nov. 21, 2012, vol. 151, pp. 1042-1054.
Breslow D.K., et al., "A Comprehensive Strategy Enabling High-Resolution Functional Analysis of the Yeast Genome," Nature Methods, Aug. 2008, vol. 5, No. 8, pp. 711-718.
Bruns P.J., et al., "Biolistic Transformation of Macro- and Micronuclei," Methods in Cell Biology, 1999, vol. 62, Chapter 27, pp. 501-512.
Byrne G.W., et al., "Multiplex Gene Regulation: a Two-tiered Approach to Transgene Regulation in Transgenic Mice," Proceedings of the National Academy of Sciences of the United States of America, Jul. 1989, vol. 86, pp. 5473-5477.
Calame K., et al., "Transcriptional Controlling Elements in the Immunoglobulin and T Cell Receptor Loci," Advances in Immunology, 1988, vol. 43, pp. 235-275.
Camper S.A., et al., "Postnatal Repression of the Alpha-fetoprotein Gene is Enhancer Independent," Genes & Development, Apr. 1989, vol. 3, No. 4, pp. 537-546.
Cassidy-Hanley D., et al., "Germline and Somatic Transformation of Mating Tetrahymena thermophila by Particle Bombardment," Genetics, May 1997, vol. 146, pp. 135-147.
Chang Y-F., et al., "The Nonsense-Mediated Decay RNA Surveillance Pathway," Annual Review of Biochemistry, 2007, vol. 76, pp. 1-74.
Chappell J., et al., "A Renaissance In RNA Synthetic Biology: New Mechanisms, Applications And Tools For The Future," Current Opinion in Chemical Biology, Oct. 2015, vol. 28, pp. 47-56.
Charneski C.A., et al., "Positively Charged Residues Are the Major Determinants of Ribosomal Velocity," PLoS Bioi, Mar. 2013, pp. 1-20, vol. 11, No. 3, Article 1001508, 20 Pages.
Chen J. et al., "Dynamic Pathways Of—1 Translational Frameshifting," Nature, Aug. 21, 2014, vol. 512, No. 7514, pp. 328-332.
Choe Y-J., et al., "Failure of RQC Machinery Causes Protein Aggregation and Proteotoxic Stress," Nature, Mar. 10, 2016, vol. 531, No. 7593, pp. 191-195, 30 pages.
Chuang H.-Y., et al., "A Decade of Systems Biology," Annual Review of Cell and Developmental Biology, 2010, vol. 26, pp. 721-744.
Collins K., et al., "Tetrahymena Thermophila," Current Biology, May 10, 2005, vol. 15, No. 9, pp. R317-R318.
Dimitrova L.N., et al., "Nascent Peptide-Dependent Translation Arrest Leads to Not4p-Mediated Protein Degradationy the Proteasome," Journal of Biological Chemistry, Apr. 17, 2009, vol. 284, No. 16, pp. 10343-10352.
Djuranovic S., et al., "MiRNA-Mediated Gene Silencing by Translational Repression Followed by mRNA Deadenylation and Decay," Science, Apr. 13, 2012, vol. 336, pp. 237-240.
Doma M.K., et al., "Endonucleolytic Cleavage of Eukaryotic mRNAs with Stalls in Translation Elongation," NIH Public Access Author Manuscript, Mar. 30, 2007, pp. 1-9, Published in final edited form as: Nature, Mar. 23, 2006, vol. 440, No. 7083, pp. 561-564.
Doudna J., et al., "The New Frontier of Genome Engineering with CRISPR-Cas9," Science, Nov. 28, 2014, vol. 346, No. 6213, with Correction, p. 1077, pp. 1258096-1258096-9.
Duffy J.B., "GAL4 System in Drosophila: A Fly Geneticist's Swiss Army Knife," Genesis, Wiley-Liss. Inc, 2002, vol. 34, pp. 1-15.
Edlund T., et al., "Cell-Specific Expression of the Rat Insulin Gene: Evidence for Role of Two Distinct 5' Flanking Elements," Science, Nov. 22, 1985, vol. 230, No. 4728, pp. 912-916.
Eisen J.A., et al., "Macronuclear Genome Sequence of the Ciliate Tetrahymena Thermophila, a Model Eukaryote," PLOS Biology, Sep. 2006, vol. 4, No. 9, e286, pp. 1620-1642.
Ferri A.L.M., et al., "Sox2 Deficiency Causes Neurodegeneration and Impaired Neurogenesis in the Adult Mouse Brain," Development, 2004, vol. 131, No. 15, pp. 3805-3819.
Forbes S.A., et al., "COSMIC: Exploring the World's Knowledge of Somatic Mutations in Human Cancer," Nucleic Acids Research, 2015, vol. 43, pp. D805-D811.
Fresno M., et al., "Inhibition of Translation in Eukaryotic Systems by Harringtonine," European Journal of Biochemistry, 1977, vol. 72, pp. 323-330.
Gari E., et al., "A Set of Vectors with a Tetracycline-Regulatable Promoter System for Modulated Gene Expression in Saccharomyces cerevisiae," Yeast, John Wiley Sons Ltd, 1997, vol. 13, pp. 837-848.
Georgi B., et al., "From Mouse to Human: Evolutionary Genomics Analysis of Human Orthologs of Essential Genes," PLOS Genetics, May 2013, vol. 9, No. 5, e1003484, pp. 1-10.
Gonzalez C., et al., "Ribosome Profiling Reveals a Cell-Type-Specific Translational Landscape in Brain Tumors," The Journal of Neuroscience, Aug. 13, 2014, vol. 34, No. 33, pp. 10924-10936.
Goto T., et al., "Hypomorphic Phenotype Of Foxn1 Gene-Modified Rats By Crispr/Cas9 System" Transgenic Research, Aug. 2016, vol. 25, pp. 533-544.
Groth A.C., et al., "Construction of Transgenic Drosophila by Using the Site-Specific Integrase From Phage PhiC31," Genetics, Apr. 2004, vol. 166, pp. 1775-1782.
Habich M., et al., "PATACSDB—The Database of PolyA Translational Attenuators in Coding Sequences," PeerJ Computer Science, 2016, vol. 2, No. e45, pp. 1-7.
Hershey J.W.B., et al., "Principles of Translational Control: An Overview," Cold Spring Harbor perspectives in biology, Dec. 1, 2012, vol. 04, No. 12, 11 Pages.
Hieter P., et al., "Mitotic Stability of Yeast Chromosomes: A Colony Color Assay That Measures Nondisjunction and Chromosome Loss," Cell, Feb. 1985, vol. 40, pp. 381-392.
Hir H.L., et al., "The Exon-Exon Junction Complex Provides a Binding Platform for Factors Involved in mRNA Export and Nonsense-Mediated mRNA Decay," The EMBO Journal, 2001, vol. 20, No. 17, pp. 4987-4997.
Hirotsune S., et al., "Graded Reduction of Pafah1b1 (List) Activity Results in Neuronal Migration Defects and Early Embryonic Lethality," Nature Genetics, Aug. 1998, vol. 19, pp. 333-339.
Hui A., et al., "Directing Ribosomes to a Single mRNA Species: A Method to Study Ribosomal RNA Mutations and Their Effects on Translation of a Single Messenger In Escherichia coli," Methods in Enzymology, 1987, vol. 153, pp. 432-452.
Hui A., et al., "Specialized Ribosome System: Preferential Translation of a Single mRNA Species by a Subpopulation of Mutated Ribosomes in Escherichia coli," Proceedings of the National Academy of Sciences of the United States of America, vol. 84, Jul. 1987, pp. 4762-4766.
Hunt R.C., et al., "Exposing Synonymous Mutations," Trend in Genetics, Jul. 2014, vol. 30, No. 7, pp. 308-321.
Ingolia N.T., et al., "The Ribosome Profiling Strategy for Monitoring Translation in Vivo by Deep Sequencing of Ribosome-Protected mRNA Fragments," Nature Protocols, 2012, vol. 7, No. 8, pp. 1534-1550.
Ingolia N.T., "Ribosome Profiling: New Views Of Translation, From Single Codons To Genome Scale," Nature Reviews Genetics, Mar. 2014, vol. 15, pp. 205-213.
International Preliminary Report on Patentability for International Application No. PCT/US2017/041766, mailed Jan. 24, 2019, 10 Pages.
International Search Report and Written Opinion for International Application No. PCT/US2017/041766, mailed Oct. 6, 2017, 13 Pages.
Invitrogen (TM): "Gateway(TM) pYES-DEST52 Vector," ThermoFisher Scientific, Catalog No. 12286019, Jun. 28, 2022, 21 pages.
Invitrogen (TM): "pBAD-DEST49 Gateway(TM) Destination Vector," ThermoFisher Scientific, Catalog No. 12283016, Jun. 28, 2022, 20 pages.

(56) References Cited

OTHER PUBLICATIONS

Ito-Harashima S., et al., "Translation Of The Poly(A) Tail Plays Crucial Roles In Nonstop mRNA Surveillance Via Translation Repression And Protein Destabilization By Proteasome In Yeast," Genes Development, 2007, vol. 21, pp. 519-524.
Joung J.K., et al., "TALENs: A Widely Applicable Technology For Targeted Genome Editing," Nature Reviews Molecular Cell Biology, 2013, vol. 14, pp. 49-55.
Karlin S., et al., "Amino Acid Runs in Eukaryotic Proteomes and Disease Associations," Proceedings of the National Academy of Sciences of the United States of America, Jan. 8, 2002, vol. 99, No. 1, pp. 333-338.
Kaufman R.J., et al., "Translational Efficiency of Polycistronic mRNAs and Their Utilization to Express Heterologous Genes in Mammalian Cells," The EMBO Journal, 1987, vol. 6, No. 1, pp. 187-193.
Kessel M., et al., "Murine Development Control Genes," Science, Jul. 27, 1990, vol. 249, No. 4967, pp. 374-379.
Koncz C., et al., "The Promoter of TL-DNA Gene 5 Controls the Tissue-Specific Expression of Chimaeric Genes Carried by a Novel Type of Agrobacterium Binary Vector," Molecular general genetics, Springer-Verlag, 1986, vol. 204, pp. 383-396.
Koutmou K.S., et al., "Ribosomes Slide on Lysine-Encoding Homopolymeric A Stretches," elife, 2015, vol. 4, No. e05534, pp. 1-18.
Kurjan J., et al., "Structure of a Yeast Pheromone Gene (MF alpha): A Putative alpha-factor Precursor contains four Tandem Copies of Mature alpha-factor," Cell, Oct. 1982, vol. 30(3), pp. 933-943.
Kuroha K., et al., "Receptor for Activated C Kinase 1 Stimulates Nascent Polypeptide-Dependent Translation Arrest," EMBO Reports, 2010, vol. 11, No. 12, pp. 956-961.
Lafave M.C., et al., "Transcription Initiation From Within P Elements Generates Hypomorphic Mutations in *Drosophila melanogaster*," Genetics, Jul. 2011, vol. 188, pp. 749-752.
Langmead B., et al., "Ultrafast and Memory-Efficient Alignment of Short DNA Sequences to the Human Genome," Genome Biology, Mar. 4, 2009, vol. 10, No. 3, 10 pages.
Lee K., et al., "Genetic Analysis Of The Shine-Dalgarno Interaction: Selection Of Alternative Functional mRNA-rRNA Combinations," RNA, Cambridge University Press, 1996, vol. 2, pp. 1270-1285.
Letzring D.P., et al., "Control Of Translation Efficiency In Yeast By Codon-anticodon Interactions," RNA, Dec. 2010, vol. 16, No. 2, pp. 2516-2528.
Li J., et al., "Relationship Between Promoter Sequence And Its Strength In Gene Expression," The European Physical Journal E, 2014, vol. 37, No. 86, pp. 1-6.
Liebman S.W., et al., "Prions In Yeast," Genetics, Aug. 2012, vol. 191, pp. 1041-1072.
Loayza-Puch F., et al., "p53 Induces Transcriptional And Translational Programs To Suppress Cell Proliferation And Growth," Genome Biology, 2013, vol. 14, Article R32, pp. 1-12.
Lu J., et al., "Electrostatics in the Ribosomal Tunnel Modulate Chain Elongation Rates," Journal of Molecular Biology, Dec. 5, 2008, vol. 384, No. 1, pp. 73-86.
Lykke-Andersen J., et al., "Human Upf Proteins Target an mRNA for Nonsense-Mediated Decay When Bound Downstream of a Termination Codon," Cell, Dec. 22, 2000, vol. 103, pp. 1121-1131.
Mano Y., et al., "Single Cell Visualization of Yeast Gene Expression Shows Correlation of Epigenetic Switching between Multiple Heterochromatic Regions through Multiple Generations," PLOS Biology, Jul. 2, 2013, vol. 11, No. 7, e1001601, pp. 1-18.
Matsuda A., et al., "The Conjugation-Specific Die5 Protein Is Required for Development of the Somatic Nucleus in both Paramecium and Tetrahymena," Eukaryotic Cell, Jul. 2010, vol. 9, No. 7, pp. 1087-1099.
Mclaughlin S.K., et al., "The RasGAP Gene, RASAL2, Is a Tumor and Metastasis Suppressor," Cancer Cell, Cell Press, Sep. 9, 2013, vol. 24, pp. 365-378.

Melnikov S., et al., "One Core, Two Shells: Bacterial And Eukaryotic Ribosomes," Nature Structural Molecular Biology, Jun. 2012, vol. 19, No. 6, pp. 560-567.
Meyers E.N., et al., "An Fgf8 Mutant Allelic Series Generated By Cre- And Flp-Mediated Recombination," Nature Genetics, Feb. 1998, vol. 18, pp. 136-141.
Motl J.A., et al., "Zygotic Expression of the Double-Stranded RNA Binding Motif Protein Drb2p Is Required for DNA Elimination in the Ciliate Tetrahymena Thermophila," Eukaryotic Cell, Dec. 2011, vol. 10, No. 12, pp. 1648-1659.
MTDH Clone ID 5298467, "*Homo sapiens* metadherin, mRNA," Jul. 17, 2006, 3 pages.
Nagy A., et al., "Dissecting The Role of N-myc in Development Using a Single Targeting Vector To Generate a Series of Alleles," Current Biology, 1998, vol. 8, No. 11, pp. 661-664, 6 Pages.
O'Hare K, et al., "Transformation of Mouse Fibroblasts to Methotrexate Resistance by a Recombinant Plasmid Expressing a Prokaryotic Dihydrofolate Reductase," Proceedings of the National Academy of Sciences of the United States of America, 1981, vol. 78, No. 3, pp. 1527-1531.
Pfeiffer B.D., et al., "Using Translational Enhancers To Increase Transgene Expression In *Drosophila*," Proceedings of the National Academy of Sciences of the United States of America, Apr. 24, 2012, vol. 109, No. 17, pp. 6626-6631.
Pinkert C.A., et al., "An Albumin Enhancer Located 10 Kb Upstream Functions along with Its Promoter to Direct Efficient, Liver-specific Expression in Transgenic Mice," Genes & Development, Cold Spring Harbor Laboratory Press, May 1987, vol. 1, No. 3, pp. 268-276.
Polylinker, "Encyclopedia of Genetics, Genomics, Proteomics and Informatics," 2008 Edition, Springer, Dordrecht, First Online Jul. 16, 2016, 3 pages, [Retrieved on Jun. 28, 2022] Retrieved from URL: https://doi.org/10.1007/978-1-4020-6754-9_13204.
Ponton F., et al., "Evaluation Of Potential Reference Genes For Reverse Transcription-qPCR Studies Of Physiological Responses In *Drosophila melanogaster*," Journal of Insect Physiology, Jun. 2011, vol. 57, pp. 840-850.
Popp M.W.L., et al., "Organizing Principles of Mammalian Nonsense-Mediated mRNA Decay," NIH Public Access Author Manuscript, Aug. 29, 2014, Annual Review of Genetics, 2013, vol. 47, pp. 139-165, 33 Pages.
Pruitt K.D., et al., "RefSeq: An Update on Mammalian Reference Sequences," Nucleic Acids Research, Database Issue, Oxford University Press, 2014, vol. 42, pp. D756-D763.
Queen C., et al., "Immunoglobulin Gene Transcription Is Activated by Downstream Sequence Elements," Cell, Jul. 1983, vol. 33, No. 3, pp. 741-748.
Rackham O., et al., "A Network Of Orthogonal Ribosome mRNA Pairs," Nature Chemical Biology, Aug. 2005, vol. 1, No. 3, pp. 159-166.
Redden H., et al., "The Synthetic Biology Toolbox For Tuning Gene Expression In Yeast," FEMS Yeast Research, Feb. 2015, vol. 15, No. 1, pp. 1-10.
Rooijers K., et al., "Ribosome Profiling Reveals Features Of Normal And Disease-associated Mitochondrial Translation," Nature Communications, 2013, vol. 4, No. 2886, pp. 1-8.
Schultz L.D., et al., "Expression and Secretion in Yeast of a 400-kDa Envelope Glycoprotein derived from Epstein-Barr Virus," Gene, 1987, vol. 54(1), pp. 113-123.
Seed B., "An LFA-3 cDNA Encodes a Phospholipid-linked Membrane Protein Homologous to its Receptor CD2," Nature, Oct. 1987, vol. 329(6142), pp. 840-842.
Shang Y., et al., "A Robust Inducible-repressible Promoter Greatly Facilitates Gene Knockouts, Conditional Expression, And Overexpression Of Homologous And Heterologous Genes In Tetrahymena Thermophila," Proceedings of the National Academy of Sciences of the United States of America, Mar. 19, 2002, vol. 99, No. 6, pp. 3734-3739.
Sherry S.T., et al., "dbSNP: The NCBI Database Of Genetic Variation," Nucleic Acids Research, 2001, vol. 29, No. 1, pp. 308-311.

(56) References Cited

OTHER PUBLICATIONS

Shoemaker C.J., et al., "Translation Drives mRNA Quality Control," Nature Structural Molecular Biology, 2012, vol. 19, No. 6, pp. 594-601.
Slater G.C., et al., "Automated Generation Of Heuristics For Biological Sequence Comparison," BMC Bioinformatics, Feb. 5, 2005, vol. 6, No. 31, pp. 1-11.
Smith D.B., et al., "Single-Step Purification of Polypeptides Expressed in *Escherichia coli* as Fusions with Glutathione S-Transferase," Gene, 1988, vol. 67, No. 1, pp. 31-40.
Takebe Y., et al., "SRα Promoter: An Efficient And Versatile Mammalian cDNA Expression System Composed Of The Simian Virus 40 Early Promoter And The R-U5 Segment Of Human T-Cell Leukemia Virus Type 1 Long Terminal Repeat," Molecular and Cellular Biology, Jan. 1988, vol. 8, No. 1, pp. 466-472.
Tsuboi T., et al., "Dom34:Hbs1 Plays a General Role in Quality-Control Systems by Dissociation of a Stalled Ribosome at the 3' End of Aberrant mRNA," Molecular Cell, May 25, 2012, vol. 46, pp. 518-529.
TTHERM_00384860, "LA Motif RNA-Binding Domain Protein [Tetrahymena Thermophila SB210]," Sep. 17, 2016, 3 Pages.

\* cited by examiner

X = (AAA)₆₋₁₂, (AAG)₆₋₁₂, (GAA)₁₂, (CGA)₁₂, (AGG)₁₂, TAA

```
WT          GCAGCGGTGAGC
             A  A  V  S

A9          GCAGCGAAAAAAAAAGTGAGC
             A  A  K  K  K  V  S

A10         GCAGCAAAAAAAAAAGTGAGC
             A  A  K  K  K  V  S

A11         GCAGCAAAAAAAAAAAACGTG
             A  A  K  K  K  T  V

A12         GCAGCAAAAAAAAAAAACGTG
             A  A  K  K  K  N  V

A13         GCAGAAAAAAAAAAAAACGTG
             A  E  K  K  K  N  V
```

| | | |
|---|---|---|
| SLU7 | GAGAAGAAGAAGAAGAAAAAGAAGAAGAAGAAGCAT | 10 Lys (9AAG/1AAA) |
| MTDH | TCCAAAAAGAAAAAAAAGAAAAAAGAAGAAGCAAGGT | 9 Lys (5AAG/4AAA) |
| NOP58 | GAGAAAAAGAAGAAAAAGAAAAAAAACAGAGAGAGA | 8 Lys (4AAG/4AAA) |
| ZCRB1 | CCAAAGAAGAAAGAAAAAAGAAAAAAAAGAAAGCT | 6 Lys (2AAG/4AAA) |
| RASAL2 | GTGGAAAAAAAGAAAAAAAAAGGACAAGAATAATTAT | 5 Lys (2AAG/3AAA) |

```
AA seq      ...AspValGluLysLyslysLysLysAspLysAsnAsn...
Human       ...gatgtggaaaaaaagaaaaaaaaggacaagaataat...
Pig         ...gacgtggaaaaaaagaaaaaaaaggacaagaataat...
Mouse       ...gatgtggaaaaaaagaaaaaaaaggacaagaataat...
Hamster     ...gatgtggaaaaaaagaaaaaaaaggacaagaataat...
Chicken     ...gatgtggaaaagaagaaaaaaaaggacaaaaataat...
Zebrafish   ...gatgtggaaaagaagaaaaaaaaggacaaaaacaac...
Frog        ...gatgttgaaaagaagaaaaaaaaagataaaaacaac...
```

FIG. 15

|  | Pro | Lys | Lys | Lys | Glu | Lys | Lys | Lys | Lys | Lys | Ala |
|---|---|---|---|---|---|---|---|---|---|---|---|
| ZCRB1 WT | CCA | AAG | AAG | AAA | GAA | AAA | AAG | AAA | AAA | AAG | AAA GCT |
| ZCRB1 411G>A | CCA | AAG | AAG | AAA | GAA | AAA | AAA | AAA | AAA | AAG | AAA GCT |
| ZCRB1 408A>G;417A>G | CCA | AAG | AAG | AAA | GAA | AAG | AAG | AAA | AAG | AAG | AAA GCT |

```
         Ser Lys Lys Lys Lys Lys Lys Lys Lys Lys Gln
Lyr (WT) TCC AAA AAG AAA AAA AAG AAA AAG AAG AAG CAA- (8As/9K)
Lyr (LG) TCC AAG AAG AAG AAG AAG AAG AAG AAG AAG CAA- (2As/9K)
Lyr (LM) TCC AAA AAA AAA AAA AAG AAA AAG AAG AAG CAA- (14As/9K)
Lyr (LA) TCC AAA AAA AAA AAA AAA AAA AAA AAA AAA CAA -(27As/9K)
```

```
LUC con

ZCRB WT  - LUC          ATG-2xHA-SEQ ID NO: 84-LUC
ZCRB -1  - LUC          ATG-2xHA-SEQ ID NO: 85-LUC
ZCRB +1  - LUC          ATG-2xHA-SEQ ID NO: 86-LUC

ZCRB 417G>A   - LUC     ATG-2xHA-SEQ ID NO: 87-LUC
ZCRB 417G>A-1 - LUC     ATG-2xHA-SEQ ID NO: 88-LUC
ZCRB 417G>A+1 - LUC     ATG-2xHA-SEQ ID NO: 89-LUC
```

```
            442 443 444 445 446 447 448 449 450 451 452
            ...Ser Lys Lys Lys Lys Lys Lys Lys Lys Lys Gln...
MTDH WT     ...TCC AAA AAG AAA AAA AAG AAA AAG AAG AAG CAA...
MTDH K447K  ...TCC AAA AAG AAA AAA AAA AAA AAG AAG AAG CAA...
                                 1341G>A
```

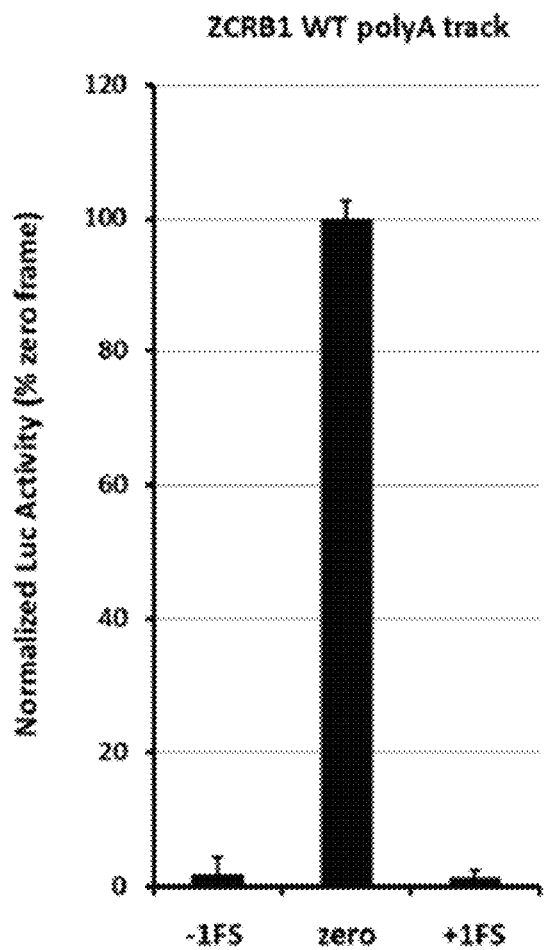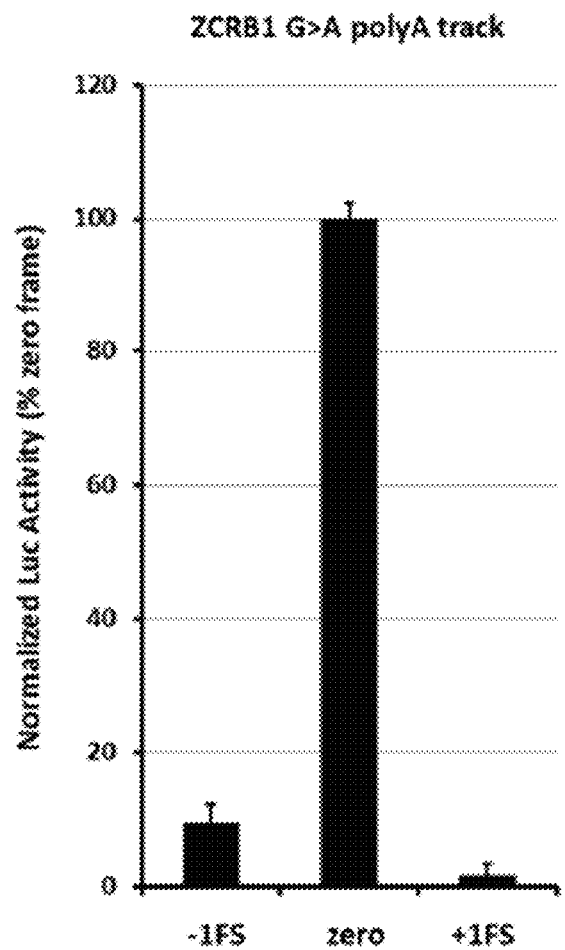
FIG. 22A  FIG. 22B

X = 6-12xLys$_{AAG}$ or 3-12Lys$_{AAA}$

WT (TRX-HA) – Ala – Val – (mCherry)
- GCA - GTG -

(AAG)$_n$ (TRX-HA) – Ala – (Lys)$_{6-12}$ – Val – (mCherry)
- GCA - (AAG)$_{6-12}$ - GTG -

(AAA)$_n$ (TRX-HA) – Ala – (Lys)$_{6-12}$ – Val – (mCherry)
- GCA - (AAA)$_{6-12}$ - GTG -

```
WT              GCAGTG
                 A  V

K2/A9   (AN)    GCAAAAAAAAATGTG
                 A  K  K  N  V

K3/A9   (AS)    GCGAAAAAAAAATCC
                 A  K  K  K  S

K2/A10  (QN)    CAAAAAAAAAATGTG
                 Q  K  K  N  V

K3/A10  (EV)    GAAAAAAAAAAGGTG
                 E  K  K  K  V

K3/A10  (QV)    CAAAAAAAAAAGGTG
                 Q  K  K  K  V

K3/A11  (AN)    GCGAAAAAAAAAAATGTG
                 A  K  K  K  N  V

K4/A11  (AV)    GCGAAAAAAAAAAAGGTG
                 A  K  K  K  K  V
```

FIG. 45A

Non-PolyA species of genomic reads (7.73%):

TGCACCCAAAAAAATTTACAAAAAAACCGTGAGCAAGGGCGA

Bold portion maps to chromosome X
Underline portion maps to chromosome 3L

SEQUENCE LISTING

```
Sequence total quantity: 116
SEQ ID NO: 1            moltype = DNA  length = 36
FEATURE                 Location/Qualifiers
misc_feature            1..36
                        note = SYNTHESIZED
source                  1..36
                        mol_type = other DNA
                        organism = synthetic construct
SEQUENCE: 1
gaagaagaag aagaagaaga agaagaagaa gaagaa                                    36

SEQ ID NO: 2            moltype = DNA  length = 18
FEATURE                 Location/Qualifiers
misc_feature            1..18
                        note = SYNTHESIZED
source                  1..18
                        mol_type = other DNA
                        organism = synthetic construct
SEQUENCE: 2
aagaagaaga agaagaag                                                        18

SEQ ID NO: 3            moltype = DNA  length = 27
FEATURE                 Location/Qualifiers
misc_feature            1..27
                        note = SYNTHESIZED
source                  1..27
                        mol_type = other DNA
                        organism = synthetic construct
SEQUENCE: 3
aagaagaaga agaagaagaa gaagaag                                              27

SEQ ID NO: 4            moltype = DNA  length = 36
FEATURE                 Location/Qualifiers
misc_feature            1..36
                        note = SYNTHESIZED
source                  1..36
                        mol_type = other DNA
                        organism = synthetic construct
SEQUENCE: 4
aagaagaaga agaagaagaa gaagaagaag aagaag                                    36

SEQ ID NO: 5            moltype = DNA  length = 18
FEATURE                 Location/Qualifiers
misc_feature            1..18
                        note = SYNTHESIZED
source                  1..18
                        mol_type = other DNA
                        organism = synthetic construct
SEQUENCE: 5
```

```
aaaaaaaaaa aaaaaaaa                                                      18

SEQ ID NO: 6              moltype = DNA  length = 27
FEATURE                   Location/Qualifiers
misc_feature              1..27
                          note = SYNTHESIZED
source                    1..27
                          mol_type = other DNA
                          organism = synthetic construct
SEQUENCE: 6
aaaaaaaaaa aaaaaaaaaa aaaaaaa                                            27

SEQ ID NO: 7              moltype = DNA  length = 36
FEATURE                   Location/Qualifiers
misc_feature              1..36
                          note = SYNTHESIZED
source                    1..36
                          mol_type = other DNA
                          organism = synthetic construct
SEQUENCE: 7
aaaaaaaaaa aaaaaaaaaa aaaaaaaaaa aaaaaa                                  36

SEQ ID NO: 8              moltype = DNA  length = 36
FEATURE                   Location/Qualifiers
misc_feature              1..36
                          note = SYNTHESIZED
source                    1..36
                          mol_type = other DNA
                          organism = synthetic construct
SEQUENCE: 8
cgacgacgac gacgacgacg acgacgacga cgacga                                  36

SEQ ID NO: 9              moltype = DNA  length = 36
FEATURE                   Location/Qualifiers
misc_feature              1..36
                          note = SYNTHESIZED
source                    1..36
                          mol_type = other DNA
                          organism = synthetic construct
SEQUENCE: 9
aggaggagga ggaggaggag gaggaggagg aggagg                                  36

SEQ ID NO: 10             moltype = DNA  length = 21
FEATURE                   Location/Qualifiers
misc_feature              1..21
                          note = SYNTHESIZED
source                    1..21
                          mol_type = other DNA
                          organism = synthetic construct
SEQUENCE: 10
gcagcgaaaa aaaaatccgt g                                                  21

SEQ ID NO: 11             moltype = DNA  length = 15
FEATURE                   Location/Qualifiers
misc_feature              1..15
                          note = SYNTHESIZED
source                    1..15
                          mol_type = other DNA
                          organism = synthetic construct
SEQUENCE: 11
gcaaaaaaaa aagtg                                                         15

SEQ ID NO: 12             moltype = DNA  length = 21
FEATURE                   Location/Qualifiers
misc_feature              1..21
                          note = SYNTHESIZED
source                    1..21
                          mol_type = other DNA
                          organism = synthetic construct
SEQUENCE: 12
gcagcaaaaa aaaaaaccgt g                                                  21

SEQ ID NO: 13             moltype = DNA  length = 21
FEATURE                   Location/Qualifiers
misc_feature              1..21
                          note = SYNTHESIZED
source                    1..21
                          mol_type = other DNA
                          organism = synthetic construct
```

```
SEQUENCE: 13
gcagaaaaaa aaaaaaccgt g                                                 21

SEQ ID NO: 14              moltype = DNA   length = 21
FEATURE                    Location/Qualifiers
misc_feature               1..21
                           note = SYNTHESIZED
source                     1..21
                           mol_type = other DNA
                           organism = synthetic construct
SEQUENCE: 14
gcagaaaaaa aaaaaacgt g                                                  21

SEQ ID NO: 15              moltype = DNA   length = 36
FEATURE                    Location/Qualifiers
misc_feature               1..36
                           note = SYNTHESIZED
source                     1..36
                           mol_type = other DNA
                           organism = synthetic construct
SEQUENCE: 15
gagaagaaga agaagaaaaa gaagaagaag aagcat                                 36

SEQ ID NO: 16              moltype = DNA   length = 36
FEATURE                    Location/Qualifiers
misc_feature               1..36
                           note = SYNTHESIZED
source                     1..36
                           mol_type = other DNA
                           organism = synthetic construct
SEQUENCE: 16
tccaaaaaga aaaaaagaa aaagaagaag caaggt                                  36

SEQ ID NO: 17              moltype = DNA   length = 36
FEATURE                    Location/Qualifiers
misc_feature               1..36
                           note = SYNTHESIZED
source                     1..36
                           mol_type = other DNA
                           organism = synthetic construct
SEQUENCE: 17
gagaaaaga agaaaagaa aaaaagaga gagaga                                    36

SEQ ID NO: 18              moltype = DNA   length = 36
FEATURE                    Location/Qualifiers
misc_feature               1..36
                           note = SYNTHESIZED
source                     1..36
                           mol_type = other DNA
                           organism = synthetic construct
SEQUENCE: 18
ccaaagaaga agaaaaaaa gaaaaaaag aaagct                                   36

SEQ ID NO: 19              moltype = DNA   length = 36
FEATURE                    Location/Qualifiers
misc_feature               1..36
                           note = SYNTHESIZED
source                     1..36
                           mol_type = other DNA
                           organism = synthetic construct
SEQUENCE: 19
gtggaaaaaa agaaaaaaaa ggacaagaat aattat                                 36

SEQ ID NO: 20              moltype = DNA   length = 36
FEATURE                    Location/Qualifiers
misc_feature               1..36
                           note = SYNTHESIZED
source                     1..36
                           mol_type = other DNA
                           organism = synthetic construct
SEQUENCE: 20
ccaaagaaga agaaaaaaa gaaaaaaag aaagct                                   36

SEQ ID NO: 21              moltype = DNA   length = 36
FEATURE                    Location/Qualifiers
misc_feature               1..36
                           note = SYNTHESIZED
source                     1..36
                           mol_type = other DNA
```

```
                                organism = synthetic construct
SEQUENCE: 21
ccaaagaaga aagaaaaaaa aaaaaaaaag aaagct                                 36

SEQ ID NO: 22           moltype = DNA   length = 36
FEATURE                 Location/Qualifiers
misc_feature            1..36
                        note = SYNTHESIZED
source                  1..36
                        mol_type = other DNA
                        organism = synthetic construct
SEQUENCE: 22
ccaaagaaga aagaaaagaa gaaaaagaag aaagct                                 36

SEQ ID NO: 23           moltype = DNA   length = 36
FEATURE                 Location/Qualifiers
misc_feature            1..36
                        note = SYNTHESIZED
source                  1..36
                        mol_type = other DNA
                        organism = synthetic construct
SEQUENCE: 23
gtggaaaaaa agaaaaaaaa ggacaagaat aattat                                 36

SEQ ID NO: 24           moltype = DNA   length = 36
FEATURE                 Location/Qualifiers
misc_feature            1..36
                        note = SYNTHESIZED
source                  1..36
                        mol_type = other DNA
                        organism = synthetic construct
SEQUENCE: 24
gtggaaaaaa aaaaaaaaaa ggacaagaat aattat                                 36

SEQ ID NO: 25           moltype = DNA   length = 36
FEATURE                 Location/Qualifiers
misc_feature            1..36
                        note = SYNTHESIZED
source                  1..36
                        mol_type = other DNA
                        organism = synthetic construct
SEQUENCE: 25
gtggaaaaaa agaaaaagaa ggacaagaat aattat                                 36

SEQ ID NO: 26           moltype = DNA   length = 36
FEATURE                 Location/Qualifiers
misc_feature            1..36
                        note = SYNTHESIZED
source                  1..36
                        mol_type = other DNA
                        organism = synthetic construct
SEQUENCE: 26
gtggaaaaga agaagaagaa ggacaagaat aattat                                 36

SEQ ID NO: 27           moltype = DNA   length = 65
FEATURE                 Location/Qualifiers
misc_feature            1..65
                        note = SYNTHESIZED
source                  1..65
                        mol_type = other DNA
                        organism = synthetic construct
SEQUENCE: 27
caccatgcac catcaccatc accatgaaaa aaaaatcact ggatatacca ccgttgatat        60
atccc                                                                   65

SEQ ID NO: 28           moltype = DNA   length = 89
FEATURE                 Location/Qualifiers
misc_feature            1..89
                        note = SYNTHESIZED
source                  1..89
                        mol_type = other DNA
                        organism = synthetic construct
SEQUENCE: 28
caccatgcac catcaccatc accatgagaa gaagaagaag aagaagaaga agaagaagat        60
cactggatat accaccgttg atatatccc                                         89

SEQ ID NO: 29           moltype = DNA   length = 68
FEATURE                 Location/Qualifiers
misc_feature            1..68
```

```
                        note = SYNTHESIZED
source                  1..68
                        mol_type = other DNA
                        organism = synthetic construct
SEQUENCE: 29
caccatgcac catcaccatc accatgaaaa aaaaaaatc actggatata ccaccgttga    60
tatatccc                                                           68

SEQ ID NO: 30           moltype = DNA  length = 71
FEATURE                 Location/Qualifiers
misc_feature            1..71
                        note = SYNTHESIZED
source                  1..71
                        mol_type = other DNA
                        organism = synthetic construct
SEQUENCE: 30
caccatgcac catcaccatc accatgaaaa aaaaaaaaaa atcactggat ataccaccgt    60
tgatatatcc c                                                        71

SEQ ID NO: 31           moltype = DNA  length = 74
FEATURE                 Location/Qualifiers
misc_feature            1..74
                        note = SYNTHESIZED
source                  1..74
                        mol_type = other DNA
                        organism = synthetic construct
SEQUENCE: 31
caccatgcac catcaccatc accatgaaaa aaaaaaaaaa aaaatcactg gatataccac    60
cgttgatata tccc                                                     74

SEQ ID NO: 32           moltype = DNA  length = 77
FEATURE                 Location/Qualifiers
misc_feature            1..77
                        note = SYNTHESIZED
source                  1..77
                        mol_type = other DNA
                        organism = synthetic construct
SEQUENCE: 32
caccatgcac catcaccatc accatgaaaa aaaaaaaaaa aaaaaaatca ctggatatac    60
caccgttgat atatccc                                                  77

SEQ ID NO: 33           moltype = DNA  length = 80
FEATURE                 Location/Qualifiers
misc_feature            1..80
                        note = SYNTHESIZED
source                  1..80
                        mol_type = other DNA
                        organism = synthetic construct
SEQUENCE: 33
caccatgcac catcaccatc accatgaaaa aaaaaaaaaa aaaaaaaaaa tcactggata    60
taccaccgtt gatatatccc                                               80

SEQ ID NO: 34           moltype = DNA  length = 83
FEATURE                 Location/Qualifiers
misc_feature            1..83
                        note = SYNTHESIZED
source                  1..83
                        mol_type = other DNA
                        organism = synthetic construct
SEQUENCE: 34
caccatgcac catcaccatc accatgaaaa aaaaaaaaaa aaaaaaaaaa aaatcactgg    60
ataccaccgt tgatatat ccc                                             83

SEQ ID NO: 35           moltype = DNA  length = 86
FEATURE                 Location/Qualifiers
misc_feature            1..86
                        note = SYNTHESIZED
source                  1..86
                        mol_type = other DNA
                        organism = synthetic construct
SEQUENCE: 35
caccatgcac catcaccatc accatgaaaa aaaaaaaaaa aaaaaaaaaa aaaaaatcac    60
tggatatacc accgttgata tatccc                                        86

SEQ ID NO: 36           moltype = DNA  length = 89
FEATURE                 Location/Qualifiers
misc_feature            1..89
                        note = SYNTHESIZED
source                  1..89
```

```
                        mol_type = other DNA
                        organism = synthetic construct
SEQUENCE: 36
caccatgcac catcaccatc accatgaaaa aaaaaaaaaa aaaaaaaaaa aaaaaaaaat    60
cactggatat accaccgttg atatatccc                                      89

SEQ ID NO: 37           moltype = DNA   length = 60
FEATURE                 Location/Qualifiers
misc_feature            1..60
                        note = SYNTHESIZED
source                  1..60
                        mol_type = other DNA
                        organism = synthetic construct
SEQUENCE: 37
cattacagat cttcttcaga aataagtttt tgttccgccc cgccctgcca ctcatcgcag    60

SEQ ID NO: 38           moltype = DNA   length = 33
FEATURE                 Location/Qualifiers
misc_feature            1..33
                        note = SYNTHESIZED
source                  1..33
                        mol_type = other DNA
                        organism = synthetic construct
SEQUENCE: 38
ggactagtat gtcaattacg aagactgaac tgg                                 33

SEQ ID NO: 39           moltype = DNA   length = 51
FEATURE                 Location/Qualifiers
misc_feature            1..51
                        note = SYNTHESIZED
source                  1..51
                        mol_type = other DNA
                        organism = synthetic construct
SEQUENCE: 39
ggactagtat gaaaaaaaaa aaaaaaaaat caattacgaa gactgaactg g              51

SEQ ID NO: 40           moltype = DNA   length = 60
FEATURE                 Location/Qualifiers
misc_feature            1..60
                        note = SYNTHESIZED
source                  1..60
                        mol_type = other DNA
                        organism = synthetic construct
SEQUENCE: 40
ggactagtat gaaaaaaaaa aaaaaaaaaa aaaaaaatc aattacgaag actgaactgg     60

SEQ ID NO: 41           moltype = DNA   length = 69
FEATURE                 Location/Qualifiers
misc_feature            1..69
                        note = SYNTHESIZED
source                  1..69
                        mol_type = other DNA
                        organism = synthetic construct
SEQUENCE: 41
ggactagtat gaaaaaaaaa aaaaaaaaaa aaaaaaaaaa aaaaaatca attacgaaga     60
ctgaactgg                                                             69

SEQ ID NO: 42           moltype = DNA   length = 69
FEATURE                 Location/Qualifiers
misc_feature            1..69
                        note = SYNTHESIZED
source                  1..69
                        mol_type = other DNA
                        organism = synthetic construct
SEQUENCE: 42
ggactagtat gaagaagaag aagaagaaga agaagaagaa gaagaagtca attacgaaga    60
ctgaactgg                                                             69

SEQ ID NO: 43           moltype = DNA   length = 53
FEATURE                 Location/Qualifiers
misc_feature            1..53
                        note = SYNTHESIZED
source                  1..53
                        mol_type = other DNA
                        organism = synthetic construct
SEQUENCE: 43
ggatcgattt acttgtcgtc atcgtccttg tagtcgtgag accatttaga ccc           53

SEQ ID NO: 44           moltype = DNA   length = 25
```

```
FEATURE                 Location/Qualifiers
misc_feature            1..25
                        note = SYNTHESIZED
source                  1..25
                        mol_type = other DNA
                        organism = synthetic construct
SEQUENCE: 44
gggagctcac acgatagcaa agcag                                              25

SEQ ID NO: 45           moltype = DNA   length = 24
FEATURE                 Location/Qualifiers
misc_feature            1..24
                        note = SYNTHESIZED
source                  1..24
                        mol_type = other DNA
                        organism = synthetic construct
SEQUENCE: 45
ggtctagata tcgttaatat ttcg                                               24

SEQ ID NO: 46           moltype = DNA   length = 39
FEATURE                 Location/Qualifiers
misc_feature            1..39
                        note = SYNTHESIZED
source                  1..39
                        mol_type = other DNA
                        organism = synthetic construct
SEQUENCE: 46
cacccgtacg aataaaatga gcattaataa agaagaagt                               39

SEQ ID NO: 47           moltype = DNA   length = 34
FEATURE                 Location/Qualifiers
misc_feature            1..34
                        note = SYNTHESIZED
source                  1..34
                        mol_type = other DNA
                        organism = synthetic construct
SEQUENCE: 47
gatatcttca attttaattt ttcttcgaag ttgc                                    34

SEQ ID NO: 48           moltype = DNA   length = 20
FEATURE                 Location/Qualifiers
misc_feature            1..20
                        note = SYNTHESIZED
source                  1..20
                        mol_type = other DNA
                        organism = synthetic construct
SEQUENCE: 48
tcttagctac gtgattcacg                                                    20

SEQ ID NO: 49           moltype = DNA   length = 21
FEATURE                 Location/Qualifiers
misc_feature            1..21
                        note = SYNTHESIZED
source                  1..21
                        mol_type = other DNA
                        organism = synthetic construct
SEQUENCE: 49
atgtgttatt aatcgattga t                                                  21

SEQ ID NO: 50           moltype = DNA   length = 20
FEATURE                 Location/Qualifiers
misc_feature            1..20
                        note = SYNTHESIZED
source                  1..20
                        mol_type = other DNA
                        organism = synthetic construct
SEQUENCE: 50
tctctttcat gcatgctagc                                                    20

SEQ ID NO: 51           moltype = DNA   length = 20
FEATURE                 Location/Qualifiers
misc_feature            1..20
                        note = SYNTHESIZED
source                  1..20
                        mol_type = other DNA
                        organism = synthetic construct
SEQUENCE: 51
aggcctacaa gaccaagggt                                                    20
```

| | | |
|---|---|---|
| SEQ ID NO: 52<br>FEATURE<br>misc_feature<br>source | moltype = DNA   length = 20<br>Location/Qualifiers<br>1..20<br>note = SYNTHESIZED<br>1..20<br>mol_type = other DNA<br>organism = synthetic construct | |
| SEQUENCE: 52<br>agagcggttt tgacgttgga | | 20 |
| SEQ ID NO: 53<br>FEATURE<br>misc_feature<br>source | moltype = DNA   length = 23<br>Location/Qualifiers<br>1..23<br>note = SYNTHESIZED<br>1..23<br>mol_type = other DNA<br>organism = synthetic construct | |
| SEQUENCE: 53<br>cccgtatgac gtaccggatt atg | | 23 |
| SEQ ID NO: 54<br>FEATURE<br>misc_feature<br>source | moltype = DNA   length = 19<br>Location/Qualifiers<br>1..19<br>note = SYNTHESIZED<br>1..19<br>mol_type = other DNA<br>organism = synthetic construct | |
| SEQUENCE: 54<br>acttcagggt cagcttgcc | | 19 |
| SEQ ID NO: 55<br>FEATURE<br>misc_feature<br>source | moltype = DNA   length = 20<br>Location/Qualifiers<br>1..20<br>note = SYNTHESIZED<br>1..20<br>mol_type = other DNA<br>organism = synthetic construct | |
| SEQUENCE: 55<br>ggctacccat acgatgttcc | | 20 |
| SEQ ID NO: 56<br>FEATURE<br>misc_feature<br>source | moltype = DNA   length = 20<br>Location/Qualifiers<br>1..20<br>note = SYNTHESIZED<br>1..20<br>mol_type = other DNA<br>organism = synthetic construct | |
| SEQUENCE: 56<br>cctccatgtg caccttgaag | | 20 |
| SEQ ID NO: 57<br>FEATURE<br>misc_feature<br>source | moltype = DNA   length = 18<br>Location/Qualifiers<br>1..18<br>note = SYNTHESIZED<br>1..18<br>mol_type = other DNA<br>organism = synthetic construct | |
| SEQUENCE: 57<br>tcaagagcgt ggtcgctg | | 18 |
| SEQ ID NO: 58<br>FEATURE<br>misc_feature<br>source | moltype = DNA   length = 20<br>Location/Qualifiers<br>1..20<br>note = SYNTHESIZED<br>1..20<br>mol_type = other DNA<br>organism = synthetic construct | |
| SEQUENCE: 58<br>caaatctcgg tgacgggcag | | 20 |
| SEQ ID NO: 59<br>FEATURE<br>misc_feature<br>source | moltype = DNA   length = 20<br>Location/Qualifiers<br>1..20<br>note = SYNTHESIZED<br>1..20<br>mol_type = other DNA<br>organism = synthetic construct | |
| SEQUENCE: 59<br>tgacgtaccg gattatgcaa | | 20 |

| | | |
|---|---|---|
| SEQ ID NO: 60<br>FEATURE<br>misc_feature<br>source | moltype = DNA length = 20<br>Location/Qualifiers<br>1..20<br>note = SYNTHESIZED<br>1..20<br>mol_type = other DNA<br>organism = synthetic construct | |
| SEQUENCE: 60<br>atatgaactg agggacagg | | 20 |
| SEQ ID NO: 61<br>FEATURE<br>misc_feature<br>source | moltype = DNA length = 20<br>Location/Qualifiers<br>1..20<br>note = SYNTHESIZED<br>1..20<br>mol_type = other DNA<br>organism = synthetic construct | |
| SEQUENCE: 61<br>gcgtgggttt gtgatcagtt | | 20 |
| SEQ ID NO: 62<br>FEATURE<br>misc_feature<br>source | moltype = DNA length = 20<br>Location/Qualifiers<br>1..20<br>note = SYNTHESIZED<br>1..20<br>mol_type = other DNA<br>organism = synthetic construct | |
| SEQUENCE: 62<br>gatcttctcc ttgcccatcc | | 20 |
| SEQ ID NO: 63<br>FEATURE<br>misc_feature<br>source | moltype = DNA length = 20<br>Location/Qualifiers<br>1..20<br>note = SYNTHESIZED<br>1..20<br>mol_type = other DNA<br>organism = synthetic construct | |
| SEQUENCE: 63<br>tgacgtaccg gattatgcaa | | 20 |
| SEQ ID NO: 64<br>FEATURE<br>misc_feature<br>source | moltype = DNA length = 20<br>Location/Qualifiers<br>1..20<br>note = SYNTHESIZED<br>1..20<br>mol_type = other DNA<br>organism = synthetic construct | |
| SEQUENCE: 64<br>atatgaactg agggacagg | | 20 |
| SEQ ID NO: 65<br>FEATURE<br>misc_feature<br>source | moltype = DNA length = 20<br>Location/Qualifiers<br>1..20<br>note = SYNTHESIZED<br>1..20<br>mol_type = other DNA<br>organism = synthetic construct | |
| SEQUENCE: 65<br>ctgaatgaac tgcaggacga | | 20 |
| SEQ ID NO: 66<br>FEATURE<br>misc_feature<br>source | moltype = DNA length = 20<br>Location/Qualifiers<br>1..20<br>note = SYNTHESIZED<br>1..20<br>mol_type = other DNA<br>organism = synthetic construct | |
| SEQUENCE: 66<br>atactttctc ggcaggagca | | 20 |
| SEQ ID NO: 67<br>FEATURE<br>misc_feature<br>source | moltype = DNA length = 20<br>Location/Qualifiers<br>1..20<br>note = SYNTHESIZED<br>1..20<br>mol_type = other DNA<br>organism = synthetic construct | |
| SEQUENCE: 67 | | |

```
gatgtaggag ggcgtggata                                              20

SEQ ID NO: 68           moltype = DNA   length = 20
FEATURE                 Location/Qualifiers
misc_feature            1..20
                        note = SYNTHESIZED
source                  1..20
                        mol_type = other DNA
                        organism = synthetic construct SEQUENCE: 68
ataggtcagg ctctcgctga                                              20

SEQ ID NO: 69           moltype = DNA   length = 20
FEATURE                 Location/Qualifiers
misc_feature            1..20
                        note = SYNTHESIZED
source                  1..20
                        mol_type = other DNA
                        organism = synthetic construct SEQUENCE: 69
agaaaatctg gcaccacacc                                              20

SEQ ID NO: 70           moltype = DNA   length = 20
FEATURE                 Location/Qualifiers
misc_feature            1..20
                        note = SYNTHESIZED
source                  1..20
                        mol_type = other DNA
                        organism = synthetic construct SEQUENCE: 70
agaggcgtac agggatagca                                              20

SEQ ID NO: 71           moltype = DNA   length = 12
FEATURE                 Location/Qualifiers
misc_feature            1..12
                        note = SYNTHESIZED
source                  1..12
                        mol_type = other DNA
                        organism = synthetic construct SEQUENCE: 71
gcagcggtga gc                                                      12

SEQ ID NO: 72           moltype = AA    length = 4
FEATURE                 Location/Qualifiers
REGION                  1..4
                        note = SYNTHESIZED
source                  1..4
                        mol_type = protein
                        organism = synthetic construct SEQUENCE: 72
AAVS                                                               4

SEQ ID NO: 73           moltype = AA    length = 7
FEATURE                 Location/Qualifiers
REGION                  1..7
                        note = SYNTHESIZED
source                  1..7
                        mol_type = protein
                        organism = synthetic construct SEQUENCE: 73
AAKKKVS                                                            7

SEQ ID NO: 74           moltype = AA    length = 7
FEATURE                 Location/Qualifiers
REGION                  1..7
                        note = SYNTHESIZED
source                  1..7
                        mol_type = protein
                        organism = synthetic construct SEQUENCE: 74
AAKKKTV                                                            7

SEQ ID NO: 75           moltype = AA    length = 7
FEATURE                 Location/Qualifiers
REGION                  1..7
                        note = SYNTHESIZED
source                  1..7
                        mol_type = protein
                        organism = synthetic construct
```

```
SEQUENCE: 75
AAKKKNV                                                                             7

SEQ ID NO: 76           moltype = AA  length = 7
FEATURE                 Location/Qualifiers
REGION                  1..7
                        note = SYNTHESIZED
source                  1..7
                        mol_type = protein
                        organism = synthetic construct
SEQUENCE: 76
AEKKKNV                                                                             7

SEQ ID NO: 77           moltype = AA  length = 12
FEATURE                 Location/Qualifiers
REGION                  1..12
                        note = SYNTHESIZED
source                  1..12
                        mol_type = protein
                        organism = synthetic construct
SEQUENCE: 77
PKKKEKKKKK KA                                                                      12

SEQ ID NO: 78           moltype = DNA  length = 33
FEATURE                 Location/Qualifiers
misc_feature            1..33
                        note = SYNTHESIZED
source                  1..33
                        mol_type = other DNA
                        organism = synthetic construct
SEQUENCE: 78
tccaaaaaga aaaaaagaa aaagaagaag caa                                                33

SEQ ID NO: 79           moltype = DNA  length = 33
FEATURE                 Location/Qualifiers
misc_feature            1..33
                        note = SYNTHESIZED
source                  1..33
                        mol_type = other DNA
                        organism = synthetic construct
SEQUENCE: 79
tccaagaaga agaagaagaa gaagaagaag caa                                               33

SEQ ID NO: 80           moltype = DNA  length = 33
FEATURE                 Location/Qualifiers
misc_feature            1..33
                        note = SYNTHESIZED
source                  1..33
                        mol_type = other DNA
                        organism = synthetic construct
SEQUENCE: 80
tccaaaaaaa aaaaaaagaa aaagaagaag caa                                               33

SEQ ID NO: 81           moltype = DNA  length = 33
FEATURE                 Location/Qualifiers
misc_feature            1..33
                        note = SYNTHESIZED
source                  1..33
                        mol_type = other DNA
                        organism = synthetic construct
SEQUENCE: 81
tccaaaaaaa aaaaaaaaaa aaaaaaaaaa caa                                               33

SEQ ID NO: 82           moltype = AA  length = 11
FEATURE                 Location/Qualifiers
REGION                  1..11
                        note = SYNTHESIZED
source                  1..11
                        mol_type = protein
                        organism = synthetic construct
SEQUENCE: 82
SKKKKKKKKK Q                                                                       11

SEQ ID NO: 83           moltype = AA  length = 10
FEATURE                 Location/Qualifiers
REGION                  1..10
                        note = SYNTHESIZED
source                  1..10
                        mol_type = protein
```

```
                              organism = synthetic construct
SEQUENCE: 83
EKKKKKDKNN                                                                       10

SEQ ID NO: 84           moltype = DNA   length = 33
FEATURE                 Location/Qualifiers
misc_feature            1..33
                        note = SYNTHESIZED
source                  1..33
                        mol_type = other DNA
                        organism = synthetic construct
SEQUENCE: 84
aagaagaaag aaaaaaagaa aaaaaagaaa gct                                             33

SEQ ID NO: 85           moltype = DNA   length = 37
FEATURE                 Location/Qualifiers
misc_feature            1..37
                        note = SYNTHESIZED
source                  1..37
                        mol_type = other DNA
                        organism = synthetic construct
SEQUENCE: 85
aagaagaaag aaaaaaagaa aaaaaagaaa gctctaa                                         37

SEQ ID NO: 86           moltype = DNA   length = 38
FEATURE                 Location/Qualifiers
misc_feature            1..38
                        note = SYNTHESIZED
source                  1..38
                        mol_type = other DNA
                        organism = synthetic construct
SEQUENCE: 86
aagaagaaag aaaaaaagaa aaaaaagaaa gctcctaa                                        38

SEQ ID NO: 87           moltype = DNA   length = 33
FEATURE                 Location/Qualifiers
misc_feature            1..33
                        note = SYNTHESIZED
source                  1..33
                        mol_type = other DNA
                        organism = synthetic construct
SEQUENCE: 87
aagaagaaag aaaaaaaaaa aaaaaagaaa gct                                             33

SEQ ID NO: 88           moltype = DNA   length = 37
FEATURE                 Location/Qualifiers
misc_feature            1..37
                        note = SYNTHESIZED
source                  1..37
                        mol_type = other DNA
                        organism = synthetic construct
SEQUENCE: 88
aagaagaaag aaaaaaaaaa aaaaaagaaa gctctaa                                         37

SEQ ID NO: 89           moltype = DNA   length = 38
FEATURE                 Location/Qualifiers
misc_feature            1..38
                        note = SYNTHESIZED
source                  1..38
                        mol_type = other DNA
                        organism = synthetic construct
SEQUENCE: 89
aagaagaaag aaaaaaaaaa aaaaaagaaa gctcctaa                                        38

SEQ ID NO: 90           moltype = DNA   length = 33
FEATURE                 Location/Qualifiers
misc_feature            1..33
                        note = SYNTHESIZED
source                  1..33
                        mol_type = other DNA
                        organism = synthetic construct
SEQUENCE: 90
tccaaaaaga aaaaaaaaaa aaagaagaag caa                                             33

SEQ ID NO: 91           moltype = DNA   length = 15
FEATURE                 Location/Qualifiers
misc_feature            1..15
                        note = SYNTHESIZED
source                  1..15
```

```
                                mol_type = other DNA
                                organism = synthetic construct
SEQUENCE: 91
gcaaaaaaaa atgtg                                                              15

SEQ ID NO: 92                   moltype = AA  length = 5
FEATURE                         Location/Qualifiers
REGION                          1..5
                                note = SYNTHESIZED
source                          1..5
                                mol_type = protein
                                organism = synthetic construct
SEQUENCE: 92
AKKNV                                                                          5

SEQ ID NO: 93                   moltype = DNA  length = 15
FEATURE                         Location/Qualifiers
misc_feature                    1..15
                                note = SYNTHESIZED
source                          1..15
                                mol_type = other DNA
                                organism = synthetic construct
SEQUENCE: 93
gcgaaaaaaa aatcc                                                              15

SEQ ID NO: 94                   moltype = AA  length = 5
FEATURE                         Location/Qualifiers
REGION                          1..5
                                note = SYNTHESIZED
source                          1..5
                                mol_type = protein
                                organism = synthetic construct
SEQUENCE: 94
AKKKS                                                                          5

SEQ ID NO: 95                   moltype = DNA  length = 15
FEATURE                         Location/Qualifiers
misc_feature                    1..15
                                note = SYNTHESIZED
source                          1..15
                                mol_type = other DNA
                                organism = synthetic construct
SEQUENCE: 95
caaaaaaaaa atgtg                                                              15

SEQ ID NO: 96                   moltype = AA  length = 5
FEATURE                         Location/Qualifiers
REGION                          1..5
                                note = SYNTHESIZED
source                          1..5
                                mol_type = protein
                                organism = synthetic construct
SEQUENCE: 96
QKKNV                                                                          5

SEQ ID NO: 97                   moltype = DNA  length = 15
FEATURE                         Location/Qualifiers
misc_feature                    1..15
                                note = SYNTHESIZED
source                          1..15
                                mol_type = other DNA
                                organism = synthetic construct
SEQUENCE: 97
gaaaaaaaaa aggtg                                                              15

SEQ ID NO: 98                   moltype = AA  length = 5
FEATURE                         Location/Qualifiers
REGION                          1..5
                                note = SYNTHESIZED
source                          1..5
                                mol_type = protein
                                organism = synthetic construct
SEQUENCE: 98
EKKKV                                                                          5

SEQ ID NO: 99                   moltype = DNA  length = 15
FEATURE                         Location/Qualifiers
misc_feature                    1..15
                                note = SYNTHESIZED
```

```
source                    1..15
                          mol_type = other DNA
                          organism = synthetic construct
SEQUENCE: 99
caaaaaaaaa aggtg                                                           15

SEQ ID NO: 100            moltype = AA   length = 5
FEATURE                   Location/Qualifiers
REGION                    1..5
                          note = SYNTHESIZED
source                    1..5
                          mol_type = protein
                          organism = synthetic construct
SEQUENCE: 100
QKKKV                                                                       5

SEQ ID NO: 101            moltype = DNA  length = 18
FEATURE                   Location/Qualifiers
misc_feature              1..18
                          note = SYNTHESIZED
source                    1..18
                          mol_type = other DNA
                          organism = synthetic construct
SEQUENCE: 101
gcgaaaaaaa aaaatgtg                                                        18

SEQ ID NO: 102            moltype = AA   length = 6
FEATURE                   Location/Qualifiers
REGION                    1..6
                          note = SYNTHESIZED
source                    1..6
                          mol_type = protein
                          organism = synthetic construct
SEQUENCE: 102
AKKKNV                                                                      6

SEQ ID NO: 103            moltype = DNA  length = 18
FEATURE                   Location/Qualifiers
misc_feature              1..18
                          note = SYNTHESIZED
source                    1..18
                          mol_type = other DNA
                          organism = synthetic construct
SEQUENCE: 103
gcgaaaaaaa aaaaggtg                                                        18

SEQ ID NO: 104            moltype = AA   length = 6
FEATURE                   Location/Qualifiers
REGION                    1..6
                          note = SYNTHESIZED
source                    1..6
                          mol_type = protein
                          organism = synthetic construct
SEQUENCE: 104
AKKKKV                                                                      6

SEQ ID NO: 105            moltype = DNA  length = 58
FEATURE                   Location/Qualifiers
misc_feature              1..58
                          note = SYNTHESIZED
source                    1..58
                          mol_type = other DNA
                          organism = synthetic construct
SEQUENCE: 105
gtaccggatt atgcgaaaaa aaaaaaaaaa aaaaaaaagt gagcaagg                       58

SEQ ID NO: 106            moltype = DNA  length = 58
FEATURE                   Location/Qualifiers
misc_feature              1..58
                          note = SYNTHESIZED
source                    1..58
                          mol_type = other DNA
                          organism = synthetic construct
SEQUENCE: 106
gtaccggatt atgcgaaaaa aaaaaaaaaa ctgaaaaaaa aaaaaaaagt gagcaagg            58

SEQ ID NO: 107            moltype = DNA  length = 58
FEATURE                   Location/Qualifiers
misc_feature              1..58
```

```
                    note = SYNTHESIZED
source              1..58
                    mol_type = other DNA
                    organism = synthetic construct
SEQUENCE: 107
gtaccggatt atgcgaaaaa aaaaaaaaaa tacaaaaaaa aaaaaaaagt gagcaagg         58

SEQ ID NO: 108         moltype = DNA  length = 58
FEATURE                Location/Qualifiers
misc_feature        1..58
                    note = SYNTHESIZED
source              1..58
                    mol_type = other DNA
                    organism = synthetic construct
SEQUENCE: 108
gtaccggatt atgcgaaaaa aaaaaaaaaa cccaaaaaaa aaaaaaaagt gagcaagg         58

SEQ ID NO: 109         moltype = DNA  length = 55
FEATURE                Location/Qualifiers
misc_feature        1..55
                    note = SYNTHESIZED
source              1..55
                    mol_type = other DNA
                    organism = synthetic construct
SEQUENCE: 109
gtaccggatt atgcgaaaaa aaaaaaaaaa aaaaaaaaaa aaaaagtgag caagg            55

SEQ ID NO: 110         moltype = DNA  length = 42
FEATURE                Location/Qualifiers
misc_feature        1..42
                    note = SYNTHESIZED
source              1..42
                    mol_type = other DNA
                    organism = synthetic construct
SEQUENCE: 110
tgcacccaaa aaaatttaca aaaaaaccgt gagcaagggc ga                          42

SEQ ID NO: 111         moltype = AA  length = 12
FEATURE                Location/Qualifiers
REGION              1..12
                    note = SYNTHESIZED
source              1..12
                    mol_type = protein
                    organism = synthetic construct
SEQUENCE: 111
DVEKKKKKDK NN                                                           12

SEQ ID NO: 112         moltype = DNA  length = 36
FEATURE                Location/Qualifiers
misc_feature        1..36
                    note = SYNTHESIZED
source              1..36
                    mol_type = other DNA
                    organism = synthetic construct
SEQUENCE: 112
gatgtggaaa aaaagaaaaa aaaggacaag aataat                                 36

SEQ ID NO: 113         moltype = DNA  length = 36
FEATURE                Location/Qualifiers
misc_feature        1..36
                    note = SYNTHESIZED
source              1..36
                    mol_type = other DNA
                    organism = synthetic construct
SEQUENCE: 113
gacgtggaaa aaaagaaaaa aaaggacaag aataat                                 36

SEQ ID NO: 114         moltype = DNA  length = 36
FEATURE                Location/Qualifiers
misc_feature        1..36
                    note = SYNTHESIZED
source              1..36
                    mol_type = other DNA
                    organism = synthetic construct
SEQUENCE: 114
gatgtggaaa agaagaaaaa aaaggacaaa aataat                                 36

SEQ ID NO: 115         moltype = DNA  length = 36
FEATURE                Location/Qualifiers
```

```
misc_feature           1..36
                       note = SYNTHESIZED
source                 1..36
                       mol_type = other DNA
                       organism = synthetic construct
SEQUENCE: 115
gatgtggaaa agaagaaaaa aaaggacaaa aacaac                    36

SEQ ID NO: 116         moltype = DNA  length = 36
FEATURE                Location/Qualifiers
misc_feature           1..36
                       note = SYNTHESIZED
source                 1..36
                       mol_type = other DNA
                       organism = synthetic construct
SEQUENCE: 116
gatgtggaaa agaagaaaaa aaaggataaa aacaac                    36
```

INCORPORATION OF INTERNAL POLYA-ENCODED POLY-LYSINE SEQUENCE TAGS AND THEIR VARIATIONS FOR THE TUNABLE CONTROL OF PROTEIN SYNTHESIS IN BACTERIAL AND EUKARYOTIC CELLS

CROSS REFERENCE TO RELATED APPLICATIONS

This application is a continuation of U.S. application Ser. No. 16/317,791, filed Jan. 14, 2019 which claims the benefit of PCT Application number PCT/US17/41766, filed Jul. 12, 2017, which claims the benefit of U.S. Provisional Application 62/361,307, filed Jul. 12, 2016, U.S. Provisional Application No. 62/427,518, filed Nov. 29, 2016, U.S. Provisional Application No. 62/437,464, filed Dec. 21, 2016, and U.S. Provisional Application No. 62/438,017, filed Dec. 22, 2016, each of the disclosures of which is hereby incorporated by reference in its entirety.

GOVERNMENTAL RIGHTS

This invention was made with government support under T32 GM007067 and RO1 GM112824 awarded by the National Institutes of Health (NIH). The government has certain rights in the invention.

REFERENCE TO A SEQUENCE LISTING

This application contains a Sequence Listing that has been submitted in Extensible Markup Language (.xml) and is hereby incorporated by reference in its entirety. The XML copy, created on Mar. 13, 2023, is named 047563-755867.xml, and is 148.025 bytes in size.

FIELD OF THE INVENTION

The present disclosure relates to modulation of protein expression.

BACKGROUND OF THE INVENTION

Gene expression in cells is a multistep process that involves transcription of genetic material from DNA to RNA and ultimately translation of mRNA into protein. These processes are subject to stringent control at all levels. Translational regulation generally controls the amount of protein generated from a given mRNA. While a majority of translational regulation mechanisms target the recruitment of ribosomes to the initiation codon, the protein synthesis machinery can also modulate translation, elongation, and termination (Dinman and Berry (2007) Cold Spring Harb. Monogr.Arch.; Hershey et al. (2012) Cold Spring Harb. Perspect. Biol. 4).

Pausing during the translational cycle—so-called ribosome stalling—is one mechanism by which the level of translation elongation can be regulated. Ribosome stalling is recognized by components of mRNA surveillance pathways, no-go decay (NGD) and non-stop decay (NSD), resulting in endonucleolytic cleavage of the stalled mRNA, ribosome rescue and proteolytic degradation of incomplete protein products (Shoemaker and Green (2012) Nat. Struct. Mol. Biol. 19, 594-601). NGD and NSD act on aberrant mRNAs that trigger translational arrest, as observed with damaged bases, stable stem-loop structures (Doma and Parker (2006) Nature 440, 561-564), rare codons (Letzring et al. (2010) RNA N. Y. N. 16, 2516-2528) or mRNAs lacking stop codons (non-stop mRNAs) (Dimitrova et al. (2009) J. Biol. Chem. 284, 10343-10352). However, these mechanisms also act on more specific types of translational pauses, such as runs of codons that encode consecutive basic amino acids (Kuroha et al. (2010) EMBO Rep. 11, 956-961; Brandman et al. (2012) Cell 151,1042-1054). It is thought that polybasic runs, as well as translation of the poly(A) tail in the case of non-stop mRNAs, cause ribosome stalling through interaction of the positively charged peptide with the negatively charged ribosome exit channel (Lu and Deutsch (2008) J. Mol. Biol. 384, 73-86). Presumably, the strength of the stall is dependent on the length and composition of the polybasic stretch, and thus the impact on overall protein expression might vary (Shoemaker and Green (2012) Nat. Struct. Mol. Biol. 19, 594-601). Given this logic, it seems plausible that such an amino acid motif may act as a gene regulatory element that would define the amount of protein translated and the stability of the mRNA. For example, structural and biophysical differences between lysine and arginine residues as well as potential mRNA sequence involvement could act to further modulate this process.

Most studies investigating the effects of polybasic sequences during translation have used reporter sequences in *E. coli* (Koutmou et al. (2015) eLIFE 10.7554/eLife.05534), yeast (Brandman et al. (2012) Cell 151, 1042-1054; Tsuboi et al. (2012) Mol. Cell. 46, 518-529) or in vitro rabbit reticulocyte lysate (Lu and Deutsch (2008) J. Mol. Biol. 384, 73-86). However, detailed mechanistic information about the nature of the stall in endogenous targets through genome-wide analyses has not yet been conducted.

SUMMARY OF THE INVENTION

In an aspect, the disclosure provides a method for modulating the level of expression of a polypeptide in a cell, the method comprising modulating the amount of consecutive adenine (A) nucleotides in at least one lysine codon in an open reading frame of a polynucleotide sequence encoding the polypeptide in the cell, thereby modulating the level of expression of the polypeptide in the cell.

In another aspect, the disclosure provides an expression vector comprising: a) a cloning site for inserting at least one polynucleotide sequence encoding a polypeptide to be expressed, and at least one polynucleotide tag sequence comprising at least one AAG lysine codon that increases expression of the at least one polynucleotide sequence when the expression vector is introduced into a cell; or b) a cloning site for inserting at least one polynucleotide sequence encoding a polypeptide to be expressed, and at least one polynucleotide tag sequence comprising at least one AAA lysine codon that decreases expression of the at least one polynucleotide sequence when the expression vector is introduced into a cell.

In another aspect, the disclsoure provides an expression vector comprising: a) at least one engineered polynucleotide sequence encoding a polypeptide to be expressed, the at least one engineered polynucleotide sequence comprising at least one engineered synonymous mutation of at least one AAA lysine codon to at least one AAG lysine codon in a coding sequence of the at least one polynucleotide sequence, wherein the synonymous mutation increases expression of the polypeptide to be expressed when the expression vector is introduced into a cell; or b) at least one engineered polynucleotide sequence encoding a polypeptide to be expressed, the at least one engineered polynucleotide sequence comprising at least one engineered synonymous mutation of at least one AAG lysine codon to at least one AAA lysine codon in a coding sequence of the at least one polynucleotide sequence, wherein the synonymous mutation decreases expression of the polypeptide to be expressed when the expression vector is introduced into a cell.

In yet another aspect, the disclosure provides a method of decreasing translation of a protein in a cell, by increasing the quantity of consecutive adenine nucleotides in an open reading frame (ORF) or an untranslated region (UTR) adjacent to the ORF in genomic DNA (gDNA). The gDNA may be modified by using a clustered regularly interspaced short palindromic repeats (CRISPR) enzyme system, zinc-finger nuclease (ZFN), or transcription activator-like effector nuclease (TALEN).

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 7A shows the scheme of assayed mCherry constructs. Thioredoxin (Trx) fusion protein was used instead of insertion of polylysine run in the middle of mCherry gene. Positions of 12 lysine (36As) insertions and HA-tagg in the constructs are labeled with blue and gray boxes, respectively. Numbers above reporter indicate distance of 36As insertion from the first nucleotide in the coding sequence. FIG. 7B shows that protein expression was monitored by western blot analyses using HA and beta-actin antibody. FIG. 7C shows that qRT-PCR analyses of mRNA abundance was normalized to neomycin resistance gene and presented as fraction of mRNA levels for WT mCherry construct without insert.

FIG. 8A shows a scheme of HBD gene with position of poly lysine and stop codon insertions. Position and length of introns as well as exons in HBD constructs are indicated. FIG. 8B shows western blot analysis of HA-HBD construct expression normalized to β-actin levels. FIG. 8C shows qRT-PCR analyses of mRNA abundance normalized to neomycin resistance gene and presented as fraction of mRNA levels for WT HBD construct without insert.

FIG. 12A shows the occupancy of ribosomal footprints for regions around different codon combinations for four lysine tracks. All combinations of one, two, three and four AAG codons per group are shown. Data for four AAA codons is not shown because only a single gene has such a sequence. The upper and lower "hinges" correspond to the first and third quartiles (the 25th and 75th percentiles). The upper and lower whiskers extend from hinges up or down at maximum of 1.5*IQR of the respective hinge. FIG. 12B shows the sequences of HA-(A9-A13)-mCherry constructs used in electroporation experiments. The WT nucleotide and amino acid sequences shown are SEQ ID NO: 71 and 72, respectively. The A9 nucleotide and amino acid sequences shown are SEQ ID NO: 10 and 73, respectively. The A10 nucleotide and amino acid sequences shown are SEQ ID NO: 11 and 73, respectively. The A11 nucleotide and amino acid sequences shown are SEQ ID NO: 12 and 74, respectively. The A12 nucleotide and amino acid sequences shown are SEQ ID NO: 13 and 75, respectively. The A14 nucleotide and amino acid sequences shown are SEQ ID 15 and 76, respectively. FIG. 12C shows western blot analyses of HA-(A9-A13)-mCherry constructs 48 hours after electroporation (HA and β-actin antibodies). FIG. 12D shows normalized protein expression using Licor western blot analyses or in vivo mCherry fluorescence measurement. β-actin or fluorescence of co-expressed GFP construct were used for normalization of the data, respectively. Each bar represents percentage of wild type mCherry (WT) expression/fluorescence. FIG. 12E shows normalized RNA levels of HA-X-mCherry constructs. Neomycin resistance gene was used for normalization of qRT-PCR data. Each bar represents percentage of wild type mCherry (WT) mRNA levels.

FIG. 13A shows the region around polyA tracks and FIG. 13B shows the region around four arginine tracks, all codons combinations together. The upper and lower "hinges" correspond to the first and third quartiles (the 25th and 75th percentiles). The upper and lower whiskers extend from hinges at 1.5*IQR of the respective hinge.

In FIG. 14A, SLU7 is SEQ ID NO: 15; MTDH is SEQ ID NO: 16; NOP58 is SEQ ID NO: 17; ZCRB1 is SEQ ID NO: 18; and RASAL2 is SEQ ID NO: 19.

FIG. 15 shows the sequence conservation of RAS Activating-Like protein 2 gene (RASAL2) at DNA and protein sequence. Polylysine sequence and nucleotides forming polyA track are in indicated in red and bold letters, respectively. The amino acid sequence shown is SEQ ID NO: 111. The human, mouse, and hamster sequence shown is SEQ ID NO: 112. The pig sequence shown is SEQ ID NO: 113. The chicken sequence shown is SEQ ID NO: 114. The zebrafish sequence shown is SEQ ID NO: 114. The frog sequence shown is SEQ ID NO: 116.

In FIG. 16A, the nucleotide sequence shown for ZCRB1 WT corresponds to nucleotides 3-30 of SEQ ID NO: 20; the nucleotide sequence shown for ZCRB1 411G>A corresponds to nucleotides 3-30 of SEQ ID NO: 21; the nucleotide sequence shown for ZCRB1 408A>G;417A>G corresponds to nucleotides 3-30 of SEQ ID NO: 22; and the amino acid sequence corresponds to residues 2-11 of SEQ ID NO: 77. In FIG. 16D, ZCRB1 WT is SEQ ID NO: 20; ZCRB1 411G>A is SEQ ID NO: 21; ZCRB1 408A>G; 417A>G is SEQ ID NO: 22; and the amino acid sequence is SEQ ID NO: 77.

FIG. 17A shows a scheme of reporter sequences with G>A and A>G synonymous mutations. The amino acid sequence shown is SEQ ID NO: 82, and the nucleotide sequences shown are SEQ ID NO: 78-81, respectively. FIG. 17B shows western blot analyses of reporter constructs with synonymous mutations. FIG. 17C shows normalized mRNA levels for reporter sequences with wild type MTDH polyA-track (Lwt) and corresponding mutants. mRNA levels are represented as fractions of wild type mCherry levels.

FIG. 18A shows a scheme of reporter sequences with G>A and A>G synonymous mutations. The amino acid sequence is SEQ ID NO: 83. The RASAL2 WT nucleic acid sequence corresponds to nucleotide 3032 of SEQ ID NO: 23. The RASAL2 G>A nucleic acid sequence corresponds to nucleotides 3-32 of SEQ ID NO: 24. The RASAL2 A>G nucleic acid sequence corresponds to nucleotides 3-32 of SEQ ID NO: 25. The RASAL2 A>G (3) nucleic acid sequence corresponds to nucleotides 3-32 of SEQ ID NO: 26. FIG. 18B shows western blot analyses of reporter constructs with synonymous mutations. FIG. 18C shows normalized mRNA levels for reporter sequences with wild type RASAL2 polyA-track (Lwt) and corresponding mutants. mRNA levels are represented as fractions of wild type mCherry levels.

FIG. 19D shows western blot analyses of HA-ZCRB1-GFP proteins from HDF cells using HA-antibody. Western blot analyses were normalized using beta-actin levels as loading controls.

FIG. 20A shows immunoprecipitation of HA-ZCRB gene constructs using anti-HA magnetic beads. ZCRB1 WT, synonymous (single 411 G>A or double 408 A>G; 417 A>G), non-sense (385 G>T, insertion of stop codon prior poly(A) track), deletion (423ΔA, equivalent to +1 frame-shift) or insertion (423 A>AA, equivalent to −1 frame-shift) mutant constructs are labelled respectively. FIG. 20B shows a scheme of luciferase constructs used to estimate frame-shifting potential for ZCRB1 WT and 411 G>A mutant polyA tracks. FIG. 20C shows luciferase levels (activity) from −1, "zero" and +1 frame constructs of wild type and G>A mutant ZCRB1 polyA track are compared. Bars represent normalized ratio of ZCRB1 G>A and ZCRB1 WT poly(A) tracks elucidates changes in the levels of luciferase expression in all three frames. FIG. 20D shows a model for function of poly(A) tracks in human genes. Poly(A)-tracks lead to three possible scenarios: Frameshifting consolidated with NMD which results in reduced output of wild type protein; Frameshifting with synthesis of both out of frame and wild type protein; and non-resolved stalling consolidated by endonucleolytic cleavage of mRNA and reduction in wild type protein levels, as in NGD pathway. Scheme for translation of mRNAs without poly(A) tracks is shown for comparison.

FIG. 21A shows the sequence of the wild type and K447K (G>A) mutant of MTDH gene. The amino acid seqeunce shown is SEQ ID NO: 82, and the nucleotide sequences shown are SEQ ID NO: 78 and 90, respectively. FIG. 21B shows western blot analyses of HA-tagged WT and K474K mutant MTDH proteins. Major additional protein product corresponds to frame-shifted MTDH protein products (−1 and +1 FS) created by insertion or delation of one nucleotide following the last nucleotide in polyA-track.

FIG. 22A and FIG. 22B show the frame-shifting efficiency of polyA tracks from ZCRB1 WT (FIG. 22A) and ZCRB G>A mutant (FIG. 22B) measured by luciferase activity. Values for −1 and +1 frame-shifts (FS) for WT and mutant polyA track are presented as fractions of luciferase activity coming from expression from zero frame construct of WT (FIG. 22A) or mutant G>A sequence (FIG. 22B).

FIG. 25A shows scheme of inserted polyA tracks in the reporter genes used in this study. Hemagglutinin (HA) tag (gray) and polyA tracks (red) were introduced in the coding region of the reporter genes next to the start AUG codon. Exon boundaries as well as termination codon (Stop) are indicated. FIG. 25B shows proposed correlation between gene products levels, mRNA and protein, and the length of inserted polyA track tags. The reduction in levels of both reporter protein and mRNA is dependent on increasing length of consecutive adenine nucleotides in the coding sequence. FIG. 25C shows scheme of translation of eukaryotic reporter mRNA with or without inserted polyA tracks. The length of inserted polyA track tag determines the protein output of the regulated reporter gene as indicated by the number of globular protein structures. Features of the eukaryotic mRNAs (m7GpppG—cap, AUG—start codon, Stop—termination codon and polyA tail), as well as HA-tag, position of the polyA track tag, ribosome and nascent polypeptide chain are illustrated in the scheme.

FIG. 26A shows percentage of mCherry fluorescence of tested LysAAG ((AAG)6-12) and LysAAA((AAA)3-12) insertion constructs compared to wild type fluorescence (WT, no insertion construct) 2 hours after promoter induction with 0.1% arabinose (w/v) in the media. mCherry fluorescence was assayed at excitation wavelength of 475±9 nm and emission was detected at 620±9 nm. Error bars indicate mean mCherry fluorescence values±standard deviation for three individual E. coli colonies for each construct. Background levels of mCherry expression can be estimated from the fluorescence of the wild type construct that was not induced with the addition of arabinose in the media (WT (NI)). FIG. 26B shows set of constructs analyzed for mCherry fluorescence was additionally assessed for protein expression levels by Western blot analysis. Equal amounts of E. coli cell lysates with Thioredoxin(Trx) fusion proteins were used for analysis. Fusion proteins were detected using HA-tag specific antibody. Positions of the fusion protein (Trx-HA-mCherry) and sizes of molecular weight markers (MWM) are indicated. FIG. 26C shows representative differential interference contrast microscopy (left panel) and the corresponding fluorescence image (right panel −25 msec exposure) of a T. thermophila cell expressing the wild type (WT) MLP1-HA-YFP fusion. Arrowheads denote the position of the macronucleus. FIG. 26D shows MPL1-HA-YFP accumulation within macronuclei of live T. thermophila cells expressing an allelic series of fusion proteins WT, (AAA)6-12, and (AAG)12, was visualized by epifluorescence microscopy. Different exposures times are indicated on the right to demonstrate the relative accumulation of each variant. FIG. 26E shows western blot analysis was performed with whole cell lysates made from T. thermophila cells expressing the MLP-HA-YFP fusion proteins. Protein from equivalent cell numbers was loaded in each lane and detected using YFP specific antibody (top panel) and normalized to the nuclear histone species, histone H3 trimethyl-lysine 4 (H3K4m) (bottom panel). Positions of the full-length fusion protein (YFP), normalization control (H3k4m), and sizes of molecular weight markers (MWM) are indicated. Degradation of excess fusion protein is readily apparent as faster migrating species below the full-length MLP1-HA-YFP. FIG. 30F shows steady state levels of fusion gene constructs measured by qRT-PCR. Relative levels of the mRNA for (AAG)12 and (AAA)6-12 are presented as percentage of the wild type (WT) construct mRNA levels. Error bars represent mean±standard deviation values (n=3).

FIG. 27A shows fluorescence images of N. benthamiana epidermal cells transiently expressing wild type (WT), (AAG)12 and (AAA)6-12 mCherry constructs. YFP expression was used as a transfection control. (FIG. 27B) Western blot analysis, (FIG. 27C) protein level estimate and (FIG. 27D) mRNA levels for transfected (−) insert control and WT, (AAG)12 and (AAA) 6-12 mCherry constructs expressed transiently in N. benthamiana epidermal cells. FIG. 27B shows primary HA-tag antibody was used for detection of HA-mCherry constructs.

Phosphinotricin acetyl transferase (BAR) specific antibody was used as a loading and normalization control (FIG. 27C). Levels of mCherry protein from different constructs were derived from detected band intensities normalized for BAR accumulation detected in the same sample. Error bars represent mean values±standard error from biological replicates (n=8). FIG. 27D shows mRNA levels for different mCherry constructs were calculated as cycle threshold (Ct) values and normalized to BAR gene mRNA values. Error bars represent mean values±standard error from biological replicates (n=3). FIG. 27E shows western blot analysis of transient mCherry constructs expression in HeLa cells. WT, 12LysAAG ((AAG)12) and 6-12LysAAA ((AAA)6-12) mCherry proteins were detected using HA-tag specific primary antibody. β-actin was used as a loading control and was detected using specific antibody. Positions of the fusion protein (HA-mCherry), normalization control (β-actin) and sizes of molecular weight markers (MWM) are indicated. FIG. 27F shows quantification of the mCherry protein levels from detected western blot intensities. Levels of mCherry were normalized to β-actin band intensities and represented as a percentage of the wild type construct values.

FIG. 28A shows diagram of third instar fruit fly larva showing approximate location of salivary glands (SG, blue), central nervous system (CNS, green) and proventriculus (PV, red). Fluorescence imaging of formaldehyde fixed SG (FIG. 28B), CNS (FIG. 28C) and PV (FIG. 28D), dissected from larvae expressing wild type (WT), (AAG)12 and (AAA)6-12 mCherry constructs. mCherry and GFP indicate images acquired by selective fluorescence filter setting. Overlay of mCherry and GFP fluorescence is shown in the merged panel.

FIG. 29A shows western blot analysis of the cell lysates from T-Rex HEK293 stable cell lines expressing doxycycline (Dox) inducible wild type (HA-mCherry) and 12LysAAA insertion construct (HA-(AAA)12-mCherry) from a single locus. Dox concentration in the media was varied from 0 to 0.1 µg/ml. Constitutively expressed δ-tubulin was used as a loading control and was detected using specific antibody. Positions of the fusion protein (HA-mCherry), normalization control (δ-tubulin) and sizes of molecular weight markers (MWM) are indicated. FIG. 29B shows quantification of the mCherry protein levels from detected western blot intensities. Levels of mCherry were normalized to δ-tubulin band intensities and represented as a percentage of the wild type construct values. Numbers indicate concentration of Dox in the media. FIG. 29C shows steady state mRNA levels of the 12LysAAA insertion construct ((AAA)12) measured by qRT-PCR. Relative levels of the mRNA for (AAA)12 are presented as percentage of the wild type (WT) construct mRNA levels. Error bars represent mean±standard deviation values (n=3). Numbers indicate final concentration of Dox in the media.

FIG. 30A shows survival of E. coli cells expressing wildtype (WT), 10LysAAG ((AAG)10) and 3-10LysAAA (AAA)3-10 chloramphenicol acetyltransferase (CAT) constructs on chloramphenicol (CAM) selective media. Pulse induced E. coli cells, expressing different CAT constructs, were plated on selective antibiotic plates with varying amounts of CAM in the media (0-100 mg/ml). Two independent clones were assessed for each construct. E. coli colonies were imaged 16 hours after plating. FIG. 30B shows assays for ADE1 gene regulation by polyA tracks ((AAA)6-12). Ability of S. cerevisiae ade1Δ cells to produce sufficient levels of functional Ade1 protein were assayed by reintroduction of single copy vector with wild type (WT), 12LysAAG ((AAG)12) and 6-12LysAAA ((AAA)6-12) Ade1 construct. Empty vector (EV) served as a negative control. Yeast colonies show diferential red coloration, on the selective SD-Ura media, which is proportional to the activity of Ade1 protein. Adenine dropout media (SD-Ade) selects for yeast cells expressing sufficient amounts of active Ade1 protein. Dilutions of the yeast cultures showing relative survival and growth are indicated.

FIG. 38A shows scheme of genetic loci expressing WT (HA-mCherry) and 12LysAAA insertion construct (HA-12LysAAA-mCherry) in stable Flp-InTM T-RexTM 293 cell lines. Position of the SV40 promoter (SV40), hygromycin B phosphotransferase (Hygromycin), antibiotic resistance gene for selection of single insertion constructs), doxycyclin-inducible CMV promoter (CMV 2× TetO2), double HA-tag (HA) and fluorescent reporter (mCherry) are indicated. Red box designates the position of in frame inserted 12 LysAAA sequence. WT construct contains no insertions at this position. FIG. 38B shows relative folds of transcriptional activation for WT and 12LysAAA mCherry loci were calculated from mRNA levels for each construct at different levels of induction by doxycycline (Dox, 0.001-0.1 µg/ml). RT-qPCR data for each construct was normalized to the mRNA levels of constitutively expressed hygromycin B phosphotransferase gene. Fold induction was calculated over the non-induced samples for each construct separately. Error bars indicate mean±standard deviation.

FIG. 44A shows position of the orotidine 5'-phosphate decarboxylase promoter and and gene (ura3 and URA3, respectively), ADE1 promoter and gene (ade1 and ADE1, respectively) and FLAG-tag (FLAG) are indicated. Red box (insert) designates the position of in frame inserted 12 LysAAG and 6-12 LysAAA sequences. WT construct contains no insertions at this position. FIG. 44B shows dot blot of yeast cell lysates expressing FLAG-tagged WT, 12 LysAAG and 6-12 LysAAA ADE1 protein from endogenous ade1 promoter. ADE1 protein was detected using anti-Flag (Sigma) antibody. 20 µg of total protein was spotted onto a nitrocellulose membrane for each construct. Ponceau S staining is used as loading control.

FIG. 45A, FIG. 45B, FIG. 45C, and FIG. 45D. Quantification of mCherry fluorescence with modified polyA track sequences. PolyA tracks designed with flanking XAA and AAY codons, where X and Y denote C/G or T/C/G nucleotides respectively, were inserted into the mCherry reporter. The number of lysine residues (K) and adenine residues (A) are noted as well as the two amino acids flanking lysine. The nucleotide and amino acid sequence for K2/A9 (AN) are SEQ ID NO: 91 and 92, respectively. The nucleotide and amino acid sequence for K3/A9 (AS) are SEQ ID NO: 93 and 94, respectively. The nucleotide and amino acid sequence for K2/A10 (QN) are SEQ ID NO: 95 and 96, respectively. The nucleotide and amino acid sequence for K3/A10 (EV) are SEQ ID NO: 97 and 98, respectively. The nucleotide and amino acid sequence for K3/A10 (QV) are SEQ ID NO: 99 and 100, respectively. The nucleotide and amino acid sequence for K3/A11 (AN) are SEQ ID NO: 101 and 102, respectively. The nucleotide and amino acid sequence for K4/A11 (AV) are SEQ ID NO: 103 and 104, respectively. (FIG. 45A). Normalized mCherry fluorescence intensity. (FIG. 45B). PolyA tracks with non-lysine codons interrupting the consecutive AAA codons were inserted into the mCherry reporter. The number of adenosine residues and interrupting codon and the protein sequences are indicated.

The nucleic acid sequences for 33As, 15A(CTG)15A, 15A (TAC)15A, 15A(CCC)15A, and 30As are SEQ ID NO: 105, 106, 107, 108, and 109, respectively. (FIG. 45C). Normalized mCherry fluorescence intensity. Error bars represent standard deviation from three different colonies (FIG. 45B and FIG. 45D).

DETAILED DESCRIPTION OF THE INVENTION

Figure 1A:
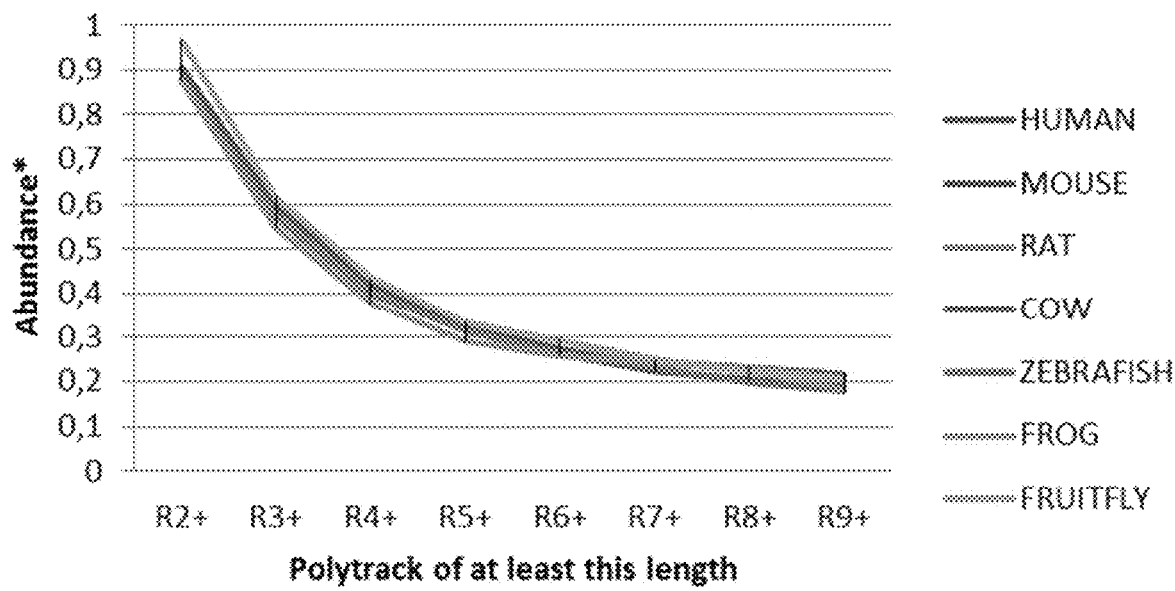
FIG. 1A and FIG. 1B show the distribution of polyarginine (FIG. 1A) and polylysine (FIG. 1B) runs of different length in several organisms. Abundance is normalized to the number of residues of certain kind in all protein isoforms (see Materials and Methods, Example 1).

The disclosure provides a method for the translational control of gene expression in cells (e.g., eukaryotic and bacterial cells). In broad terms, the disclosure is based on polyA-triggered ribosome stalling and frameshifting leading to mRNA degradation and an alteration of protein output. The disclosure involves inserting a series of protein sequence tags that differ by several codons to allow tunable amounts of translation, and thus protein output in cells. Control of protein production can be further modulated by differential localization of such sequence tags (e.g. N- or C-terminal) as well as through proteasome and non-sense mediated decay (NMD) inhibition.

Aspects of the disclosure allow for control of protein production at the level of translation based on the insertion into genes of interest of predefined lengths of tagging sequences encoding poly-lysine with iterated AAA and/or AAG codons. These strings of codons induce site-specific cleavage of the mRNA, likely through stalling and frameshifting of the ribosome, as well as inhibition of endogenous stalling and frameshifting of the ribosome, respectively. As such, this system allows differential control of protein expression based on single or multiple base changes within a polylysine track situated within a coding sequence. A wide range of protein output can be achieved by inserting a variety of polyA (e.g., synonymous G-A lysine mutations) and disrupted polyA sequences (e.g., synonymous A-G lysine mutations) within an ORF of a gene.

The presently disclosed subject matter can be used for a variety of research, diagnostic, and/or therapeutic applications for which tunable regulation of protein expression in cells is desired. In one example, the presently disclosed subject matter can be used to achieve site specific mRNA cleavage triggered by a ribosome translating a polynucleotide comprising a polylysine track comprising at least one AAA lysine codon in its coding sequence. In another example, the presently disclosed subject matter involves peptidyl-tRNA drop off on polyA sequences in eukaryotes, archaea, and bacteria. In yet another example, the presently disclosed subject matter can be used to achieve differential expression of recombinant proteins based on single or multiple base changes inside of a polynucleotide tag sequence comprising at least one AAA lysine codon and/or at least one AAG lysine codon, or at least one polylysine track comprising such lysine codons. In a further example, the presently disclosed subject matter provides different sequence tags that specify differential effects on protein output in bacterial, archaeal, and eukaryoic cells.

In sum, the presently disclosed subject matter can be used for the regulation of protein translation in eukaryotic, archaeal, and bacterial systems, the tunable down regulation of essential cellular genes, the controlled expression of proteins and analysis of these effects on cell homeostasis, assays for translational control at various steps of the translation cycle, and the estimation of mRNA translation and turnover, among other uses.

I. Methods for Modulating the Level of Expression of Polypeptides in Cells

In an aspect, the presently disclosed subject matter provides a method for modulating the level of expression of a polypeptide in a cell, the method comprising modulating the amount of consecutive adenine (A) nucleotides in at least one lysine codon in an open reading frame of a polynucleotide sequence encoding the polypeptide in the cell, thereby modulating the level of expression of the polypeptide in the cell.

As used herein, "modulating" broadly means to cause or facilitate a qualitative or quantitative change, alteration, or modification in a molecule, a process, pathway, or phenomenon of interest. As used herein, "expression" refers to the process by which a polynucleotide is transcribed from a DNA template (such as into an mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a cell.

A "gene," as used herein, refers to a polynucleotide containing at least one open reading frame that is capable of encoding a particular protein after being transcribed and translated. As used herein, a "gene product" is the biochemical material, either RNA or protein, resulting from expression of a gene. A measurement of the amount of gene product is sometimes used to infer how active a gene is. As used herein, "gene expression" is the process by which information from a gene is used in the synthesis of a functional gene product. As used herein, a "reporter gene" refers to a gene that produces a gene product that is easily detected. Examples of reporter genes include, but are not limited to, bioluminescent, fluorescent, computed tomography (CT), magnetic resonance imaging (MRI), positron emission tomography (PET), single-photon emission computed tomography (SPECT) reporter genes, and the like. In some aspects, the reporter gene is a bioluminescent reporter gene (e.g., firefly luciferase). In some aspects, the reporter gene is a fluorescent reporter gene (e.g., a fluorescent protein (GFP, mCherry, etc.).

The terms "polynucleotide", "polynucleotide sequence", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The terms "polypeptide," "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; non-limiting examples of such modifications include disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, "modulating the level of expression" refers to causing or facilitating a qualitative or quantitative change, alteration, or modification in the amount of at least one polypeptide produced in a cell as a result of translation of at least one polynucleotide sequence (e.g., mRNA) encoding such at least one polypeptide. The phrase "modulating the amount of consecutive A nucleotides" means changing the linear sequence of nucleotides that are linked together by phosphodiester bonds in at least one polynucleotide sequence encoding at least one polypeptide of interest to be expressed in a cell a way that increases or decreases the number of contiguous A nucleotides in a targeted region of such polynucleotide sequence.

The presently disclosed subject matter demonstrates that a synonymous lysine mutation consisting of a single AAG-to-AAA codon in a polyA or polylysine track of a nucleic acid sequence (e.g., gene or mRNA) encoding a protein of interest decreases expression of the protein and mRNA stability. Conversely, the presently disclosed subject matter demonstrates that a synonymous lysine mutation consisting of a single AAA-to-AAG codon in a polyA or polylysine track of a nucleic acid sequence (e.g., gene or mRNA) encoding a protein of interest increases expression of the protein and mRNA stability. Put differently, increasing the length of consecutive A nucleotides, for example, by changing selected AAG lysine codons to AAA lysine codons reduces protein expression and mRNA stability, whereas decreasing the length of consecutive A nucleotides, for example, by changing selected AAA lysine codons to AAG lysine codons increases protein expression and mRNA stability.

Accordingly, some aspects of the presently disclosed subject matter contemplate methods for decreasing the level of expression of a polypeptide in a cell, for example, by increasing the amount of consecutive A nucleotides in at least one lysine codon in an open reading frame of a polynucleotide sequence encoding at least one polypeptide in at least one cell.

The terms "decrease", "reduced", "reduction", "decrease" or "inhibit" are all used herein generally to mean a decrease by a statistically significant amount. However, for avoidance of doubt, "reduced", "reduction", "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90%, where the decrease is less than 100%. In one embodiment, the decrease includes a 100% decrease (e.g. absent level as compared to a reference sample), or any decrease between 10-100% as compared to a reference level.

In some embodiments, modulating the amount of consecutive A nucleotides in at least one lysine codon comprises increasing the amount of consecutive A nucleotides in at least one AAG lysine codon in the open reading frame of the polynucleotide sequence encoding the polypeptide in a cell, thereby decreasing the level of expression of the polypeptide in the cell. In the contexts of decreasing the level of expression of a polypeptide in a cell, the methods contemplated herein can decrease protein translation and mRNA stability by at least about 10%, 20%, 30%, 40%, 50%, 60%, 70%, 80, 90%, or as much as 100% as compared to a reference level (e.g., an objective measure of the level of expression of at least one polypeptide in a cell employing the method compared to the level of expression of at least one polypeptide in the cell in the absence of employing the method).

The presently disclosed subject matter contemplates using any technique available to the skilled artisan for increasing the amount of consecutive A nucleotides in at least one AAG lysine codon in an open reading frame of a polynucleotide sequence encoding at least one polypeptide in at least one cell.

In some embodiments, increasing the amount of consecutive A nucleotides in the at least one lysine codon comprises introducing at least one synonymous G to A nucleotide mutation into at least one AAG lysine codon. As used herein, "synonymous" in the context of a "nucleotide mutation" refers to a change in the nucleotide of a codon which does not alter the amino acid encoded by such codon. To introduce at least one synonymous G to A nucleotide mutation into at least one AAG lysine codon in an open reading frame of at least one polynucleotide sequence, at least one AAG lysine codon must be identified in the open reading frame. Methods of identifying at least one AAG lysine codon in an open reading frame of at least one polynucleotide encoding at least one polypeptide of interest are well known to the skilled artisan. For example, the position of at least one AAG lysine codon in an open reading frame of at least one polynucleotide encoding at least one polypeptide can be determined using publicly available sequence databases and bioinformatics tools (e.g., BLAST searching, mRNA mapping, etc.). When the position of at least one AAG lysine codon in an open reading frame of at least one polynucleotide encoding at least one polypeptide is determined, at least one synonymous G to A nucleotide mutation can be introduced into such at least one AAG lysine codon, for example, using site directed mutagenesis. It should be appreciated, however, it is the number of consecutive A nucleotides that controls the levels of protein expression and mRNA stability. As such, it may be advantageous to identify at least one AAG lysine codon that is flanked by an upstream codon that ends with an A nucleotide (e.g., UUA (Leu), AUA (Ile), GUA (Val), UCA (Ser), CCA (Pro), ACA (Thr), GCA (Ala), UAU (Tyr), CAA (Gln), AAA (Lys), GAA (Glu), CGA (Arg), AGA (Arg), and GGA (Gly)) and/or is flanked by a downstream codon that begins with an A nucleotide (e.g., AUU (Ile), AUC (Ile), AUA (Ile), AUG (Met), ACU (Thr), ACC (Thr), ACA (Thr), ACG (Thr), AAU (Asn), AAC (Asn), AAA (Lys), AAG (Lys), AGU (Ser), AGC (Ser), AGA (Arg), and AGG (Arg)) for introduction of at least one synonymous G to A nucleotide mutation, for example, to increase the number of consecutive A nucleotides in the polynucleotide sequence with the resultant decrease in the level of expression of at least one polypeptide encoded by such polynucleotide sequence. Accordingly, in some embodiments, the method comprises introducing at least one synonymous G to A nucleotide mutation into at least one AAG lysine codon that is flanked by an upstream codon that ends with an A nucleotide and/or is flanked by a downstream codon that begins with an A nucleotide.

Generally, it is believed that the greater the increase in the number of consecutive A nucleotides in at least one polynucleotide sequence encoding at least one polypeptide, the greater the decrease will be in the level of expression of the at least one polypeptide. The skilled artisan will appreciate that the increase in the number of consecutive A nucleotides introduced into at least one polynucleotide sequence in this manner will be limited by the number of AAG lysine codons in the open reading frame of such polynucleotide sequence, as well as those AAG lysine codons that are flanked by upstream codons ending with A nucleotides and/or are flanked by downstream codons beginning with A nucleotides.

In some embodiments, at least one synonymous G to A nucleotide mutation is introduced into at least one AAG lysine codon in an open reading frame of at least one polynucleotide sequence. In some embodiments, at least two, at least three, at least four, at least five, at least six, at least seven, at least eight, at least nine, at least 10, at least 11, at least 12, or at least n synonymous G to A nucleotide mutations (where n is a positive integer greater than or equal to 13 and less than or equal to the number of AAG lysine codons in a particular polynucleotide sequence) are introduced into at least two, at least three, at least four, at least five, at least six, at least seven, at least eight, at least nine, at least 10, at least 11, at least 12, or at least n AAG lysine codons (where n is a positive integer greater than or equal to 13 and less than or equal to the number of AAG lysine codons in a particular polynucleotide sequence) in an open reading frame of at least one polynucleotide sequence.

In other embodiments, increasing the amount of consecutive A nucleotides in the at least one lysine codon comprises inserting at least one AAA lysine codon into the open reading frame of the polynucleotide sequence encoding the polypeptide in the cell. It should be appreciated that any amount of at least one AAA lysine codons can be inserted into an open reading frame of at least one polynucleotide sequence encoding at least one polypeptide in a cell. In general, the greater the amount of consecutive A nucleotides inserted into an open reading frame of at least one polynucleotide sequence, the greater the decrease in the level of expression of at least one polypeptide encoded by the at least one polynucleotide sequence. In this way, levels of expression of at least one polypeptide can be controlled in a cell. In some embodiments, at least one (AAA) lysine codon is inserted into an open reading frame of at least one polynucleotide sequence encoding at least one polypeptide of interest in a cell. In some embodiments, at least two, at least three, at least four, at least five, at least six, at least seven, at least eight, at least nine, at least 10, at least eleven, at least 12, or at least n AAA lysine codons ((AAA)n) (where n is a positive integer greater than or equal to 13) are inserted into an open reading frame of at least one polynucleotide sequence encoding at least one polypeptide of interest in a cell. In some embodiments, at least one, at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, or at least n A nucleotides ((A)n) (where n is a positive integer greater than or equal to 37) are inserted into an open reading frame of at least one polynucleotide sequence encoding at least one polypeptide of interest in a cell.

The AAA lysine codons and/or consecutive A nucleotides can be inserted in the form of one or more polynucleotide sequence tags designed for tunable expression of at least one polypeptide in a cell. In some embodiments, at least one polyA polynucleotide sequence tag can be inserted in an open reading frame, for example, in between an upstream codon ending with an A nucleotide and a downstream codon beginning with an A nucleotide. In some embodiments, two or more polyA polynucleotide sequence tags can be inserted adjacent to each other or spaced apart by intervening polynucleotides sequences in the open reading frame.

The presently disclosed subject matter contemplates insertion of at least one AAA lysine codon, a consecutive number of A nucleotides, and/or a polyA polynucleotide sequence tag into any portion of an open reading frame in at least one polynucleotide encoding at least one polypeptide in a cell. In some embodiments, at least one AAA lysine codon is inserted into a coding sequence of the open reading frame. In some embodiments, two or more polyA polynucleotide sequence tags are inserted into a coding sequence of at least one polypeptide. In some embodiments, at least one AAA lysine codon is inserted into a 5' untranslated region (UTR) of at least one polynucleotide encoding a polypeptide in a cell. In some embodiments, a polyA polynucleotide sequence tag is inserted into a 5' UTR of at least one polynucleotide encoding a polypeptide of interest. In some embodiments, at least one AAA lysine codon is inserted into an exon of at least one polynucleotide encoding a polypeptide of interest. In some embodiments, a polyA polynucleotide sequence tag is inserted into an exon of at least one polynucleotide encoding a polypeptide of interest. In some embodiments, at least one AAA lysine codon is inserted into an exon/intron boundary of at least one polynucleotide encoding a polypeptide of interest. In some embodiments, a polyA polynucleotide sequence tag is inserted into an exon/intron boundary of at least one polynucleotide encoding a polypeptide of interest. In some embodiments, at least one AAA lysine codon is inserted into an intron of at least one polynucleotide encoding a polypeptide of interest. In some embodiments, a polyA polynucleotide sequence tag is inserted into an intron of at least one polynucleotide encoding a polypeptide of interest. In some embodiments, at least one AAA lysine codon is inserted into a 3' UTR of at least one polynucleotide encoding a polypeptide of interest. In some embodiments, a polyA polynucleotide sequence tag is inserted into a 3' UTR of at least one polynucleotide encoding a polypeptide of interest.

In some embodiments, at least one polyA polynucleotide sequence tag comprises one or more AAG lysine codons, for example, for tunable expression of at least one polypeptide of interest encoded by at least one polynucleotide into which the at least one polyA polynucleotide sequence tag is inserted. Examples of such polyA nucleotide sequence tags include at least one AAA lysine codon preceded or followed by at least one AAG lysine codon, a first AAA lysine codon and a second AAA lysine codon flanking an AAG lysine codon, alternating AAG and AAA lysine codons (e.g., (AAG-AAA)n (where n is a positive integer greater than or equal to 1), triple repeats comprising combinations of AAG and AAA lysine codons (e.g., (AAA-AAG-AAA)n, (AAG-AAA-AAA)n, (AAA-AAA-AAG)n, where each n is a positive integer greater than or equal to 1), quadruple repeats, etc. In some embodiments, n is 1. In some embodiments, n is 2. In some embodiments, n is 3. In some embodiments, n is 4. In some embodiments, n is 5. In some embodiments, n is 6. In some embodiments, n is 6. In some embodiments, n is 8. In some embodiments, n is 9. In some embodiments, n is 10. In some embodiments, n is 11. In some embodiments, n is 12.

Some aspects of the presently disclosed subject matter contemplate methods for increasing the level of expression of a polypeptides in a cell, for example, by decreasing the amount of consecutive A nucleotides in at least one lysine codon in an open reading frame of a polynucleotide sequence encoding at least one polypeptide in at least one cell.

The terms "increased", 'increase", "enhance" or "activate" are all used herein to generally mean an increase by a statically significant amount; for the avoidance of any doubt, the terms "increased", "increase", "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

In some embodiments, modulating the amount of consecutive A nucleotides in the at least one lysine codon comprises decreasing the amount of consecutive A nucleotides in the at least one AAA lysine codon in an open reading frame of at least one polynucleotide sequence encoding at least one polypeptide of interest in a cell, thereby increasing the level of expression of the polypeptide in the cell. In the contexts of increasing the level of expression of a polypeptide in a cell, the methods contemplated herein can increase protein translation and mRNA stability, by at least about 10%, 20%, 30%, 40%, 50%, 60%, 70%, 80, 90%, or as much as 100%, at least about a 2-fold, or at least about a 3-fold, or at least about a 4-fold, or at least about a 5-fold or at least about a 10-fold increase, or any increase between 2-fold and 10-fold or greater as compared to a reference level (e.g., an objective measure of the level of expression of at least one polypeptide in a cell employing the method compared to the level of expression of at least one polypeptide in the cell in the absence of employing the method).

The presently disclosed subject matter contemplates using any technique available to the skilled artisan for decreasing the amount of consecutive A nucleotides in at least one lysine codon in an open reading frame of a polynucleotide sequence encoding at least one polypeptide of interest. In some embodiments, decreasing the amount of consecutive A nucleotides in at least one lysine codon comprises introducing at least one synonymous A to G nucleotide mutation into the at least one AAA lysine codon. To introduce at least one synonymous A to G nucleotide mutation into at least one AAA lysine codon in an open reading frame of at least one polyucleotide sequence, at least one AAA lysine codon must be identified in the open reading frame using methods which are well known to the skilled artisan. When the position of at least one AAA lysine codon in an open reading frame of at least one polynucleotide encoding at least one polypeptide is determined, at least one synonymous A to G nucleotide mutation can be introduced into such at least one AAA lysine codon, for example, using site directed mutagenesis. It should be appreciated, however, it is the number of consecutive A nucleotides that controls the levels of protein expression and mRNA stability. As such, it may be advantageous to identify at least one AAA lysine codon flanked by an upstream codon that ends with an A nucleotide (e.g., UUA (Leu), AUA (Ile), GUA (Val), UCA (Ser), CCA (Pro), ACA (Thr), GCA (Ala), UAU (Tyr), CAA (Gln), AAA (Lys), GAA (Glu), CGA (Arg), AGA (Arg), and GGA (Gly)) and/or flanked by a downstream codon that begins with an A nucleotide (e.g., AUU (Ile), AUC (Ile), AUA (Ile), AUG (Met), ACU (Thr), ACC (Thr), ACA (Thr), ACG (Thr), AAU (Asn), AAC (Asn), AAA (Lys), AAG (Lys), AGU (Ser), AGC (Ser), AGA (Arg), andAGG (Arg)) to introduce at least one synonymous A to G nucleotide mutation into, for example, to decrease the number of consecutive A nucleotides in the polynucleotide sequence with the resultant increase in the level of expression of at least one polypeptide encoded by such polynucleotide sequence. Accordingly, in some embodiments, the method comprises introducing at least one synonymous A to G nucleotide mutation into at least one AAA lysine codon flanked by an upstream codon that ends with an A nucleotide and/or flanked by a downstream codon that begins with an A nucleotide.

Generally, it is believed that the greater the decrease in the number of consecutive A nucleotides in at least one polynucleotide sequence encoding at least one polypeptide of interest, the greater the increase will be in the level of expression of the at least one polypeptide of interest. The skilled artisan will appreciate that the decrease in the number of consecutive A nucleotides in at least one polynucleotide sequence will be limited by the number of consecutive A nucleotides in such sequence, and in particular embodiments by the number of AAA lysine codons in the open reading frame of such polynucleotide sequence.

In some embodiments, at least one synonymous A to G nucleotide mutation is introduced into at least one AAA lysine codon in an open reading frame of at least one polynucleotide sequence encoding a polypeptide of interest. In some embodiments, at least two, at least three, at least four, at least five, at least six, at least seven, at least eight, at least nine, at least 10, at least 11, at least 12, or at least n synonymous A to G nucleotide mutations (where n is a positive integer greater than or equal to 13 and less than or equal to the number of AAA lysine codons in a particular polynucleotide sequence) are introduced into at least two, at least three, at least four, at least five, at least six, at least seven, at least eight, at least nine, at least 10, at least 11, at least 12, or at least n AAA lysine codons (where n is a positive integer greater than or equal to 13 and less than or equal to the number of AAA lysine codons in a particular polynucleotide sequence) in an open reading frame of at least one polynucleotide sequence.

In other embodiments, decreasing the amount of consecutive A nucleotides in at least one lysine codon comprises inserting at least one AAG lysine codon into the open reading frame of at least one polynucleotide sequence encoding at least one polypeptide of interest. It should be appreciated that any amount of at least one AAG lysine codons can be inserted into an open reading frame of at least one polynucleotide sequence encoding at least one polypeptide of interest. In general, the greater the amount of AAG lysine codons inserted into an open reading frame of at least one polynucleotide sequence, the greater the increase in the level of expression of at least one polypeptide encoded by the at least one polynucleotide sequence. In this way, levels of expression of at least one polypeptide can be controlled in a cell. In some embodiments, at least one (AAG) lysine codon is inserted into an open reading frame of at least one polynucleotide sequence encoding at least one polypeptide of interest. In some embodiments, at least two, at least three, at least four, at least five, at least six, at least seven, at least eight, at least nine, at least 10, at least eleven, at least 12, or at least n AAG lysine codons ((AAG)n) (where n is a positive integer greater than or equal to 13) are inserted into an open reading frame of at least one polynucleotide sequence encoding at least one polypeptide of interest.

The AAG lysine codons can be inserted in the form of one or more poly AAG lysine polynucleotide sequence tags designed for tunable expression of at least one polypeptide in a cell. In some embodiments, at least one polyAAG lysine polynucleotide sequence tag can be inserted in an open reading frame. In some embodiments, two or more polyAAG lysine polynucleotide sequence tags can be inserted in the open reading frame.

The presently disclosed subject matter contemplates insertion of at least one AAG lysine codon, and/or a polyAAG lysine polynucleotide sequence tag into any portion of an open reading frame in at least one polynucleotide encoding at least one polypeptide of interest. In some embodiments, at least one AAG lysine codon is inserted into a coding sequence of at least one polynucleotide encoding a polypeptide of interest. In some embodiments, at least one poly AAG lysine polynucleotide sequence tag is inserted into a coding sequence of at least one polynucleotide encoding a polypeptide of interest. In some embodiments, at least one AAG lysine codon is inserted into a 5' untranslated region (UTR) of at least one polynucleotide encoding a polypeptide of interest. In some embodiments, a polyAAG lysine polynucleotide sequence tag is inserted into a 5' UTR of at least one polynucleotide encoding a polypeptide of interest. In some embodiments, at least one AAG lysine codon is inserted into an exon/intron boundary of at least one polynucleotide encoding a polypeptide of interest. In some embodiments, a polyAAG lysine polynucleotide sequence tag is inserted into an exon/intron boundary of at least one polynucleotide encoding a polypeptide of interest. In some embodiments, at least one AAG lysine codon is inserted into an intron of at least one polynucleotide encoding a polypeptide of interest. In some embodiments, at least one polyAAG lysine polynucleotide sequence tag is inserted into an intron of at least one polynucleotide encoding a polypeptide of interest. In some embodiments, at least one AAG lysine codon is inserted into a 3' UTR of at least one polynucleotide encoding a polypeptide of interest. In some embodiments, at least one polyAAG lysine polynucleotide sequence tag is inserted into a 3' UTR of at least one polynucleotide encoding a polypeptide of interest.

In some embodiments, at least one polyAAG lysine polynucleotide sequence tag comprises one or more AAA lysine codons, for example, for tunable expression of at least one polypeptide of interest encoded by at least one polynucleotide into which the at least one polyAAG lysine polynucleotide ssequence tag is inserted. Examples of such polyAAG lysine polynucleotide sequence tags include at least one AAG lysine codon preceded or followed by at least one AAA lysine codon, a first AAG lysine codon and a second AAG lysine codon flanking an AAA lysine codon, alternating AAA and AAG lysine codons (e.g., (AAA-AAG)n (where n is a positive integer greater than or equal to 1), triple repeats comprising combinations of AAA and AAG lysine codons (e.g., (AAG-AAA-AAG)n, (AAA-AAG-AAG)n, (AAG-AAG-AAA)n, where each n is a positive integer greater than or equal to 1), quadruple repeats, etc. In some embodiments, n is 1. In some embodiments, n is 2. In some embodiments, n is 3. In some embodiments, n is 4. In some embodiments, n is 5. In some embodiments, n is 6. In some embodiments, n is 6. In some embodiments, n is 8. In some embodiments, n is 9. In some embodiments, n is 10. In some embodiments, n is 11. In some embodiments, n is 12.

In some embodiments, at least one AAG lysine codon is inserted into at least one polynucleotide sequence for expression at an N-terminus or C-terminus of at least one polypeptide of interest to be expressed in a cell. In some embodiments, at least one polyAAG lysine polynucleotide sequence tag comprises a N-terminus tag. In some embodiments, at least one polyAAG lysine polynucleotide sequence tag comprises a C-terminus tag.

Those skilled in the art will appreciate that the manner in which at least one synonymous lysine mutation (e.g., at least one synonymous A to G nucleotide mutation or at least one synonymous G to A nucleotide mutation) is introduced into at least one lysine codon, the manner in which at least one lysine codon (e.g., at least one AAA lysine codon or at least one AAG lysine codon) is inserted into an open reading frame of at least one polynucleotide sequence enoding a polypeptide of interest, and/or the manner in which at least one polylysine sequence tag (e.g., at least one polyA track or polyA polynucleotide sequence tag or at least one polyAAG lysine track or polyAAG lysine polynucleotide sequence tag) is inserted into an open reading frame of at least one polynucleotide sequence encoding a polypeptide of interest depends on whether at least one polynucleotide encoding at least one polypeptide of interest is an endogenous polynucleotide sequence in a cell, or an exogenous polynucleotide sequence encoding a heterologous protein to be expressed in a cell.

In some embodiments, at least one polynucleotide sequence comprises an endogenous polynucleotide sequence and the step of modulating the amount of consecutive A nucleotides in the at least one lysine codon includes selecting an endogenouous polynucleotide sequence in the cell that comprises at least one lysine codon, and editing the endogenous polynucleotide sequence in the cell. The presently disclosed subject matter contemplates editing endogenous polynucleotide sequences in cells that is available to the skilled artisan. In some embodiments, editing the endogenous polynucleotide sequence in the cell comprises contacting the cell with an engineered nuclease selected from the group consisting of a CRISPR-Cas system, CRISPR-Cpf1 system, a zinc finger nuclease (ZFN), a transcription activator-like effector nuclease (TALEN), and a meganuclease.

In other embodiments, at least one polynucleotide sequence comprises an exogenous polynucleotide sequence and the step of modulating the amount of consecutive A nucleotides in the at least one lysine codon includes providing an expression vector comprising an exogenous polynucleotide sequence comprising at least one AAA lysine codon or at least one AAG lysine codon inserted thereinto operably linked to a promoter that drives expression of the exogenous polynucleotide in the cell, and contacting the cell with the expression vector.

In some embodiments, at least one lysine codon comprises at least one polylysine track selected from the group consisting of AAA lysine codons, AAG lysine codons, and combinations thereof. In some embodiments, at least one polylysine track comprises between 4 and 36 A nucleotides. In some embodiments, at least one polylysine track comprises at least 11 consecutive A nucleotides in at least three consecutive lysine codons.

In some embodiments, exogenouc polynucleotide sequences comprising at least one lysine codon and/or at least one polylysine track, and/or at least one polyA polynucleotide sequence tag and/or at least one polyAAG lysine polynucleotide sequence tag can be synthesized utilizing in vitro transcription methods which are well known to the skilled artisan.

In some embodiments, at least one lysine codon, at least one polyA polynucleotide sequence tag, and/or at least one polylysine track is not a polyA tail. In some embodiments, at least one lysine codon, at least one polyA polynucleotide sequence tag, and/or at least one polylysine (polyA) track is not located in the 3' UTR or downstream of the 3' UTR.

Ii. Expression Vectors

Aspects of the presently disclosed subject matter relate to expression vectors for the tunable expression of polypeptides of interest in cells. The presently disclosed expression vectors comprise at least one polynucleotide comprising at least one lysine codon, at least one polylysine track, at least one polyA polynucleotide sequence tag, and/or at least one polyAAG lysine polynucleotide sequence tag.

In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell.

Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the presently disclosed subject matter in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed.

Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel (1990) Gene Expression Technology: Methods in Enzymology 185, Academic Press, San Diego, Calif. Regulatory elements include those that direct constitutive expression of a nucleotide sequence in many types of host cell and those that direct expression of the nucleotide sequence only in certain host cells (e.g., tissue-specific regulatory sequences). In some embodiments, the promoter is an inducible promoter that is active in response to specific stimuli.

A cell-specific promoter may direct expression primarily in a desired cell of interest, such as muscle cell, a neuron, a skin cell, a blood cell, an immune cell, a liver cell, a pancreatic cell, a spleen cell, etc. In some embodiments, the promoter is a tissue-specific promoter that is active in specific tissues. In some embodiments, the promoter is a tumor-specific promoter that is active specifically in tumor cells. Regulatory elements may also direct expression in a temporal-dependent manner, such as in a cell-cycle dependent or developmental stage-dependent manner, which may or may not also be tissue or cell-type specific.

In some embodiments, a vector comprises one or more pol III promoters, one or more pol II promoters, one or more pol I promoters, or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) (e.g., Boshart et al. (1985) Cell 41:521-530), the SV40 promoter, the dihydrofolate reductase promoter, the β-actin promoter, the phosphoglycerol kinase (PGK) promoter, and the EF1α promoter.

Also encompassed by the term "regulatory element" are enhancer elements, such as WPRE; CMV enhancers; the R-U5' segment in LTR of HTLV-I (Takebe et al. (1988) Mol. Cell. Biol.8:466-472); SV40 enhancer; and the intron sequence between exons 2 and 3 of rabbit β-globin (O'Hare et al. (1981) Proc. Natl. Acad. Sci. USA. 78(3):1527-31). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). Advantageous vectors include lentiviruses and adeno-associated viruses, and types of such vectors can also be selected for targeting particular types of cells.

As used herein the term "wild type" is a term of the art understood by skilled persons and means the typical form of an organism, strain, gene or characteristic as it occurs in nature as distinguished from mutant or variant forms.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

Vectors may be introduced and propagated in a prokaryote. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins.

Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson (1988) Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A. respectively, to the target recombinant protein.

Examples of suitable inducible non-fusion *E. coli* expression vectors include pTrc (Amrann et al. (1988) Gene 69:301-315) and pET 11d (Studier et al. (1990) Gene Expression Technology: Methods in Enzymology 185, Academic Press, San Diego, Calif.).

In some embodiments, a vector is a yeast expression vector. Examples of vectors for expression in yeast *Saccharomyces* cerivisae include pYepSec1 (Baldari, et al.(1987) EMBO J. 6: 229-234), pMFa (Kuijan and Herskowitz (1982) Cell 30: 933-943), pJRY88 (Schultz et al. (1987) Gene 54: 113-123), pYES2 (Invitrogen Corporation, San Diego, Calif.), and picZ (InVitrogen Corp, San Diego, Calif.).

In some embodiments, a vector is capable of driving expression of one or more sequences in mammalian cells using a mammalian expression vector. Examples of mammalian expression vectors include pCDM8 (Seed (1987) Nature 329: 840) and pMT2PC (Kaufman et al. (1987) EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook et al. (1989) Molecular Cloning: A Laboratory Manual. 2nd ed., Cold Spring Harbor Laboratory, Cold Spring Harbor Laboratory Press, Cold Spring Harbor, N.Y..

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1: 268-277), lymphoid-specific promoters (Calame and Eaton (1988) Adv. Immunol. 43: 235-275), in particular promoters of T cell receptors (Winoto and Baltimore (1989) EMBO J.8: 729-733) and immunoglobulins (Baneiji et al. (1983) Cell 33: 729-740; Queen and Baltimore (1983) Cell 33: 741-748), neuron-specific promoters (e.g., the neurofilament promoter; Byrne and Ruddle (1989) Proc. Natl. Acad. Sci. USA 86: 5473-5477), pancreas-specific promoters (Edlund et al.(1985) Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss (1990) Science 249: 374-379) and the α-fetoprotein promoter (Campes and Tilghman (1989) Genes Dev. 3: 537-546).

In some aspects, the presently disclosed subject matter provides an expression vector comprising a cloning site for inserting at least one polynucleotide sequence encoding a polypeptide to be expressed, and at least one polynucleotide tag sequence comprising at least one AAG lysine codon that increases expression of the at least one polynucleotide sequence when the expression vector is introduced into a cell. In some embodiments, at least one polynucleotide tag sequence comprises at least one polylysine track comprising at least two consecutive AAG lysine codons. In some embodiments, at least one polylysine track comprises at least two consecutive AAG lysine codons selected from the group consisting of (AAG)2, (AAG)3, (AAG)6, and (AAG) 12. In some embodiments, at least one polylysine track comprises at least n consecutive AAG lysine codons (i.e., (AAG)n), where n is a positive integer greater than or equal to 13.

In some aspects, the presently disclosed subject matter provides an expression vector comprising a cloning site for inserting at least one polynucleotide sequence encoding a polypeptide to be expressed, and at least one polynucleotide tag sequence comprising at least one AAA lysine codon that decreases expression of the at least one polynucleotide sequence when the expression vector is introduced into a cell. In some embodiments, at least one polynucleotide tag sequence comprises at least one polylysine track comprising at least two consecutive AAA lysine codons. wherein the and wherein the at least one polylysine track in b) comprises at least two consecutive AAA lysine codons selected from the group consisting of (AAA)2, (AAA)3, (AAA)6, and (AAA) 12. In some embodiments, at least one polylysine track comprises at least n consecutive AAA lysine codons (i.e., (AAA)n), where n is a positive integer greater than or equal to 13.

In some aspects, the presently disclosed subject matter provides an expression vector comprising at least one engineered polynucleotide sequence encoding a polypeptide to be expressed, the at least one engineered polynucleotide sequence comprising at least one engineered synonymous mutation of at least one AAA lysine codon to at least one AAG lysine codon in a coding sequence of the at least one polynucleotide sequence, wherein the synonymous mutation increases expression of the polypeptide to be expressed when the expression vector is introduced into a cell. In some embodiments, at least one engineered polynucleotide sequence comprises at least one polylysine track comprising at least two consecutive lysine codons in the coding sequence. In some embodiments, at least one polylysine track comprises at least two consecutive AAG lysine codons selected from the group consisting of (AAG)2, (AAG)3, (AAG)6, and (AAG)12. In some embodiments, at least one polylysine track comprises at least n consecutive AAG lysine codons (i.e., (AAG)n where n is a positive integer greater than or equal to 13).

In some aspects, the presently disclosed subject matter provides an expression vector comprising at least one engineered polynucleotide sequence encoding a polypeptide to be expressed, the at least one engineered polynucleotide sequence comprising at least one engineered synonymous mutation of at least one AAG lysine codon to at least one AAA lysine codon in a coding sequence of the at least one polynucleotide sequence, wherein the synonymous mutation decreases expression of the polypeptide to be expressed when the expression vector is introduced into a cell.

In some embodiments, at least one engineered polynucleotide sequence comprises at least one polylysine track comprising at least two consecutive lysine codons in the coding sequence. In some embodiments, at least one polylysine track comprises at least two consecutive AAA lysine codons selected from the group consisting of (AAA)2, (AAA)3, (AAA)6, and (AAA)12. In some embodiments, at least one polylysine track comprises at least n consecutive AAA lysine codons (i.e., (AAA)n where n is a positive integer greater than or equal to 13).

In some embodiments, at least one polylysine track comprises at least 11 consecutive A nucleotides in at least three consecutive lysine codons, prior to enginnering the at least one engineered polynucleotide sequence to include the at least one engineered synonymous mutation.

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

In aspects of the presently disclosed subject matter the terms "chimeric RNA", "chimeric guide RNA", "guide RNA", "single guide RNA" and "synthetic guide RNA" are used interchangeably and refer to the polynucleotide sequence comprising the guide sequence. The term "guide sequence" refers to the about 20 bp sequence within the guide RNA that specifies a target sequence and may be used interchangeably with the terms "guide" or "spacer".

A target sequence may comprise any polynucleotide, such as DNA or RNA polynucleotides. In some embodiments, a target sequence is located in the nucleus or cytoplasm of a cell. In some embodiments, the target sequence may be within an organelle of a eukaryotic cell, for example, mitochondrion or chloroplast. A sequence or template that may be used for recombination into the targeted locus comprising the target sequences is referred to as an "editing template" or "editing polynucleotide" or "editing sequence". In aspects of the presently disclosed subject matter, an exogenous template polynucleotide may be referred to as an editing template. In an aspect of the presently disclosed subject matter the recombination is homologous recombination.

In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length.

Iii. Isolated Recombinant Cells

Aspects of the presently disclosed subject matter relate to an isolated recombinant cell comprising an expression vector of the presently disclosed subject matter. In some embodiments, host cells which contain the constructs and vectors of the presently disclosed subject matter are also encompassed, e.g. in vitro cells such as cultured cells, e.g., bacterial or eukaryotic cells which are used to store generate or manipulate the vectors, and the like. In some embodiments, the isolated recombinant cell or host cell is a mammalian cell. In some embodiments, the isolated recombinant cell or host cell is a human cell. In some embodiments, the cell is selected from the group consisting of a bacterial cell and a eukaryotic cell. In some embodiments, the eukaryotic cell is a mammalian cell. In some embodiments, the eukaryotic cell is a human cell.

Iv. Kits

Aspects of the presently disclosed subject matter relate to kits for modulating the expression levels of polypeptides in cells. In general, a presently disclosed kit contains some or all of the components, reagents, supplies, and the like to practice a method according to the presently disclosed subject matter.

In some embodiments, the term "kit" may refer to any intended article of manufacture (e.g., a package or a container) comprising at least one of the presently disclosed engineered nuclease, expression vector, isolated recombinant cell comprising the expression vector, and instructions for modulating expression of an endogenous polypeptide using an engineered nuclease or recombinant polypeptide of interest using the expression vector and/or the isolated recombinant cell. The kit can be packaged in a divided or undivided container, such as a carton, bottle, ampule, tube, etc. The presently disclosed compositions can be packaged in dried, lyophilized, or liquid form. Additional components provided can include vehicles for reconstitution of dried components. Preferably all such vehicles are sterile and apyrogenic so that they are suitable for injection into a patient without causing adverse reactions.

The polynucleotide sequences for use in the methods, expression vectors, and kits of the presently disclosed subject matter may encode one or more bioactive molecules functional in the treatment of a disease, disorder, or condition. The one or more bioactive molecules may be selected from the group consisting of proteins, polypeptides, peptides, drugs, enzymes, and hormones.

In some embodiments, the kit can be used for hightthroughput purification and quantification of a recombinant polypeptide of interest to be expressed. The kit may include a presently disclosed expression vector for expressing a recombinant polypeptide of interest in a host cell. In some embodiments, the kit includes an affinity chromatography resin, a proteolytic enzyme, an internal quantification standard, a matrix for MALDI-TOF mass spectrometry, and instructions for use. In some embodiments, the kit includes at least one buffer selected from the group consisting of a lysis buffer, a denaturing buffer, an affinity chromatography binding buffer, an affinity chromatography washing buffer, an affinity chromatography elution buffer, and a proteolytic digestion buffer. In some embodiments, the kit for high throughput purification and quantification includes at least one multi-well plate. In some embodiments, the kit for high throughput purification and quantification includes a partially or fully automated high throughput purification and quantification system.

V. Methods of Producing Polypeptides

Aspects of the presently disclosed subject matter relate to methods of producing a polypeptide of interest (e.g., a recombinant polypeptide) that involve culturing a recombinant cell of the presently disclosed subject matter in vitro under conditions suitable for the tunable expression of the polypeptide of interest in the cell. In some embodiments, the method optionally includes recovering the polypeptide of interest. In some embodiments, a kit of the presently disclosed subject matter can be used to produce a polypeptide of interest.

Vi. Recombinant Polypeptides

Aspects of the presently disclosed subject matter relate to recombinant polypeptides produced according to a method of the presently disclosed subject matter. In some aspects, a recombinant polypeptide of interest can be produced using an expression vector of the presently disclosed subject matter. In other aspects, a recombinant polypeptide of interest can be produced in an isolated recombinant cell of the presently disclosed subject matter. In certain easpects, a recombinant polypeptide of interest can be produced using a kit of the presently disclosed subject matter. As used herein, "polypeptide of interest" refers to any polypeptide for which the tunable regulation of its expression is desired in cells. In some embodiments, the polypeptide of interest comprises a therapeutic antibody, peptide, protein, or enzyme. In some embodiments, the polypeptide of interest comprises a naturally occurring polypeptide. In some embodiments, the polypeptide of interest comprises a variant of a naturally occurring polypeptide. In some embodiments, the polypeptide of interest comprises a fusion protein. In some embodiments, the polypeptide of interest comprises a label or tag. In some embodimenst, the polypeptide of interest comprises a reporter. In some embodiments, the polypeptide of interest comprises at least one N-terminus HA tag and/or at least one C-terminus reporter, such as a fluorescent protein. In some embodiments, the polypeptide of interest is a naturally occurring mammalian protein or a variant thereof. In some embodiments, the polypeptide of interest comprises a human protein or a variant thereof. In some embodiments, the polypeptide of interest comprises a C-terminus polylysine track or tag (e.g., a polyA polynucleotide sequence tag, a polyAAG lysine polynucleotide sequenc tag, etc.). In some embodiments, the polypeptide of interest comprises a N-terminus polylysine track or tag (e.g., a polyA polynucleotide sequence tag, a polyAAG lysine polynucleotide sequenc tag, etc.).

Vii. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Figure 1B:
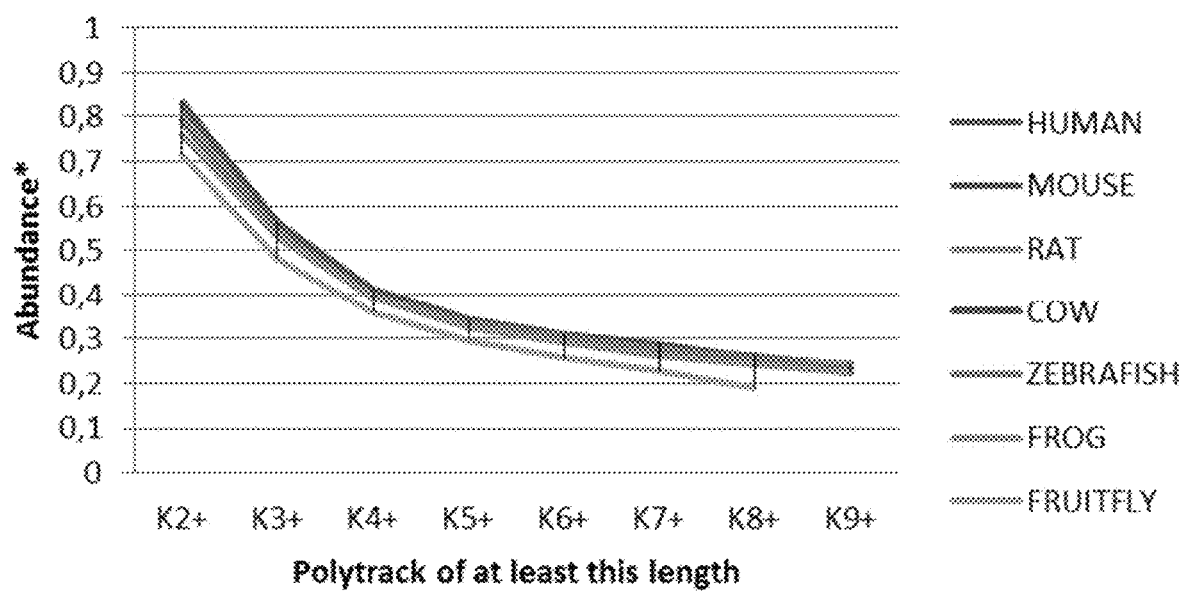
Figure 2A:
FIG. 2A, FIG. 2B, FIG. 2C, and FIG. 2D show a cartoon of reporter constructs used in electroporation experiments (FIG. 2A), western blot analyses of HA-X-mCherry constructs 48 hours after electroporation (FIG. 2B; HA and β-actin antibodies), normalized protein expression using Licor western blot analyses or in vivo mCherry fluorescence measurement (FIG. 2C; β-actin or fluorescence of co-expressed GFP construct were used for normalization of the data, respectively; each bar represents percentage of wild type mCherry (WT) expression/fluorescence), and normalized RNA levels of HA-X-mCherry constructs (FIG. 2D; neomycin-resistance gene was used for normalization of qRT-PCR data; each bar represents percentage of wild type mCherry (WT) mRNA levels).
Figure 2B:
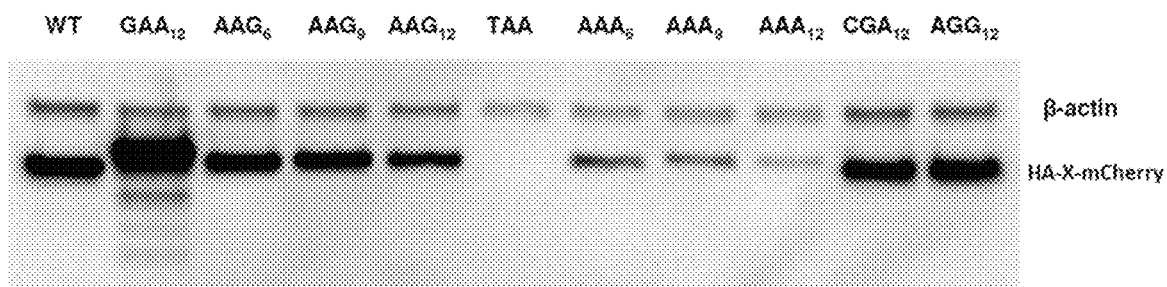
Figure 2C:
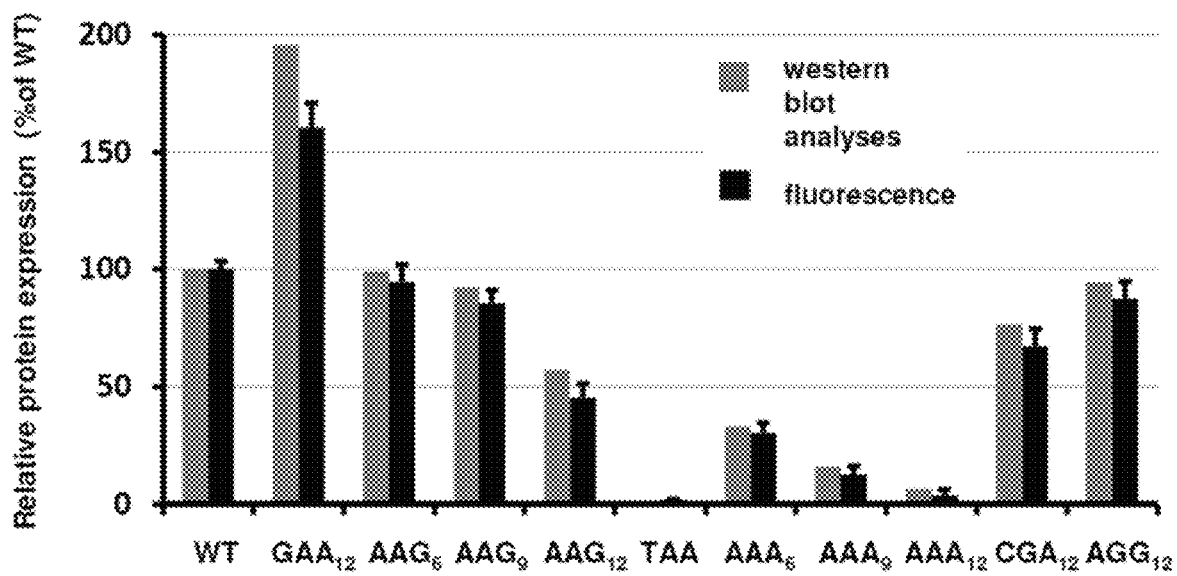
Figure 2D:
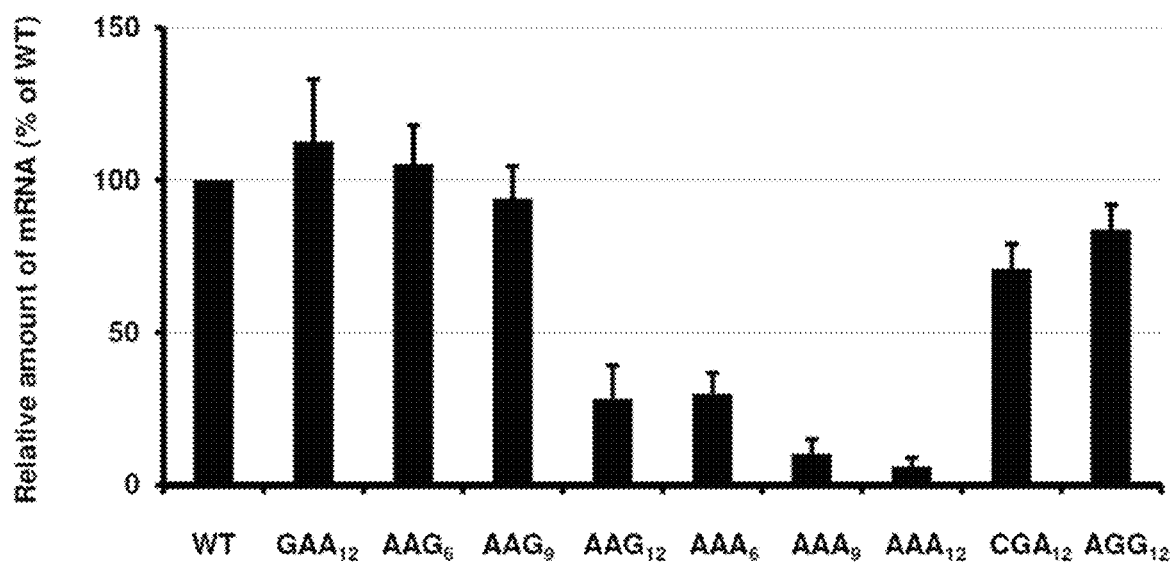
Figure 3A:
FIG. 3A and FIG. 3B show the expression of HA-X-mCherry reporters in Chinese Hamster Ovary cells. Western blot analysis of reporter expression was normalized to β-actin levels (FIG. 3A). qRT-PCR analyses of mRNA abundance was normalized to neomycin resistance gene and presented as fraction of mRNA levels for mCherry construct without insert (FIG. 3B).
Figure 3B:
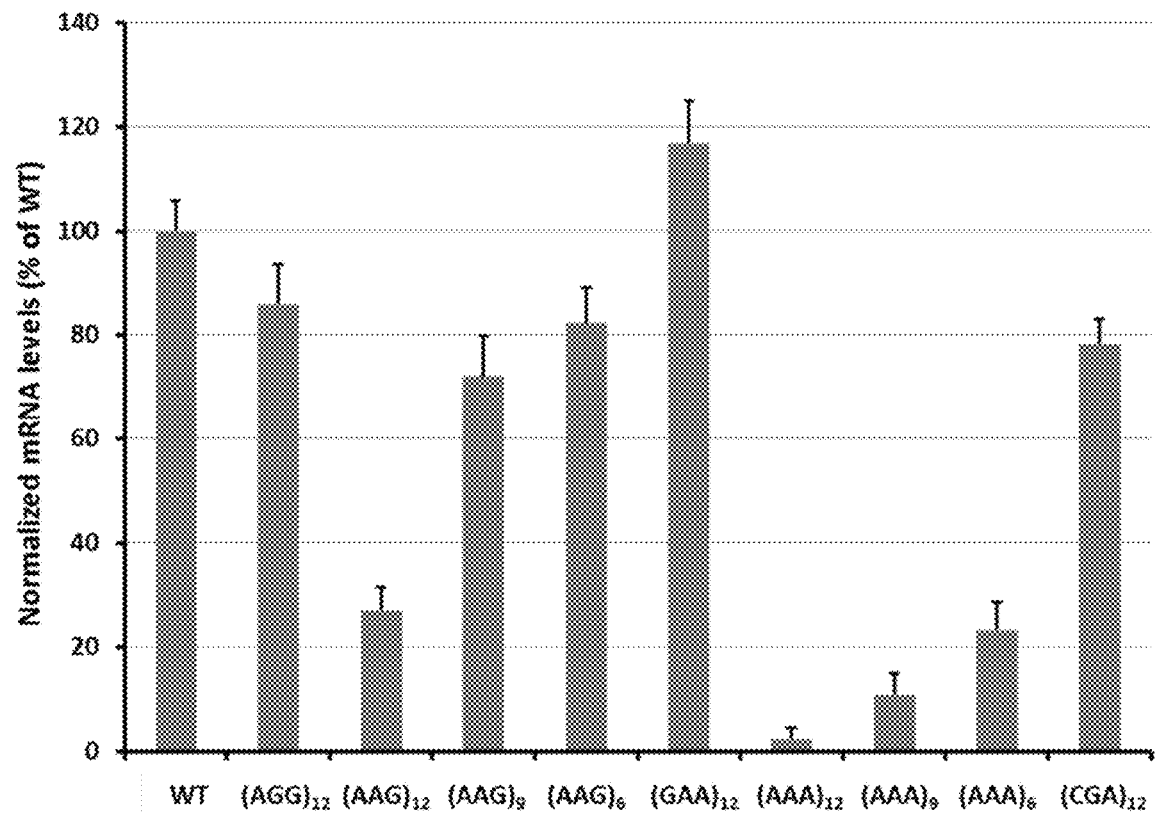
Figure 4A:
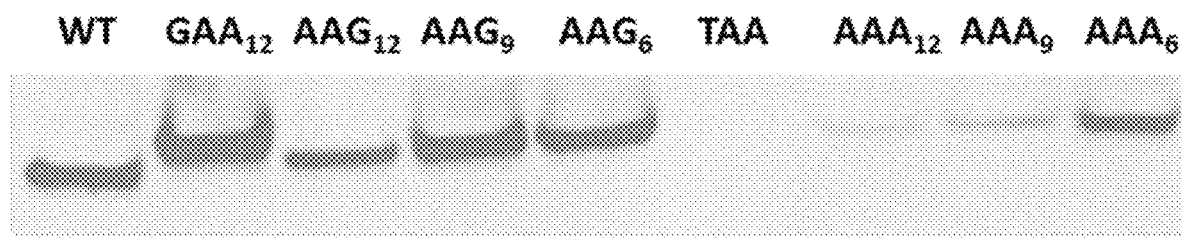
FIG. 4A and FIG. 4B show the expression of HA-X-mCherry reporters in *Drosophila* S2 cells. Western blot analysis of reporter expression was normalized to total protein amount (FIG. 4A). qRT-PCR analyses of mRNA abundance was normalized to levels of endogenous GAPDH mRNA and presented as fraction of mRNA levels for mCherry construct without insert (FIG. 4B).
Figure 4B:
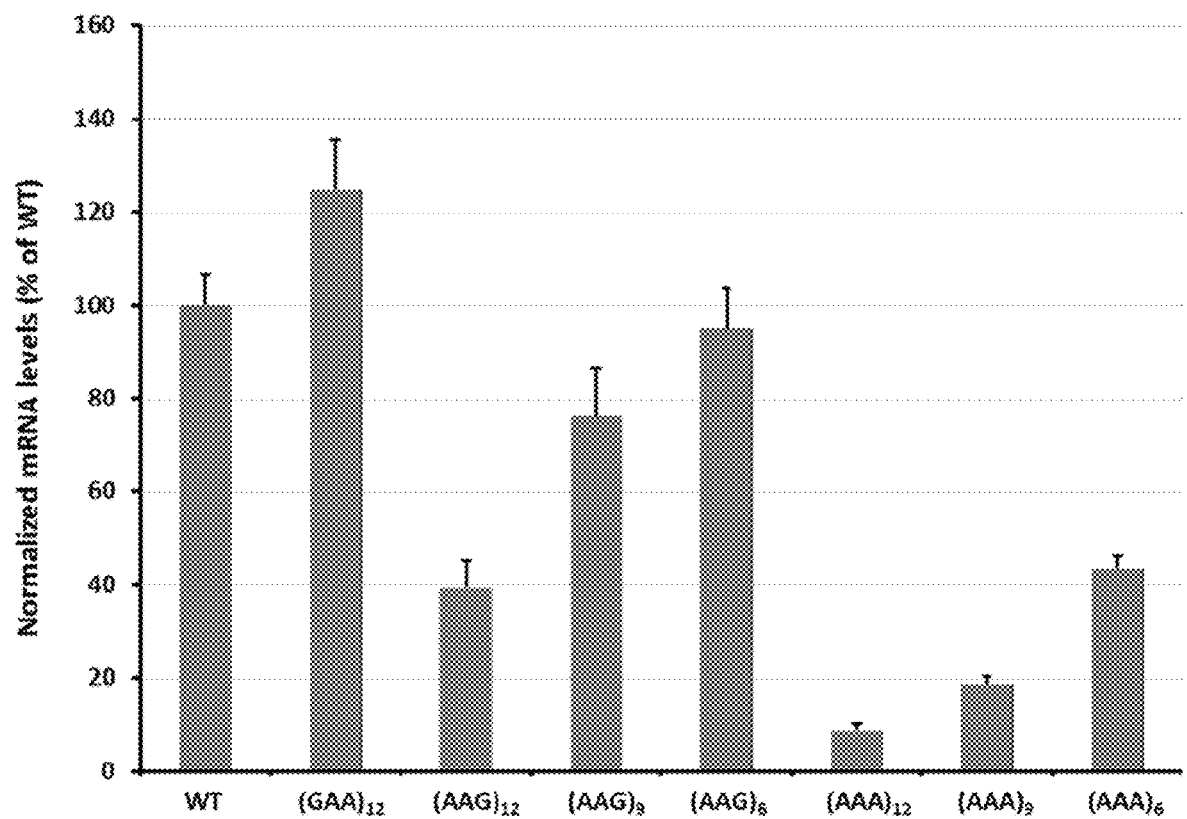

EXAMPLE 1: In Translational Regulation, Poly(A) Coding Sequences in Human Cells Unexpectedly Induce Ribosome Pausing Directly, without a Role for the Encoded Basic Peptide Bioinformatic analysis can be used as an initial approach to ask whether there are evolutionary constraints that limit the abundance of polybasic amino acid residues. Runs of polybasic residues in coding sequences of genes from many eukaryotic organisms are under-represented when compared to runs of other amino acids (Karlin et al. (2002) Proc. Natl. Acad. Sci. U.S.A 99, 333-338). Interestingly, polyarginine runs have a similar abundance to polylysine runs at each segment length across multiple organisms (FIG. 1A, FIG. 1B). A series of mCherry reporters were developed to evaluate the effects of polybasic sequences on translation efficiency (output). The reporter construct consists of a double HA-tag, a run of control or polybasic sequences, followed by the mCherry reporter sequence (HAmCherry, FIG. 2A). As a control for DNA transfection and in vivo fluorescence measurements, a construct with green fluorescent protein (GFP) was also created. The reporters were used to ask whether the polybasic sequences influence translation of reporter sequences in neonatal human fibroblasts (HDFs) as well as in Drosophila S2 cells and Chinese hamster ovary cells (CHO) (FIG. 2B, FIG. 2C, FIG. 3A, FIG. 3B, FIG. 4A, FIG. 4B). Expression of the mCherry reporter was followed using fluorescence at 610 nm in vivo or western blot analyses of samples collected 48 hours after transfection (FIG. 2B, FIG. 2C). The stability of reporter mRNAs was determined using standard quantitative reverse transcription polymerase chain reaction assay (qRT-PCR, (Djuranovic et al. (2012) Science. 336, 237-240) (FIG. 2D). By careful primer design, this method allows estimation of the level of endonucleolytic cleavage on mRNAs with stalled ribosome complexes.

Figure 5A:
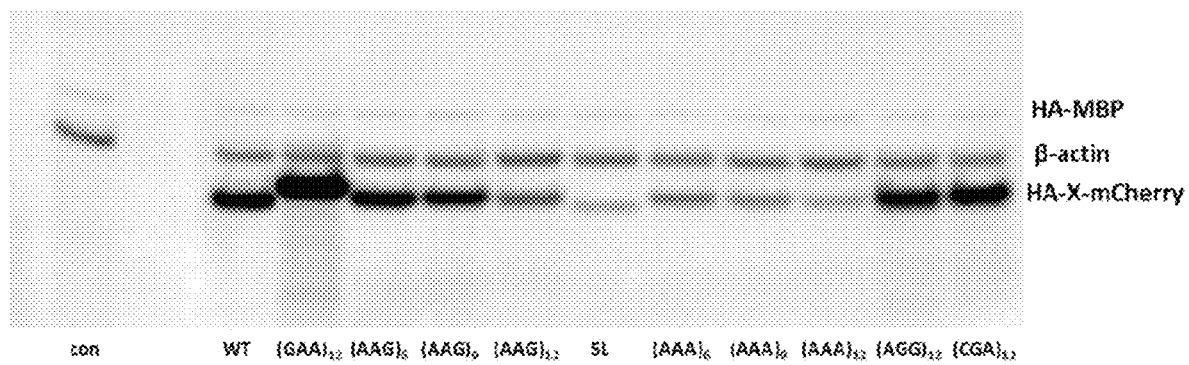
FIG. 5A and FIG. 5B show the expression of HA-X-mCherry reporters from T7-RNA polymerase in vitro transcribed mCherry mRNAs in neonatal human fibroblasts (HDFs). HA-MBP mRNAs were in vitro transcribed and co-electroporated into HDFs as a control for electroporation efficiency and western blot normalization. β-actin was used as a control for the total protein amounts (FIG. 5A). Each lane was subjected to Bio-Rad quantification analyses to determine the levels of expression shown on the graph below (FIG. 5B).
Figure 5B:
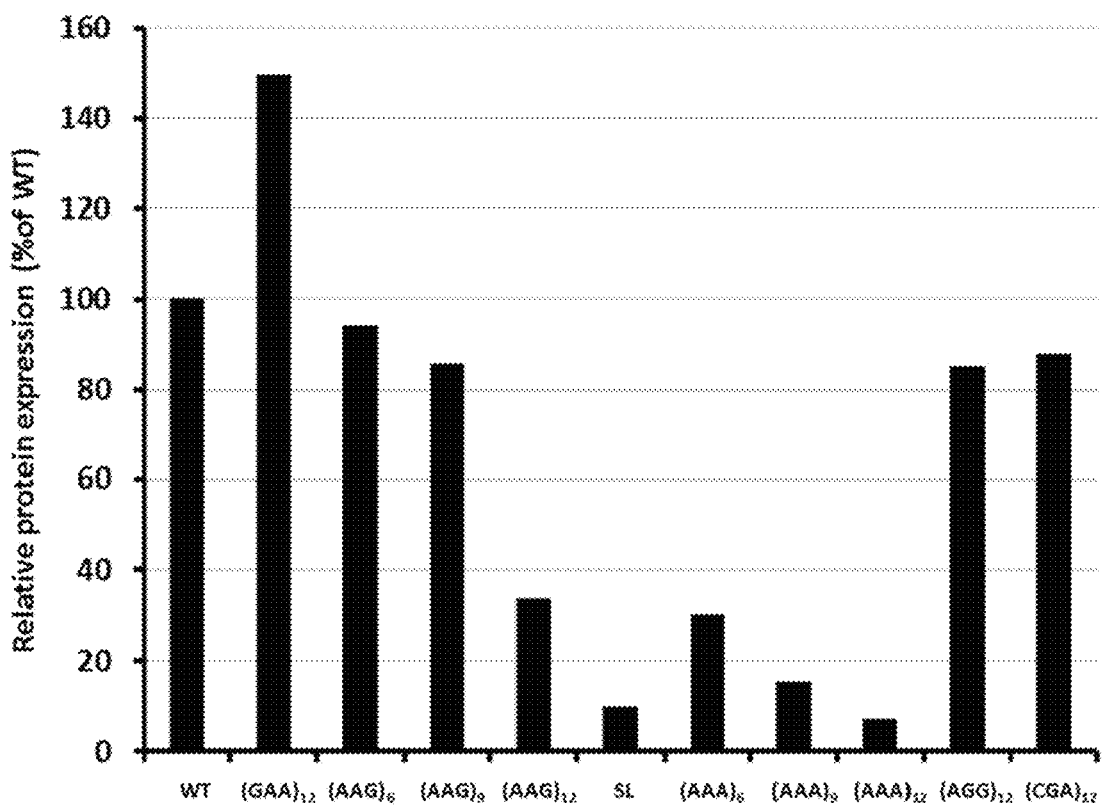
Figure 6A:
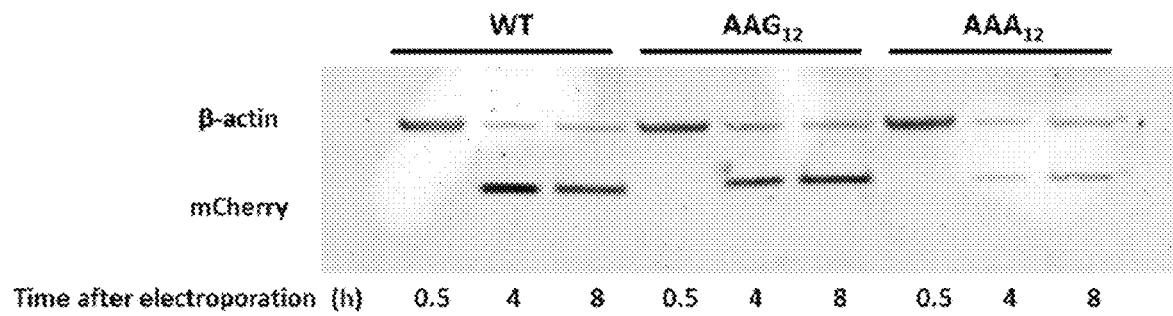
FIG. 6A, FIG. 6B, and FIG. 6C show the differential stability of electroporated mRNAs from HA-X-mCherry reporters is translation dependent. In vitro transcribed mCherry mRNAs were electroporated in HDFs. Protein (FIG. 6A) and mRNA (FIG. 6B) levels were assessed by western blot analyses or qRT-PCR. HA-(AAA)12-mCherry construct shows significant reduction in protein levels as well as in mRNA stability. Addition of translation initiation inhibitor, herringtonine, completely abolishes effect on mRNA stability (FIG. 6C).
Figure 6B:
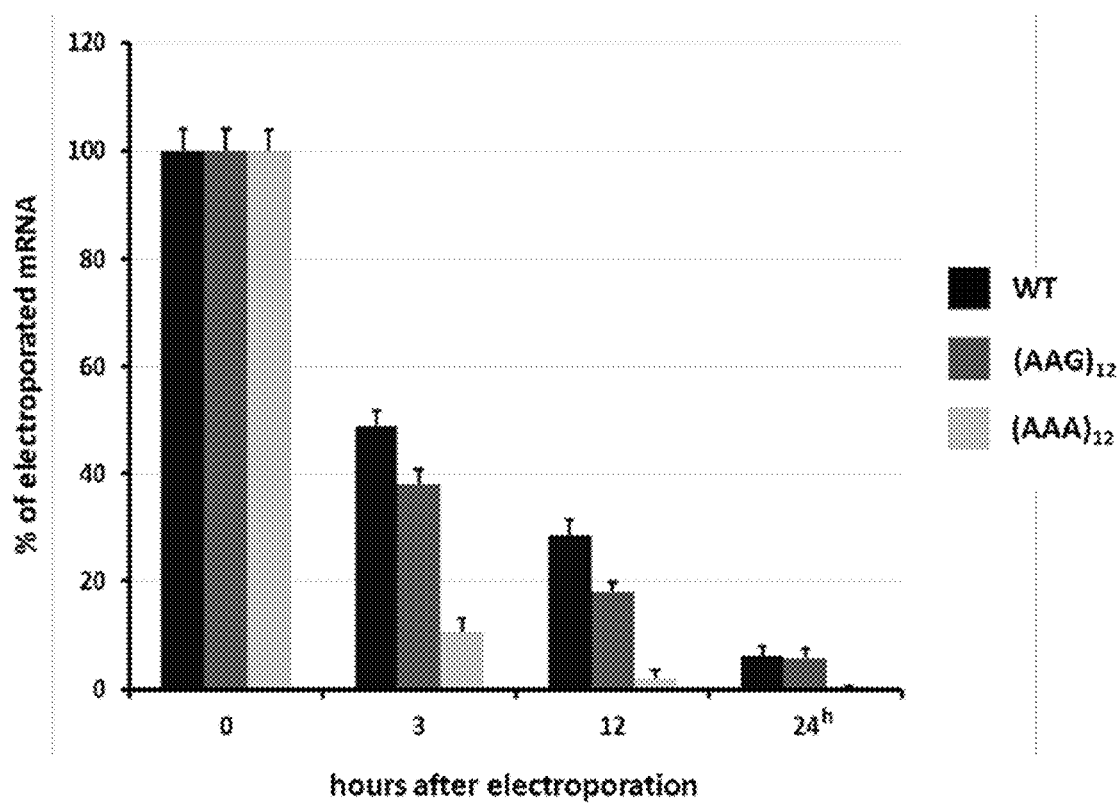
Figure 6C:
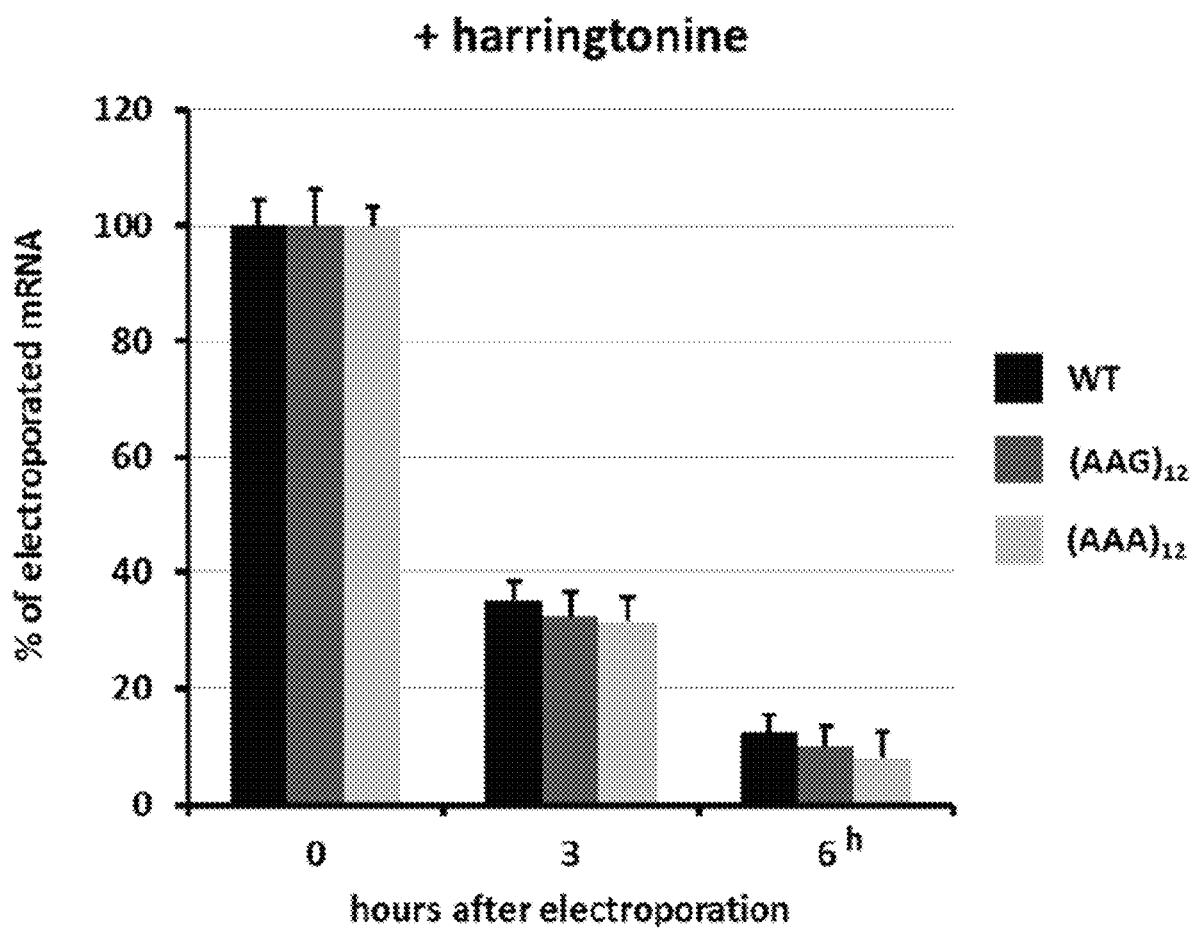
Figure 7A:
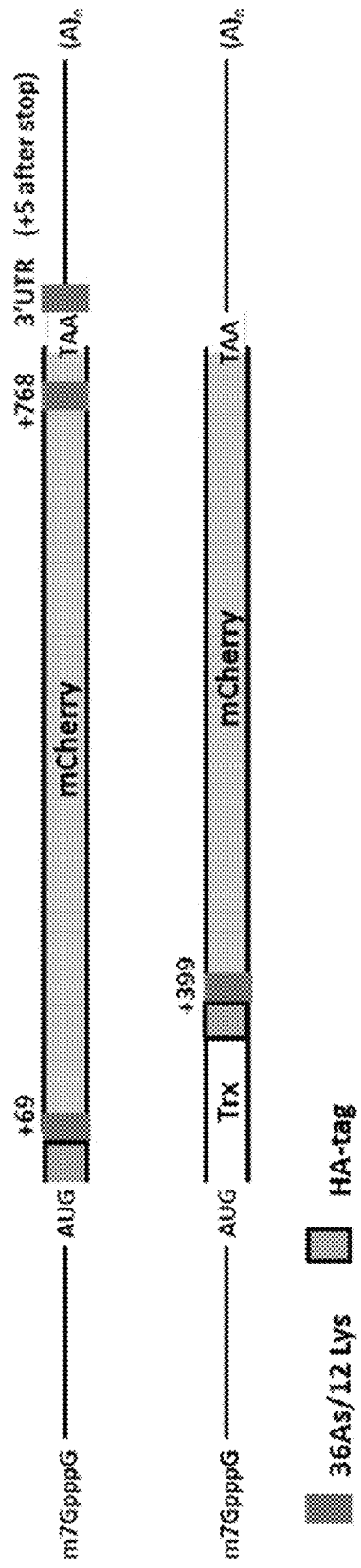
FIG. 7A, FIG. 7B, and FIG. 7C show that insertion of polylysine mCherry constructs in the coding sequence results in the same protein reduction and decreased mRNA stability.
Figure 7B:
Figure 7C:
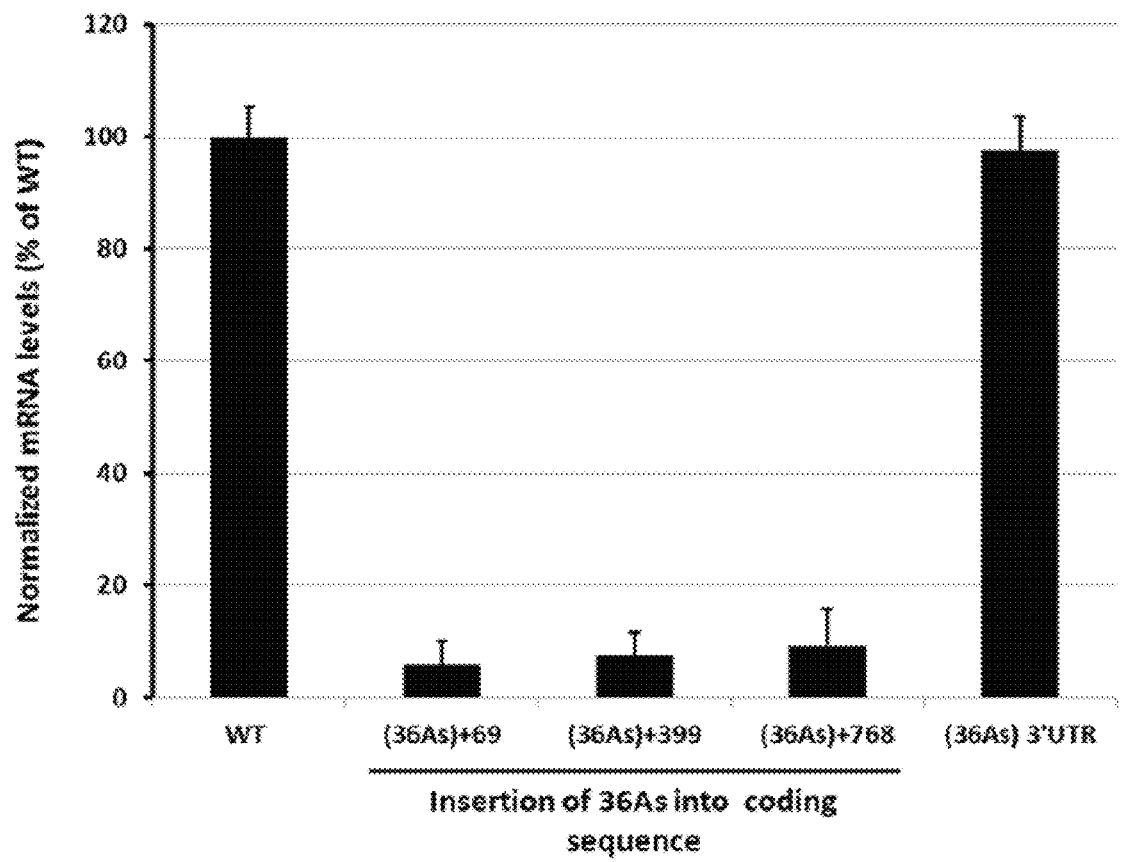

The results of DNA transfections indicate that strings of lysine codons specifically inhibit translation and decrease the stability of the mCherry reporter mRNA while up to 12 arginine codons (AGG and CGA) have much less, if any effect, on either translation or mRNA stability (FIG. 2B, FIG. 2C, FIG. 2D, FIG. 3A, FIG. 3B, FIG. 4A, FIG. 4B). The potency of translational repression by lysine codons is clearly seen with as few as six AAA-coded lysines (AAA6) and increases with the length of the homo-polymeric amino acid run. It is also noted that the levels of expressed mCherry reporters (FIG. 2B, FIG. 2C) correlate with the stability of their mRNAs (FIG. 2D), consistent with earlier published observations (Doma and Parker (2006) Nature 440, 561-564; Dimitrova et al. (2009) J. Biol. Chem. 284,10343-10352; Tsuboi et al. (2012) Mol. Cell. 46, 518-529). To control for possible transcriptional artifacts due to the effects of homopolymeric sequence on transcription by RNA polymerase, mRNAs synthesized in vitro by T7 RNA polymerase were electroporated directly into HDF cells. Previous studies established that T7 RNA polymerase is able to transcribe such homopolymeric sequences with high fidelity (Koutmou et al. (2015) eLIFE 10.7554/eLife.05534; Djuranovic et al. (2012) Science. 336, 237-240). Results of the mRNA electroporation work reproduced DNA transfection experiments, consistent with models of translational repression triggered by lysine codons (FIG. 5A, FIG. 5B). To assess whether the stability of polylysine reporter mRNAs is dependent on translation, the translation initiation inhibitor harringtonine (Fresno et al. (1977) Eur. J. Biochem. FEBS. 72, 323-330) was introduced into HDF cells prior to mRNA electroporation. In this case, a significant change in mRNA stability between wild type and polylysine-encoding mCherry constructs was not observed (FIG. 6A, FIG. 6B, FIG. 6C); these data indicate that accelerated decay of polylysine mCherry mRNAs is dependent on translation. Consistent with this observation, the insertion of 36As (sequence equivalent to twelve lysine AAA codons) after the stop codon, in the 3'UTR region, did not affect the protein expression level or mRNA stability of the assayed construct (FIG. 7A, FIG. 7B, FIG. 7C). Insertion of polylysine codons at different positions along the coding sequence drastically reduced reporter expression and mRNA levels independent of the relative position in the construct. As such, it follows that the observed changes in mRNA stability (FIG. 2D) result from translation-dependent processes.

Figure 8A:
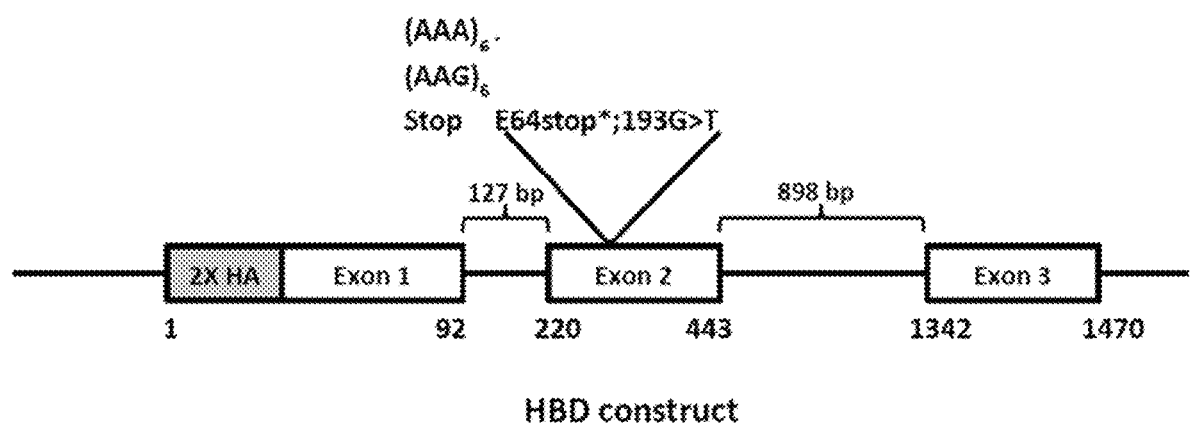
FIG. 8A, FIG. 8B, and FIG. 8C show the expression of HA-tagged hemoglobin (delta chain; HBD) constructs with natural introns in HDF cells.
Figure 8B:
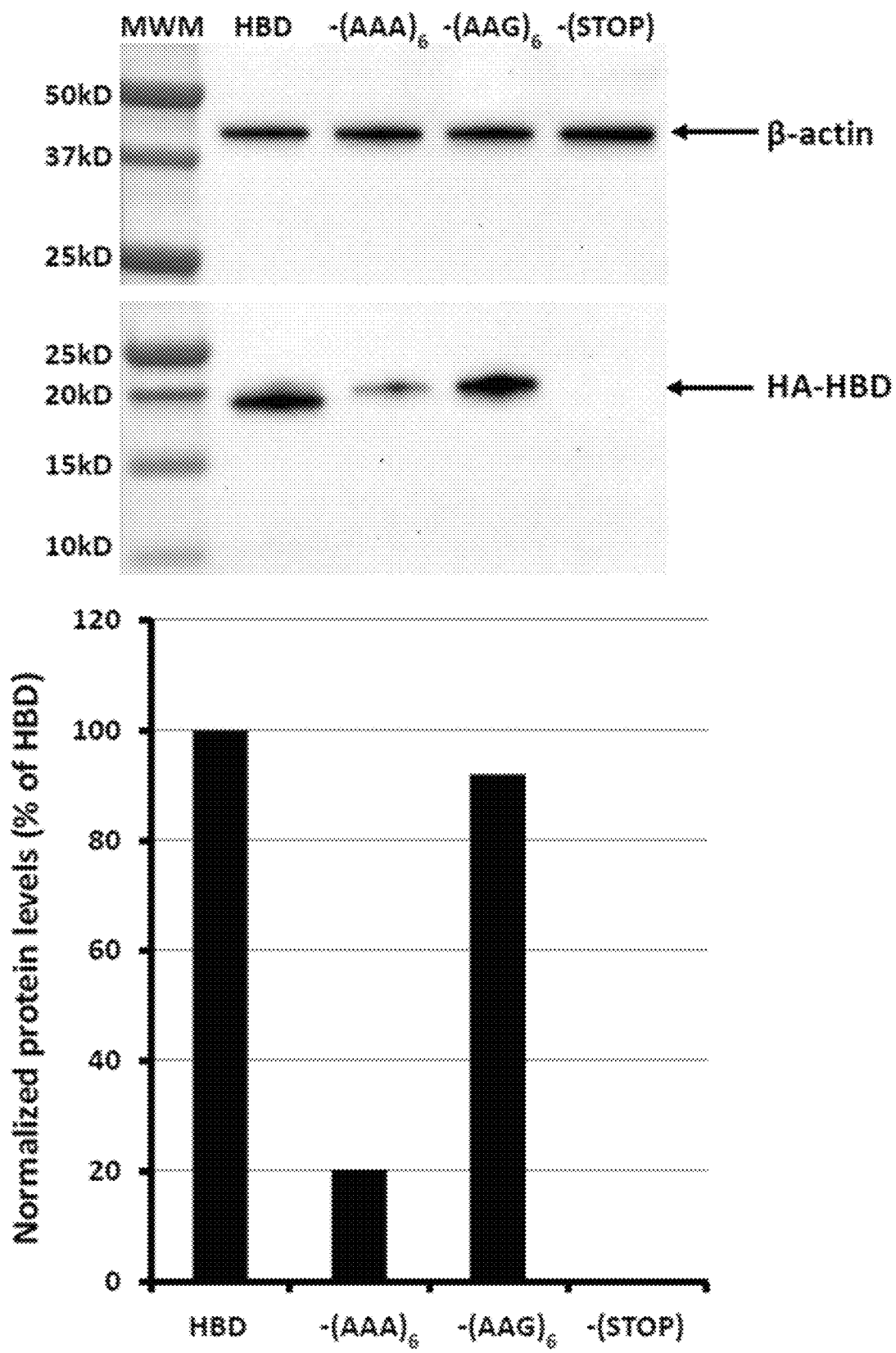
Figure 8C:
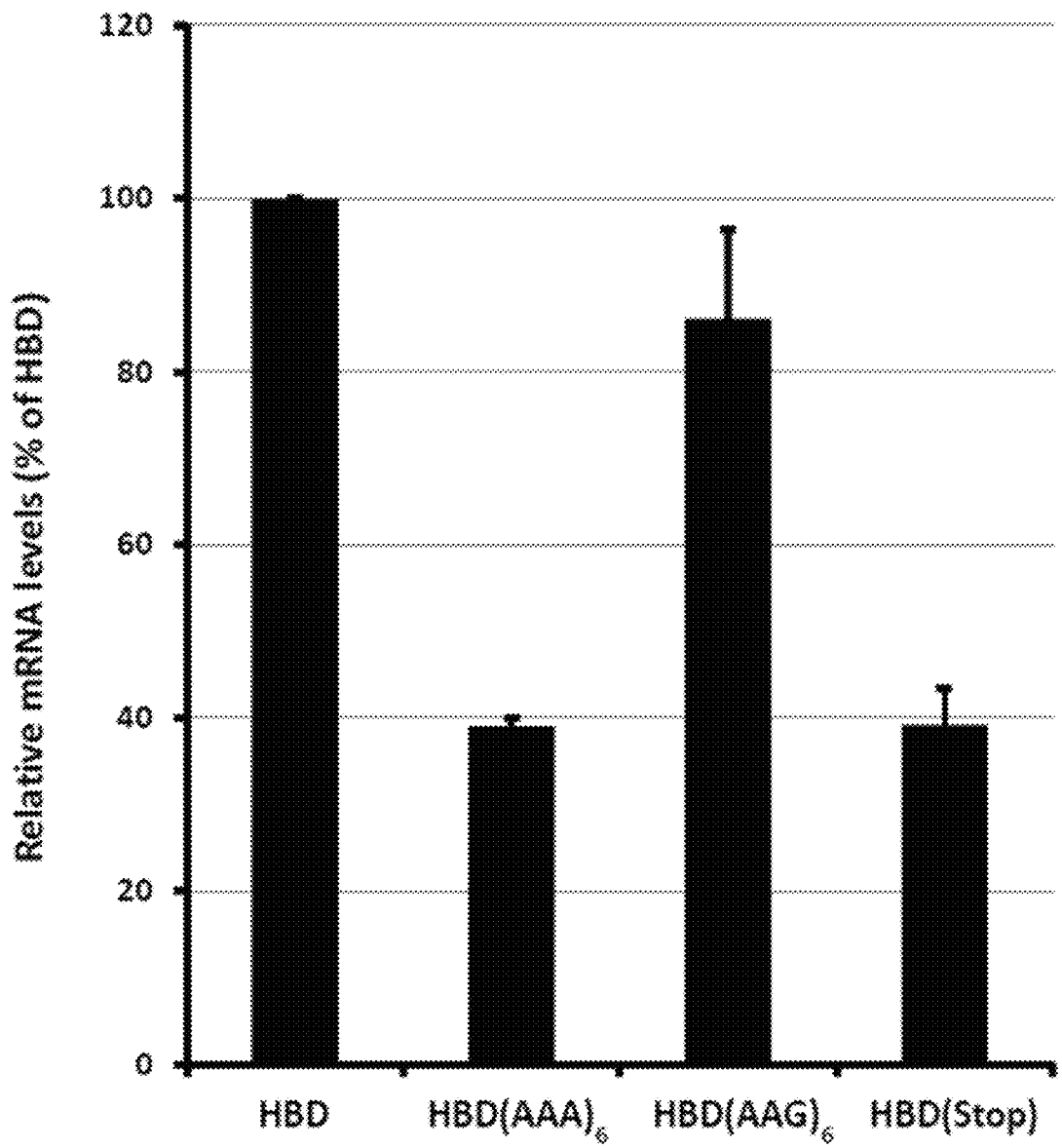

The most striking observation from these data is that the production of polylysine constructs is codon dependent; runs of polylysine residues coded by AAA codons have a much larger effect on the protein output from reporter constructs than an equivalent run of lysine AAG codons (FIG. 2B, FIG. 2C, FIG. 2D, FIG. 3A, FIG. 3B, FIG. 4A, FIG. 4B, FIG. 5A, FIG. 5B, FIG. 6A, FIG. 6B, FIG. 6C, FIG. 7A, FIG. 7B, FIG. 7C, FIG. 8A, FIG. 8B, FIG. 8C). This effect is unlikely to be driven by the intron-less nature of the reporter since constructs containing human hemoglobin gene (delta chain, HBD) with two introns showed the same effect on protein output and RNA stability (FIG. 8A, FIG. 8B, FIG. 8C). It is also noted that this effect is unlikely to be driven simply due to tRNALys abundance, since the relative protein expression and mRNA stability are comparable in cells from various species that do not share similar tRNA abundance profiles (gtrnadb.ucsc.edu/; FIG. 2A, FIG. 2B, FIG. 2C, FIG. 2D, FIG. 3A, FIG. 3B, FIG. 4A, FIG. 4B, FIG. 5A, FIG. 5B, FIG. 6A, FIG. 6B, FIG. 6C, FIG. 7A, FIG. 7B, FIG. 7C, FIG. 8A, FIG. 8B, FIG. 8C). Furthermore, the human genome encodes a comparable number of tRNA genes for AAA and AAG codons (gtrnadb.ucsc.edu/Hsapi19/) and general codon usage is similar (0.44 vs 0.56, AAA vs AAG). The generality of codon-dependent polylysine protein production was recently documented in E. coli cells where a single tRNALys(UUU) decodes both AAA and AAG codons (Koutmou et al. (2015) eLIFE 10.7554/eLife.05534).

Figure 9:
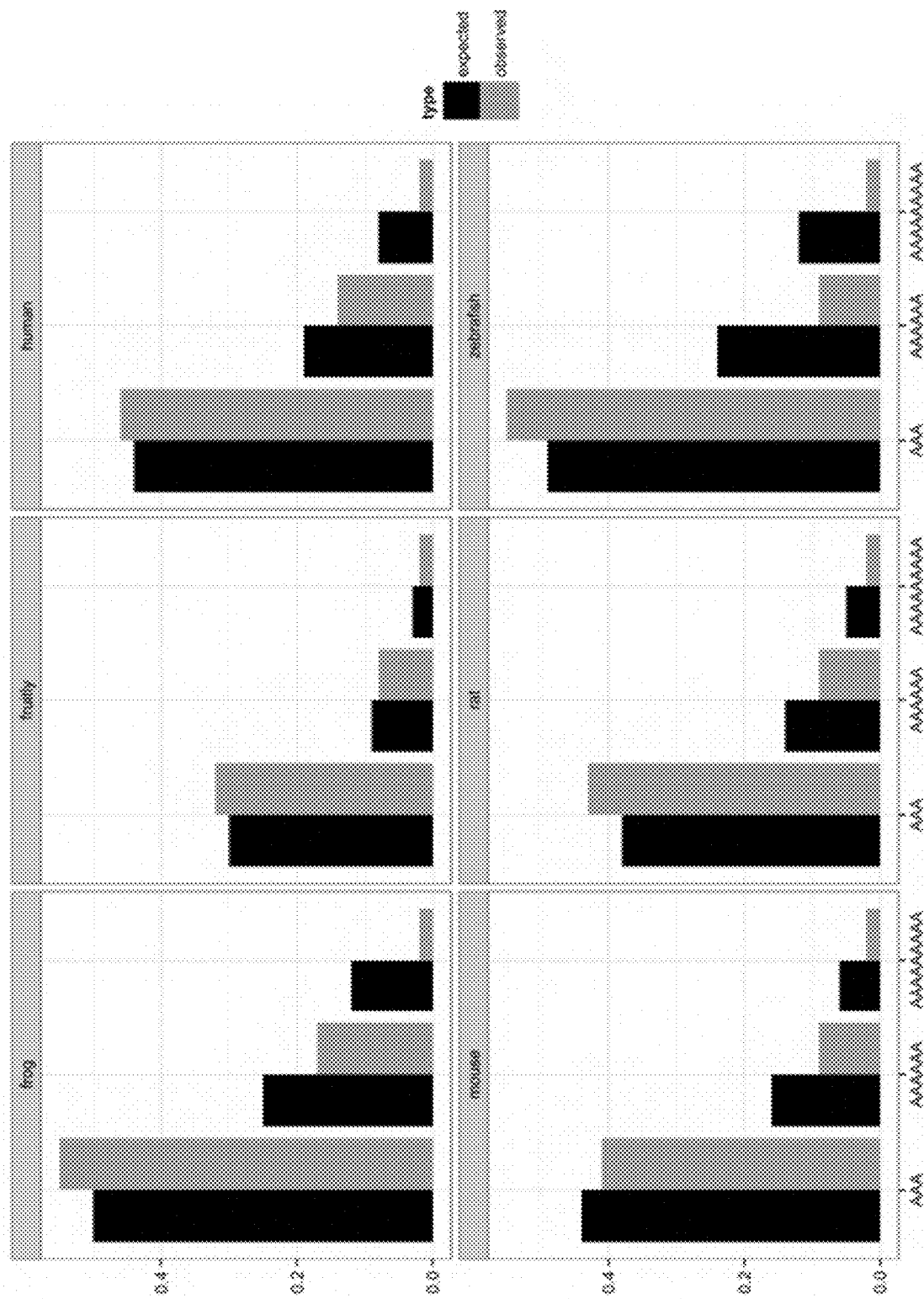
FIG. 9 shows a comparison of usage of AAA in single, double and triple lysine runs across several organisms. Expected values (black bars) are based on Kazusa database, while observed (yellow bars) are calculated from all isoforms of proteins available in NCBI RefSeq database.
Figure 10:
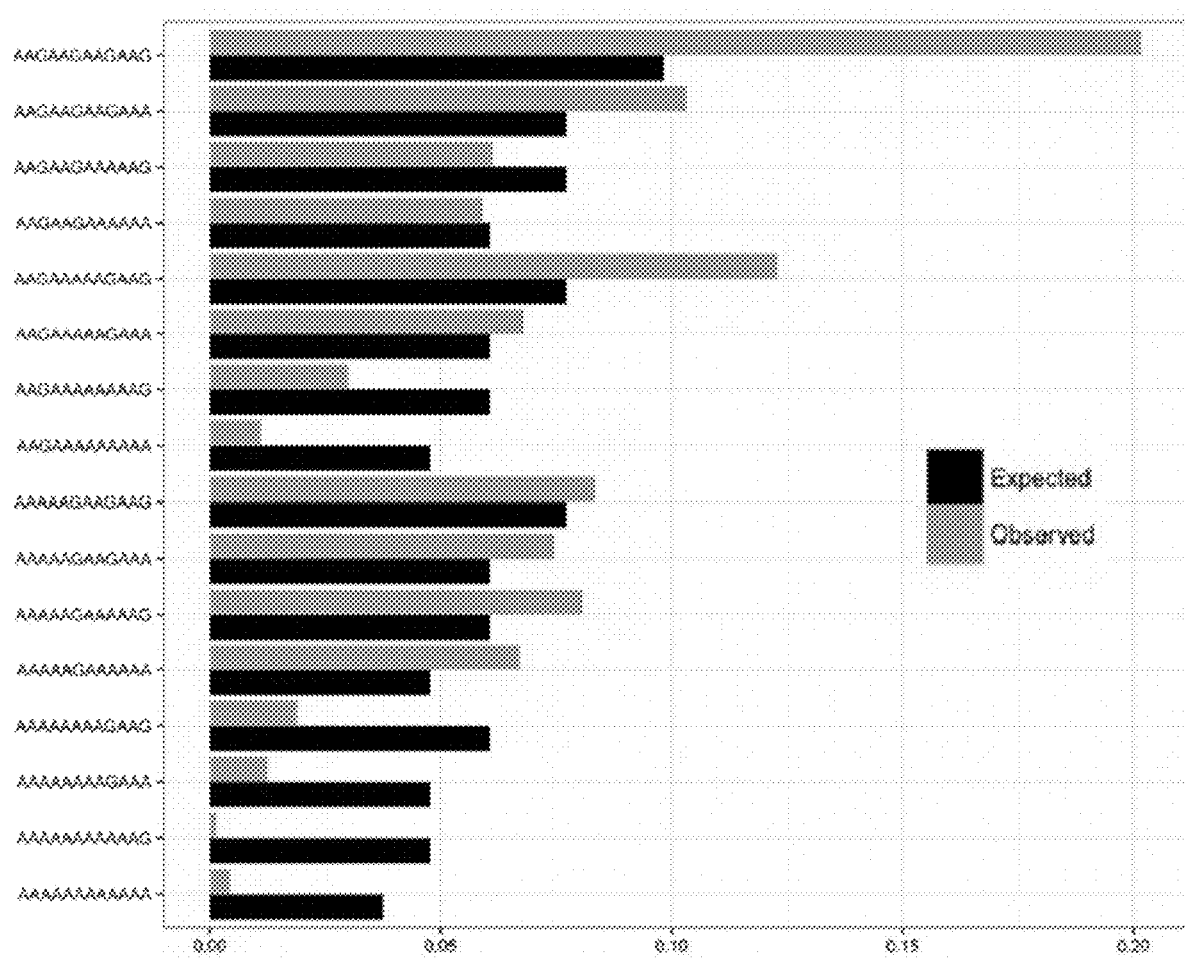
FIG. 10 shows observed codon usage in all isoforms of human proteins vs. expected (based on the proportions 0.44 to 0.56, AAA to AAG for all lysines) in the tracks of four consecutive lysines. From top to bottom along the y-axis, the sequences correspond to SEQ ID NOs 71-86 respectively.
Figure 11:
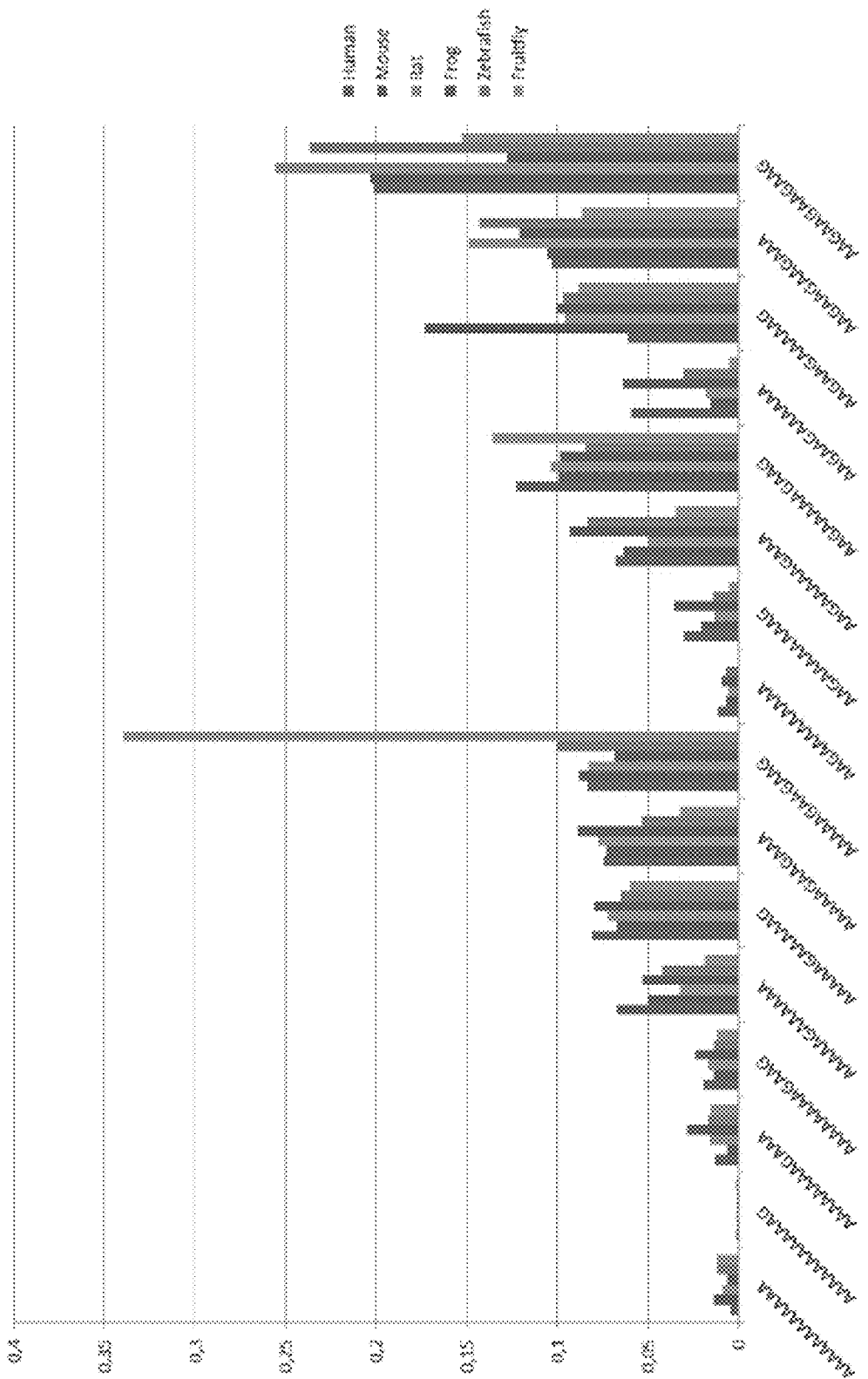
FIG. 11 shows codon distribution in four-lysine tracks in different organisms. All protein isoforms sequences and sequences of corresponding mRNAs were taken into account. The script checks all tracks of four consecutive lysines, even when overlapping (if there is a track of five lysines, it will report two nucleotide strings of length 12). From left to right along the x-axis, the sequences correspond to SEQ ID Nos 87-102 respectively.

In light of these experimental observations, codon usage and the distribution of lysine codons in polylysine tracks in various species was systematically explored (FIG. 9). Remarkably, a strong under-representation of poly(A) nucleotide runs in regions coding for iterated lysines (even with as few as three lysines) in human genes is found (FIG. 9). When there are four iterated lysine residues, the difference between expected (from data for all lysine residues) and observed codon usage for four AAA codons in a row is over one order of magnitude (FIG. 10). Notably, similar patterns of codon usage in lysine poly(A) tracks are observed in other vertebrates (FIG. 11).

Figure 12A:
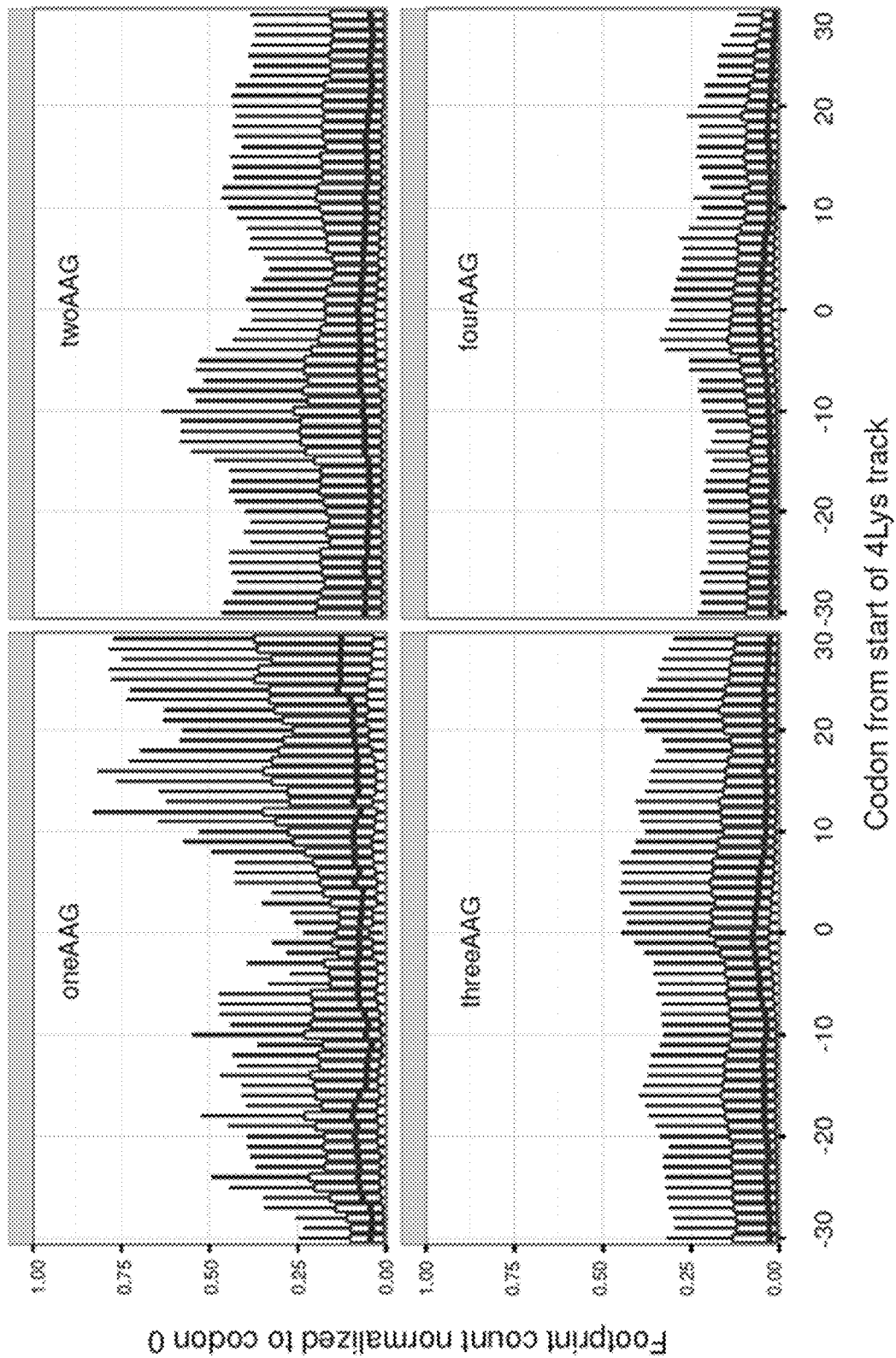
FIG. 12A, FIG. 12B, FIG. 12C, FIG. 12D, and FIG. 12E shows HA-(A9-A13)-mCherry construct sequences and protein expression.

Ribosome profiling data have the potential to reveal features of pausing on polybasic stretches throughout the genome (Ingolia (2014) Nat. Rev. Gen. 15, 205-213). A cumulative analysis of three ribosome profiling datasets from human cells for regions encoding four lysines in a row revealed that the occupancy pattern on four lysines encoded by three AAA and one AAG codon is different from the pattern for two, three and four AAG codons in four lysine-tracks (FIG. 12A). The latter three resemble the occupancy pattern for tracks of arginines (FIG. 13A, FIG. 13B), which is similar to the ribosome stalling on runs of basic amino acids observed by other researchers (Charneski and Hurst (2013) PLoS Biol. 11, e1001508). This suggests that the observed effect on protein output and mRNA stability is dependent on nucleotide, not simply the amino acid sequence. Additionally, the first example (with three AAA and one AAG codon) has a region of increased ribosome occupancy found additionally after the analyzed region (FIG. 12A). Together, these data suggest that attenuation of translation on poly(A) nucleotide tracks occurs via a different mechanism than just the interaction of positively charged residues with the negatively charged ribosomal exit tunnel.

Figures 12B, 12C:
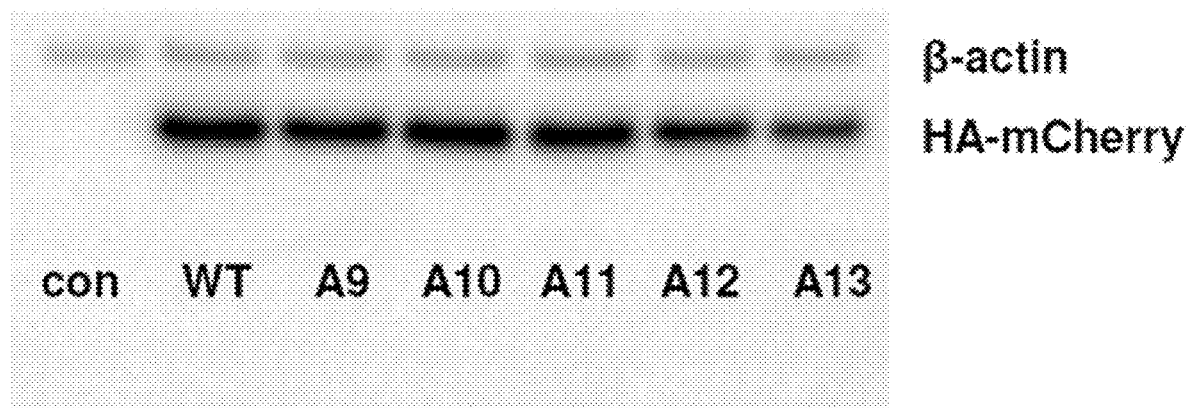
Figure 12D:
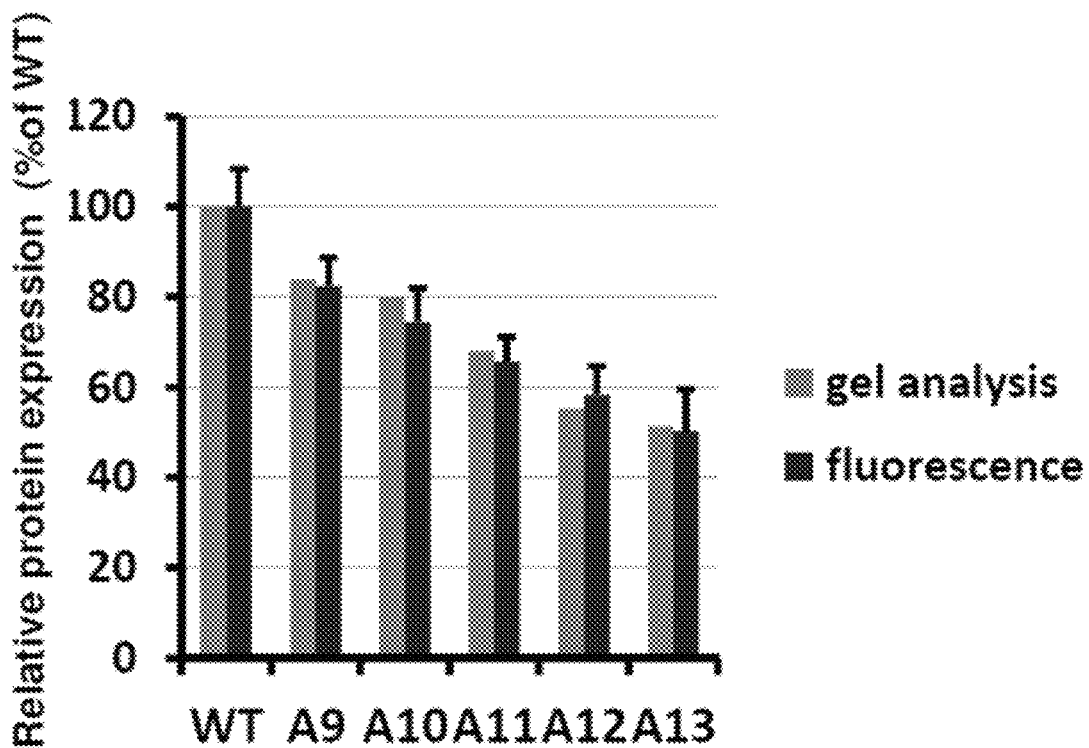
Figure 12E:
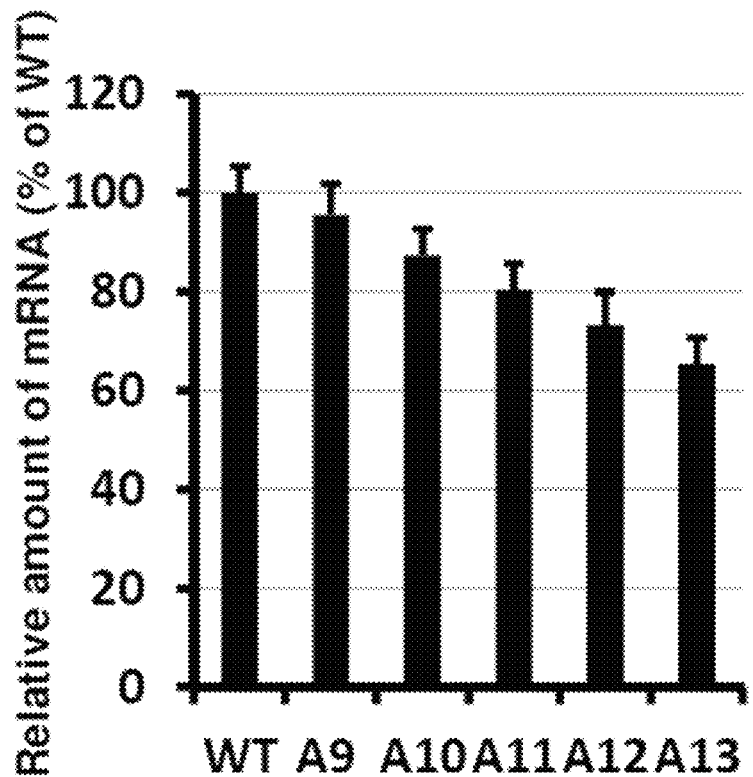

In order to probe the potential impact of the observed disparities in codon distribution for runs of three and four consecutive lysine codons, runs of three lysine resides with various numbers of consecutive As (A9-A13) were inserted into the mCherry reporter construct (FIG. 12B). As in the previous experiments (FIG. 2B, FIG. 2C), the expression of the mCherry reporter as well as the stability of the mRNA was followed (FIG. 12C, FIG. 12D, FIG. 12E). It was found that the insertion of sequences with 12 or more consecutive As reduces mCherry reporter expression by more than 50% with comparable effects on mRNA stability. Importantly, in each construct, no more than three lysines are encoded so the increasing effect on protein output must result from consecutive As, not Ks.

Figure 14A:
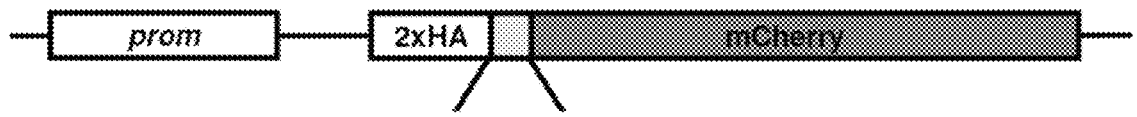
FIG. 14A, FIG. 14B, FIG. 14C, and FIG. 14D show the sequences of polylysine runs from human genes incorporated into HA-X-mCherry constructs (FIG. 14A; continuous runs of lysine residues are labeled; number of lysine residues and ratio of AAG and AAA codons for each constructs are indicated), normalized protein expression using in vivo mCherry reporter fluorescence (FIG. 14B; fluorescence of co-transfected GFP was used to normalize the data; each bar represents percentage of wild type mCherry (WT) expression/fluorescence), normalized RNA levels of HA-X-mCherry constructs (FIG. 14C; neomycin resistance gene was used for normalization of qRT-PCR data; each bar represents percentage of wild type mCherry (WT) mRNA levels), and smoothed Gaussian kernel density estimate of positions of polyA tracks along the gene (FIG. 14D; position of polyA segment is expressed as a ratio between number of first residue of polyA track and length of a gene).
Figure 14B:
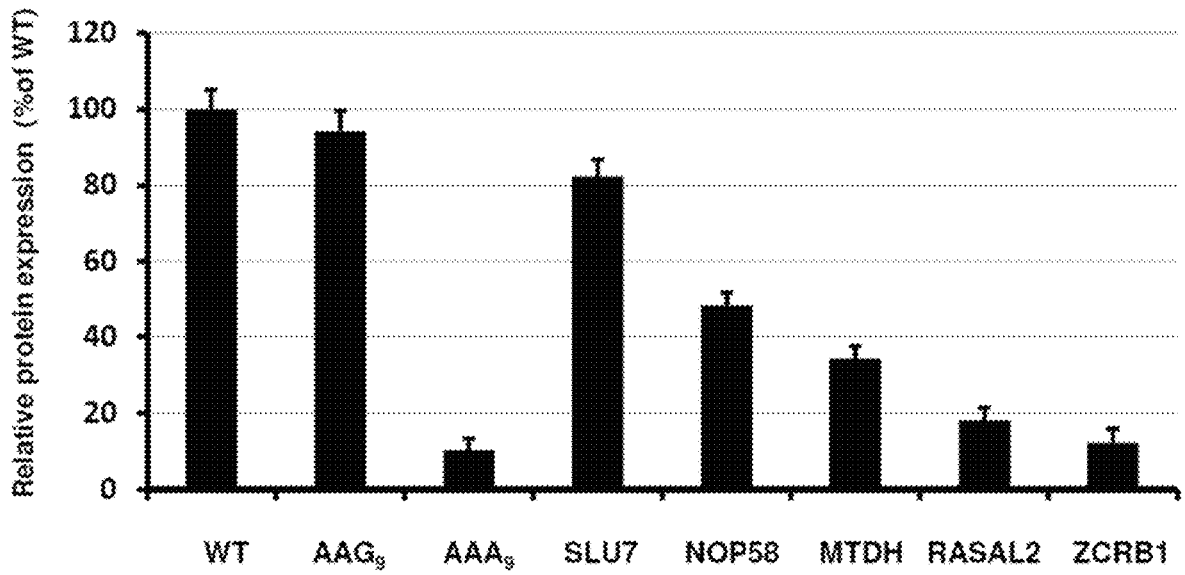
Figure 14C:
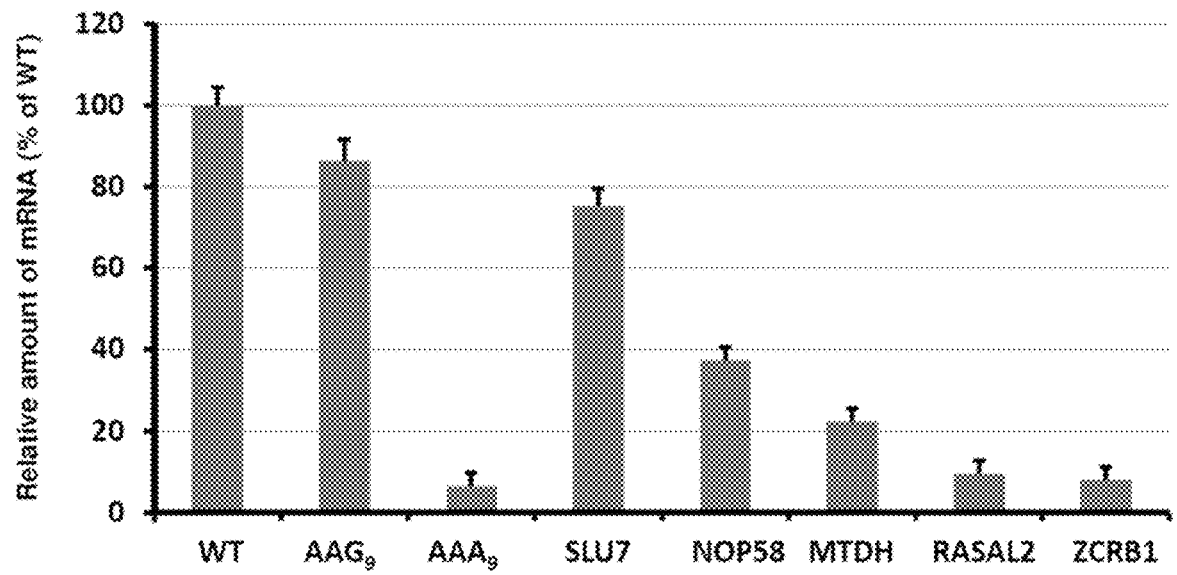

Next, it was asked whether polylysine sequences from naturally occurring genes have the same general effect on expression of reporter protein. To take an unbiased approach, different lengths of homopolymeric lysine runs and various distributions of AAA and AAG codons were selected (FIG. 14A). Reporter constructs with lysine runs were electroporated into HDF cells and relative amounts of reporter expression and mRNA stability were evaluated (FIG. 14B, FIG. 14C). As with the designed sequences in FIG. 12B, the observed decreases in reporter protein expression and mRNA stability correlated with the number of consecutive A nucleotides and not with total number of lysine codons in the chosen sequences. The reporter experiments together (FIG. 2B, FIG. 2C, FIG. 2D, FIG. 3A, FIG. 3B, FIG. 4A, FIG. 4B, FIG. 5A, FIG. 5B, FIG. 6A, FIG. 6B, FIG. 6C, FIG. 7A, FIG. 7B, FIG. 7C, FIG. 8A, FIG. 8B, FIG. 8C, FIG. 12B, FIG. 12C, FIG. 12D, FIG. 12E, FIG. 14A, FIG. 14B, FIG. 14C) argue that the repressive effects of the polylysine sequence are caused by iterated poly(A) tracks rather than by runs of encoded lysine residues. Similar effects were recently documented in in vivo and in vitro experiments with E. coli cells or a purified translational system, respectively (Koutmou et al. (2015) eLIFE 10.7554/eLife.05534). The differences observed in expression of reporter sequences with poly(A) nucleotide tracks from human genes favor the possibility that such regions in natural genes play a "translational attenuator" role that can modulate overall protein expression.

TABLE 1 shows a table of overrepresentation of gene ontology terms for 456 genes containing polyA tracks in heir coding regions up to P-value of 0.05

| Term | Background frequency | Sample frequency | Expected | +/− | P-value |
|---|---|---|---|---|---|
| nucleic acid binding (GO:0003676) | 3799 | 149 | 7.614e+01 | + | 60651e−15 |
| heterocyclic compound binding (GO:1901363) | 5648 | 189 | 1.132e+02 | + | 5.339e−13 |
| RNA binding (GO:0003723) | 1500 | 79 | 3.006e+01 | + | 7.430e−13 |
| organinc cyclic compound binding (GO:0097159) | 5717 | 190 | 1.146e+02 | + | 8.553e−13 |
| poly(A) RNA binding (GO:0044822) | 1122 | 62 | 2.249e+01 | + | 1.388e−10 |
| binding (G0:0005488) | 12444 | 316 | 2.494e+02 | + | 5.325e−09 |
| DNA binding (GO:0003677) | 2322 | 87 | 4.654e+01 | + | 1.491e−06 |
| protein binding (GO:0005515) | 8307 | 219 | 1.665e+02 | + | 3.725e−05 |
| ion binding (GO:0043167) | 5844 | 166 | 1.171e+02 | + | 3.815e−05 |
| chromatin binding (GO:0003682) | 409 | 26 | 8.197e+00 | + | 6.569e−05 |
| zinc ion binding (GO:0008270) | 1181 | 49 | 2.367e+01 | + | 2.713e−04 |
| molecular_function (GO:0003674) | 15480 | 353 | 3.103e+02 | + | 3.165e−04 |
| transition metal ion binding (GO:0046914) | 1417 | 52 | 2.840e+01 | + | 3.844e−03 |
| ATP binding (GO:0005524) | 1430 | 52 | 2.886e+01 | + | 4.880e−03 |
| nucleotide binding (GO:0000166) | 2264 | 73 | 4.538e+01 | + | 6.077e−03 |
| nucleoside phosphate binding (GO:1901265) | 2265 | 73 | 4.540e+01 | + | 6.164e−03 |
| adenyl ribonucleotide binding (GO:0032559) | 1465 | 52 | 2.936e+01 | + | 9.081e−03 |
| adenyl nucleotide binding (GO:0030554) | 1483 | 52 | 2.972e+01 | + | 1.235e−02 |
| protein serine/threonine kinase activity (GO:0004674) | 434 | 22 | 8.698e+00 | + | 1.523e−02 |
| nucleoside-triphosphate activity (GO:0017111) | 707 | 30 | 1.417e+01 | + | 2.103e−02 |
| purine ribonucleotide triphosphate binding (GO:0035639) | 1760 | 58 | 3.527e+01 | + | 2.439e−02 |
| purine ribonucleotide binding (GO:0032555) | 1801 | 59 | 3.610e+01 | + | 2.486e−02 |
| purine ribonucleoside binding (GO:0032550) | 1769 | 58 | 3.545e+01 | + | 2.783e−02 |
| purine nucleoside binding (GO:0001883) | 1772 | 58 | 3.551e+01 | + | 2.908e−02 |
| ribonucleoside binding (GO:0032549) | 1773 | 58 | 3.553e+01 | + | 2.950e−02 |
| ribonucleotide binding (GO:0032553) | 1816 | 59 | 3.640e+01 | + | 3.087e−02 |
| purine nucleotide binding (GO:0017676) | 1821 | 59 | 3.650e+01 | + | 3.315e−02 |
| nucleoside binding (GO:0001882) | 1785 | 58 | 3.574e+01 | + | 3.409e−02 |
| protein kinase activity (GO:0004672) | 591 | 26 | 1.184e+01 | + | 3.421e−02 |
| helicase activity (GO:0004386) | 145 | 11 | 2.906+00 | + | 3.556e−02 |
| small molecule binding (GO:0036094) | 2539 | 76 | 5.089e+01 | + | 4.353e−02 |

Figure 13A:
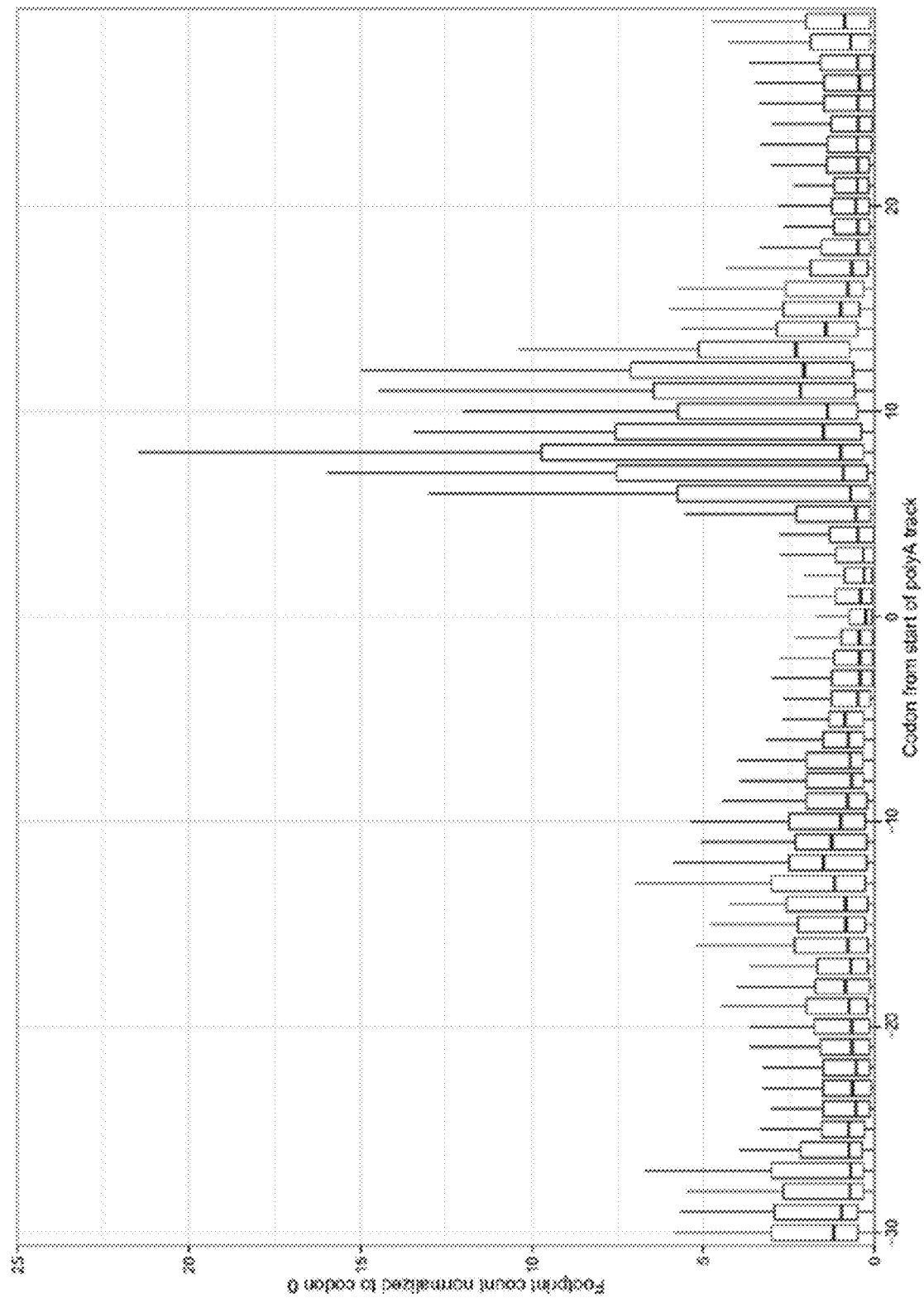
FIG. 13A and FIG. 13B show the occupancy of ribosomal footprints from three different data sets.
Figure 13B:
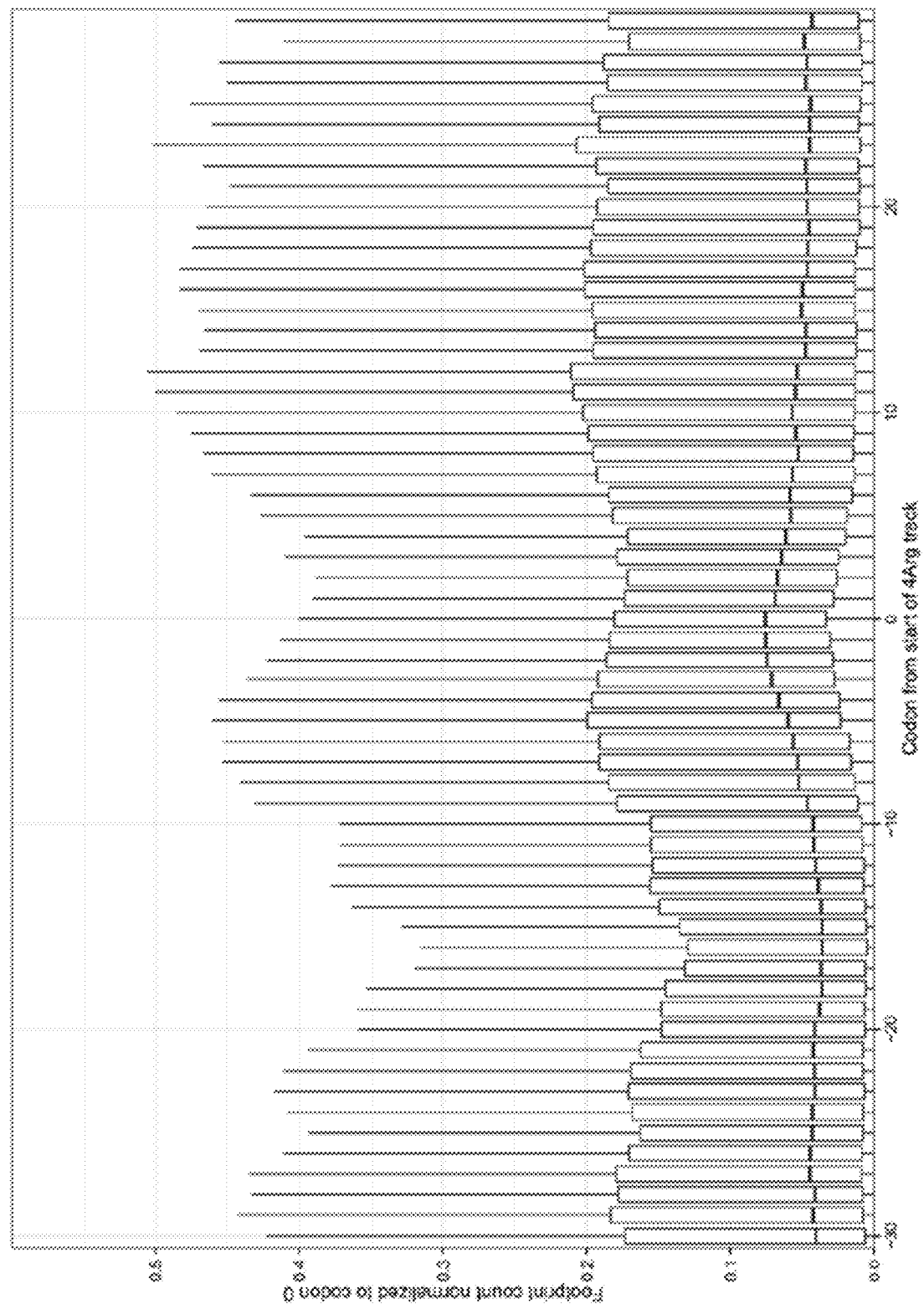
Figure 14D:
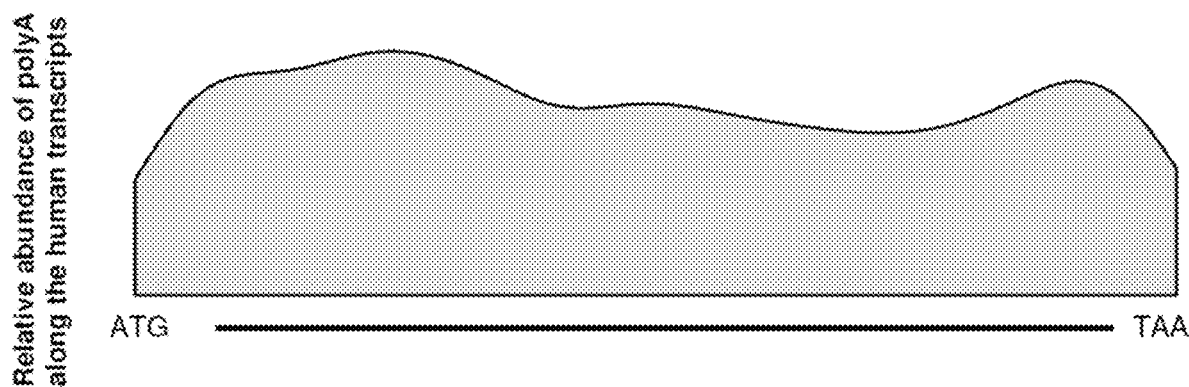
Figure 16A:
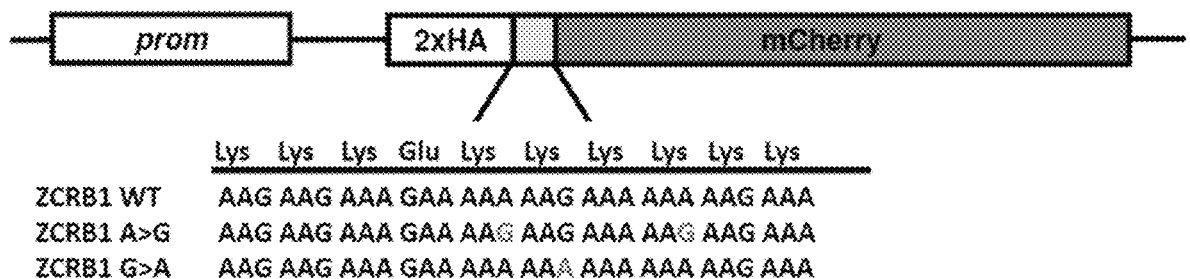
FIG. 16A, FIG. 16B, FIG. 16C, FIG. 16D, FIG. 16E, and FIG. 16F show the scheme of constructs with ZCRB1 gene polyA tracks used for analyses of synonymous mutations (FIG. 16A), western blot analyses and normalized protein expression of ZCRB1 reporter constructs with synonymous mutations (FIG. 16B; HA and β-actin antibodies; each bar represents percentage of wild type ZCRB1-mCherry (WT) expression), normalized RNA levels of ZCRB1 reporter constructs with synonymous mutations (FIG. 16C; neomycin resistance gene was used for normalization of qRT-PCR data; each bar represents percentage of wild type ZCRB1-mCherry construct (WT) mRNA levels), the scheme of full-length HA-tagged ZCRB gene constructs (FIG. 16D; position and mutations in polyA tracks are indicated), western blot analysis and normalized protein expression of ZCRB1 gene constructs with synonymous mutations (FIG. 16E; each bar represents percentage of wild type HA-ZCRB1 (WT) expression, and normalized RNA levels of ZCRB1 gene constructs (FIG. 16F; neomycin resistance gene was used for normalization of qRT-PCR data).
Figure 16B:
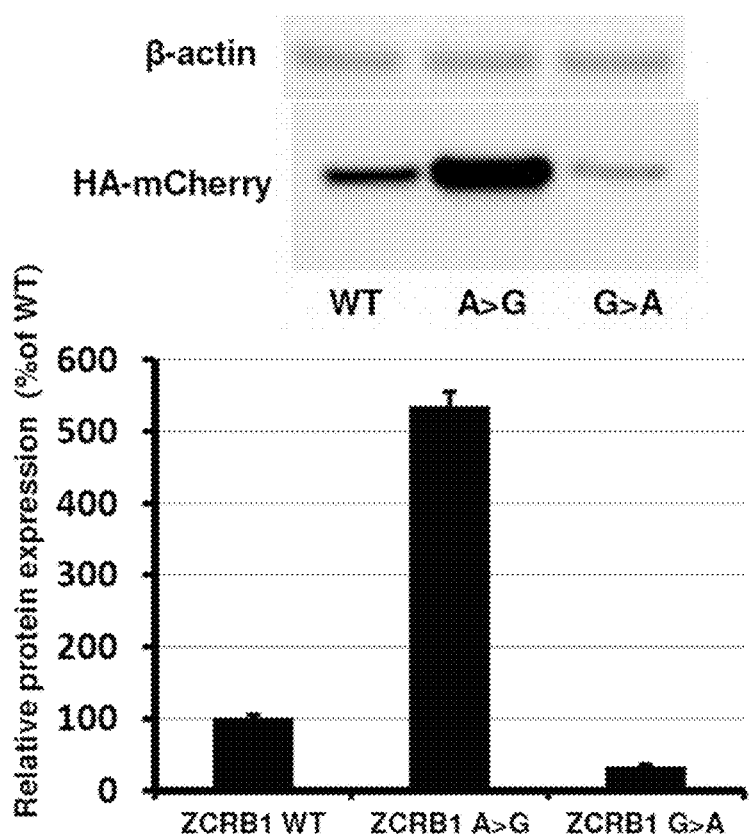
Figures 16C, 16D:
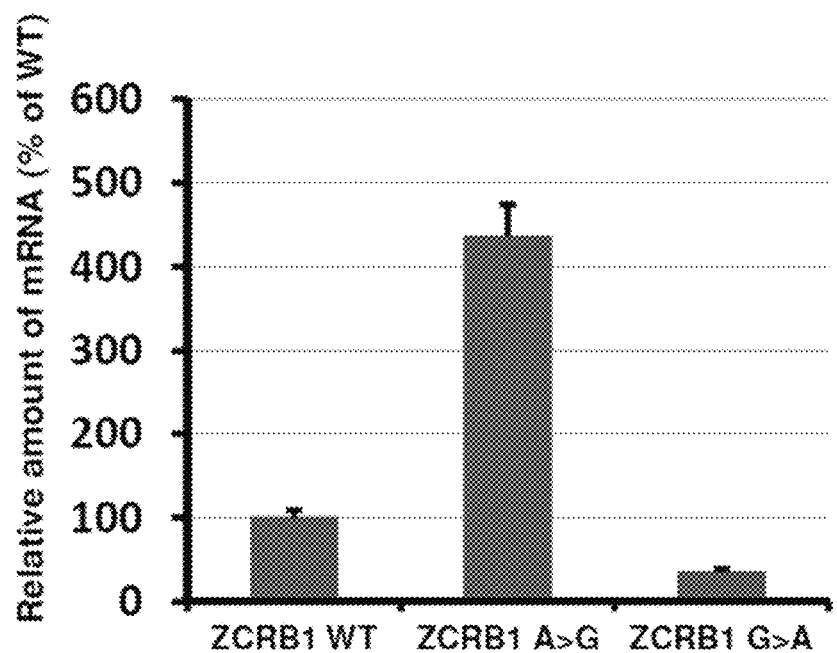
Figure 16E:
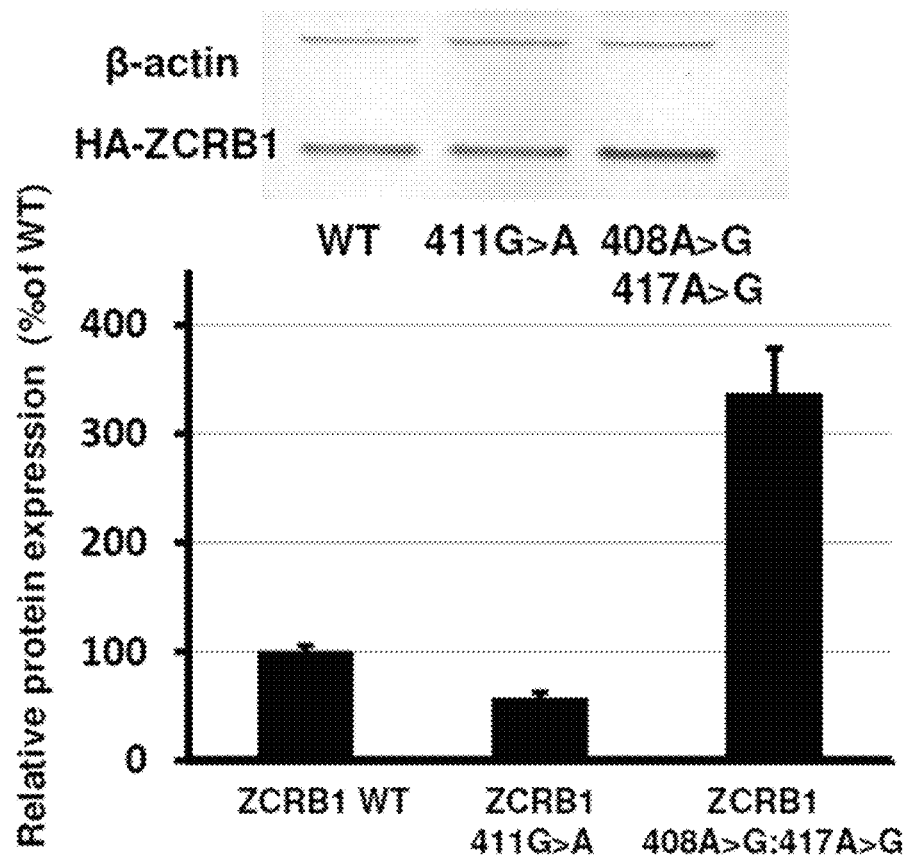
Figure 16F:
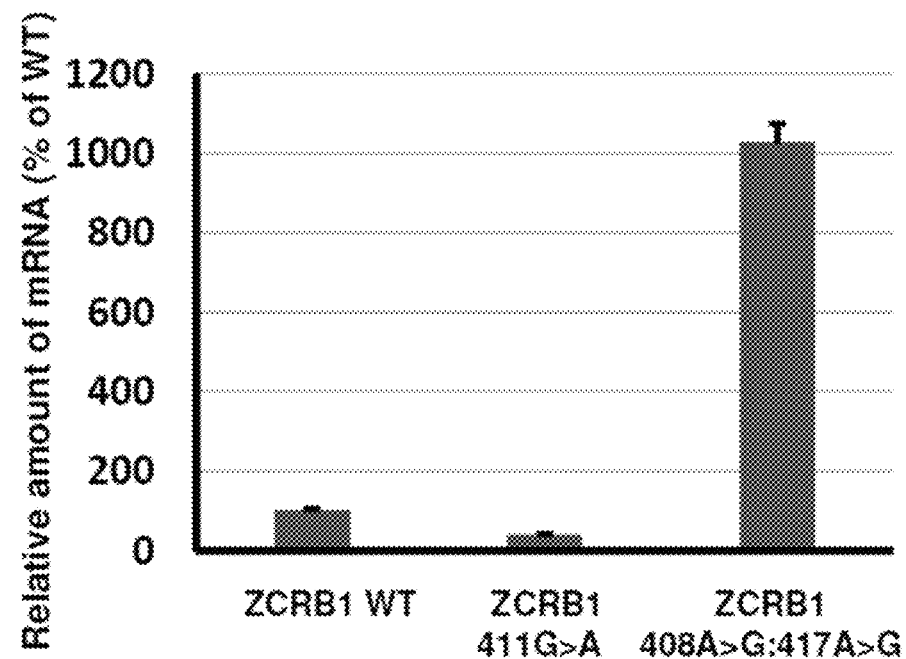
Figures 17A, 17B:
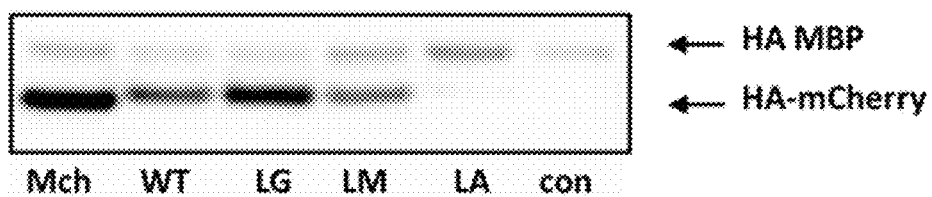
FIG. 17A, FIG. 17B, and FIG. 17C show synonymous mutations in mCherry reporter with metadherin (MTDH, Lyric(Lyr)) polyA track.
Figures 17C, 18A:
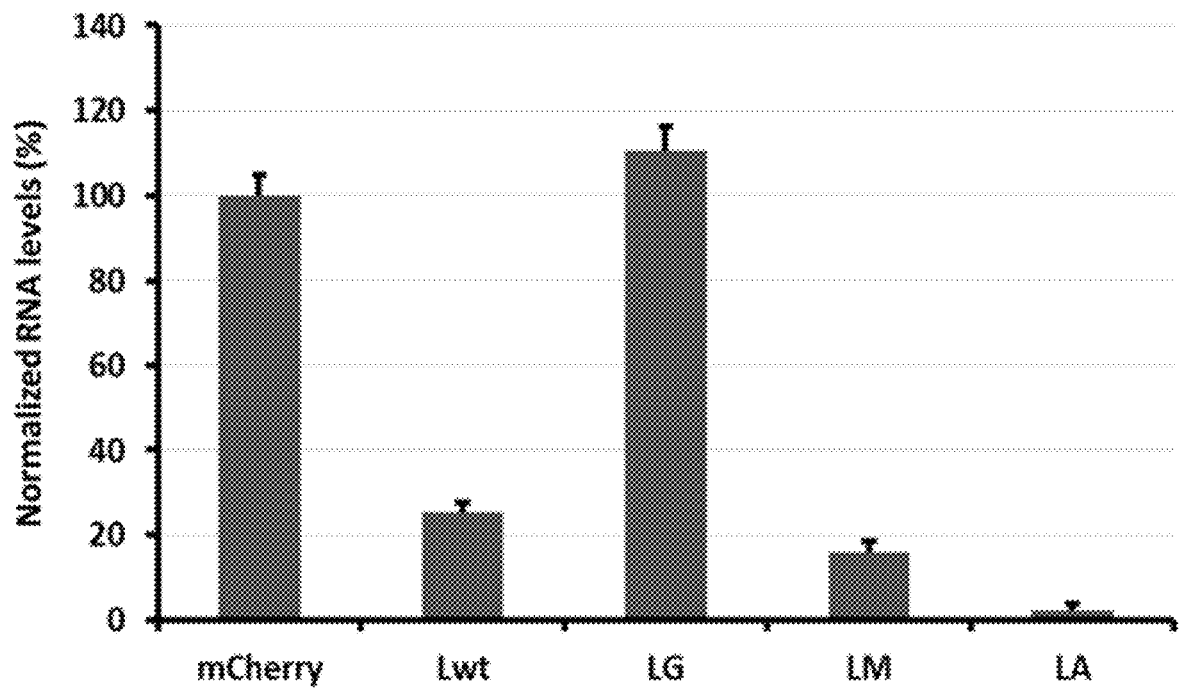
FIG. 18A, FIG. 18B, and FIG. 18C show synonymous mutations in mCherry reporter with RASAL2 polyA track.
Figure 18B:
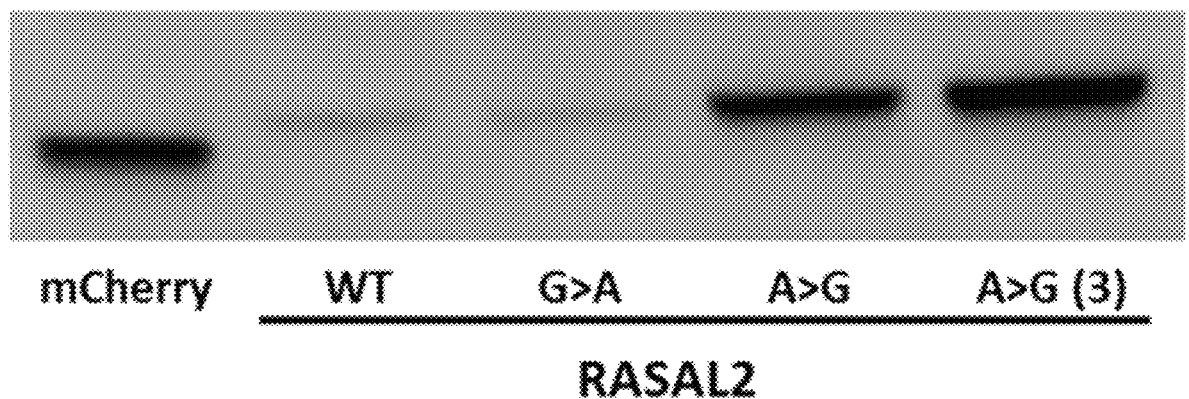
Figure 18C:
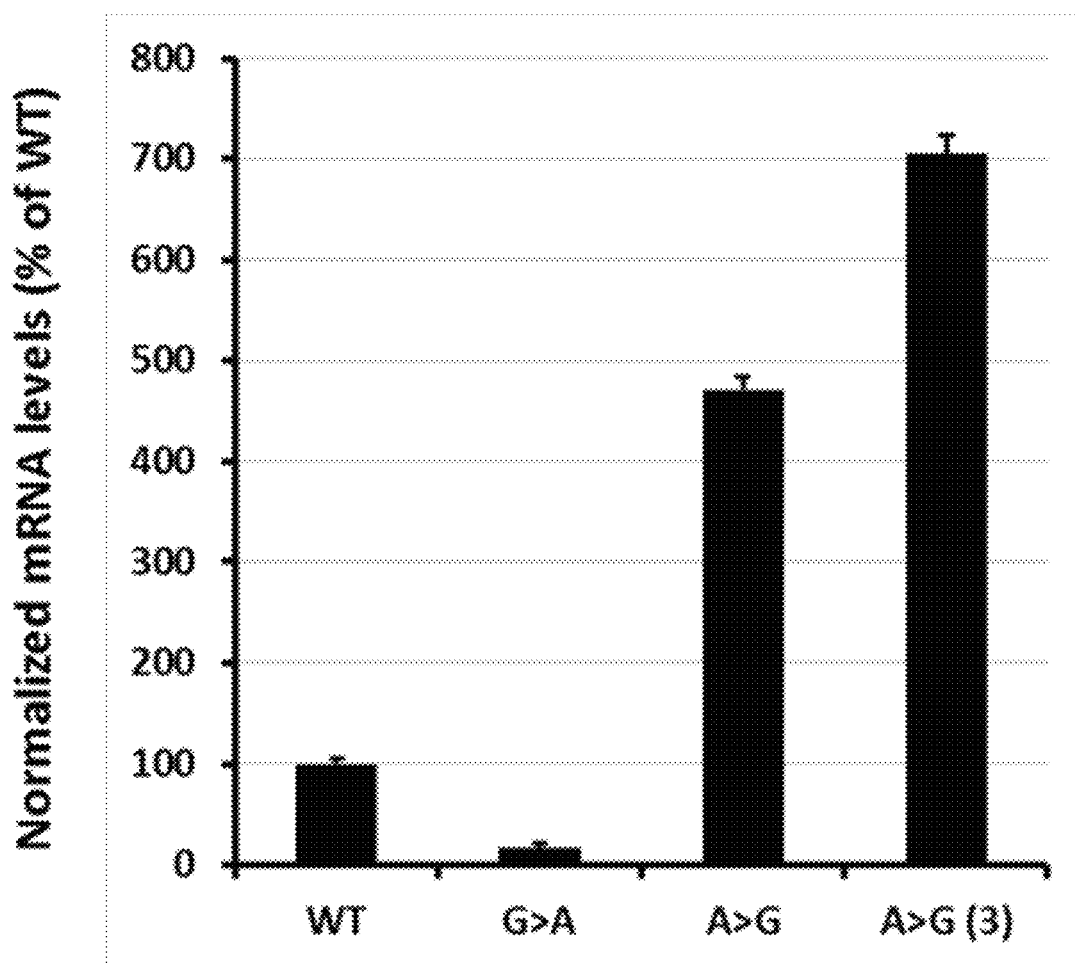
Figure 19A:
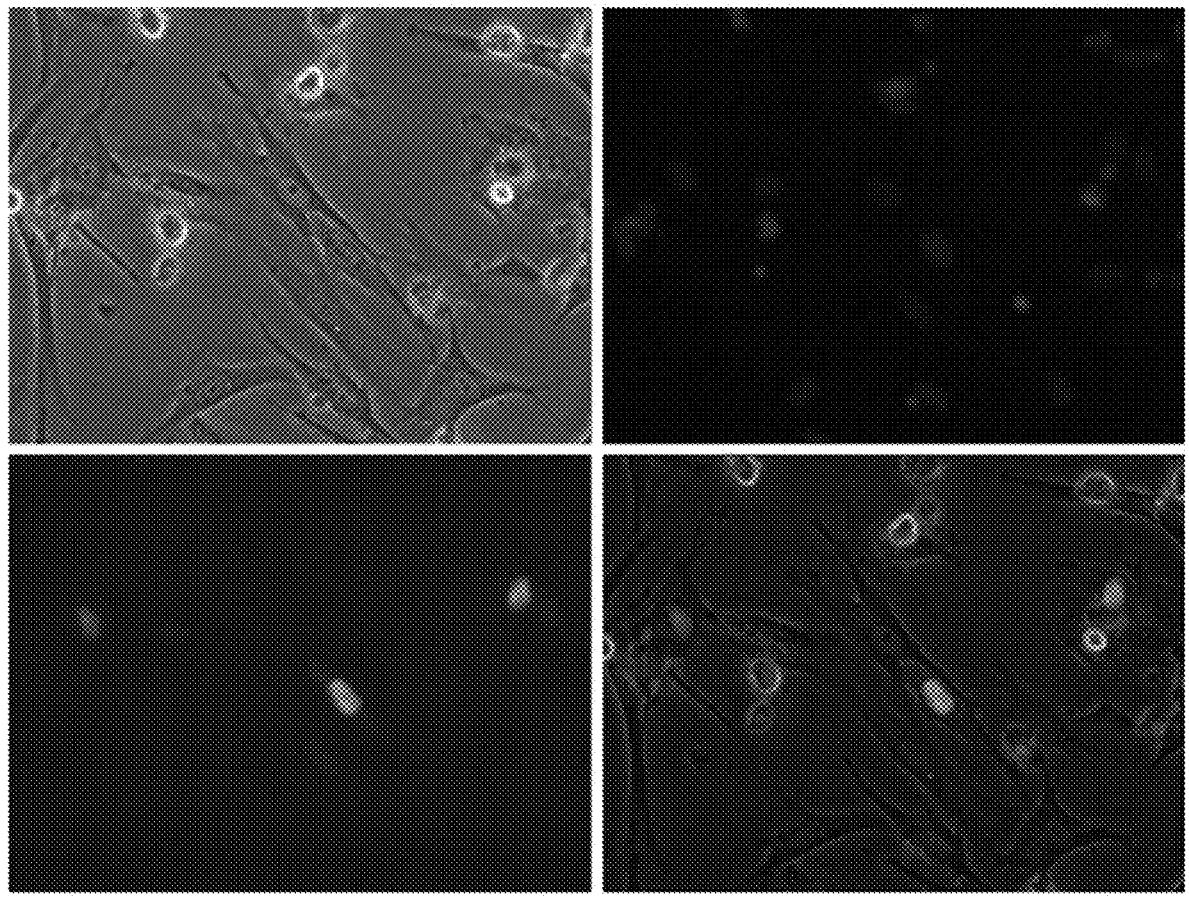
FIG. 19A, FIG. 19B, FIG. 19C, and FIG. 19D show expression analysis of N-terminally HA- and C-terminaly GFP-tagged ZCRB1 gene and its synonymous mutants in HDF cells using Evos-FL microscopy. Cell images were taken 24 hours post electroporation using same optical settings. Cell nuclei were made visible using Hoechst 33342 dye. Images of HDF cells expressing double-tagged ZCRB1 wild type (WT) protein (FIG. 19A) ZCRB1 K137K:411 G>A (FIG. 19B) and ZCRB1 K136K:408 A>G; K139K:417 A>G (FIG. 19C) mutants. Images for each channel (trans, DAPI and GFP) were taken separately and overlay image was composed using EVOS FL digital software.
Figure 19B:
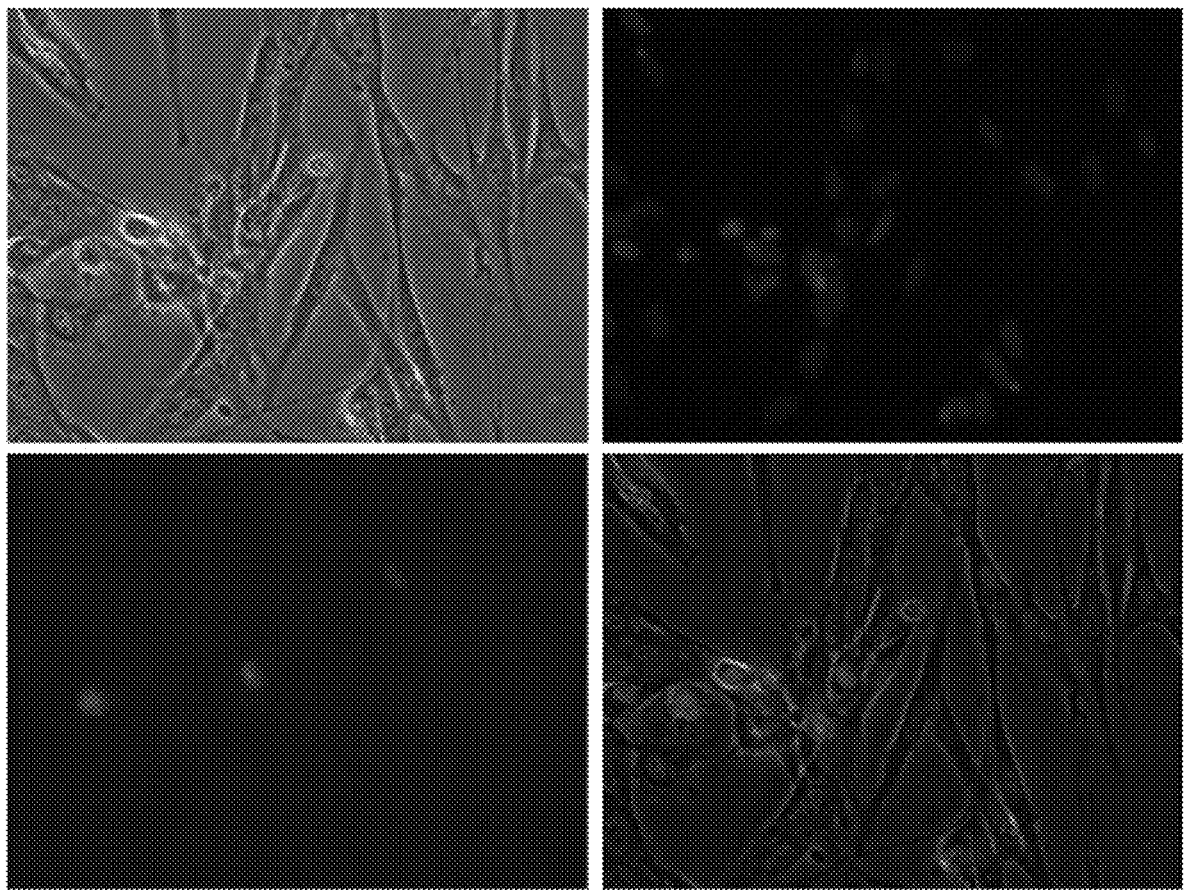
Figure 19C:
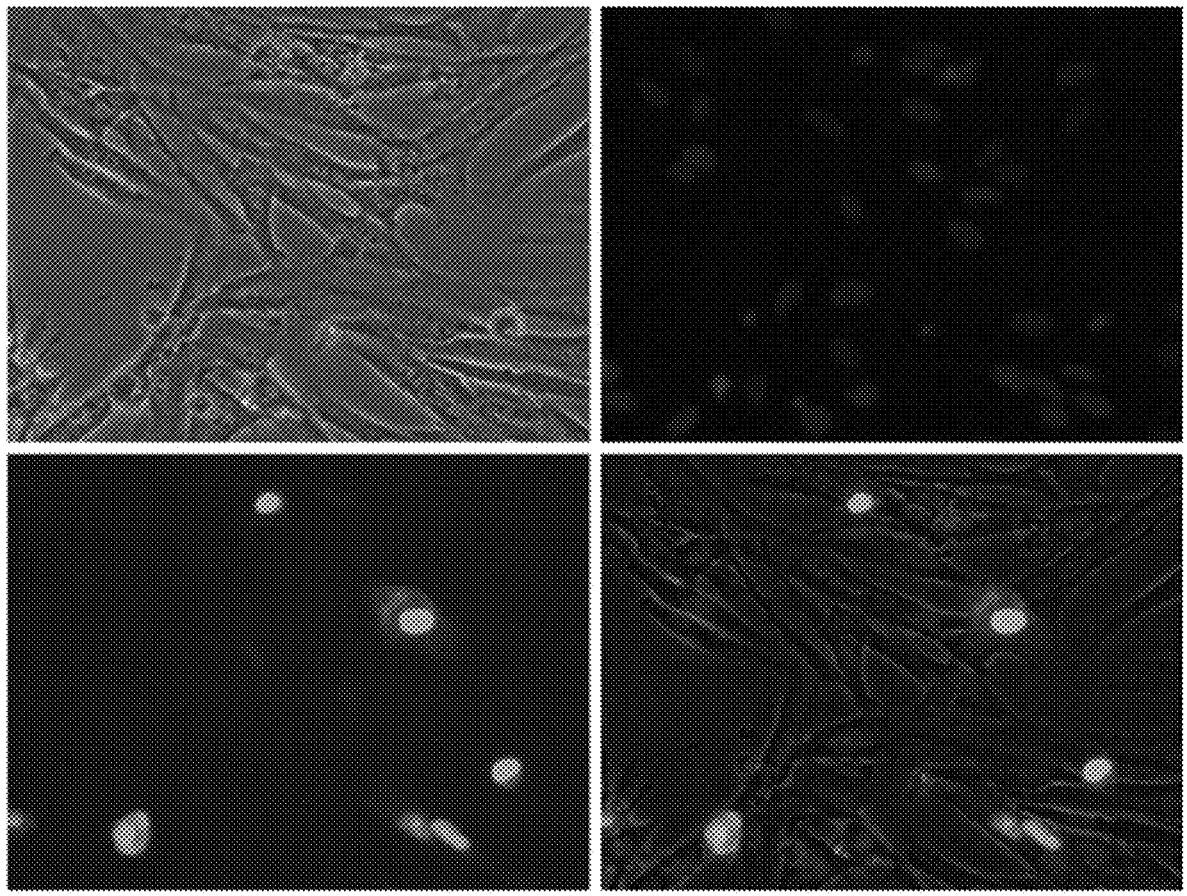
Figure 19D:
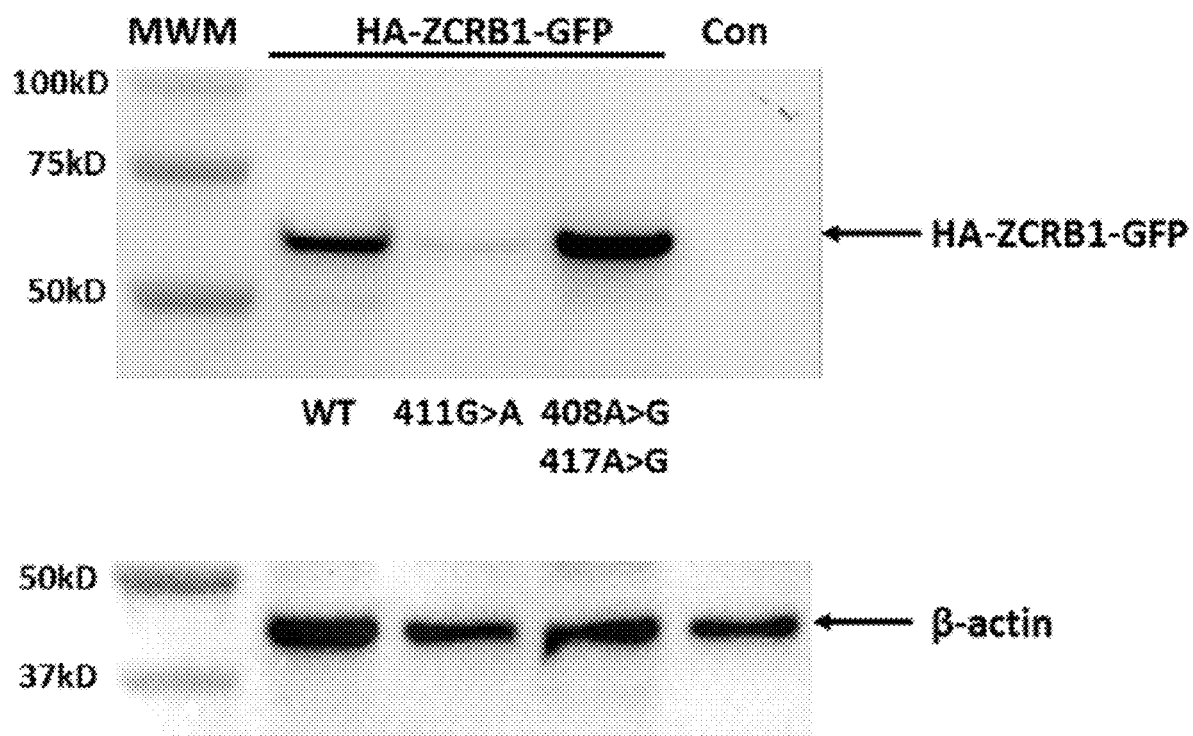

Based on the results with insertion of 12 consecutive A nucleotides (FIG. 12C) and endogenous A-rich sequences (FIG. 14B), it is proposed that a run of 11As in a stretch of 12 nucleotides (12A-1 pattern) will typically yield a measurable effect on protein expression. Since the A string did not require beginning in any particular codon frame, the sequence may not necessarily encode four consecutive lysines. As such, the 12A-1 pattern has been used to search the cDNA sequence database for multiple organisms (NCBI RefSeq resource; Pruitt et al. (2014) Nucleic Acids Res. 42, D756-763). This query revealed over 1800 mRNA sequences from over 450 human genes; the proportion was similar in other vertebrates (Table 5). Gene ontology analyses revealed an over-representation of nucleic acid binding proteins, especially RNA binding and poly(A) RNA binding proteins (Table 1). The positions of poly(A) tracks are distributed uniformly along these identified sequences with no significant enrichment towards either end of the coding region (FIG. 14D). The proteins encoded by these mRNAs are often conserved among eukaryotes; of the 7636 protein isoforms coded by mRNA with poly(A) tracks from human, mouse, rat, cow, frog, zebrafish and fruit fly, 3877 are classified as orthologous between at least two organisms. These orthologous proteins share very similar codon usage in the poly-lysine track, as seen in the example of the RASAL2 tumor suppressor protein (McLaughlin et al. (2013) Cancer Cell. 24, 365-378) (FIG. 15). These observations are consistent with the idea that poly(A) tracks may regulate specific sets of genes in these different organisms. Additional analyses of the ribosome profiling data for mRNAs from selected pools of genes (12A-1 pattern genes) showed an increased number of ribosome footprints (RPFs) in sequences following the poly(A) tracks (FIG. 13A, FIG. 13B). The observed pattern was similar, albeit more pronounced, to the pattern observed for four lysine tracks encoded by three AAA codons and one AAG (FIG. 2A), despite the fact that in many cases the selected pattern did not encode four lysines.

Given the strong sequence conservation and possible role in modulation of protein expression, the effects of mutations in poly(A) tracks were further explored. The reporter constructs containing poly(A) nucleotide tracks from endogenous genes (ZCRB1, MTDH and RASAL2) were used to evaluate effects of synonymous lysine mutations in these poly(A) tracks on protein expression (FIG. 16A, FIG. 16B, FIG. 16C, FIG. 17A, FIG. 17B, FIG. 17C, FIG. 18A, FIG. 18B, FIG. 18C). In each construct, mutations were made that changed selected AAG codons to AAA, increasing the length of consecutive As. Alternatively, AAA to AAG changes were introduced to create interruptions in poly(A) tracks. Reporter constructs with single AAG-to-AAA changes demonstrate consistent decreases in protein expression and mRNA stability. Conversely, AAA-to-AAG changes result in increases in protein expression and mRNA stability (FIG. 16B, FIG. 16C, FIG. 17A, FIG. 17B, FIG. 17C, FIG. 18A, FIG. 18B, FIG. 18C).

It was next asked whether the same synonymous mutations have similar effects when cloned in the full-length coding sequence of the ZCRB1 gene (FIG. 16D, FIG. 16E, FIG. 16F, FIG. 19A, FIG. 19B, FIG. 19C, FIG. 19D). Indeed, the effects on protein and mRNA levels observed with the mCherry reporter sequences are reproduced within the context of the complete coding sequence of the ZCRB1 gene (and mutated variant). Mutation of single AAG-to-AAA codons in the poly(A) track of the ZCRB1 gene (K137K; 411G>A) resulted in a significant decrease in both protein expression and mRNA stability (FIG. 16E, FIG. 16F, FIG. 19A, FIG. 19B, FIG. 19C, FIG. 19D); substitution of two AAA codons with synonymous AAG codons (K136K: 408 A>G; K139K:417A>G) resulted in increases in both recombinant ZCRB1 protein output and mRNA stability. Generally, mutations resulting in longer poly(A) tracks reduced protein expression and mRNA stability, while synonymous substitutions that result in shorter poly(A) nucleotide tracks increased both protein expression and mRNA stability. From these observations, it is suggested that synonymous mutations in poly(A) tracks could modulate protein production from these genes.

Figures 21A, 21B:
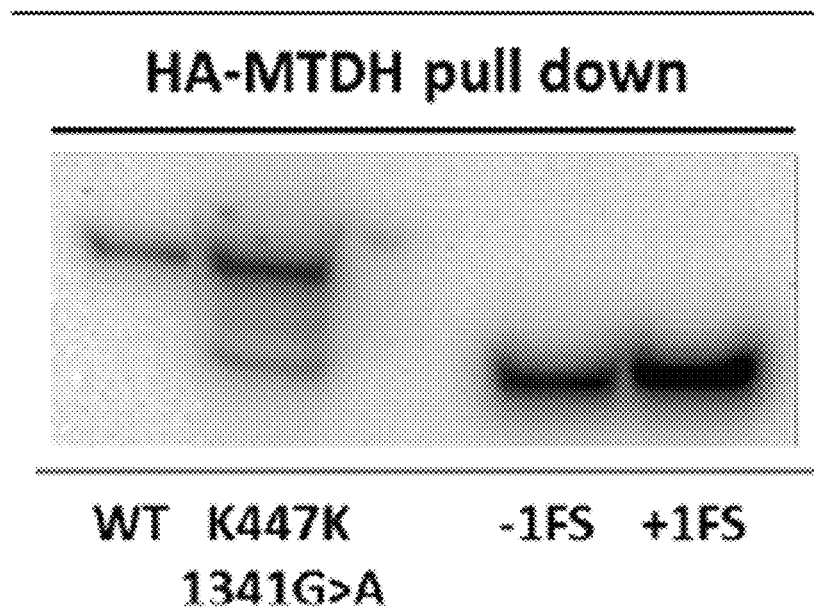
FIG. 21A and FIG. 21B show that the introduction of COSMIC database reported synonymous mutation K447K (1341 G>A) in full length recombinant MTDH gene.

Poly(A) tracks resemble ribosome "slippery" sequences that have been associated with translational frame-shifts (Belfield et al. (2007) Nucleic Acids Res. 35, 1322-1332; Chen et al. (2014) Nature 512, 328-332). Recent studies suggest that polyA tracks can induce "sliding" of *E. coli* ribosomes resulting in frame-shifting (Koutmou et al. (2015) eLIFE 10.7554/eLife.05534; Yan et al. (2015) Cell 160(5), 870-81). Therefore, potential frame-shifted products of overexpressed ZCRB1 variants were looked for by immunoprecipitation using an engineered N-terminally located HA-tag. It was observed that the presence of a protein product of the expected size results from possible frame-shifting in the construct with increased length A tracks (ZCRB K137K (411G>A) mutant) (FIG. 21A). The presence of potential frame-shifted protein products was not observed in WT or control double synonymous mutations K136K(408 A>G): K139K(417A>G). Interestingly, it was noted that the K137K-synonymous change represents a recurrent cancer mutation found in the COSMIC database (COSMIC stands for Catalogue of Somatic Mutations in Cancer, cancer.sanger.ac.uk; Forbes et al. (2014) Nucleic Acids Res.) for ZCRB1 gene; cancersangerac.uk/cosmic/mutation/overview?id=109189). Similar results were obtained when immuno-precipitations were compared of overexpressed and HA-tagged wild type MTDH gene and a K451 K (1353 G>A) variant, yet another cancer-associated mutation (cancer.sanger.ac.uk/cosmic/mutation/overview?id=150510; FIG. 22A, FIG. 22B).

Figures 20A, 20B:
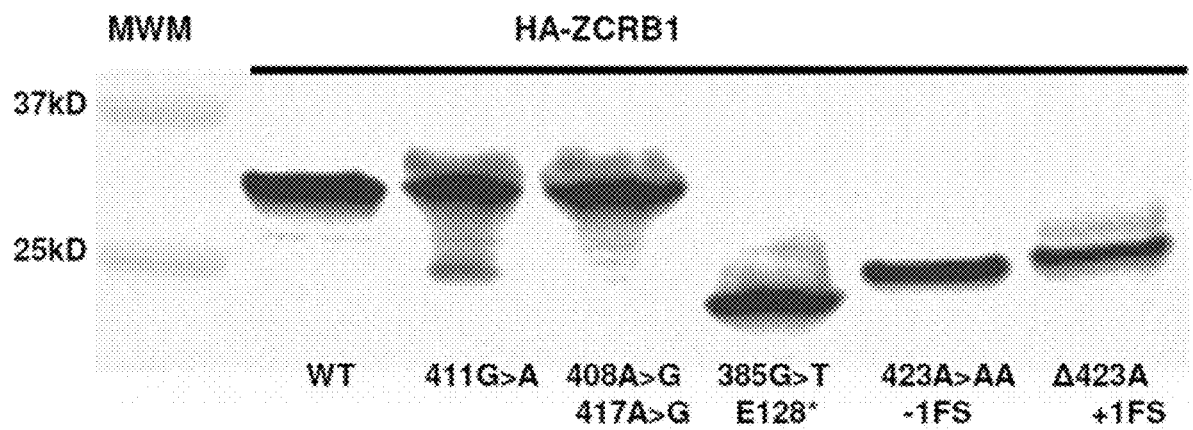
FIG. 20A, FIG. 20B, FIG. 20C, and FIG. 20D show a scheme using luciferase constructs and luciferase expression.
Figure 20C:
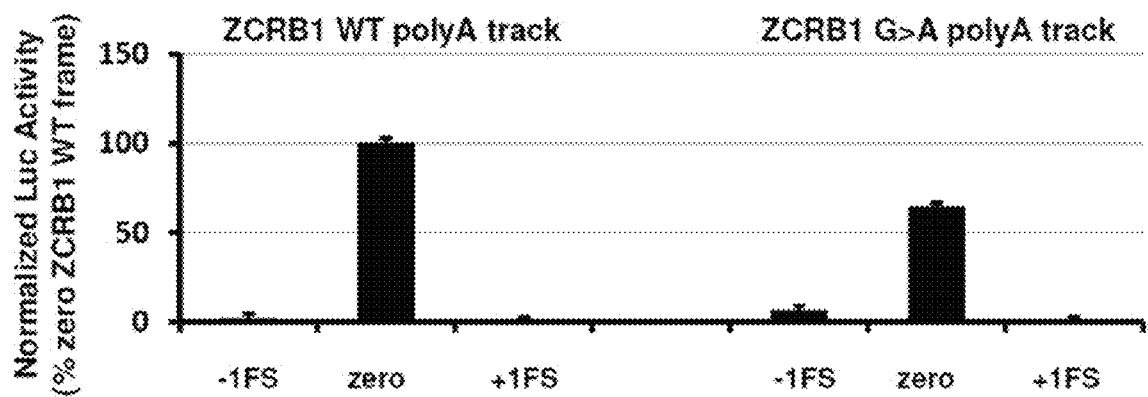

To further document the extent and direction of frame-shifting in the ZCRB1 transcript, polyA tracks were introduced from WT ZCRB1 and a K137K ZCRB1 mutant into a *Renilla* luciferase reporter gene. Single or double nucleotide(s) were introduced downstream in the reporter sequence following the A track, thus creating +1 and −1 frame-shift (FS) constructs, respectively (FIG. 20B). When compared to wild type ZCRB1 polyA track, the G>A mutant shows decreases in full length luciferase protein expression (approximately 40% reduction in "zero" frame); additionally, the G>A mutant exhibits an increase in expression of −1 FS frame construct (which is not observed in the wild type ZCRB1 poly(A) track −1 FS construct) (FIG. 20C). The total amount of luciferase protein activity from the −1 FS ZCRB1 G>A mutant construct is approximately 10% of that expressed from the "zero" frame mutant construct (FIG. 20C, FIG. 22A, FIG. 22B). No significant change in luciferase expression was detected in samples electroporated with +1 FS constructs where expression from these constructs resulted in background levels of luciferase activity (FIG. 21A, FIG. 21B).

Figure 20D:
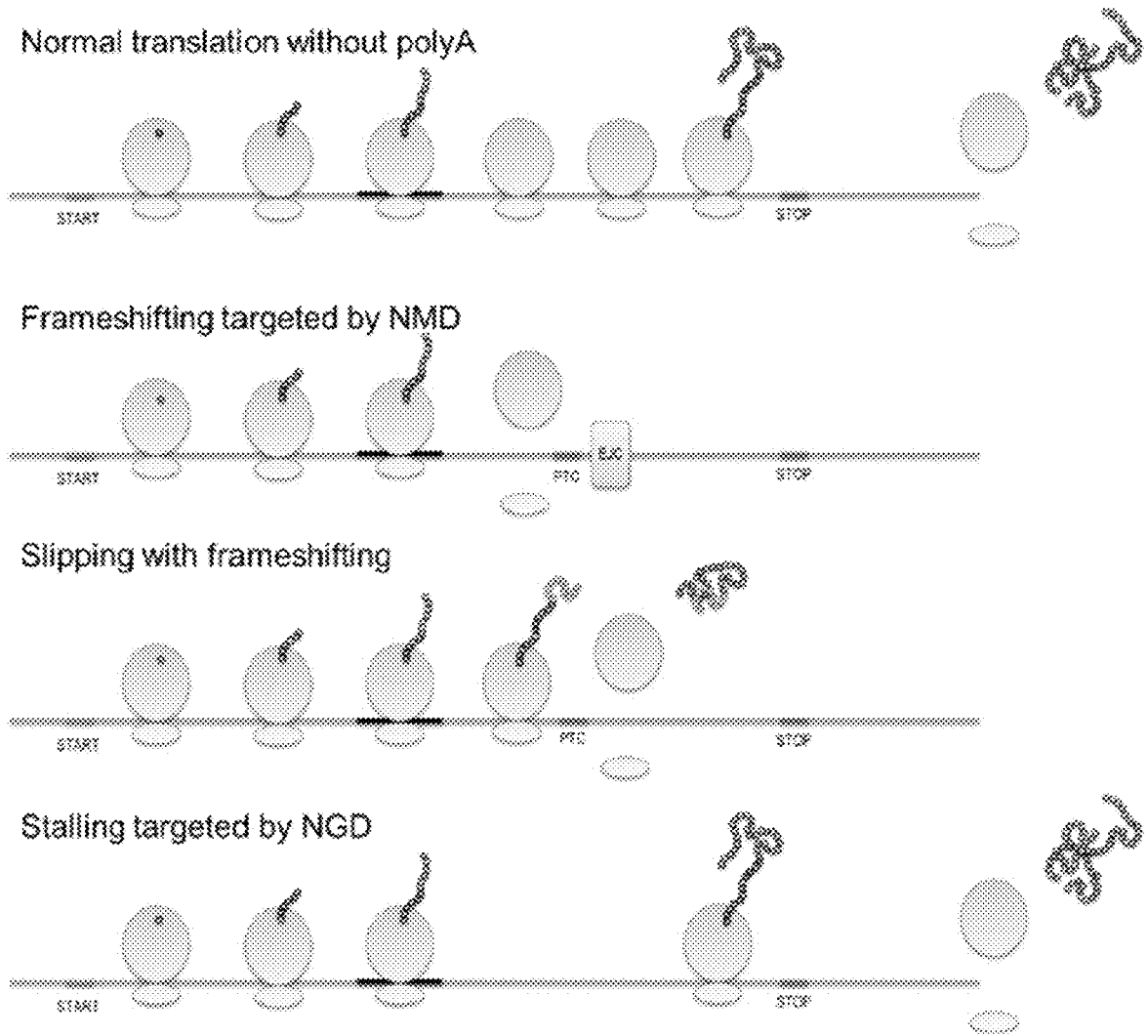

Frame-shifting and recognition of out-of-frame premature stop codons can lead to nonsense-mediated mRNA decay (NMD) that results in targeted mRNA decay (Belew et al. (2011) Nucleic Acids Res. 39, 2799-2808; Belew et al. (2014) Nature. 512, 265-269). Previous efforts suggest that NMD may play a role in determining the stability of poly(A) track-containing mRNAs. Deletion of NMD factor Upf1p in yeast cells partially rescues mRNA levels from constructs with simple poly(A) tracks (Koutmou et al. (2015) eLIFE 10.7554/eLife.05534). The complete set of human poly(A) track-containing genes have been analyzed to see whether they would be likely targets for NMD as a result of frame-shifting on the poly(A) track (based on the usual rules for NMD; Lykke-Andersen et al. (2000) Cell. 103,1121-1131; Le Hir et al. (2001) EMBO J. 20, 4987-4997; Chang et al. (2007) Annu. Rev. Biochem. 76, 51-74; Popp and Maquat (2013) Annu. Rev. Genet. 47, 139-165). Based on the position of the poly(A) tracks, and their position relative to possible PTCs in the −1 and +1 frame, and the location of downstream exon-intron boundaries, a part of the genes of interest would likely be targeted by NMD as a result of frame-shifting during poly(A)-mediated stalling (these transcripts and position of PTCs are listed in Table 2). The considerable number of human poly(A) track genes may not elicit NMD response since PTCs in both −1 and +1 frame following poly(A) tracks are less than 50 nucleotides away from established exon-intron boundaries. While the majority of frame-shift events seem to lead to proteins that would be truncated immediately after poly(A) tracks, in a few cases a novel peptide chain of substantial length may be produced (Table 3). As such, the outcome of poly(A) track stalling and slipping may include a scenario in which a frame-shifted protein product is synthesized in addition to the full-length gene product (scheme shown in FIG. 20D). The possible role and presence of such fragments from poly(A) track genes and their variants is still to be elucidated.

TABLE 2 shows a table of mRNAs that have intron-exon boundary closer than 50 nucleotides downstream from a stop codon arising from frameshifting over polyA tracks. These genes would fall in the category of non "classical" NMD targets if frameshifting occurs on polyA track.

| mRNA GI number | end of polyA region | nearest stop codon | location of stop codon | location of downstream intron-exon boundary | mRNA GI number | end of polyA region | nearest stop codon | location of downstream intron-exon boundary |
|---|---|---|---|---|---|---|---|---|
| 315360663 | 465 | TAG | 472 | 491 | 239787843 | 177 | TAG | 321 |
| 315360663 | 465 | TGA | 467 | 491 | 217035143 | 1437 | TAG | 1467 |
| 54792083 | 710 | TAG | 839 | 849 | 188035876 | 1539 | TAA | 1553 |
| 61743937 | 294 | TAA | 310 | 327 | 188035876 | 1539 | TGA | 1545 |
| 61743937 | 294 | TAG | 324 | 327 | 312283645 | 1473 | TAA | 1503 |
| 61743937 | 294 | TGA | 306 | 327 | 291084574 | 1802 | TAG | 2242 |
| 41350197 | 346 | TGA | 385 | 398 | 291084574 | 1802 | TGA | 1832 |
| 42542385 | 1274 | TAA | 1312 | 1342 | 312434029 | 1760 | TAA | 1790 |
| 115430109 | 97 | TAA | 139 | 171 | 21536424 | 476 | TAA | 508 |
| 115430109 | 97 | TAG | 321 | 340 | 21536424 | 476 | TGA | 515 |
| 115430109 | 97 | TGA | 162 | 171 | 312283632 | 1760 | TAA | 1790 |
| 38327633 | 431 | TGA | 452 | 470 | 393185915 | 487 | TAG | 498 |
| 148596997 | 396 | TGA | 411 | 416 | 393185915 | 487 | TGA | 523 |
| 146133847 | 192 | TAA | 473 | 499 | 187761329 | 1522 | TGA | 1553 |
| 146133847 | 192 | TAG | 200 | 246 | 557786140 | 263 | TAA | 265 |
| 189163500 | 2545 | TAG | 2788 | 2813 | 296278211 | 1102 | TAA | 1184 |
| 214010231 | 475 | TAA | 748 | 780 | 296278220 | 493 | TAA | 575 |
| 284795238 | 986 | TAG | 997 | 1014 | 257467646 | 2736 | TGA | 2785 |
| 284795238 | 986 | TGA | 1001 | 1014 | 385648269 | 3155 | TAA | 3253 |
| 332205944 | 3430 | TAA | 3688 | 3732 | 385648269 | 3155 | TAG | 3260 |
| 283549152 | 927 | TGA | 996 | 1015 | 27894332 | 928 | TAG | 1071 |
| 325197190 | 472 | TAA | 484 | 515 | 27894332 | 928 | TGA | 942 |
| 325197190 | 472 | TGA | 502 | 515 | 350606366 | 375 | TAA | 464 |
| 325197194 | 1713 | TAA | 1725 | 1756 | 350606366 | 375 | TAG | 434 |
| 325197194 | 1713 | TAG | 1743 | 1756 | 317008579 | 4447 | TGA | 4458 |
| 325197181 | 768 | TAA | 780 | 811 | 209915559 | 770 | TAG | 825 |
| 325197181 | 768 | TGA | 798 | 811 | 296278213 | 618 | TAA | 700 |
| 332205942 | 3451 | TAA | 3709 | 3753 | 350606370 | 621 | TAA | 710 |
| 378786661 | 207 | TAA | 304 | 352 | 350606370 | 621 | TAG | 680 |
| 378786661 | 207 | TAG | 351 | 352 | 350606369 | 438 | TAG | 497 |
| 378786661 | 207 | TGA | 364 | 408 | 385648267 | 3393 | TAA | 3491 |
| 367460089 | 3008 | TAA | 3256 | 3288 | 385648267 | 3393 | TAG | 3498 |
| 378786660 | 315 | TAA | 412 | 460 | 61744441 | 448 | TGA | 466 |
| 378786660 | 315 | TAG | 459 | 460 | 312283650 | 1601 | TAA | 1631 |
| 378786660 | 315 | TGA | 472 | 516 | 589811545 | 2995 | TGA | 3044 |
| 387528005 | 1266 | TAG | 1416 | 1437 | 387527983 | 928 | TGA | 942 |
| 57863258 | 885 | TAG | 938 | 947 | 197245388 | 940 | TAA | 1013 |
| 380420368 | 574 | TAG | 821 | 842 | 197245388 | 940 | TGA | 968 |
| 527317397 | 1917 | TGA | 1941 | 1958 | 262399360 | 1971 | TAG | 2015 |
| 543173130 | 2544 | TAG | 2847 | 2872 | 262399359 | 1962 | TAG | 2006 |
| 347954818 | 953 | TGA | 1010 | 1038 | 283806678 | 8679 | TAG | 8790 |
| 564473350 | 2511 | TAA | 2513 | 2521 | 189242611 | 609 | TAG | 944 |
| 585420399 | 1248 | TAG | 1381 | 1407 | 365812503 | 1512 | TAG | 1515 |
| 585420411 | 916 | TAG | 1049 | 1075 | 365812503 | 1512 | TGA | 1522 |
| 256542287 | 192 | TAA | 473 | 499 | 153792693 | 6916 | TAG | 6952 |
| 256542287 | 192 | TAG | 200 | 246 | 70980548 | 254 | TAG | 312 |
| 223634474 | 186 | TAA | 467 | 493 | 38683845 | 918 | TAA | 924 |
| 223634474 | 186 | TAG | 194 | 240 | 38683845 | 918 | TAG | 959 |
| 585866348 | 1248 | TAG | 1381 | 1407 | 38683845 | 918 | TGA | 981 |
| 110349755 | 889 | TGA | 926 | 951 | 148612837 | 2289 | TAG | 2586 |
| 110349753 | 889 | TGA | 926 | 951 | 47419908 | 2793 | TAA | 2807 |
| 544583528 | 866 | TAA | 980 | 1012 | 47419908 | 2793 | TAG | 2821 |
| 93277100 | 828 | TAA | 855 | 903 | 47419908 | 2793 | TGA | 2795 |
| 145699132 | 2771 | TAA | 2772 | 2777 | 21361597 | 1222 | TGA | 1225 |
| 93141224 | 645 | TAG | 649 | 667 | 291190786 | 1506 | TAG | 1514 |
| 527317380 | 612 | TAA | 693 | 696 | 67944632 | 259 | TAG | 391 |
| 32967604 | 1594 | TAG | 1683 | 1697 | 67944631 | 259 | TAG | 391 |
| 72377390 | 216 | TAA | 281 | 318 | 67944633 | 415 | TAG | 547 |
| 153251835 | 867 | TAA | 901 | 905 | 122114650 | 3206 | TAA | 3430 |
| 153251835 | 867 | TGA | 872 | 905 | 109715821 | 865 | TAA | 991 |
| 215272324 | 361 | TGA | 421 | 464 | 109715821 | 865 | TAG | 1082 |
| 46255020 | 219 | TGA | 226 | 247 | 109715821 | 865 | TGA | 917 |
| 116063563 | 3480 | TAA | 3534 | 3538 | 154354989 | 1512 | TAG | 1515 |

TABLE 2-continued shows a table of mRNAs that have intron-exon boundary closer than 50 nucleotides downstream from a stop codon arising from frameshifting over polyA tracks. These genes would fall in the category of non "classical" NMD targets if frameshifting occurs on polyA track.

| mRNA GI number | end of polyA region | nearest stop codon | location of stop codon | location of downstream intron-exon boundary | mRNA GI number | end of polyA region | nearest stop codon | location of downstream intron-exon boundary |
|---|---|---|---|---|---|---|---|---|
| 116063563 | 3480 | TGA | 3509 | 3538 | 154354989 | 1512 | TGA | 1522 |
| 194473999 | 931 | TAA | 998 | 1004 | 47419910 | 2895 | TAA | 2909 |
| 56550119 | 511 | TAA | 525 | 559 | 47419910 | 2895 | TAG | 2923 |
| 56550119 | 511 | TAG | 531 | 559 | 47419910 | 2895 | TGA | 2897 |
| 564473377 | 1659 | TAA | 1661 | 1669 | 216548486 | 1594 | TGA | 1632 |
| 151301227 | 2638 | TAA | 2698 | 2723 | 189491764 | 1859 | TGA | 1943 |
| 451172080 | 719 | TAG | 775 | 808 | 189242610 | 609 | TAG | 944 |
| 451172080 | 719 | TGA | 770 | 808 | 315360659 | 761 | TAG | 768 |
| 94538358 | 192 | TAA | 473 | 499 | 315360659 | 761 | TGA | 763 |
| 94538358 | 192 | TAG | 200 | 246 | 114155141 | 2355 | TAA | 2463 |
| 119637838 | 1257 | TAG | 1275 | 1304 | 114155141 | 2355 | TAG | 2450 |
| 119637838 | 1257 | TGA | 1288 | 1304 | 75677575 | 956 | TAA | 959 |
| 49640008 | 6092 | TAA | 6105 | 6154 | 75677575 | 956 | TAG | 971 |
| 49640008 | 6092 | TGA | 6114 | 6154 | 325197180 | 604 | TAA | 616 |
| 49640010 | 4801 | TAA | 4814 | 4863 | 325197180 | 604 | TGA | 634 |
| 49640010 | 4801 | TGA | 4823 | 4863 | 189409141 | 1081 | TAA | 1134 |
| 239787903 | 1353 | TAA | 1428 | 1472 | 189409141 | 1081 | TAG | 1156 |
| 239787903 | 1353 | TAG | 1469 | 1472 | 91208427 | 6031 | TAA | 6289 |
| 239787903 | 1353 | TGA | 1442 | 1472 | 115527086 | 2080 | TGA | 2087 |
| 55749880 | 458 | TGA | 519 | 549 | 125656164 | 2810 | TAG | 2926 |
| 225579091 | 2672 | TAA | 2683 | 2705 | 61635914 | 967 | TGA | 974 |
| 225579091 | 2672 | TGA | 2695 | 2705 | 183227692 | 581 | TAA | 618 |
| 125987600 | 747 | TAA | 858 | 889 | 183227692 | 581 | TGA | 625 |
| 187828563 | 1100 | TAA | 1112 | 1153 | 51873042 | 1122 | TAG | 1187 |
| 451172082 | 569 | TGA | 733 | 764 | 189163502 | 2545 | TAG | 2788 |
| 451172084 | 533 | TAG | 589 | 622 | 148746212 | 2045 | TAG | 2114 |
| 451172084 | 533 | TGA | 584 | 622 | 148746212 | 2045 | TGA | 2099 |
| 451172086 | 533 | TGA | 697 | 728 | 122937397 | 8679 | TAG | 8790 |
| 270483794 | 1195 | TGA | 1196 | 1203 | 284795235 | 1103 | TAG | 1114 |
| 209870068 | 878 | TAA | 940 | 985 | 284795235 | 1103 | TGA | 1118 |
| 72377376 | 305 | TAG | 370 | 407 | 392307008 | 2145 | TAA | 2393 |
| 63054847 | 785 | TGA | 789 | 820 | 124107605 | 853 | TAA | 861 |
| 573459699 | 766 | TAA | 781 | 801 | 124107605 | 853 | TGA | 864 |
| 573459699 | 766 | TGA | 893 | 915 | 385648266 | 3527 | TAA | 3625 |
| 116642876 | 1399 | TAG | 1450 | 1493 | 385648266 | 3527 | TAG | 3632 |
| 116642876 | 1399 | TGA | 1457 | 1493 | 325053711 | 956 | TAA | 959 |
| 188219548 | 1077 | TAA | 1084 | 1113 | 325053711 | 956 | TAG | 971 |
| 188219548 | 1077 | TAG | 1103 | 1113 | 325053712 | 956 | TAA | 959 |
| 544583488 | 906 | TAA | 1020 | 1052 | 325053712 | 956 | TAG | 971 |
| 543173126 | 2619 | TAG | 2922 | 2947 | 392307006 | 2628 | TAA | 2876 |
| 544346128 | 1063 | TAG | 1145 | 1189 | 459215048 | 2072 | TAG | 2147 |
| 544346128 | 1063 | TGA | 1232 | 1257 | 388490157 | 3286 | TGA | 3323 |
| 170650704 | 667 | TAA | 807 | 830 | 32483358 | 2382 | TAA | 2485 |
| 170650704 | 667 | TAG | 798 | 830 | 32483358 | 2382 | TGA | 2449 |
| 544583450 | 918 | TAA | 1032 | 1064 | 291290967 | 5965 | TAG | 6092 |
| 289547540 | 894 | TAA | 992 | 1033 | 291084578 | 1907 | TAG | 2347 |
| 367460086 | 2981 | TAA | 3229 | 3261 | 291084578 | 1907 | TGA | 1937 |
| 51243064 | 631 | TGA | 638 | 656 | 307746920 | 769 | TAG | 802 |
| 215599550 | 501 | TAG | 662 | 689 | 32483365 | 2349 | TAA | 2452 |
| 475505353 | 3017 | TAA | 3256 | 3290 | 32483365 | 2349 | TGA | 2416 |
| 122937226 | 703 | TAA | 731 | 738 | 531990837 | 1144 | TAA | 1153 |
| 122937226 | 703 | TAG | 855 | 869 | 531990837 | 1144 | TGA | 1184 |
| 122937395 | 987 | TAA | 1025 | 1028 | 32483360 | 2382 | TAA | 2485 |
| 122937395 | 987 | TAG | 1032 | 1072 | 32483360 | 2382 | TGA | 2449 |
| 122937395 | 987 | TGA | 1020 | 1028 | 22027649 | 707 | TAG | 787 |
| 57863256 | 971 | TAG | 1024 | 1033 | 22027649 | 707 | TGA | 782 |
| 451172081 | 569 | TAG | 625 | 658 | 350606365 | 491 | TAA | 580 |
| 451172081 | 569 | TGA | 620 | 658 | 350606365 | 491 | TAG | 550 |
| 87298936 | 1370 | TAA | 1453 | 1487 | 459215047 | 2072 | TAG | 2147 |
| 138175816 | 1579 | TAA | 1583 | 1610 | 291575138 | 897 | TAG | 1023 |
| 138175816 | 1579 | TGA | 1580 | 1610 | 531990838 | 858 | TAA | 868 |
| 150036261 | 475 | TAA | 575 | 602 | 531990838 | 858 | TGA | 899 |
| 150036261 | 475 | TGA | 476 | 493 | 353411933 | 747 | TAG | 751 |
| 315360661 | 566 | TAG | 573 | 592 | 313661425 | 3742 | TGA | 3757 |
| 315360661 | 566 | TGA | 568 | 592 | 257467647 | 3543 | TGA | 3592 |
| 38373672 | 3210 | TAG | 3474 | 3489 | 388490159 | 3786 | TGA | 3823 |
| 38373672 | 3210 | TGA | 3244 | 3290 | 531990840 | 822 | TAA | 832 |
| 544346132 | 1174 | TAG | 1256 | 1300 | 531990840 | 822 | TGA | 863 |
| 544346132 | 1174 | TGA | 1343 | 1368 | 354682004 | 903 | TAG | 1487 |
| 116805347 | 219 | TGA | 261 | 278 | 354682006 | 1473 | TAA | 1583 |
| 157502183 | 1552 | TAA | 1882 | 1906 | 354682006 | 1473 | TAG | 1484 |

TABLE 2-continued shows a table of mRNAs that have intron-exon boundary closer than 50 nucleotides downstream from a stop codon arising from frameshifting over polyA tracks. These genes would fall in the category of non "classical" NMD targets if frameshifting occurs on polyA track.

| mRNA GI number | end of polyA region | nearest stop codon | location of stop codon | location of downstream intron-exon boundary | mRNA GI number | end of polyA region | nearest stop codon | location of downstream intron-exon boundary |
|---|---|---|---|---|---|---|---|---|
| 23111022 | 714 | TAG | 721 | 740 | 354682006 | 1473 | TGA | 1572 |
| 23111022 | 714 | TGA | 716 | 740 | 32483364 | 2349 | TAA | 2452 |
| 32967602 | 1594 | TAG | 1683 | 1697 | 32483364 | 2349 | TGA | 2416 |
| 573459727 | 352 | TAA | 367 | 387 | 305410828 | 910 | TAG | 942 |
| 573459727 | 352 | TGA | 479 | 501 | 467091961 | 1974 | TAA | 1981 |
| 573459714 | 617 | TAA | 632 | 652 | 467091961 | 1974 | TAG | 2146 |
| 573459714 | 617 | TGA | 744 | 766 | 467091961 | 1974 | TGA | 1990 |
| 574275032 | 622 | TGA | 629 | 633 | 401664559 | 8145 | TAG | 8151 |
| 574275429 | 622 | TGA | 629 | 633 | 163792200 | 1425 | TAG | 1542 |
| 574275427 | 622 | TGA | 629 | 633 | 119829186 | 1344 | TAA | 1374 |
| 574275776 | 622 | TGA | 629 | 633 | 119829186 | 1344 | TGA | 1363 |
| 574275778 | 557 | TGA | 564 | 568 | 305410830 | 1079 | TAG | 1111 |
| 169234948 | 317 | TAG | 360 | 370 | 284004924 | 591 | TAA | 593 |
| 169234948 | 317 | TGA | 336 | 370 | 224994180 | 967 | TGA | 974 |
| 557636701 | 3791 | TAA | 3834 | 3870 | 270483791 | 1363 | TGA | 1364 |
| 557636701 | 3791 | TGA | 3826 | 3870 | 305410832 | 747 | TAG | 780 |
| 344925844 | 1128 | TGA | 1241 | 1282 | 307746901 | 1016 | TAG | 1048 |
| 115298681 | 736 | TGA | 746 | 787 | 270132520 | 4540 | TAA | 4667 |
| 61743939 | 295 | TAA | 310 | 327 | 153791627 | 1121 | TAG | 1132 |
| 61743939 | 295 | TAG | 324 | 327 | 153791627 | 1121 | TGA | 1136 |
| 61743939 | 295 | TGA | 306 | 327 | 166235162 | 541 | TAA | 591 |
| 289547543 | 894 | TAA | 992 | 1033 | 193788631 | 841 | TAG | 883 |
| 7705934 | 473 | TAG | 718 | 750 | 193788631 | 841 | TGA | 857 |
| 209870072 | 451 | TAA | 514 | 559 | 194353965 | 6584 | TAG | 6589 |
| 209870078 | 917 | TAA | 979 | 1024 | 217330569 | 1221 | TAG | 1261 |
| 209870070 | 704 | TAA | 766 | 811 | 217330573 | 1408 | TAG | 1448 |
| 215599561 | 320 | TAG | 481 | 508 | 51873044 | 1026 | TAG | 1091 |
| 544583540 | 918 | TAA | 1032 | 1064 | 119395733 | 9174 | TAG | 9307 |
| 284172494 | 1574 | TAA | 1651 | 1685 | 217330567 | 1513 | TAG | 1553 |
| 239582713 | 995 | TAG | 1343 | 1371 | 51873046 | 1122 | TAG | 1187 |
| 225579094 | 2815 | TAA | 2826 | 2848 | 299782586 | 1712 | TGA | 1735 |
| 225579094 | 2815 | TGA | 2838 | 2848 | 289547522 | 1454 | TAG | 1494 |
| 110347419 | 1175 | TAA | 1181 | 1221 | 574269958 | 1379 | TAA | 1458 |
| 110347419 | 1175 | TAG | 1192 | 1221 | 574269958 | 1379 | TAG | 1385 |
| 110347419 | 1175 | TGA | 1187 | 1221 | 574272532 | 1583 | TAA | 1662 |
| 284795233 | 1121 | TAG | 1132 | 1149 | 574272532 | 1583 | TAG | 1589 |
| 284795233 | 1121 | TGA | 1136 | 1149 | 574272304 | 1192 | TAA | 1271 |
| 544583452 | 918 | TAA | 1032 | 1064 | 574272304 | 1192 | TAG | 1198 |
| 399498564 | 848 | TAG | 902 | 943 | 574271714 | 1478 | TAA | 1557 |
| 399498564 | 848 | TGA | 906 | 943 | 574271714 | 1478 | TAG | 1484 |
| 399498565 | 851 | TAA | 863 | 904 | 574271316 | 1379 | TAA | 1458 |
| 223005861 | 4124 | TGA | 4130 | 4134 | 574271316 | 1379 | TAG | 1385 |
| 155029543 | 670 | TAG | 810 | 848 | 574273241 | 1478 | TAA | 1557 |
| 155029541 | 801 | TAG | 941 | 979 | 574273241 | 1478 | TAG | 1484 |
| 157739935 | 1035 | TAA | 1036 | 1063 | 574269522 | 1427 | TAA | 1506 |
| 38202203 | 1157 | TAA | 1292 | 1305 | 574269522 | 1427 | TAG | 1433 |
| 388240807 | 1129 | TAA | 1135 | 1175 | 558472849 | 1026 | TAG | 1091 |
| 388240807 | 1129 | TAG | 1146 | 1175 | 156523967 | 855 | TAA | 867 |
| 388240807 | 1129 | TGA | 1141 | 1175 | 156523967 | 855 | TAG | 864 |
| 67782329 | 488 | TAG | 1321 | 1324 | 156523967 | 855 | TGA | 873 |
| 542133168 | 2773 | TAA | 2877 | 2887 | 112382209 | 1093 | TAA | 1108 |
| 542133168 | 2773 | TAG | 2838 | 2887 | 112382209 | 1093 | TAG | 1174 |
| 542133173 | 2334 | TAA | 2438 | 2448 | 112382209 | 1093 | TGA | 1097 |
| 542133173 | 2334 | TAG | 2399 | 2448 | 111120330 | 2052 | TAA | 2059 |
| 542133166 | 2690 | TAA | 2794 | 2804 | 111120330 | 2052 | TAG | 2224 |
| 542133166 | 2690 | TAG | 2755 | 2804 | 111120330 | 2052 | TGA | 2068 |
| 542133167 | 2827 | TAA | 2931 | 2941 | 88703042 | 692 | TAA | 713 |
| 542133167 | 2827 | TAG | 2892 | 2941 | 109255233 | 1177 | TAG | 1255 |
| 542133171 | 2646 | TAA | 2750 | 2760 | 88703040 | 587 | TAA | 608 |
| 542133171 | 2646 | TAG | 2711 | 2760 | 112789561 | 683 | TGA | 836 |
| 542133176 | 1321 | TAA | 1425 | 1435 | 126032349 | 10872 | TAG | 10941 |
| 542133176 | 1321 | TAG | 1386 | 1435 | 62244047 | 946 | TAG | 963 |
| 542133175 | 1388 | TAA | 1492 | 1502 | 226437633 | 186 | TAA | 452 |
| 542133175 | 1388 | TAG | 1453 | 1502 | 226437633 | 186 | TAG | 496 |
| 542133172 | 2571 | TAA | 2675 | 2685 | 226437633 | 186 | TGA | 209 |
| 542133172 | 2571 | TAG | 2636 | 2685 | 199559531 | 1216 | TAA | 1223 |
| 365192531 | 3074 | TAA | 3322 | 3354 | 189163519 | 4030 | TAA | 4062 |
| 239787905 | 1468 | TAA | 1543 | 1587 | 189163519 | 4030 | TAG | 4116 |
| 239787905 | 1468 | TAG | 1584 | 1587 | 189163519 | 4030 | TGA | 4051 |
| 239787905 | 1468 | TGA | 1557 | 1587 | 199559437 | 1154 | TAA | 1161 |
| 393185909 | 180 | TAG | 191 | 237 | 199559489 | 1301 | TAA | 1308 |

TABLE 2-continued shows a table of mRNAs that have intron-exon boundary closer than 50 nucleotides downstream from a stop codon arising from frameshifting over polyA tracks. These genes would fall in the category of non "classical" NMD targets if frameshifting occurs on polyA track.

| mRNA GI number | end of polyA region | nearest stop codon | location of stop codon | location of downstream intron-exon boundary | mRNA GI number | end of polyA region | nearest stop codon | location of downstream intron-exon boundary |
|---|---|---|---|---|---|---|---|---|
| 393185909 | 180 | TGA | 216 | 237 | 199558961 | 1216 | TAA | 1223 |
| 542133170 | 2639 | TAA | 2743 | 2753 | 205360986 | 300 | TAA | 372 |
| 542133170 | 2639 | TAG | 2704 | 2753 | 205360986 | 300 | TAG | 387 |
| 95147341 | 3226 | TAA | 3230 | 3264 | 205360986 | 300 | TGA | 304 |
| 95147341 | 3226 | TAG | 3238 | 3264 | 305410834 | 1016 | TAG | 1048 |
| 95147341 | 3226 | TGA | 3247 | 3264 | 32479524 | 1140 | TAG | 1659 |
| 34577113 | 1789 | TAG | 1857 | 1898 | 215982795 | 767 | TAG | 823 |
| 542133169 | 2639 | TAA | 2743 | 2753 | 349501056 | 1573 | TAG | 1613 |
| 542133169 | 2639 | TAG | 2704 | 2753 | 305410827 | 909 | TAG | 942 |
| 422398891 | 320 | TAA | 417 | 438 | 349501055 | 1573 | TAG | 1613 |
| 422398891 | 320 | TAG | 526 | 529 | 349501059 | 916 | TAG | 956 |
| 284795244 | 1103 | TAG | 1114 | 1131 | 349501060 | 1573 | TAG | 1613 |
| 284795244 | 1103 | TGA | 1118 | 1131 | 32479526 | 1373 | TAG | 1892 |
| 301500638 | 762 | TAA | 887 | 905 | 167860144 | 1425 | TAA | 1448 |
| 151301203 | 1982 | TAA | 2027 | 2050 | 167860144 | 1425 | TGA | 1473 |
| 151301203 | 1982 | TGA | 2030 | 2050 | 305410836 | 693 | TAG | 726 |
| 573459695 | 1552 | TAA | 1882 | 1906 | 386781570 | 946 | TAG | 963 |
| 422398886 | 320 | TAA | 417 | 438 | 167830435 | 2605 | TGA | 2714 |
| 296080784 | 530 | TGA | 663 | 703 | 167830432 | 658 | TAG | 857 |
| 300244517 | 499 | TAA | 535 | 547 | 167830432 | 658 | TGA | 660 |
| 300244517 | 499 | TAG | 517 | 547 | 594191052 | 1137 | TAA | 1416 |
| 300244517 | 499 | TGA | 502 | 547 | 594191052 | 1137 | TAG | 1236 |
| 296278216 | 1064 | TAA | 1146 | 1187 | 55956799 | 426 | TAA | 429 |
| 527317401 | 2486 | TGA | 2588 | 2594 | 113204614 | 8646 | TAG | 8716 |
| 313661424 | 3736 | TGA | 3751 | 3795 | 113204616 | 8646 | TAG | 8716 |
| 52145311 | 2119 | TAA | 2152 | 2183 | 296939603 | 2391 | TAA | 2823 |
| 52145311 | 2119 | TGA | 2139 | 2183 | 296939601 | 2391 | TAA | 2823 |
| 300797236 | 693 | TAG | 800 | 808 | 27765081 | 2101 | TAA | 2199 |
| 422398893 | 337 | TAA | 434 | 455 | 27765081 | 2101 | TAG | 2288 |
| 422398893 | 337 | TAG | 543 | 546 | 27765081 | 2101 | TGA | 2196 |
| 574274904 | 622 | TGA | 629 | 633 | 157266316 | 2444 | TAA | 2455 |
| 296278222 | 341 | TAA | 423 | 464 | 157266316 | 2444 | TAG | 2447 |
| 422398882 | 337 | TAA | 434 | 455 | 27765075 | 428 | TAA | 526 |
| 544346208 | 1454 | TAG | 1536 | 1580 | 27765075 | 428 | TAG | 615 |
| 544346208 | 1454 | TGA | 1623 | 1648 | 27765075 | 428 | TGA | 523 |
| 291084569 | 1795 | TAG | 2235 | 2249 | 207113159 | 4478 | TGA | 4515 |
| 291084569 | 1795 | TGA | 1825 | 1860 | 304376300 | 4364 | TGA | 4401 |
| 284795242 | 1103 | TAG | 1114 | 1131 | 207113158 | 4247 | TGA | 4284 |
| 284795242 | 1103 | TGA | 1118 | 1131 | 207113161 | 4367 | TGA | 4404 |
| 313661429 | 3451 | TGA | 3466 | 3510 | 207113163 | 4250 | TGA | 4287 |
| 324711032 | 1276 | TAG | 1294 | 1323 | 236463299 | 559 | TAA | 595 |
| 324711032 | 1276 | TGA | 1307 | 1323 | 236463299 | 559 | TAG | 574 |
| 313661427 | 3610 | TGA | 3625 | 3669 | 236463299 | 559 | TGA | 587 |
| 555943904 | 605 | TAG | 608 | 654 | 236463163 | 559 | TAA | 595 |
| 555943904 | 605 | TGA | 718 | 744 | 236463163 | 559 | TAG | 574 |
| 301500639 | 738 | TAA | 863 | 881 | 236463163 | 559 | TGA | 587 |
| 302191685 | 381 | TAA | 404 | 441 | 349501083 | 1110 | TAG | 1150 |
| 422398895 | 337 | TAA | 434 | 455 | 315360665 | 835 | TAG | 842 |
| 422398895 | 337 | TAG | 543 | 546 | 315360665 | 835 | TGA | 837 |
| 422398884 | 320 | TAA | 417 | 438 | 387527982 | 915 | TAG | 1058 |
| 422398884 | 320 | TAG | 544 | 547 | 387527982 | 915 | TGA | 929 |
| 300244513 | 239 | TAA | 275 | 287 | 402513678 | 237 | TAA | 246 |
| 300244513 | 239 | TAG | 257 | 287 | 402513678 | 237 | TAG | 257 |
| 300244513 | 239 | TGA | 242 | 287 | 305410841 | 927 | TAG | 959 |
| 313661433 | 3604 | TGA | 3619 | 3663 | 305410838 | 905 | TAG | 937 |
| 300244516 | 430 | TAA | 466 | 478 | 305410844 | 1074 | TAG | 1106 |
| 300244516 | 430 | TAG | 448 | 478 | 574957022 | 893 | TAA | 901 |
| 300244516 | 430 | TGA | 433 | 478 | 574957022 | 893 | TAG | 1028 |
| 527317400 | 2615 | TGA | 2717 | 2723 | 574957022 | 893 | TGA | 920 |
| 422398870 | 337 | TAA | 434 | 455 | 574957031 | 1965 | TAA | 1973 |
| 422398870 | 337 | TAG | 561 | 564 | 574957031 | 1965 | TAG | 2100 |
| 555943722 | 605 | TAG | 608 | 654 | 574957031 | 1965 | TGA | 1992 |
| 555943722 | 605 | TGA | 718 | 744 | 386268034 | 971 | TAG | 1012 |
| 284004933 | 616 | TAA | 618 | 625 | 386268035 | 971 | TAG | 1012 |
| 296278218 | 560 | TAA | 642 | 683 | 386268037 | 971 | TAG | 1012 |
| 574275184 | 577 | TGA | 584 | 588 | 223555916 | 1674 | TAA | 1693 |
| 574275536 | 666 | TGA | 673 | 677 | 223555916 | 1674 | TGA | 1687 |
| 386781586 | 575 | TAG | 592 | 638 | 396578113 | 1329 | TAA | 1399 |
| 300797255 | 693 | TAG | 800 | 808 | 396578113 | 1329 | TGA | 1452 |
| 386781549 | 946 | TAG | 963 | 1009 | 396578116 | 1117 | TAA | 1187 |
| 557947981 | 412 | TAA | 718 | 752 | 396578116 | 1117 | TGA | 1240 |

TABLE 2-continued shows a table of mRNAs that have intron-exon boundary closer than 50 nucleotides downstream from a stop codon arising from frameshifting over polyA tracks. These genes would fall in the category of non "classical" NMD targets if frameshifting occurs on polyA track.

| mRNA GI number | end of polyA region | nearest stop codon | location of stop codon | location of downstream intron-exon boundary | mRNA GI number | end of polyA region | nearest stop codon | location of downstream intron-exon boundary |
|---|---|---|---|---|---|---|---|---|
| 557947981 | 412 | TGA | 430 | 435 | 95147334 | 3551 | TAA | 3660 |
| 110347424 | 1113 | TAA | 1119 | 1159 | 160707983 | 2206 | TAG | 2264 |
| 110347424 | 1113 | TAG | 1130 | 1159 | 154146192 | 1034 | TAA | 1086 |
| 110347424 | 1113 | TGA | 1125 | 1159 | 154146192 | 1034 | TGA | 1050 |
| 110347417 | 1104 | TAA | 1110 | 1150 | 145275203 | 1841 | TAA | 1907 |
| 110347417 | 1104 | TAG | 1121 | 1150 | 154146222 | 954 | TAA | 1006 |
| 110347417 | 1104 | TGA | 1116 | 1150 | 154146222 | 954 | TGA | 970 |
| 53729338 | 2711 | TAA | 2714 | 2749 | 120953299 | 4732 | TAG | 4829 |
| 53729336 | 2290 | TAA | 2293 | 2328 | 120953299 | 4732 | TGA | 4784 |
| 94538369 | 841 | TAG | 883 | 905 | 189409139 | 1021 | TAA | 1074 |
| 94538369 | 841 | TGA | 857 | 905 | 189409139 | 1021 | TAG | 1096 |
| 160707983 | 2206 | TAA | 2238 | 2272 | 239787837 | 233 | TAG | 377 |

TABLE 3 shows a table showing peptides arising from possible frame-shifting on polyA tracks. Direction of frame-shift, gene name and peptide sequences following polyA track are shown in table. Additional analyses of possible eukaryotic linear motifs (ELMs) found in these peptides is included.

| Frameshift | Gene name | Sequence | ELMs |
|---|---|---|---|
| minus one | ALS2CR12 | TKKFEMESGEE | ELME000117 ELME000085 ELME000064 |
| minus one | APTX | LEFFQYRIL | ELME000355 ELME000370 ELME000120 |
| minus one | ASTE1 | EETEYQLF | ELME000370 ELME000236 ELME000120 ELME000352 |
| minus one | BRCA1 | QPNASQAQQKPTTHGR | ELME000202 ELME000353 ELME000239 ELME000070 |
| minus one | C10orf90 | RTKEKGDLTK | ELME000351 |
| minus one | CASP5 | DVLLYDTIFQIFNNRNCLS | ELME000020 ELME000336 ELME000370 ELME000335 ELME000120 ELME000352 |
| minus one | CCDC146 | SWNKKSKR | ELME000011 ELME000285 ELME000278 |
| minus one | CCDC148 | LGQEKTEVARNG | ELME000355 |
| minus one | CCDC168 | KKVSKLGSQGWRNQ | ELME000202 ELME000351 ELME000008 ELME000053 |
| minus one | CDYL | RQSIWFGGKA | ELME000351 ELME000197 |
| minus one | CENPQ | HLKDLSSEGQTKH | ELME000334 ELME000053 |
| minus one | CEP290 | HYQLQVQELTDL | ELME000086 ELME000163 |
| minus one | CHEK1 | YLNPWKKIDSAPLALL | ELME000182 ELME000085 ELME000084 ELME000355 ELME000081 |
| minus one | CHRM5 | EEKLYWQGNSKLP | ELME000352 ELME000137 |
| minus one | CNTLN | MLKMTRNGCCTFRNFLKDSFLLPHIY | ELME000146 ELME000336 ELME000079 ELME000337 ELME000355 ELME000370 ELME000369 |
| minus one | CNTRL | AAQTRLSEL | ELME000086 ELME000285 |
| minus one | CPNE3 | TRIQVLSV | ELME000333 ELME000091 ELME000365 |
| minus one | DHX36 | TFGILKCSISEKSCLRMECKRNW | ELME000336 ELME000162 ELME000368 ELME000063 ELME000103 ELME000360 ELME000370 ELME000108 ELME000064 ELME000100 |

TABLE 3-continued shows a table showing peptides arising from possible frame-shifting on polyA tracks. Direction of frame-shift, gene name and peptide sequences following polyA track are shown in table. Additional analyses of possible eukaryotic linear motifs (ELMs) found in these peptides is included.

| Frameshift | Gene name | Sequence | ELMs |
|---|---|---|---|
| minus one | DIAPH3 | TDFFVLWKASGTIQFNCK | ELME000368 ELME000085 ELME000370 ELME000328 |
| minus one | DYNC1I2 | TRRRKLLLLCKKNQILKKKGEKLK HCFKAWG | ELME000146 ELME000149 ELME000106 ELME000108 ELME000231 ELME000012 ELME000233 ELME000102 |
| minus one | EIF2AK2 | LLQKLLSKK | ELME000045 ELME000355 |
| minus one | FAM133A | SKDETEKEKD | ELME000285 ELME000220 ELME000064 |
| minus one | FBXO38 | DVYPSCSSTTASTVGNSSSHNTASQS PDF | ELME000136 ELME000202 ELME000063 ELME000159 ELME000197 ELME000239 ELME000070 ELME000352 ELME000053 |
| minus one | FILIP1 | EILLLAQNEPCPQSQLLHFPERRLQKV EEAHLQTGPHPLFR | ELME000202 ELME000173 ELME000335 ELME000108 ELME000012 ELME000352 ELME000102 |
| minus one | GON4L | TKRKRDGRGQEGTLAYDLKLDDMLDR TLEDGAKQHN | ELME000147 ELME000108 ELME000220 ELME000365 ELME000100 ELME000102 |
| minus one | GOPC | KEAQLEAEVKLLRKENEAL | ELME000232 ELME000351 ELME000335 ELME000365 ELME000089 ELME000102 |
| minus one | GPATCH4 | KEAERGGRSYSI | ELME000091 ELME000351 |
| minus one | HMGXB4 | RRTKREREEKSQKRRTCRPTRCS | ELME000271 ELME000202 ELME000101 ELME000351 ELME000062 ELME000108 ELME000220 ELME000276 ELME000100 ELME000008 ELME000102 ELME000053 |
| minus one | IFI16 | PKKRLDPKG | ELME000106 ELME000108 ELME000100 |
| minus one | IQCA1 | EEEKGKTTQESQKTKERNKGEK | ELME000117 ELME000202 ELME000063 ELME000220 ELME000064 ELME000352 ELME000053 |
| minus one | JARID2 | SHSQYHLSPPG | ELME000367 ELME000249 ELME000136 ELME000159 ELME000285 |
| minus one | KNOP1 | HQEGDALPGHSKPSRSMESS | ELME000063 ELME000287 ELME000239 ELME000053 |
| minus one | KRCC1 | NKAKKGQRRKCFGTSLFLD | ELME000336 ELME000353 ELME000108 ELME000102 |
| minus one | LPIN2 | GERNTNRT | ELME000062 |
| minus one | MAST4 | SGKVTKSLSASALSLMIPGDMFAVSPL GSPMSPHSLSSDPSSSRDSSPSRDSS AASASPHQPIVIHSSGKNYGFTIRAIRV YVGDSDIYTVHHIVWNVEEGSPACQA GLKAGDLITHINGEPVHGLVHTEVIELLL KSG | ELME000155 ELME000182 ELME000367 ELME000336 ELME000136 ELME000149 ELME000147 ELME000337 ELME000085 ELME000063 ELME000159 ELME000173 ELME000335 ELME000062 ELME000285 ELME000313 ELME000153 ELME000365 ELME000148 ELME000239 ELME000052 ELME000321 ELME000053 |
| minus one | MED19 | KRILNGKGRRKRRRKRRIDIVQTTQVW AAPRPAAAAAY | ELME000271 ELME000146 ELME000202 ELME000101 ELME000103 ELME000093 ELME000351 ELME000108 ELME000278 ELME000012 ELME000233 ELME000369 ELME000052 ELME000276 ELME000100 ELME000270 ELME000102 |
| minus one | MGA | MGSDEFDISPRISKQQEGSSASSVDLG QMF | ELME000136 ELME000085 ELME000063 ELME000159 ELME000062 ELME000365 ELME000197 ELME000053 |
| minus one | MIS18BP1 | SIPTYVKKRKTTNHSSQMTVH | ELME000182 ELME000271 ELME000202 ELME000063 ELME000062 ELME000285 ELME000108 ELME000070 ELME000100 |

TABLE 3-continued shows a table showing peptides arising from possible frame-shifting on polyA tracks. Direction of frame-shift, gene name and peptide sequences following polyA track are shown in table. Additional analyses of possible eukaryotic linear motifs (ELMs) found in these peptides is included.

| Frameshift | Gene name | Sequence | ELMs |
|---|---|---|---|
| minus one | MKNK1 | HQQPRACVY | ELME000008 ELME000270 ELME000102 ELME000053 |
| minus one | MORC4 | IITEDSLPSLEAILNYSIFNRENDLLAQF DAIPGKKGTRVLIWNIRR | ELME000336 ELME000149 ELME000147 ELME000063 ELME000355 ELME000106 ELME000093 ELME000120 ELME000341 ELME000012 ELME000287 ELME000069 ELME000365 ELME000233 ELME000070 ELME000052 ELME000008 ELME000137 |
| minus one | MYH10 | QAHIQDLEEQLDEEEGARQKLQLEKVT AEAKIKKMEEEILLLEDQNSKFIKEKKL MEDRIAECSSQLAEEEEKAKNLAKIR | ELME000342 ELME000146 ELME000117 ELME000149 ELME000202 ELME000106 ELME000333 ELME000335 ELME000353 ELME000365 ELME000233 ELME000239 |
| minus one | NEK3 | QQNQDSFGK | ELME000353 |
| minus one | NGFRAP1 | LIMANIHQENEEMEQPMQNGEEDRPL GG | ELME000355 |
| minus one | NIPBL | ILTHRRLGVLQE | ELME000355 ELME000106 ELME000108 ELME000012 ELME000102 |
| minus one | NPIPB15 | KTKQNPRSKNK | ELME000351 |
| minus one | NR3C1 | FSRPLQESHKKP | ELME000117 ELME000336 ELME000355 |
| minus one | NUP85 | RWCQVAPLSISS | ELME000351 |
| minus one | OSBPL1A | LSEALETLA | ELME000086 ELME000355 |
| minus one | PA2G4 | GLQDCRECHQWGNIRRK | ELME000108 ELME000012 ELME000060 ELME000102 |
| minus one | PHLPP1 | RRIHGQYIHCHAKETWNCWAEAWWC RCPLSYQA | ELME000182 ELME000160 ELME000091 ELME000351 ELME000108 ELME000012 ELME000365 ELME000102 |
| minus one | PLXNC1 | QILTSYIFGKQTAFLFASG | ELME000182 ELME000198 ELME000353 ELME000197 ELME000052 |
| minus one | PPP1R10 | CHLRLPSQAP | ELME000354 ELME000367 ELME000202 ELME000334 |
| minus one | PRPF40A | QAKQLRKRNWEA | ELME000271 ELME000353 ELME000108 ELME000278 ELME000012 ELME000100 ELME000102 |
| minus one | PXK | FSSKEVKTICS | ELME000146 ELME000355 |
| minus one | RNF145 | AAKEKLEAV | ELME000285 ELME000365 ELME000089 |
| minus one | SENP7 | YPRVSCYFQVITRKDTQSY | ELME000182 ELME000368 ELME000337 ELME000202 ELME000370 ELME000062 ELME000120 ELME000220 ELME000365 ELME000197 ELME000239 ELME000008 ELME000102 ELME000053 |
| minus one | SGOL1 | VPQKKMHKSVSS | ELME000336 |
| minus one | SH3RF1 | FVEVAFWRLH | ELME000368 ELME000355 ELME000370 |
| minus one | SLC46A3 | SPIFAFQEEVQKKVSR | ELME000117 ELME000011 ELME000285 |
| minus one | SMAD5 | CHGGTGESLEQSRTAE | ELME000354 ELME000336 ELME000053 |
| minus one | SPATA16 | ATSNCSAK | ELME000085 ELME000285 ELME000070 |
| minus one | TAF1D | RYQPTGRPRGRPEGRRNPIYS | ELME000103 ELME000093 ELME000351 ELME000122 ELME000108 ELME000097 ELME000012 ELME000095 ELME000102 |

TABLE 3-continued shows a table showing peptides arising from possible frame-shifting on polyA tracks. Direction of frame-shift, gene name and peptide sequences following polyA track are shown in table. Additional analyses of possible eukaryotic linear motifs (ELMs) found in these peptides is included.

| Frameshift | Gene name | Sequence | ELMs |
|---|---|---|---|
| minus one | TAOK1 | SGFQSRRRIYSISKQKKK | ELME000011 ELME000285 ELME000108 ELME000012 ELME000065 ELME000051 ELME000061 ELME000102 |
| minus one | TDRD5 | HNRRFARS | ELME000108 ELME000012 ELME000102 |
| minus one | TFDP2 | SGLACLPILLRNVRIWR | ELME000285 |
| minus one | TMEM254 | KKIEAKNGDPNDCSEFLRSVWVVFWP QSIPYQNLGPLGPFTQYLVDHHHTLLC NGYWLAWLIHVGESLYAIVLCK | ELME000020 ELME000155 ELME000182 ELME000317 ELME000336 ELME000079 ELME000368 ELME000160 ELME000202 ELME000084 ELME000351 ELME000370 ELME000335 ELME000120 ELME000081 ELME000052 |
| minus one | U2SURP | IWNSSKKN | ELME000355 ELME000070 |
| minus one | ULK4 | RECWAVPLAAYTV | ELME000091 ELME000351 ELME000369 |
| minus one | VEZF1 | KLHLCALTA | ELME000091 ELME000351 |
| minus one | ZC3H13 | WKSQERENLGLIS | ELME000149 ELME000355 ELME000333 ELME000231 |
| minus one | ZMYM5 | IDAAEHRLYENEKNDGVLLLYT | ELME000149 ELME000084 ELME000355 ELME000321 |
| minus one | ZRANB2 | QRESSWSCIY | ELME000080 ELME000199 ELME000368 ELME000147 ELME000063 ELME000370 ELME000062 ELME000353 |
| plus one | ABCC2 | SLGPKKMFQNPG | ELME000146 ELME000285 |
| plus one | ALS2CR12 | MTKKFEMESGEE | ELME000117 ELME000085 ELME000064 |
| plus one | ANKHD1-EIF4EBP3 | GTEKETGRR | ELME000093 |
| plus one | ANKHD1 | GTEKETGRR | ELME000093 |
| plus one | ANKRD49 | GKRPKQIASLGC | ELME000091 ELME000108 ELME000100 ELME000270 |
| plus one | APAF1 | ITNLSRLVVRPHTDAVYHACF | ELME000155 ELME000355 ELME000371 ELME000070 ELME000052 |
| plus one | APTX | IGILSIQNTS | ELME000355 ELME000333 ELME000053 |
| plus one | APTX | WNSFNTEYF | ELME000063 ELME000355 ELME000089 |
| plus one | BBX | KKSKMDRHG | ELME000351 |
| plus one | BEND2 | YQPCCIGICR | ELME000355 |
| plus one | BLM | VSSKSVSEGRDG | ELME000063 ELME000064 ELME000321 |
| plus one | BRCA1 | YNQMPVRHSRNLQLME | ELME000355 ELME000106 ELME000062 ELME000120 |
| plus one | C10orf90 | RTKEKGDLTK | ELME000351 |
| plus one | C16orf45 | KLQKQREDE | ELME000351 |
| plus one | CAPN3 | SPSSSFRTEQTATRSWVWTRSQRRAK AKQA | ELME000146 ELME000011 ELME000147 ELME000337 ELME000202 ELME000063 ELME000285 ELME000108 ELME000365 ELME000197 ELME000239 ELME000102 ELME000053 |
| plus one | CASP5 | DVLLYDTIFQIFNNRNCLS | ELME000020 ELME000336 ELME000370 ELME000335 ELME000120 ELME000352 |

TABLE 3-continued shows a table showing peptides arising from possible frame-shifting on polyA tracks. Direction of frame-shift, gene name and peptide sequences following polyA track are shown in table. Additional analyses of possible eukaryotic linear motifs (ELMs) found in these peptides is included.

| Frameshift | Gene name | Sequence | ELMs |
| --- | --- | --- | --- |
| plus one | CASP5 | RMCCFMTPSSRYSTTATASV | ELME000358 ELME000136 ELME000063 ELME000159 ELME000351 ELME000062 ELME000365 ELME000239 ELME000053 |
| plus one | CCDC122 | VLFNLKNELHELEKEIAAISAE | ELME000085 ELME000002 ELME000365 |
| plus one | CCDC146 | CLGTRSQN | ELME000354 |
| plus one | CCDC148 | WAKKKQKWQEME | ELME000271 ELME000201 ELME000355 ELME000278 |
| plus one | CEP290 | IIINFKCRSLQIF | ELME000355 ELME000106 |
| plus one | CHD9 | RRRYRREAI | ELME000101 ELME000103 ELME000351 ELME000108 ELME000012 ELME000089 ELME000102 |
| plus one | CHRM5 | WKRSCTGRGTASY | ELME000355 ELME000173 ELME000062 ELME000108 ELME000100 ELME000053 |
| plus one | CNTRL | QHKLDYQNC | ELME000084 ELME000353 |
| plus one | EIF2AK2 | FYRNYSQRN | ELME000202 ELME000084 ELME000355 ELME000070 |
| plus one | EIF5B | TEGQKTEF | ELME000086 |
| plus one | ERC2 | ATGPHRREGDTGR | ELME000285 ELME000108 ELME000102 |
| plus one | ERO1LB | ARERLFSLLQG | ELME000045 ELME000368 ELME000149 ELME000370 ELME000285 ELME000231 ELME000061 |
| plus one | EXOC1 | NCFLCATVTTERPVQ | ELME000336 ELME000353 |
| plus one | FAM133A | SQRMKQRKKRM | ELME000271 ELME000011 ELME000101 ELME000285 ELME000108 ELME000100 ELME000270 ELME000102 |
| plus one | FAM227B | DSSFVSIYTHLWENVPRIFEALLIMESK | ELME000182 ELME000368 ELME000063 ELME000370 ELME000120 ELME000047 ELME000365 ELME000352 |
| plus one | FAM81B | TEIVFQKYQIYKK | ELME000370 |
| plus one | FILIP1 | WRYYSWPRTSHVPSHNYYIFQREDSRKWKRRICRQAHIPYS | ELME000182 ELME000271 ELME000355 ELME000103 ELME000370 ELME000062 ELME000120 ELME000108 ELME000278 ELME000012 ELME000048 ELME000239 ELME000052 ELME000100 ELME000163 ELME000102 ELME000053 |
| plus one | FOXP3 | MRTPPHPVIISAHTHRKKFGLLEERGLRLPHRTAWFFFSV | ELME000358 ELME000155 ELME000367 ELME000085 ELME000063 ELME000106 ELME000333 ELME000091 ELME000351 ELME000370 ELME000365 ELME000102 |
| plus one | GGNBP2 | KKKKSKILKCDEHIQKLGSCITDP | ELME000271 ELME000146 ELME000007 ELME000351 ELME000173 ELME000278 ELME000008 |
| plus one | GYPC | GVETPPAKSAEKK | ELME000358 ELME000136 ELME000085 ELME000159 ELME000239 |
| plus one | HMGXB4 | REGQRERERRKAKKEEHVGLPGVL | ELME000155 ELME000271 ELME000146 ELME000101 ELME000103 ELME000351 ELME000108 ELME000002 ELME000278 ELME000233 ELME000102 |
| plus one | HYDIN | EIESDFLATTNTTKAQEEQTSS | ELME000117 ELME000336 ELME000070 ELME000352 ELME000053 |

TABLE 3-continued shows a table showing peptides arising from possible frame-shifting on polyA tracks. Direction of frame-shift, gene name and peptide sequences following polyA track are shown in table. Additional analyses of possible eukaryotic linear motifs (ELMs) found in these peptides is included.

| Frameshift | Gene name | Sequence | ELMs |
| --- | --- | --- | --- |
| plus one | IGHMBP2 | QRTSGHRSAHGGGL | ELME000085 ELME000062 ELME000353 ELME000053 |
| plus one | IL1R2 | DHSCDHFPPQDHISFSGVKTDNPV | ELME000368 ELME000085 ELME000370 ELME000352 ELME000053 |
| plus one | IQCA1 | KKKKKEKQPKKAKKQKKGTKEK | ELME000271 ELME000146 ELME000351 ELME000278 ELME000276 ELME000008 |
| plus one | JARID2 | GPTLSTISALL | ELME000085 ELME000063 ELME000365 |
| plus one | KCNC1 | KHIPRPPQLGSPNY | ELME000155 ELME000199 ELME000136 ELME000159 ELME000351 ELME000005 |
| plus one | KDM4D | HDCGGVSPFGKQ | ELME000136 ELME000159 |
| plus one | KNOP1 | TRREMPSQATPSPPGPWRAA | ELME000358 ELME000155 ELME000006 ELME000136 ELME000202 ELME000063 ELME000159 ELME000108 ELME000102 |
| plus one | LARP7 | DRVEASSLPEVRTGKRKRSSSEDAES LAPRSK | ELME000271 ELME000093 ELME000173 ELME000062 ELME000108 ELME000365 ELME000064 ELME000100 ELME000061 ELME000008 ELME000352 ELME000270 ELME000102 |
| plus one | LOC101929870 | QKSFPSEGQRQRRSLFLDSNSRENLG WLAKLTREQNILPEAEKPHALSGGG | ELME000146 ELME000336 ELME000085 ELME000063 ELME000101 ELME000106 ELME000062 ELME000353 ELME000108 ELME000231 ELME000012 ELME000365 ELME000233 ELME000051 ELME000102 |
| plus one | LPIN2 | KEKEIQTGQ | ELME000351 |
| plus one | MPP3 | PPMSPACEDTAAPFDEQQQEMAASAA FIDRHYGHLVDAVLVKEDLQGAYSQLK VVLEKLSKDTHWVPVSWVR | ELME000146 ELME000336 ELME000136 ELME000368 ELME000147 ELME000202 ELME000085 ELME000063 ELME000159 ELME000333 ELME000370 ELME000120 ELME000326 ELME000313 ELME000365 ELME000197 ELME000233 ELME000052 |
| plus one | NAA35 | SPIEPRDHNEPSISEHVCWNV | ELME000147 ELME000285 ELME000365 ELME000064 |
| plus one | NCOA7 | SQTKCRDSLSCSYKDSYWEGR | ELME000336 ELME000162 ELME000062 ELME000285 ELME000064 ELME000321 ELME000053 |
| plus one | NEK3 | PSRIRIALG | ELME000146 ELME000012 ELME000365 |
| plus one | NHLRC2 | CTTLAGTGDT | ELME000354 |
| plus one | NIPBL | KKRKAYEPK | ELME000271 ELME000351 ELME000108 ELME000278 ELME000100 ELME000102 |
| plus one | NIPBL | RFLPTGGWGCYRR | ELME000106 ELME000351 ELME000370 ELME000012 |
| plus one | NPIPB15 | KKQNKTHAPKTN | ELME000351 ELME000070 |
| plus one | NR3C1 | NSAGHYRSLTRNL | ELME000146 ELME000085 ELME000353 ELME000120 ELME000334 |
| plus one | OSBPL1A | CQKHWRRWP | ELME000354 ELME000160 ELME000108 ELME000012 ELME000102 |
| plus one | PDZD9 | ERGVSNKVKTSVHNLSKTQQTKLTV | ELME000336 ELME000202 ELME000091 ELME000365 ELME000070 ELME000352 |
| plus one | PEG10 | GVEEGARIQASIPTE | ELME000365 ELME000051 ELME000060 |
| plus one | PPFIA2 | RLGQLRGFMETEAAAQESLG | ELME000117 ELME000351 ELME000140 ELME000239 |

TABLE 3-continued shows a table showing peptides arising from possible frame-shifting on polyA tracks. Direction of frame-shift, gene name and peptide sequences following polyA track are shown in table. Additional analyses of possible eukaryotic linear motifs (ELMs) found in these peptides is included.

| Frameshift | Gene name | Sequence | ELMs |
| --- | --- | --- | --- |
| plus one | PPP1R10 | TVTYGCQAKPL | ELME000163 |
| plus one | PRR14L | CEENVCRS | ELME000354 ELME000079 |
| plus one | QTRTD1 | LGKTGDHTMDIPGCLLYTKTGSAPHLT HHTL | ELME000182 ELME000336 ELME000147 ELME000085 ELME000355 ELME000173 ELME000052 ELME000053 |
| plus one | RALGPS2 | SSAPNAVAFTRRFNH | ELME000085 ELME000285 ELME000328 ELME000108 ELME000012 ELME000102 |
| plus one | RBPJ | MERDGCSEQESQPCAFIG | ELME000117 ELME000202 ELME000064 ELME000352 ELME000053 |
| plus one | RNF10 | RNRSSCSAPQSSTP | ELME000085 ELME000063 ELME000351 ELME000062 ELME000239 ELME000070 ELME000053 |
| plus one | RNF145 | WLQRRNWRQC | ELME000355 ELME000108 ELME000102 |
| plus one | RYR1 | RKISQSAQT | ELME000202 ELME000085 ELME000351 ELME000008 |
| plus one | SENP7 | HIRGCPVTSKSSPERQLKVMLTNVLWT DLGRKFRKTLPRND | ELME000146 ELME000336 ELME000136 ELME000063 ELME000106 ELME000159 ELME000093 ELME000062 ELME000153 ELME000278 ELME000365 ELME000064 ELME000239 ELME000052 ELME000102 ELME000053 |
| plus one | SENP7 | YPRVSCYFQVITRKGLTTK | ELME000182 ELME000146 ELME000368 ELME000337 ELME000370 ELME000062 ELME000120 ELME000365 ELME000197 ELME000239 ELME000102 |
| plus one | SGOL1 | FPKKKCTNLSVP | ELME000271 ELME000367 ELME000365 ELME000233 ELME000070 ELME000008 |
| plus one | SLC26A8 | KKGPERAPFLVSFVQ | ELME000336 ELME000149 ELME000351 ELME000328 |
| plus one | SLC46A3 | AQFLHSRRKFRKKCHV | ELME000271 ELME000336 ELME000011 ELME000285 ELME000108 ELME000278 ELME000102 |
| plus one | SLC4A7 | KEEAERMLQDDDDTVHLPFEGGSLLQI PVKA | ELME000155 ELME000367 ELME000149 ELME000147 ELME000091 ELME000351 ELME000335 ELME000240 ELME000052 |
| plus one | SLCO5A1 | SVDAVSDDDVLKEKSNNSEQADKKVS SMGFGKDVRDLPRAAVRI | ELME000063 ELME000106 ELME000091 ELME000198 ELME000285 ELME000365 ELME000197 ELME000233 ELME000070 ELME000008 |
| plus one | SLCO5A1 | SVDAVSDDDVLKEKSNNSEQADKKVS SMGFGKDVRGVIIVPSAGVGIVLGGYI | ELME000085 ELME000063 ELME000198 ELME000285 ELME000365 ELME000197 ELME000233 ELME000070 ELME000008 |
| plus one | SPG11 | IFLKKRKEL | ELME000011 ELME000355 ELME000108 ELME000100 ELME000102 |
| plus one | SYCP1 | QENTNIFIGNT | ELME000353 |
| plus one | TCF25 | EKQEKQHGRSIGKRTRRYRSHPRED | ELME000101 ELME000103 ELME000093 ELME000108 ELME000278 ELME000012 ELME000048 ELME000100 ELME000352 ELME000102 |

TABLE 3-continued shows a table showing peptides arising from possible frame-shifting on polyA tracks. Direction of frame-shift, gene name and peptide sequences following polyA track are shown in table. Additional analyses of possible eukaryotic linear motifs (ELMs) found in these peptides is included.

| Frameshift | Gene name | Sequence | ELMs |
|---|---|---|---|
| plus one | TDRD5 | ATTEDLQEA | ELME000285 ELME000052 |
| plus one | TERF1 | SRRATESRIPVSKSQP | ELME000146 ELME000062 ELME000285 ELME000108 ELME000239 ELME000008 ELME000102 |
| plus one | TFDP2 | QVDWPAYQFCSGMSESG | ELME000085 ELME000063 ELME000370 ELME000353 |
| plus one | THOC2 | KERCTALQDKLLEEEKKOMEHVORVL QRLKLEKDNWL | ELME000351 ELME000062 ELME000002 |
| plus one | TMEM254 | KENRSQEWRPK | ELME000202 ELME000351 ELME000070 |
| plus one | TNRC6B | ATQKVTEQKTKVPE | ELME000011 ELME000285 ELME000053 |
| plus one | TRAPPC10 | QHPSPNLYCGQ | ELME000182 ELME000136 ELME000159 ELME000353 ELME000163 |
| plus one | TRDN | CRSRTTQGKKTGKERKTCGTSKVTKE RTLRN | ELME000354 ELME000147 ELME000202 ELME000063 ELME000093 ELME000173 ELME000062 ELME000220 ELME000064 ELME000052 ELME000102 ELME000053 |
| plus one | TRDN | RNKDTGERTEES | ELME000351 ELME000053 |
| plus one | TRPC1 | IASGIPGFVLIYIDVWPVQL | ELME000020 ELME000182 ELME000085 ELME000355 ELME000333 ELME000091 ELME000120 ELME000083 ELME000047 ELME000365 ELME000081 |
| plus one | ULK4 | LESAGLFPWLHTQC | ELME000086 ELME000085 ELME000355 |
| plus one | VEZF1 | QNFICVHLLQ | ELME000353 |
| plus one | WNK1 | QEESSLKQQVEQSSASQTGIKQLPSAS TGIPTASTTSASVSTQVE | ELME000147 ELME000202 ELME000085 ELME000063 ELME000106 ELME000353 ELME000365 ELME000064 ELME000239 ELME000053 |
| plus one | ZCRB1 | LLNQKKKLRK | ELME000271 ELME000011 ELME000355 ELME000278 ELME000102 |
| plus one | ZDHHC3 | DEHESRFWPPLLSRLGQPLCHARPRE GRPVPVCGLKDPDRHGHSDTSPHHST TVPSVLMNV | ELME000136 ELME000368 ELME000063 ELME000159 ELME000370 ELME000173 ELME000365 ELME000233 ELME000239 ELME000369 ELME000352 ELME000053 |
| plus one | ZFHX3 | STPFSFHS | ELME000285 |
| plus one | ZMYM5 | LLMLQNTDYMKMRKMMVCCCCT | ELME000355 ELME000122 ELME000120 ELME000095 ELME000102 |

Figure 23:
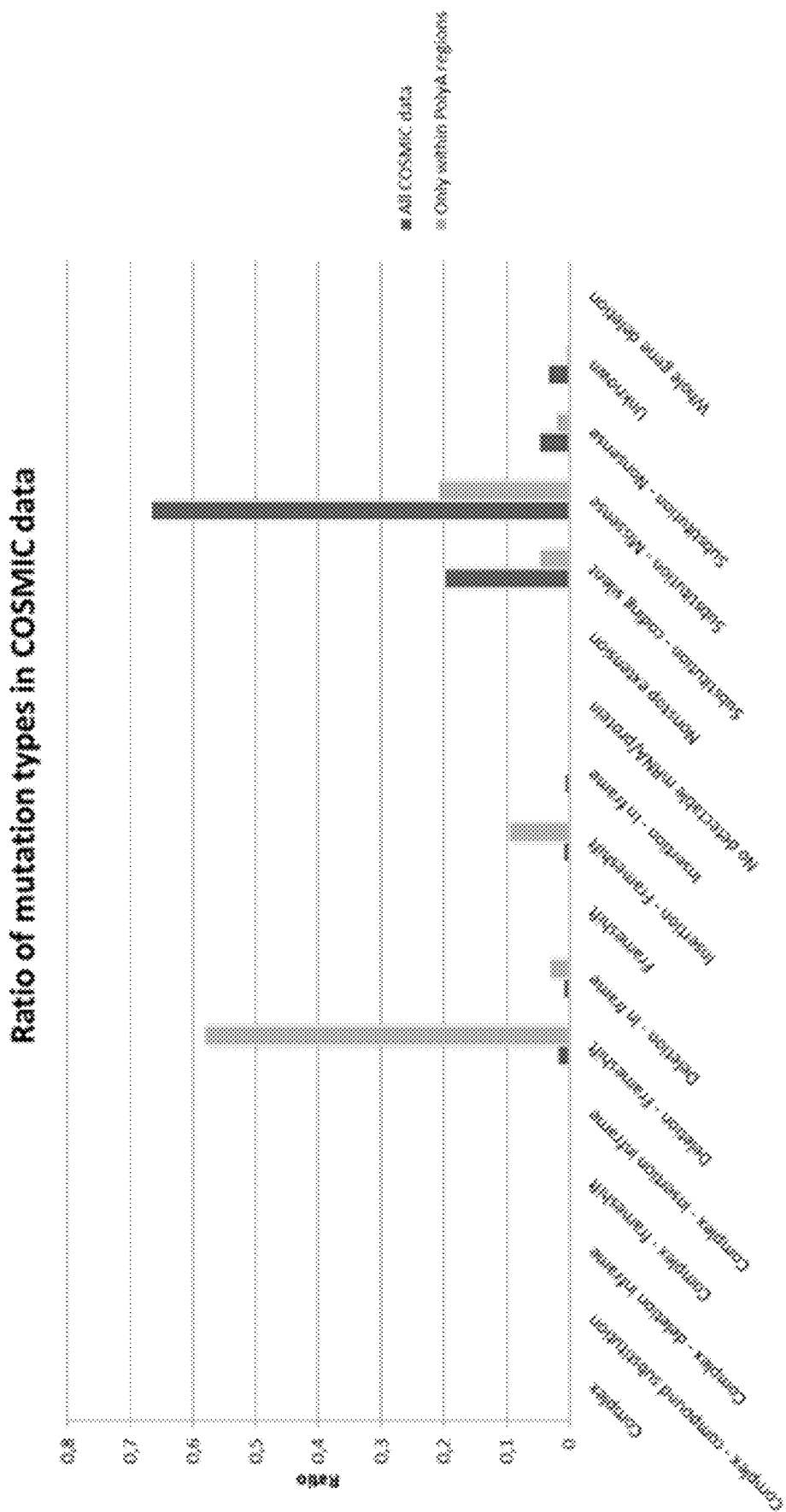
FIG. 23 shows the proportion of mutation types in polyA segments vs all mutation types. Data has been generated from COSMIC database. There is a dramatic shift in the distribution of mutations in polyA segments from substitutions (all COSMIC data) to frameshifts (polyA segments).
Figure 24:
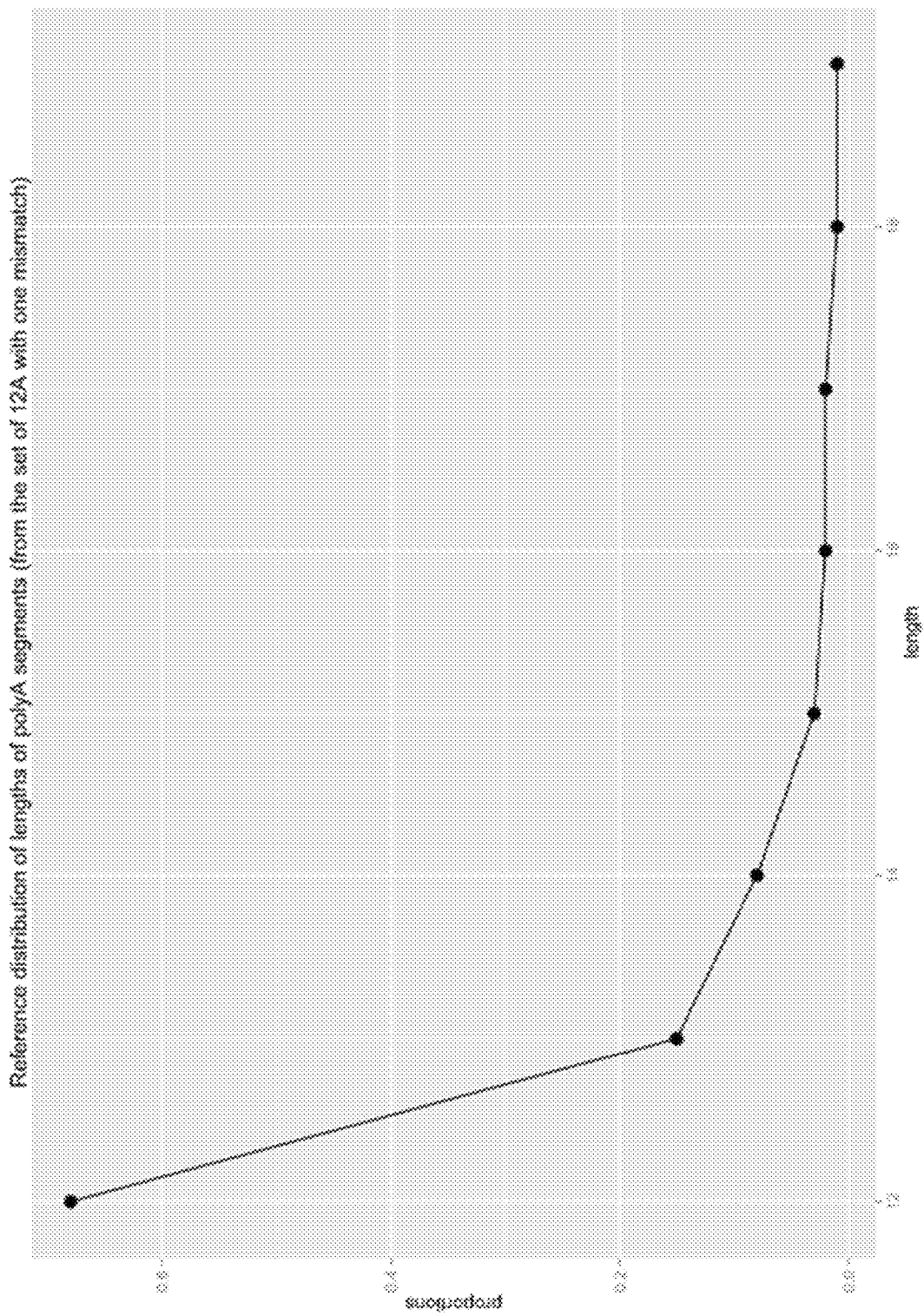
FIG. 24 shows the normalized distribution of lengths for polyA regions identified as 12 As allowing for one mismatch up to length 19 in human transcripts.
Figure 25A:
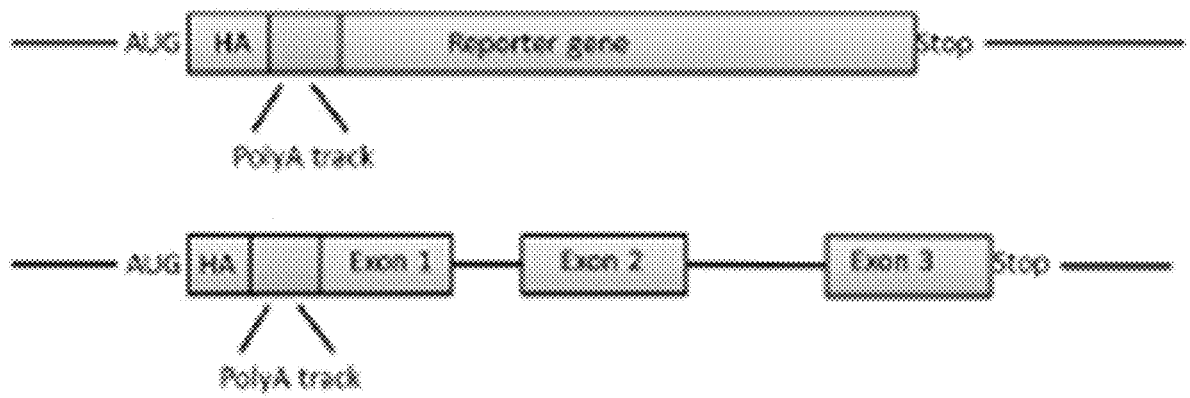
FIG. 25A, FIG. 25B, and FIG. 25C show design and mechanism of polyA track tag regulated gene expression.
Figure 25B:
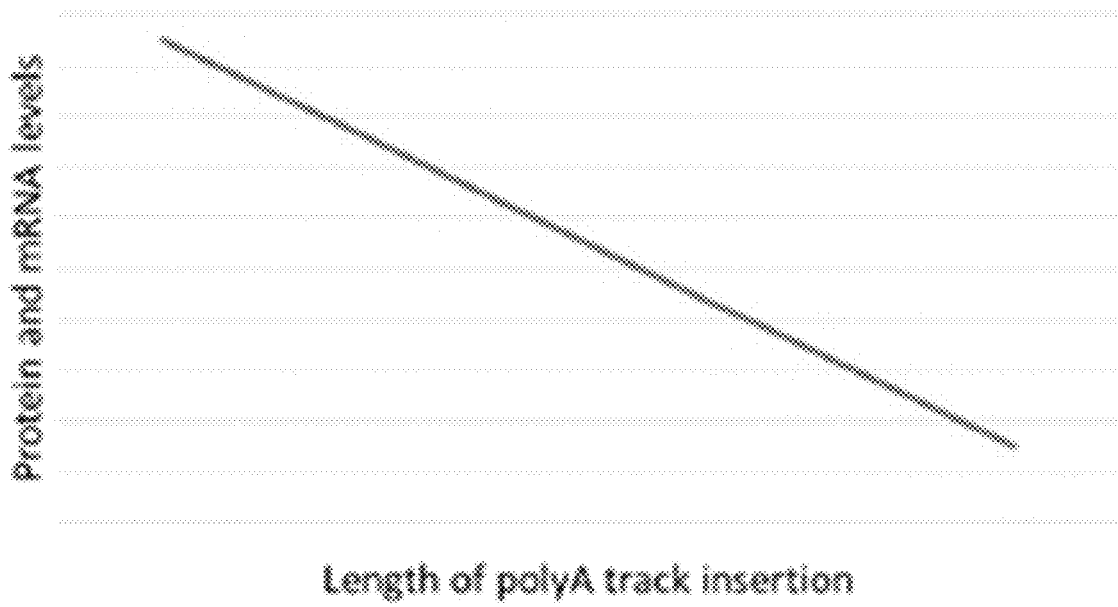
Figure 25C:
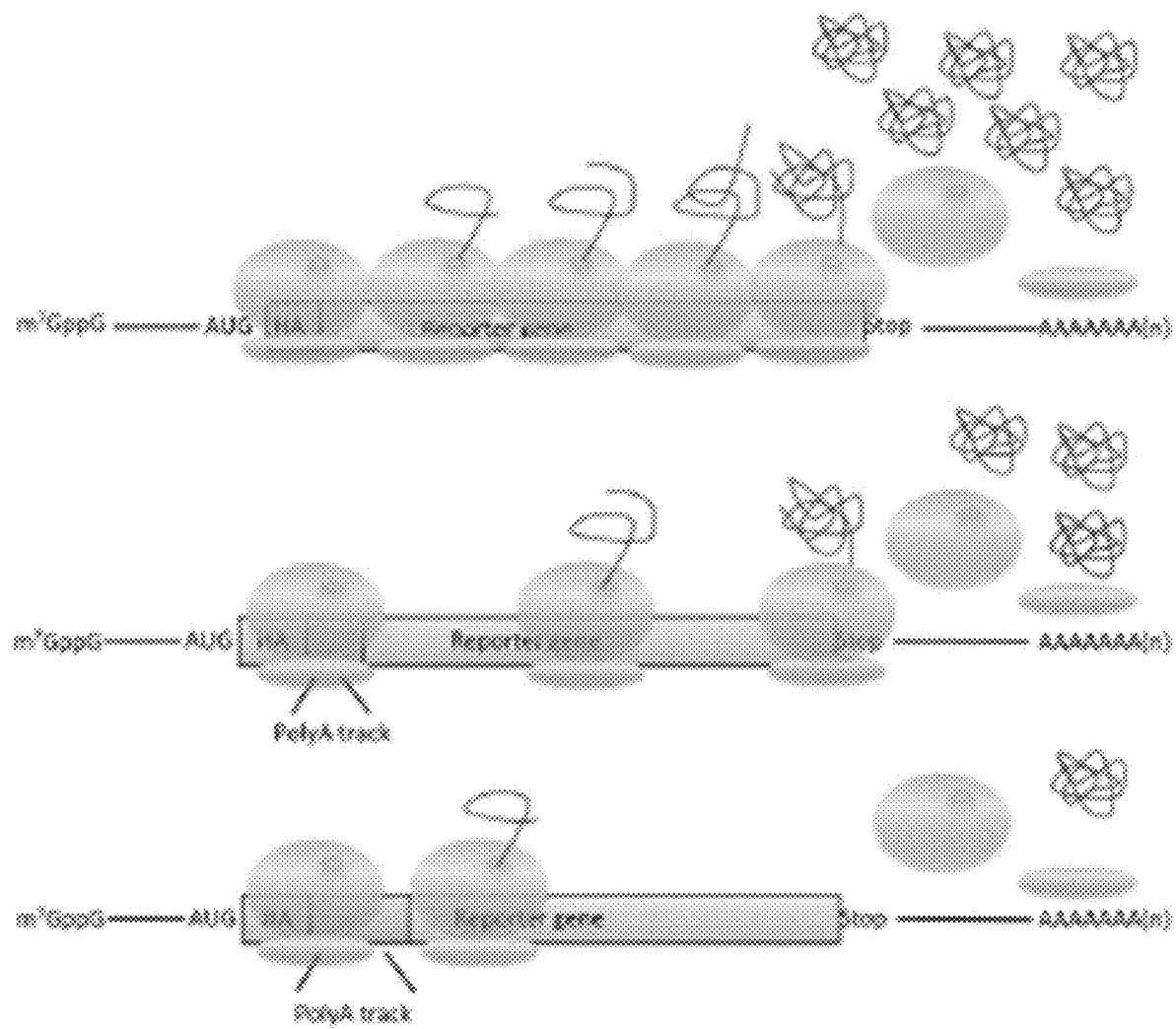

In conclusion, the presently disclosed subject matter demonstrates that lysine coding poly(A) nucleotide tracks in human genes act as translational attenuators. It is shown that the effect is dependent on nucleotide, not amino acid sequence, and the attenuation occurs in a distinct manner from previously described polybasic amino acid runs. These "poly(A) translational attenuators" are highly conserved across vertebrates, implying that they might play an important role in balancing gene dosage. Presence of such a regulatory function is further supported by negative selection against single nucleotide variants in human poly(A) segments both in dbSNP and COSMIC databases (FIG. 23; Table 4; Based on dbSNP data, it was found that variations in polyA region are less common than in randomly chosen section of the same length in genes that do not contain polyA segment (1,8k segments vs 71k segments, one random all transcripts, mean of 0.44 vs 0.49 variations per segment, p-value 0.008 with permutation test and 0.009 with Welch t-test). Almost 300 genes from the original set of 456 had no variation within polyA segment reported in dbSNP). However, it is not yet clear what the effects stemming from synonymous mutation in poly(A) tracks are. Results point to either alterations in protein-levels (altered gene dosage) or to the production of frame-shifted products in the cell. As such, these translational attenuation mechanisms may supplement the already large number of mechanisms through which synonymous mutations can exert biological effects (reviewed in Hunt et al. (2014) Trends Genet. TIG. 30, 308-321).

TABLE 4

Shows a table of genes with mutations within the polyA region reported in the COSMIC database.

| Gene name | mutation (nucleotide) | mutation (protein) | Type of mutation |
|---|---|---|---|
| AASDH | c.342delA | p.K114fs*14 | Deletion - Frameshift |
| ABCA5 | c.733G>A | p.E245K | Substitution - Missense |
| ABCA5 | c.742_743insA | p.I248fs*12 | Insertion - Frameshift |
| ABCA5 | c.742A>T | p.I248L | Substitution - Missense |
| ABCA5 | c.742delA | p.I248fs*1 | Deletion - Frameshift |
| ABCC2 | c.882G>C | p.K294N | Substitution - Missense |
| ACBD3 | c.568delA | p.R190fs*43 | Deletion - Frameshift |
| ADAL | c.644delA | p.E218fs*33 | Deletion - Frameshift |
| ADAL_ENST00000428046 | c.563delA | p.E191fs*33 | Deletion - Frameshift |
| AHI1 | c.910_911insA | p.T304fs*6 | Insertion - Frameshift |
| AHI1 | c.910delA | p.T304fs*23 | Deletion - Frameshift |
| AHI1 | c.911C>A | p.T304K | Substitution - Missense |
| AIM2 | c.1027A>C | p.T343P | Substitution - Missense |
| AIM2 | c.1027delA | p.T343fs? | Deletion - Frameshift |
| AKD1_ENST00000424296 | c.2091A>G | p.K697K | Substitution - coding silent |
| AKD1_ENST00000424296 | c.2098_2099delGA | p.E700fs*33 | Deletion - Frameshift |
| AKD1_ENST00000424296 | c.2098G>A | p.E700K | Substitution - Missense |
| AL118506.1 | c.48G>A | p.K16K | Substitution - coding silent |
| ALS2CR12 | c.777A>C | p.K259N | Substitution - Missense |
| ALS2CR12 | c.778A>G | p.K260E | Substitution - Missense |
| ANKHD1 | c.4385A>G | p.K1462R | Substitution - Missense |
| ANKHD1 | c.4386G>A | p.K1462K | Substitution - coding silent |
| ANKHD1-EIF4EBP3 | c.4385A>G | p.K1462R | Substitution - Missense |
| ANKHD1-EIF4EBP3 | c.4386G>A | p.K1462K | Substitution - coding silent |
| ANKRD12 | c.2806_2809delAAAC | p.K936fs*22 | Deletion - Frameshift |
| ANKRD1 | c.215_216insA | p.K73fs*10 | Insertion - Frameshift |
| ANKRD1 | c.216G>T | p.K72N | Substitution - Missense |
| ANKRD1 | c.223C>T | p.L75L | Substitution - coding silent |
| ANKRD26 | c.1340_1341insA | p.N447fs*5 | Insertion - Frameshift |
| ANKRD32_ENST00000265140 | c.987A>C | p.E329D | Substitution - Missense |
| ANKRD36C | c.2517_2518insA | p.Q840fs*11 | Insertion - Frameshift |
| ANKRD36C | c.2713A>G | p.K905E | Substitution - Missense |
| ANKRD36C | c.2716T>C | p.C906R | Substitution - Missense |
| ANKRD36C_ENST00000420871 | c.2517_2518insA | p.Q840fs*11 | Insertion - Frameshift |
| ANKRD36C_ENST00000420871 | c.2713A>G | p.K905E | Substitution - Missense |
| ANKRD36C_ENST00000420871 | c.2716T>C | p.C906R | Substitution - Missense |
| ANKRD49 | c.200delA | p.M70fs*32 | Deletion - Frameshift |
| APAF1 | c.1798_1799delAA | p.N602fs*23 | Deletion - Frameshift |
| APAF1 | c.1798delA | p.N602fs*8 | Deletion - Frameshift |
| APAF1 | c.1799A>G | p.K600R | Substitution - Missense |
| ARHGAP18 | c.1418T>G | p.M473R | Substitution - Missense |
| ARHGAP18 | c.492delA | p.K164fs*54 | Deletion - Frameshift |
| ASH1L | c.2134delA | p.R712fs*23 | Deletion - Frameshift |
| ASTE1 | c.1884_1885delAA | p.R632fs*10 | Deletion - Frameshift |
| ASTE1 | c.1892A>G | p.K631R | Substitution - Missense |
| ASTE1 | c.1894_1895insA | p.R632fs*11 | Insertion - Frameshift |
| ASTE1 | c.1894delA | p.R632fs*33 | Deletion - Frameshift |
| ATAD2 | c.354_355insA | p.E119fs*18 | Insertion - Frameshift |
| ATAD2 | c.354delA | p.E119fs*8 | Deletion - Frameshift |
| ATL1 | c.1665G>T | p.K555N | Substitution - Missense |
| ATR | c.2320_2321insA | p.I774fs*3 | Insertion - Frameshift |
| ATR | c.2320delA | p.I774fs*5 | Deletion - Frameshift |
| BARD1 | c.623_624insA | p.K209fs*5 | Insertion - Frameshift |
| BARD1 | c.623delA | p.K208fs*4 | Deletion - Frameshift |
| BARD1_ENST00000260947 | c.623_624insA | p.K209fs*5 | Insertion - Frameshift |
| BARD1_ENST00000260947 | c.623delA | p.K208fs*4 | Deletion - Frameshift |
| BAT2D1 | c.464delA | p.E158fs*66 | Deletion - Frameshift |
| BAT2D1_ENST00000392078 | c.464delA | p.E158fs*66 | Deletion - Frameshift |
| BEND5 | c.545A>G | p.K182R | Substitution - Missense |
| BEND5 | c.545delA | p.K182fs*15 | Deletion - Frameshift |
| BEND5 | c.546G>A | p.K182K | Substitution - coding silent |
| BEND5_ENST00000371833 | c.1052A>G | p.K351R | Substitution - Missense |
| BEND5_ENST00000371833 | c.1052delA | p.K351fs*15 | Deletion - Frameshift |
| BEND5_ENST00000371833 | c.1053G>A | p.K351K | Substitution - coding silent |
| BPTF | c.2874delA | p.I961fs*1 | Deletion - Frameshift |
| BPTF_ENST00000335221 | c.3252delA | p.I1087fs*1 | Deletion - Frameshift |
| BRCA1 | c.1960_1961insA | p.Y655fs*18 | Insertion - Frameshift |
| BRCA1 | c.1961_1961delA | p.K654fs*47 | Deletion - Frameshift |
| BRCA1 | c.1961_1962insA | p.Y655fs*18 | Insertion - Frameshift |
| BRCA1 | c.1961delA | p.K654fs*47 | Deletion - Frameshift |
| BRCA1_ENST00000471181 | c.1961delA | p.K654fs*47 | Deletion - Frameshift |
| BRCA2 | c.8941G>A | p.E2981K | Substitution - Missense |
| C10orf68 | c.555G>A | p.K185K | Substitution - coding silent |
| C10orf6 | c.1002A>G | p.E334E | Substitution - coding silent |
| C10orf90 | c.1991A>T | p.K664M | Substitution - Missense |
| C10orf90 | c.1992_1993GA>TT | p.K664_K665>N* | Complex - compound substitution |

TABLE 4-continued

Shows a table of genes with mutations within the polyA region reported in the COSMIC database.

| Gene name | mutation (nucleotide) | mutation (protein) | Type of mutation |
|---|---|---|---|
| C10orf90 | c.1998delA | p.E667fs*7 | Deletion - Frameshift |
| C10orf96 | c.605A>C | p.E202A | Substitution - Missense |
| C12orf45 | c.544delA | p.K184fs*>2 | Deletion - Frameshift |
| C13orf40 | c.2236_2237insA | p.I746fs*40 | Insertion - Frameshift |
| C13orf40 | c.2236delA | p.I746fs*1 | Deletion - Frameshift |
| C14orf102 | c.261G>T | p.K87N | Substitution - Missense |
| C14orf102 | c.268_269insA | p.R90fs*7 | Insertion - Frameshift |
| C14orf102 | c.268delA | p.R90fs*69 | Deletion - Frameshift |
| C14orf23 | c.342_343insA | p.T117fs*20 | Insertion - Frameshift |
| C14orf23 | c.342delA | p.T117fs*8 | Deletion - Frameshift |
| C14orf23 | c.345A>C | p.K115N | Substitution - Missense |
| C14orf23 | c.346_347insAAC | p.K116_T117insQ | Insertion - In frame |
| C14orf38 | c.1890A>G | p.K630K | Substitution - coding silent |
| C14orf38 | c.1894_1895insA | p.N632fs*6 | Insertion - Frameshift |
| C14orf38 | c.1895_1896insA | p.N632fs*6 | Insertion - Frameshift |
| C16orf45 | c.310G>T | p.E104* | Substitution - Nonsense |
| C16orf45 | c.317C>A | p.T106N | Substitution - Missense |
| C16orf88 | c.647A>C | p.K216T | Substitution - Missense |
| C16orf88 | c.652delA | p.I218fs*41 | Deletion - Frameshift |
| C18orf34 | c.874delA | p.M292fs*3 | Deletion - Frameshift |
| C18orf34_ENST00000383096 | c.874delA | p.M292fs*3 | Deletion - Frameshift |
| C1orf131 | c.416G>A | p.R139K | Substitution - Missense |
| C1orf9 | c.850G>T | p.E284* | Substitution - Nonsense |
| C1orf9_ENST00000367723 | c.1327G>T | p.E443* | Substitution - Nonsense |
| C2orf77 | c.407A>G | p.K136R | Substitution - Missense |
| C2orf77_ENST00000447353 | c.407A>G | p.K136R | Substitution - Missense |
| C3orf77 | c.1885delA | p.A632fs*5 | Deletion - Frameshift |
| C3orf77_ENST00000309765 | c.1885delA | p.A632fs*5 | Deletion - Frameshift |
| C6orf103_ENST00000367493 | c.1813delA | p.K607fs*>6 | Deletion - Frameshift |
| C6orf10 | c.1543G>A | p.E515K | Substitution - Missense |
| CAMKK2_ENST00000392474 | c.1601C>A | p.T534K | Substitution - Missense |
| CAMSAP1L1 | c.3748_3749insA | p.Q1253fs*12 | Insertion - Frameshift |
| CAMSAP1L1 | c.3749delA | p.K1252fs*19 | Deletion - Frameshift |
| CAPN3_ENST00000397163 | c.1788_1789insA | p.T599fs*33 | Insertion - Frameshift |
| CASP5 | c.153_154delAA | p.K51fs*3 | Deletion - Frameshift |
| CASP5 | c.154delA | p.T52fs*26 | Deletion - Frameshift |
| CASP5_ENST00000393141 | c.240_241delAA | p.K80fs*3 | Deletion - Frameshift |
| CASP5_ENST00000393141 | c.241delA | p.T81fs*26 | Deletion - Frameshift |
| CCBL1_ENST00000427720 | c.375_376delAA | p.K125fs*>34 | Deletion - Frameshift |
| CCDC108_ENST00000295729 | c.438delA | p.K146fs*3 | Deletion - Frameshift |
| CCDC148 | c.1260delA | p.K420fs*15 | Deletion - Frameshift |
| CCDC150 | c.838_839insA | p.E284fs*13 | Insertion - Frameshift |
| CCDC150 | c.839delA | p.E284fs*14 | Deletion - Frameshift |
| CCDC150 | c.847A>G | p.K283E | Substitution - Missense |
| CCDC150 | c.850G>A | p.E284K | Substitution - Missense |
| CCDC175 | c.1890A>G | p.K630K | Substitution - coding silent |
| CCDC34_ENST00000328697 | c.720A>G | p.L240L | Substitution - coding silent |
| CCDC34_ENST00000328697 | c.731_732insA | p.N244fs*3 | Insertion - Frameshift |
| CCDC34_ENST00000328697 | c.731delA | p.N244fs*28 | Deletion - Frameshift |
| CCT8L1 | c.1642_1643insA | p.I552fs*6 | Insertion - Frameshift |
| CCT8L2 | c.1654_1655insA | p.I552fs*6 | Insertion - Frameshift |
| CCT8L2 | c.1654delA | p.I552fs*4 | Deletion - Frameshift |
| CD46 | c.509A>G | p.N170S | Substitution - Missense |
| CDHR3_ENST00000542731 | c.2259 – 2dela | p.? | Unknown |
| CDKL2 | c.222_223insA | p.R75fs*7 | Insertion - Frameshift |
| CDKL2 | c.222delA | p.K74fs*5 | Deletion - Frameshift |
| CDYL | c.216_217insA | p.G75fs*13 | Insertion - Frameshift |
| CDYL | c.217delA | p.K76fs*25 | Deletion - Frameshift |
| CDYL | c.219A>G | p.K73K | Substitution - coding silent |
| CEP164 | c.336_337insA | p.E117fs*88 | Insertion - Frameshift |
| CEP164 | c.337delA | p.K116fs*22 | Deletion - Frameshift |
| CEP164 | c.347A>G | p.K116R | Substitution - Missense |
| CEP290 | c.828delA | p.E277fs*16 | Deletion - Frameshift |
| CHD2 | c.3724_3725insA | p.Y1246fs*13 | Insertion - Frameshift |
| CHD2 | c.3725delA | p.K1245fs*4 | Deletion - Frameshift |
| CHD2_ENST00000394196 | c.3725delA | p.K1245fs*4 | Deletion - Frameshift |
| CHD7 | c.1922A>T | p.K641I | Substitution - Missense |
| CHD7_ENST00000423902 | c.1922A>T | p.K641I | Substitution - Missense |
| CHEK1 | c.668A>C | p.E223A | Substitution - Missense |
| CHEK1 | c.668delA | p.T226fs*14 | Deletion - Frameshift |
| CHEK1 | c.675A>G | p.K225K | Substitution - coding silent |
| CIR1 | c.865delA | p.I289fs*51 | Deletion - Frameshift |
| CNTRL_ENST00000373855 | c.1328delA | p.I446fs*1 | Deletion - Frameshift |
| COL17A1 | c.1170delA | p.E391fs*12 | Deletion - Frameshift |
| COL17A1 | c.1171G>C | p.E391Q | Substitution - Missense |
| CPNE3 | c.771G>A | p.K257K | Substitution - coding silent |

TABLE 4-continued

Shows a table of genes with mutations within the polyA region reported in the COSMIC database.

| Gene name | mutation (nucleotide) | mutation (protein) | Type of mutation |
|---|---|---|---|
| CPNE3 | c.771G>T | p.K257N | Substitution - Missense |
| CWC27 | c.995delA | p.V335fs*1 | Deletion - Frameshift |
| CWF19L2_ENST00000282251 | c.279G>T | p.K93N | Substitution - Missense |
| CWF19L2_ENST00000282251 | c.287delA | p.K96fs*41 | Deletion - Frameshift |
| DCLRE1C | c.1706A>C | p.K569T | Substitution - Missense |
| DCLRE1C | c.1708delA | p.R570fs*6 | Deletion - Frameshift |
| DCLRE1C_ENST00000378278 | c.2051A>C | p.K684T | Substitution - Missense |
| DCLRE1C_ENST00000378278 | c.2053delA | p.R685fs*6 | Deletion - Frameshift |
| DDX18 | c.327G>T | p.K109N | Substitution - Missense |
| DDX18 | c.333G>T | p.K111N | Substitution - Missense |
| DDX59 | c.1294A>G | p.K432E | Substitution - Missense |
| DDX59_ENST00000331314 | c.1294A>G | p.K432E | Substitution - Missense |
| DENR | c.317delA | p.K108fs*10 | Deletion - Frameshift |
| DHX36 | c.2560delA | p.R854fs*4 | Deletion - Frameshift |
| DHX36 | c.2564A>T | p.K855I | Substitution - Missense |
| DHX36 | c.460_461insA | p.M154fs*3 | Insertion - Frameshift |
| DHX36 | c.460delA | p.M154fs*27 | Deletion - Frameshift |
| DHX36 | c.461_462insA | p.M154fs*3 | Insertion - Frameshift |
| DHX36 | c.578delA | p.N193fs*25 | Deletion - Frameshift |
| DIAPH2 | c.208G>T | p.E70* | Substitution - Nonsense |
| DIAPH3 | c.952A>C | p.K318Q | Substitution - Missense |
| DIAPH3 | c.958delA | p.I320fs*20 | Deletion - Frameshift |
| DNAH6 | c.6440G>T | p.R2147I | Substitution - Missense |
| DNAJC1 | c.578_579insA | p.T194fs*18 | Insertion - Frameshift |
| DNAJC2 | c.590_591insA | p.N197fs*4 | Insertion - Frameshift |
| DNAJC2 | c.590delA | p.N197fs*8 | Deletion - Frameshift |
| DSEL | c.2905_2906insA | p.R969fs*4 | Insertion - Frameshift |
| DSEL | c.2905delA | p.R969fs*16 | Deletion - Frameshift |
| DSEL | c.2910A>C | p.K970N | Substitution - Missense |
| DSEL | c.2910A>T | p.K970N | Substitution - Missense |
| DYNC1I2 | c.97delA | p.E36fs*34 | Deletion - Frameshift |
| DYNC2H1_ENST00000398093 | c.832A>C | p.N278H | Substitution - Missense |
| EEA1 | c.2428A>C | p.K810Q | Substitution - Missense |
| EFCAB7 | c.1138_1139insA | p.I380fs*7 | Insertion - Frameshift |
| EHBP1 | c.1026delA | p.N344fs*2 | Deletion - Frameshift |
| EIF2AK2 | c.1531G>T | p.E511* | Substitution - Nonsense |
| EIF3J | c.222G>C | p.K74N | Substitution - Missense |
| EIF3J | c.223delA | p.I77fs*1 | Deletion - Frameshift |
| EIF3J | c.229delA | p.I77fs*1 | Deletion - Frameshift |
| EML6 | c.4063delA | p.K1357fs*9 | Deletion - Frameshift |
| EML6 | c.4071G>T | p.K1357N | Substitution - Missense |
| ENSG00000121031 | c.10811delA | p.N3604fs*48 | Deletion - Frameshift |
| ENSG00000121031 | c.496_497insA | p.I166fs*11 | Insertion - Frameshift |
| ENSG00000121031 | c.496delA | p.I166fs*6 | Deletion - Frameshift |
| ENSG00000174501 | c.4764_4765insA | p.Q1589fs*11 | Insertion - Frameshift |
| ENSG00000174501 | c.4960A>G | p.K1654E | Substitution - Missense |
| ENSG00000174501 | c.4963T>C | p.C1655R | Substitution - Missense |
| ENSG00000188423 | c.651A>G | p.K217K | Substitution - coding silent |
| ENSG00000188423 | c.658_659delGA | p.E220fs*33 | Deletion - Frameshift |
| ENSG00000188423 | c.658G>A | p.E220K | Substitution - Missense |
| ENSG00000225516 | c.313A>C | p.K105Q | Substitution - Missense |
| ENSG00000268852 | c.52A>T | p.K18* | Substitution - Nonsense |
| ERC2 | c.1528delA | p.T510fs*21 | Deletion - Frameshift |
| ERC2_ENST00000288221 | c.1528delA | p.T510fs*21 | Deletion - Frameshift |
| ERCC4 | c.1461G>C | p.K487N | Substitution - Missense |
| ERICH1 | c.487delA | p.R163fs*3 | Deletion - Frameshift |
| ERO1LB | c.188A>C | p.K63T | Substitution - Missense |
| ESCO2 | c.1117G>C | p.D373H | Substitution - Missense |
| F5 | c.3096G>C | p.K1032N | Substitution - Missense |
| F5 | c.3102A>C | p.K1034N | Substitution - Missense |
| F8 | c.3632A>C | p.K1211T | Substitution - Missense |
| F8 | c.3637delA | p.I1213fs*5 | Deletion - Frameshift |
| F8 | c.3638T>G | p.I1213S | Substitution - Missense |
| F8_ENST00000360256 | c.3632A>C | p.K1211T | Substitution - Missense |
| F8_ENST00000360256 | c.3637delA | p.I1213fs*5 | Deletion - Frameshift |
| F8_ENST00000360256 | c.3638T>G | p.I1213S | Substitution - Missense |
| FAM133A | c.150T>G | p.N50K | Substitution - Missense |
| FAM178A | c.1002A>G | p.E334E | Substitution - coding silent |
| FAM186A_ENST00000327337 | c.2261delA | p.K754fs*2 | Deletion - Frameshift |
| FAM200B | c.170_173delAAGT | p.S59fs*9 | Deletion - Frameshift |
| FAM200B_ENST00000422728 | c.170_173delAAGT | p.S59fs*9 | Deletion - Frameshift |
| FAM83F_ENST00000536633 | c.1065delA | p.K357fs*8 | Deletion - Frameshift |
| FAM9A | c.477_478insA | p.Q160fs*8 | Insertion - Frameshift |
| FAM9A | c.477delA | p.K159fs*3 | Deletion - Frameshift |
| FAM9A | c.480A>G | p.Q160Q | Substitution - coding silent |
| FASTKD1 | c.2213G>T | p.R738I | Substitution - Missense |

TABLE 4-continued

Shows a table of genes with mutations within the polyA region reported in the COSMIC database.

| Gene name | mutation (nucleotide) | mutation (protein) | Type of mutation |
|---|---|---|---|
| FASTKD1 | c.2216A>G | p.K739R | Substitution - Missense |
| FASTKD1 | c.2220delA | p.K740fs*10 | Deletion - Frameshift |
| FAT4 | c.12401delA | p.K4136fs*17 | Deletion - Frameshift |
| FBXO38 | c.2083delA | p.N697fs*32 | Deletion - Frameshift |
| FBXO38 | c.2085A>G | p.K695K | Substitution - coding silent |
| FERMT2 | c.452A>C | p.K151T | Substitution - Missense |
| FERMT2 | c.455delA | p.K152fs*4 | Deletion - Frameshift |
| FERMT2 | c.456G>A | p.K152K | Substitution - coding silent |
| FERMT2 | c.456G>AG | p.K153fs*5 | Complex - frameshift |
| FEZ2 | c.837G>T | p.K279N | Substitution - Missense |
| FEZ2 | c.838A>G | p.K280E | Substitution - Missense |
| FLG | c.476_477insA | p.E160fs*10 | Insertion - Frameshift |
| FLG | c.477_478insA | p.E160fs*10 | Insertion - Frameshift |
| FLJ45831 | c.312G>T | p.K104N | Substitution - Missense |
| FRA10AC1 | c.694_695insA | p.R232fs*4 | Insertion - Frameshift |
| FRA10AC1 | c.694delA | p.R232fs*>84 | Deletion - Frameshift |
| FRA10AC1_ENST00000371426 | c.694_695insA | p.R232fs*4 | Insertion - Frameshift |
| FRA10AC1_ENST00000371426 | c.694delA | p.R232fs*67 | Deletion - Frameshift |
| GIMAP7 | c.776delA | p.I261fs*1 | Deletion - Frameshift |
| GOLGA4 | c.4091delA | p.V1367fs*10 | Deletion - Frameshift |
| GPR110 | c.95_96insA | p.E33fs*6 | Insertion - Frameshift |
| GPR110 | c.95_96insT | p.K32fs*7 | Insertion - Frameshift |
| GPR110_ENST00000371243 | c.95_96insA | p.E33fs*6 | Insertion - Frameshift |
| GRK4_ENST00000398052 | c.656delA | p.R222fs*2 | Deletion - Frameshift |
| GRK4_ENST00000398052 | c.666_669delAATA | p.I223fs*10 | Deletion - Frameshift |
| GRK4_ENST00000398052 | c.668T>A | p.I223K | Substitution - Missense |
| GRLF1 | c.570A>T | p.K190N | Substitution - Missense |
| GRLF1_ENST00000317082 | c.570A>T | p.K190N | Substitution - Missense |
| GRLF1_ENST00000317082 | c.578A>C | p.K193T | Substitution - Missense |
| HELLS | c.454delA | p.N154fs*29 | Deletion - Frameshift |
| HERC5 | c.409_410insA | p.I140fs*19 | Insertion - Frameshift |
| HERC5 | c.410delA | p.I140fs*1 | Deletion - Frameshift |
| HERC5 | c.416A>T | p.K139I | Substitution - Missense |
| HMGXB4 | c.1163delA | p.K391fs*33 | Deletion - Frameshift |
| HMGXB4 | c.1173G>A | p.K391K | Substitution - coding silent |
| HMMR | c.1990_1991delAA | p.K666fs*3 | Deletion - Frameshift |
| HMMR | c.1990delA | p.K666fs*11 | Deletion - Frameshift |
| IQGAP2 | c.4364G>T | p.R1455I | Substitution - Missense |
| ITIH5_ENST00000397146 | c.2020C>A | p.Q674K | Substitution - Missense |
| ITPR2 | c.3123 − 1G>A | p.? | Unknown |
| ITPR2 | c.3127G>T | p.E1043* | Substitution - Nonsense |
| JMJD1C | c.5357A>G | p.E1786G | Substitution - Missense |
| JMJD1C | c.5364delA | p.E1789fs*45 | Deletion - Frameshift |
| JMJD1C_ENST00000399262 | c.6068A>G | p.E2023G | Substitution - Missense |
| JMJD1C_ENST00000399262 | c.6075delA | p.E2026fs*45 | Deletion - Frameshift |
| KCNC1 | c.1362_1363insA | p.K458fs*16 | Insertion - Frameshift |
| KCNC1 | c.1363delA | p.K457fs*20 | Deletion - Frameshift |
| KCNC1_ENST00000265969 | c.1362_1363insA | p.K458fs*16 | Insertion - Frameshift |
| KCNC1_ENST00000265969 | c.1363delA | p.K457fs*20 | Deletion - Frameshift |
| KCNQ1 | c.1257G>T | p.K419N | Substitution - Missense |
| KCNQ1 | c.1258delA | p.K422fs*10 | Deletion - Frameshift |
| KDM2B_ENST00000377071 | c.75A>C | p.K25N | Substitution - Missense |
| KDM2B_ENST00000377071 | c.77delA | p.K26fs*81 | Deletion - Frameshift |
| KDM2B_ENST00000377071 | c.82_83delAC | p.T28fs*8 | Deletion - Frameshift |
| KDM4D | c.271delA | p.K93fs*4 | Deletion - Frameshift |
| KIAA1279 | c.1509delA | p.I506fs*1 | Deletion - Frameshift |
| KIAA1731 | c.1649G>A | p.R550K | Substitution - Missense |
| KIAA1731_ENST00000325212 | c.1649G>A | p.R550K | Substitution - Missense |
| KIAA2018 | c.3045A>C | p.K1015N | Substitution - Missense |
| KIAA2018 | c.3046_3047delAA | p.N1016fs*8 | Deletion - Frameshift |
| KIAA2018 | c.3046_3047insA | p.N1016fs*9 | Insertion - Frameshift |
| KIAA2018 | c.3046A>C | p.N1016H | Substitution - Missense |
| KIAA2018 | c.3047delA | p.N1016fs*23 | Deletion - Frameshift |
| KIAA2026_ENST00000399933 | c.2069delA | p.K690fs*3 | Deletion - Frameshift |
| KIAA2026_ENST00000399933 | c.2074T>C | p.L692L | Substitution - coding silent |
| KIF5B | c.1045G>T | p.E349* | Substitution - Nonsense |
| KIF6 | c.1458G>C | p.K486N | Substitution - Missense |
| KIF6_ENST00000287152 | c.1458G>C | p.K486N | Substitution - Missense |
| KRCC1 | c.715A>G | p.K239E | Substitution - Missense |
| LAMB4 | c.4803A>T | p.K1601N | Substitution - Missense |
| LMOD2_ENST00000458573 | c.1432A>C | p.K478Q | Substitution - Missense |
| LMOD2_ENST00000458573 | c.1437G>T | p.K479N | Substitution - Missense |
| LRRC17 | c.597A>C | p.K199N | Substitution - Missense |
| LRRIQ1 | c.818A>G | p.E273G | Substitution - Missense |
| LRRIQ1_ENST00000393217 | c.4615_4616insA | p.I1542fs*8 | Insertion - Frameshift |
| LRRIQ1_ENST00000393217 | c.4616delA | p.I1542fs*17 | Deletion - Frameshift |

TABLE 4-continued

Shows a table of genes with mutations within the polyA region reported in the COSMIC database.

| Gene name | mutation (nucleotide) | mutation (protein) | Type of mutation |
|---|---|---|---|
| LRRIQ1_ENST00000393217 | c.4623A>G | p.K1541K | Substitution - coding silent |
| LRRIQ1_ENST00000393217 | c.4624A>G | p.I1542V | Substitution - Missense |
| LRRIQ1_ENST00000393217 | c.4625T>A | p.I1542N | Substitution - Missense |
| LRRIQ1_ENST00000393217 | c.5095_5096insA | p.N1702fs*13 | Insertion - Frameshift |
| LRRIQ1_ENST00000393217 | c.5096delA | p.N1702fs*20 | Deletion - Frameshift |
| LTN1 | c.1597_1598delAA | p.N536fs*2 | Deletion - Frameshift |
| LTN1 | c.1607delA | p.N536fs*33 | Deletion - Frameshift |
| LTN1 | c.1608T>G | p.N536K | Substitution - Missense |
| MAP7D3 | c.2567A>C | p.K856T | Substitution - Missense |
| MAP9 | c.1733A>C | p.K578T | Substitution - Missense |
| MARCKS | c.454delA | p.K155fs*12 | Deletion - Frameshift |
| MCF2 | c.773T>A | p.I258K | Substitution - Missense |
| MCF2 | c.774A>T | p.I258I | Substitution - coding silent |
| MCF2 | c.780_781insA | p.L261fs*6 | Insertion - Frameshift |
| MCF2_ENST00000370573 | c.773T>A | p.I258K | Substitution - Missense |
| MCF2_ENST00000370573 | c.774A>T | p.I258I | Substitution - coding silent |
| MCF2_ENST00000370573 | c.780_781insA | p.L261fs*6 | Insertion - Frameshift |
| MCF2_ENST00000370578 | c.1208T>A | p.I403K | Substitution - Missense |
| MCF2_ENST00000519895 | c.953T>A | p.I318K | Substitution - Missense |
| MCF2_ENST00000519895 | c.954A>T | p.I318I | Substitution - coding silent |
| MCF2_ENST00000519895 | c.960_961insA | p.L321fs*6 | Insertion - Frameshift |
| MIS18BP1 | c.471delA | p.K157fs*24 | Deletion - Frameshift |
| MLH3 | c.1755_1756insA | p.E586fs*3 | Insertion - Frameshift |
| MLH3 | c.1755delA | p.E586fs*24 | Deletion - Frameshift |
| MLH3 | c.1756G>T | p.E586* | Substitution - Nonsense |
| MLH3_ENST00000355774 | c.1755_1756insA | p.E586fs*3 | Insertion - Frameshift |
| MLH3_ENST00000355774 | c.1755delA | p.E586fs*24 | Deletion - Frameshift |
| MLH3_ENST00000355774 | c.1756G>T | p.E586* | Substitution - Nonsense |
| MORC1 | c.2634A>C | p.E878D | Substitution - Missense |
| MORC1 | c.2641_2642insA | p.I881fs*11 | Insertion - Frameshift |
| MORC1 | c.2641delA | p.I881fs*1 | Deletion - Frameshift |
| MPP3 | c.1538C>T | p.T513M | Substitution - Missense |
| MPP6 | c.910delA | p.K306fs*4 | Deletion - Frameshift |
| MTDH | c.1341G>A | p.K447K | Substitution - coding silent |
| MTDH | c.1342A>T | p.K448* | Substitution - Nonsense |
| MTIF2 | c.1975T>A | p.F659I | Substitution - Missense |
| MYCBP2 | c.1124delA | p.K375fs*4 | Deletion - Frameshift |
| MYCBP2_ENST00000357337 | c.1124delA | p.K375fs*4 | Deletion - Frameshift |
| MYCBP2_ENST00000407578 | c.1238delA | p.K413fs*4 | Deletion - Frameshift |
| MYT1L | c.182G>T | p.R61I | Substitution - Missense |
| MYT1L | c.187A>G | p.T63A | Substitution - Missense |
| NAA16 | c.1883G>C | p.R628T | Substitution - Missense |
| NAA35 | c.1692G>A | p.K564K | Substitution - coding silent |
| NAA35 | c.1693delA | p.K567fs*6 | Deletion - Frameshift |
| NEK1 | c.3156A>G | p.K1052K | Substitution - coding silent |
| NEK1_ENST00000507142 | c.3156A>G | p.K1052K | Substitution - coding silent |
| NHLRC2 | c.1517_1518insA | p.N508fs*13 | Insertion - Frameshift |
| NHLRC2 | c.1522A>C | p.N508H | Substitution - Missense |
| NIPBL | c.1507delA | p.R505fs*35 | Deletion - Frameshift |
| NIPBL_ENST00000448238 | c.1507delA | p.R505fs*35 | Deletion - Frameshift |
| NKRF | c.700A>C | p.K234Q | Substitution - Missense |
| NKRF_ENST00000542113 | c.745A>C | p.K249Q | Substitution - Missense |
| NKTR | c.1297_1298insA | p.V436fs*2 | Insertion - Frameshift |
| NOL7 | c.707delA | p.K238fs*16 | Deletion - Frameshift |
| NOL7 | c.716delA | p.N240fs*14 | Deletion - Frameshift |
| NOP58 | c.1564delA | p.K524fs*>6 | Deletion - Frameshift |
| NUFIP1 | c.494delA | p.K165fs*38 | Deletion - Frameshift |
| NUP85 | c.127 + 2T>C | p.? | Unknown |
| OR6C76 | c.921_922insA | p.H312fs*>2 | Insertion - Frameshift |
| OR6C76 | c.921C>A | p.H307Q | Substitution - Missense |
| OR6C76 | c.922_923delAA | p.K311fs*>2 | Deletion - Frameshift |
| OR6C76 | c.922delA | p.K311fs*>2 | Deletion - Frameshift |
| OR6C76 | c.932A>C | p.K311T | Substitution - Missense |
| PA2G4 | c.1108delA | p.K372fs*16 | Deletion - Frameshift |
| PA2G4 | c.1116G>T | p.K372N | Substitution - Missense |
| PARP14 | c.4200G>T | p.K1400N | Substitution - Missense |
| PARP14_ENST00000474629 | c.4689G>T | p.K1563N | Substitution - Missense |
| PCDH7 | c.2685A>G | p.K895K | Substitution - coding silent |
| PCDH7_ENST00000361762 | c.2826A>G | p.K942K | Substitution - coding silent |
| PCDHA12 | c.552delA | p.D187fs*8 | Deletion - Frameshift |
| PCDHA12 | c.559G>T | p.D187Y | Substitution - Missense |
| PDCL2 | c.253A>G | p.K85E | Substitution - Missense |
| PDCL2 | c.262A>C | p.K88Q | Substitution - Missense |
| PKD2L2 | c.904delA | p.I304fs*1 | Deletion - Frameshift |
| PKD2L2 | c.916G>T | p.E306* | Substitution - Nonsense |
| PKD2L2_ENST00000508883 | c.916G>T | p.E306* | Substitution - Nonsense |

TABLE 4-continued

Shows a table of genes with mutations within the polyA region reported in the COSMIC database.

| Gene name | mutation (nucleotide) | mutation (protein) | Type of mutation |
|---|---|---|---|
| PLXNC1 | c.4192delA | p.I1400fs*21 | Deletion - Frameshift |
| PLXNC1 | c.4196A>C | p.K1399T | Substitution - Missense |
| PNISR | c.806A>G | p.K269R | Substitution - Missense |
| PNISR | c.807_808insA | p.A270fs*6 | Insertion - Frameshift |
| PPFIA2 | c.2527A>G | p.K843E | Substitution - Missense |
| PPFIA2 | c.2529A>G | p.K843K | Substitution - coding silent |
| PPP1R10 | c.924A>G | p.K308K | Substitution - coding silent |
| PPP1R10 | c.930delA | p.V311fs*79 | Deletion - Frameshift |
| PPP2R3C | c.67_68insA | p.S23fs*2 | Insertion - Frameshift |
| PPP2R3C | c.67delA | p.S23fs*5 | Deletion - Frameshift |
| PRKDC | c.10814delA | p.N3605fs*48 | Deletion - Frameshift |
| PRKDC | c.496_497insA | p.I166fs*11 | Insertion - Frameshift |
| PRKDC | c.496delA | p.I166fs*6 | Deletion - Frameshift |
| PRPF40A | c.1167 + 3A>T | p.? | Unknown |
| PRPF40A_ENST00000359961 | c.1560 + 3A>T | p.? | Unknown |
| PRPF40A_ENST00000410080 | c.1479 + 3A>T | p.? | Unknown |
| PRR11 | c.58delA | p.E23fs*9 | Deletion - Frameshift |
| PTHLH_ENST00000354417 | c.557delA | p.K186fs*12 | Deletion - Frameshift |
| PTPLAD1 | c.1074G>T | p.K358N | Substitution - Missense |
| PTPLAD1 | c.1077A>C | p.K359N | Substitution - Missense |
| PTPRC | c.2404G>T | p.E802* | Substitution - Nonsense |
| PTPRZ1 | c.5636delA | p.K1879fs*34 | Deletion - Frameshift |
| PTPRZ1_ENST00000393386 | c.5636delA | p.K1879fs*34 | Deletion - Frameshift |
| PXK | c.1367_1368insA | p.R459fs*15 | Insertion - Frameshift |
| PXK_ENST00000356151 | c.1367_1368insA | p.R459fs*15 | Insertion - Frameshift |
| PYHIN1 | c.416_417insA | p.P142fs*3 | Insertion - Frameshift |
| PYHIN1 | c.423_424insA | p.P142fs*3 | Insertion - Frameshift |
| PYHIN1 | c.424C>A | p.P142T | Substitution - Missense |
| PYHIN1_ENST00000368135 | c.424C>A | p.P142T | Substitution - Missense |
| PYH1N1_ENST00000392254 | c.424C>A | p.P142T | Substitution - Missense |
| Q99543-2 | c.590_591insA | p.N197fs*4 | Insertion - Frameshift |
| Q99543-2 | c.590delA | p.N197fs*8 | Deletion - Frameshift |
| RAD23B_ENST00000457811 | c.312_313delAA | p.K108fs*38 | Deletion - Frameshift |
| RALGAPA1 | c.5582delA | p.N1861fs*6 | Deletion - Frameshift |
| RALGAPA1_ENST00000307138 | c.5582delA | p.N1861fs*6 | Deletion - Frameshift |
| RASAL2 | c.1097A>G | p.E366G | Substitution - Missense |
| RASAL2 | c.1104_1105insA | p.D372fs*4 | Insertion - Frameshift |
| RASAL2 | c.1104G>C | p.K368N | Substitution - Missense |
| RASAL2 | c.1105_1106insA | p.D372fs*4 | Insertion - Frameshift |
| RASAL2 | c.1105delA | p.K371fs*7 | Deletion - Frameshift |
| RASAL2 | c.1111_1112insA | p.D372fs*4 | Insertion - Frameshift |
| RASAL2 | c.1112_1113insA | p.D372fs*4 | Insertion - Frameshift |
| RASAL2_ENST00000367649 | c.1151A>G | p.E384G | Substitution - Missense |
| RASAL2_ENST00000367649 | c.1158_1159insA | p.D390fs*4 | Insertion - Frameshift |
| RASAL2_ENST00000367649 | c.1158G>C | p.K386N | Substitution - Missense |
| RASAL2_ENST00000367649 | c.1159_1160insA | p.D390fs*4 | Insertion - Frameshift |
| RASAL2_ENST00000367649 | c.1159delA | p.K389fs*7 | Deletion - Frameshift |
| RASAL2_ENST00000367649 | c.1165_1166insA | p.D390fs*4 | Insertion - Frameshift |
| RASAL2_ENST00000367649 | c.1166_1167insA | p.D390fs*4 | Insertion - Frameshift |
| RASAL2_ENST00000462775 | c.707A>G | p.E236G | Substitution - Missense |
| RASAL2_ENST00000462775 | c.714_715insA | p.D242fs*4 | Insertion - Frameshift |
| RASAL2_ENST00000462775 | c.714G>C | p.K238N | Substitution - Missense |
| RASAL2_ENST00000462775 | c.715_716insA | p.D242fs*4 | Insertion - Frameshift |
| RASAL2_ENST00000462775 | c.715delA | p.K241fs*7 | Deletion - Frameshift |
| RBM43 | c.205G>T | p.E69* | Substitution - Nonsense |
| RBM43 | c.213_214insA | p.V72fs*18 | Insertion - Frameshift |
| RBM43 | c.213delA | p.V72fs*13 | Deletion - Frameshift |
| RBMX2 | c.491delA | p.K166fs*29 | Deletion - Frameshift |
| RBMX2 | c.498_499insA | p.K170fs*30 | Insertion - Frameshift |
| RBMX2 | c.503A>C | p.K168T | Substitution - Missense |
| RBMX2 | c.505A>G | p.K169E | Substitution - Missense |
| RBMX2 | c.506A>G | p.K169R | Substitution - Missense |
| RBMX2 | c.511_514delGAAA | p.E171fs*23 | Deletion - Frameshift |
| RBPJ | c.202delA | p.E71fs*21 | Deletion - Frameshift |
| RBPJ | c.204A>G | p.K68K | Substitution - coding silent |
| RBPJ_ENST00000348160 | c.205delA | p.E72fs*21 | Deletion - Frameshift |
| RBPJ_ENST00000348160 | c.207A>G | p.K69K | Substitution - coding silent |
| RDX | c.628A>C | p.N210H | Substitution - Missense |
| REV3L | c.4543G>A | p.E1515K | Substitution - Missense |
| REV3L | c.4543G>T | p.E1515* | Substitution - Nonsense |
| REV3L | c.4550T>C | p.I1517T | Substitution - Missense |
| REV3L_ENST00000358835 | c.4777G>T | p.E1593* | Substitution - Nonsense |
| REV3L_ENST00000358835 | c.4784T>C | p.I1595T | Substitution - Missense |
| RG9MTD1 | c.384delA | p.K131fs*3 | Deletion - Frameshift |
| RIF1 | c.4507delA | p.K1505fs*18 | Deletion - Frameshift |
| RNASEH2B | c.917A>C | p.K306T | Substitution - Missense |

TABLE 4-continued

Shows a table of genes with mutations within the polyA region reported in the COSMIC database.

| Gene name | mutation (nucleotide) | mutation (protein) | Type of mutation |
|---|---|---|---|
| RNASEH2B | c.926T>A | p.I309N | Substitution - Missense |
| RNASEH2B | c.926T>C | p.I309T | Substitution - Missense |
| RNF145 | c.68A>G | p.K23R | Substitution - Missense |
| RNF145 | c.68delA | p.K23fs*17 | Deletion - Frameshift |
| RNF145 | c.69G>A | p.K23K | Substitution - coding silent |
| RNF145 | c.70A>G | p.K24E | Substitution - Missense |
| RNF145 | c.71A>G | p.K24R | Substitution - Missense |
| RNF145 | c.79_80delAA | p.N27fs*43 | Deletion - Frameshift |
| RNF145 | c.80delA | p.N27fs*13 | Deletion - Frameshift |
| RNF145 | c.81C>A | p.N27K | Substitution - Missense |
| RNPC3 | c.346_347insA | p.R120fs*3 | Insertion - Frameshift |
| RNPC3 | c.347delA | p.R120fs*18 | Deletion - Frameshift |
| ROCK1_ENST00000399799 | c.149A>C | p.K50T | Substitution - Missense |
| RPL9 | c.150G>A | p.K50K | Substitution - coding silent |
| RPL9 | c.158A>G | p.K53R | Substitution - Missense |
| RPL9 | c.159G>T | p.K53N | Substitution - Missense |
| RSPO3 | c.659_660insA | p.P223fs*2 | Insertion - Frameshift |
| RYR1 | c.8508G>T | p.K2836N | Substitution - Missense |
| RYR1 | c.8509delA | p.T2839fs*89 | Deletion - Frameshift |
| SAT1_ENST00000379251 | c.439delA | p.N150fs*13 | Deletion - Frameshift |
| SCAF11 | c.2995_2999delGAAAA | p.E999fs*2 | Deletion - Frameshift |
| SCAF11 | c.3002_3003insA | p.N1001fs*2 | Insertion - Frameshift |
| SCAF11 | c.3002delA | p.N1001fs*5 | Deletion - Frameshift |
| SCAPER | c.2603delA | p.N868fs*8 | Deletion - Frameshift |
| SCAPER | c.2605A>T | p.K869* | Substitution - Nonsense |
| SCAPER | c.2613delA | p.A872fs*4 | Deletion - Frameshift |
| SCAPER_ENST00000538941 | c.1867A>T | p.K623* | Substitution - Nonsense |
| SCAPER_ENST00000538941 | c.1875delA | p.A626fs*4 | Deletion - Frameshift |
| SEC63 | c.1586delA | p.K529fs*4 | Deletion - Frameshift |
| SEC63 | c.1587G>T | p.K529N | Substitution - Missense |
| SENP7 | c.230A>G | p.K77R | Substitution - Missense |
| SENP7_ENST00000394095 | c.230A>G | p.K77R | Substitution - Missense |
| SEPT7_ENST00000469679 | c.683C>A | p.A228E | Substitution - Missense |
| SH3RF1 | c.2151G>A | p.K717K | Substitution - coding silent |
| SHPRH | c.495_496insA | p.E166fs*7 | Insertion - Frameshift |
| SHPRH | c.495delA | p.E166fs*3 | Deletion - Frameshift |
| SLC16A12_ENST00000371790 | c.83G>C | p.R28T | Substitution - Missense |
| SLC22A9 | c.1005A>C | p.K335N | Substitution - Missense |
| SLC22A9 | c.995delA | p.K335fs*67 | Deletion - Frameshift |
| SLC45A2 | c.865A>C | p.K289Q | Substitution - Missense |
| SLC46A3 | c.154A>C | p.K52Q | Substitution - Missense |
| SLC46A3_ENST00000380814 | c.154A>C | p.K52Q | Substitution - Missense |
| SLC4A7 | c.3450G>C | p.K1150N | Substitution - Missense |
| SLCO5A1 | c.1148A>G | p.K383R | Substitution - Missense |
| SLCO5A1 | c.1150T>G | p.F384V | Substitution - Missense |
| SLTM | c.1539delA | p.E514fs*8 | Deletion - Frameshift |
| SLTM | c.1540G>T | p.E514* | Substitution - Nonsense |
| SMAD5 | c.137A>G | p.K46R | Substitution - Missense |
| SMC1B_ENST00000357450 | c.2444C>G | p.T815S | Substitution - Missense |
| SMC2 | c.814delA | p.I274fs*1 | Deletion - Frameshift |
| SMC2 | c.822A>G | p.I274M | Substitution - Missense |
| SMC2_ENST00000303219 | c.822A>G | p.I274M | Substitution - Missense |
| SMC2L1 | c.814delA | p.I274fs*1 | Deletion - Frameshift |
| SMC2L1 | c.822A>G | p.I274M | Substitution - Missense |
| SMNDC1 | c.567C>A | p.N189K | Substitution - Missense |
| SNX6 | c.538A>T | p.K180* | Substitution - Nonsense |
| SP100_ENST00000341950 | c.1349_1350insA | p.K455fs*>20 | Insertion - Frameshift |
| SPATA1 | c.1345delA | p.I452fs*1 | Deletion - Frameshift |
| SPEF2 | c.711G>A | p.K237K | Substitution - coding silent |
| SPEF2 | c.712A>G | p.K238E | Substitution - Missense |
| SPEF2_ENST00000356031 | c.2649_2650delAA | p.K886fs*2 | Deletion - Frameshift |
| SPEF2_ENST00000356031 | c.2649delA | p.K886fs*8 | Deletion - Frameshift |
| SPEF2_ENST00000356031 | c.711G>A | p.K237K | Substitution - coding silent |
| SPEF2_ENST00000356031 | c.712A>G | p.K238E | Substitution - Missense |
| SPINK5 | c.2459delA | p.K823fs*101 | Deletion - Frameshift |
| SREK1IP1 | c.363A>C | p.K121N | Substitution - Missense |
| SYCP1 | c.2891_2892insA | p.L968fs*5 | Insertion - Frameshift |
| SYCP1 | c.2892delA | p.K967fs*2 | Deletion - Frameshift |
| SYCP2 | c.3062_3063insT | p.N1024fs*3 | Insertion - Frameshift |
| SYCP2 | c.3071delA | p.N1024fs*26 | Deletion - Frameshift |
| TAF1B | c.187_188delAA | p.N66fs*3 | Deletion - Frameshift |
| TAF1B | c.187_189delAAA | p.K65delK | Deletion - In frame |
| TAF1B | c.187delA | p.N66fs*26 | Deletion - Frameshift |
| TAF1B | c.198C>A | p.N66K | Substitution - Missense |
| TAF1D | c.281_282insA | p.K95fs*28 | Insertion - Frameshift |
| TAF1D | c.281delA | p.K94fs*26 | Deletion - Frameshift |

TABLE 4-continued

Shows a table of genes with mutations within the polyA region reported in the COSMIC database.

| Gene name | mutation (nucleotide) | mutation (protein) | Type of mutation |
|---|---|---|---|
| TAF7L | c.1331A>C | p.Q444P | Substitution - Missense |
| TAF7L | c.1333A>C | p.K445Q | Substitution - Missense |
| TAOK1_ENST00000261716 | c.1738G>A | p.E580K | Substitution - Missense |
| TCF25 | c.384_385insA | p.Q132fs*27 | Insertion - Frameshift |
| TCF25 | c.385delA | p.K131fs*17 | Deletion - Frameshift |
| TCF25 | c.393_394insA | p.Q132fs*27 | Insertion - Frameshift |
| TCOF1 | c.4127delA | p.E1379fs*>33 | Deletion - Frameshift |
| TCOF1_ENST00000504761 | c.4358delA | p.E1456fs*>33 | Deletion - Frameshift |
| TCP1 | c.730A>C | p.T244P | Substitution - Missense |
| TDRD5 | c.1243G>A | p.E415K | Substitution - Missense |
| TET1_ENST00000373644 | c.57C>A | p.N19K | Substitution - Missense |
| TET1_ENST00000373644 | c.58delA | p.K22fs*23 | Deletion - Frameshift |
| TEX10 | c.11_13delAAA | p.K4delK | Deletion - In frame |
| TEX10 | c.13delA | p.R5fs*10 | Deletion - Frameshift |
| TEX15 | c.5122delA | p.R1708fs*3 | Deletion - Frameshift |
| TFAM | c.432delA | p.E148fs*2 | Deletion - Frameshift |
| TFAM | c.441 + 2T>G | p.? | Unknown |
| TFAM_ENST00000395377 | c.376delA | p.T126fs*6 | Deletion - Frameshift |
| THOC2 | c.2531A>G | p.K844R | Substitution - Missense |
| THOC2_ENST00000245838 | c.2768A>G | p.K923R | Substitution - Missense |
| TIF1 | c.2574G>A | p.K858K | Substitution - coding silent |
| TMEM97 | c.518_519insA | p.*177fs? | Insertion - Frameshift |
| TMEM97 | c.519delA | p.K176fs? | Deletion - Frameshift |
| TNRC6A | c.104A>C | p.K35T | Substitution - Missense |
| TNRC6B_ENST00000301923 | c.179A>G | p.K60R | Substitution - Missense |
| TNRC6B_ENST00000301923 | c.180G>A | p.K60K | Substitution - coding silent |
| TNRC6B_ENST00000301923 | c.182A>C | p.K61T | Substitution - Missense |
| TNRC6B_ENST00000454349 | c.113A>G | p.K38R | Substitution - Missense |
| TNRC6B_ENST00000454349 | c.114G>A | p.K38K | Substitution - coding silent |
| TNRC6B_ENST00000454349 | c.116A>C | p.K39T | Substitution - Missense |
| TPR | c.2055A>C | p.E685D | Substitution - Missense |
| TPR | c.2056A>T | p.K686* | Substitution - Nonsense |
| TRDN | c.1145A>G | p.K382R | Substitution - Missense |
| TRIM24 | c.2676G>A | p.K892K | Substitution - coding silent |
| TRIM59 | c.594G>T | p.Q198H | Substitution - Missense |
| TRIM59 | c.604delA | p.S202fs*3 | Deletion - Frameshift |
| TRMT6 | c.458delA | p.K153fs*9 | Deletion - Frameshift |
| TRPC1 | c.509A>G | p.K170R | Substitution - Missense |
| TTF1 | c.1007_1008insA | p.K337fs*9 | Insertion - Frameshift |
| TTF1 | c.1007delA | p.K336fs*87 | Deletion - Frameshift |
| TWISTNB | c.932_933insA | p.K312fs*6 | Insertion - Frameshift |
| TWISTNB | c.932delA | p.K311fs*15 | Deletion - Frameshift |
| TWISTNB | c.933G>T | p.K311N | Substitution - Missense |
| TWISTNB | c.935_936insG | p.R313fs*5 | Insertion - Frameshift |
| TWISTNB | c.938G>A | p.R313K | Substitution - Missense |
| ULK4_ENST00000301831 | c.1778delA | p.K593fs*17 | Deletion - Frameshift |
| USP36 | c.2874_2879delGAAAAA | p.K959_K960delKK | Deletion - In frame |
| USP36_ENST00000312010 | c.2874_2879delGAAAAA | p.K959_K960delKK | Deletion - In frame |
| USP36_ENST00000312010 | c.2874G>A | p.K958K | Substitution - coding silent |
| USP40 | c.3468G>T | p.K1156N | Substitution - Missense |
| USP40 | c.3477_3478insA | p.Q1160fs*20 | Insertion - Frameshift |
| USP40 | c.3477delA | p.K1159fs*12 | Deletion - Frameshift |
| USP40_ENST00000450966 | c.3468G>T | p.K1156N | Substitution - Missense |
| USP40_ENST00000450966 | c.3477_3478insA | p.Q1160fs*20 | Insertion - Frameshift |
| USP40_ENST00000450966 | c.3477delA | p.K1159fs*12 | Deletion - Frameshift |
| VAX1 | c.473A>C | p.K158T | Substitution - Missense |
| VAX1 | c.477A>G | p.K159K | Substitution - coding silent |
| VAX1 | c.477delA | p.K159fs*>28 | Deletion - Frameshift |
| VAX1 | c.478C>G | p.Q160E | Substitution - Missense |
| VAX1 | c.480A>C | p.Q160H | Substitution - Missense |
| VAX1 | c.483G>T | p.K161N | Substitution - Missense |
| WDHD1 | c.1827G>A | p.K609K | Substitution - coding silent |
| WNK1 | c.1738_1749ins? | p.? | Unknown |
| WNK1 | c.1739delA | p.K583fs*11 | Deletion - Frameshift |
| WNK1 | c.1740A>G | p.E580E | Substitution - coding silent |
| WNK1 | c.1749G>T | p.K583N | Substitution - Missense |
| WNK1_ENST00000537687 | c.1739delA | p.K583fs*11 | Deletion - Frameshift |
| WNK1_ENST00000537687 | c.1740A>G | p.E580E | Substitution - coding silent |
| WNK1_ENST00000537687 | c.1749G>T | p.K583N | Substitution - Missense |
| ZC3H13 | c.3719G>C | p.S1240T | Substitution - Missense |
| ZC3H13 | c.3719G>T | p.S1240I | Substitution - Missense |
| ZCCHC9 | c.189G>T | p.K63N | Substitution - Missense |
| ZCCHC9 | c.196G>T | p.E66* | Substitution - Nonsense |
| ZCRB1 | c.411G>A | p.K137K | Substitution - coding silent |
| ZCRB1 | c.419_420insA | p.K141fs*4 | Insertion - Frameshift |
| ZCRB1 | c.419delA | p.K140fs*13 | Deletion - Frameshift |

TABLE 4-continued

Shows a table of genes with mutations within the polyA region reported in the COSMIC database.

| Gene name | mutation (nucleotide) | mutation (protein) | Type of mutation |
|---|---|---|---|
| ZFHX3 | c.1031A>T | p.N344I | Substitution - Missense |
| ZFR | c.1074_1075insA | p.E359fs*27 | Insertion - Frameshift |
| ZFR | c.1074delA | p.E359fs*4 | Deletion - Frameshift |
| ZMAT1 | c.1276A>T | p.K426* | Substitution - Nonsense |
| ZMAT1 | c.1277A>T | p.K426I | Substitution - Missense |
| ZMAT1 | c.1278A>G | p.K426K | Substitution - coding silent |
| ZMAT1_ENST00000372782 | c.1789A>T | p.K597* | Substitution - Nonsense |
| ZMAT1_ENST00000372782 | c.1790A>T | p.K597I | Substitution - Missense |
| ZMAT1_ENST00000372782 | c.1791A>G | p.K597K | Substitution - coding silent |
| ZMYM5_ENST00000337963 | c.1934delA | p.N645fs*>25 | Deletion - Frameshift |
| ZNF236 | c.1373delA | p.M461fs*1 | Deletion - Frameshift |
| ZNF236_ENST00000543926 | c.1373delA | p.M461fs*1 | Deletion - Frameshift |
| ZNF34 | c.664delA | p.T222fs*15 | Deletion - Frameshift |
| ZNF518A | c.2777delA | p.T929fs*2 | Deletion - Frameshift |
| ZNF518A_ENST00000371192 | c.2777delA | p.T929fs*2 | Deletion - Frameshift |
| ZNF600 | c.194_195insA | p.L66fs*4 | Insertion - Frameshift |
| ZNF644 | c.871delA | p.R291fs*7 | Deletion - Frameshift |
| ZNF644 | c.872G>T | p.R291I | Substitution - Missense |

Materials and Methods for Example 1

Cell Culture

HDF cells were cultured in Dulbecco's modified Eagle's medium (Gibco) and supplemented with 10% fetal bovine serum, 5% MEM non-essential amino acids (100×, Gibco), 5% penicillin and streptomycin (Gibco), and L-glutamine (Gibco). T-Rex-CHO cells were grown in Ham's F12K medium (ATCC) with the same supplements. Drosophila S2 cells were cultured in Express Five SFM Medium (Invitrogen) supplemented with 100 units per milliliter penicillin, 100 units per milliliter streptomycin (Gibco) and 45 ml of 200 mM L-glutamine (Gibco) per 500 ml of medium.

Plasmids and mRNA were introduced to the cells by the Neon® Transfection System (Invitrogen) with 100 μl tips according to cell specific protocols (www.lifetechnologies.com/us/en/home/life-science/cell-culture/transfection/transfection-selection-misc/neon-transfection-system/neon-protocols-cell-line-data.html). Cells electroporated with DNA plasmids were harvested after 48 hours if not indicated differently. Cells electroporated with mRNA were harvested after 4 hours, if not indicated differently. All transfections in S2 cells were performed using Effectene reagent (Qiagen).

DNA Constructs mCherry reporter constructs were generated by PCR amplification of an mCherry template with forward primers containing the test sequence at the 5' end and homology to mCherry at the 3' end. The test sequence for each construct is listed in Table 5. The PCR product was purified by NucleoSpin Gel and PCR Clean-up kit (Macherey-Nagel) and integrated into the pcDNA-DEST40, pcDNA-DEST53 or pMT-DEST49 expression vector by the Gateway cloning system (Invitrogen). Luciferase constructs were generated by the same method.

Whole gene constructs were generated by PCR amplification from gene library database constructs from Thermo (MTDH CloneId:5298467) or Life Technologies GeneArt Strings DNA Framents (ZCRB1) and cloned in pcDNA-DEST40 vector for expression. Synonymous mutations in the natural gene homopolymeric lysine runs were made by site directed mutagenesis. Human beta-globin gene (HBD, delta chain) was amplified from genomic DNA isolated from HDF cells. Insertions of poly(A)-track, AAG-codons or pre-mature stop codon in HBD constructs were made by site directed mutagenesis. Sequences of inserts are in the Table 5.

TABLE 5

Sequences of mCherry inserts

| Construct | Sequence inserted between 2HA tag and mCherry | SEQ ID NO: |
|---|---|---|
| WT | No sequence inserted | |
| GAA₁₂ | GAA GAA GAA GAA GAA GAA GAA GAA GAA GAA GAA GAA | 1 |
| AAG₆ | AAG AAG AAG AAG AAG AAG | 2 |
| AAG₉ | AAG AAG AAG AAG AAG AAG AAG AAG AAG | 3 |
| AAG₁₂ | AAG AAG AAG AAG AAG AAG AAG AAG AAG AAG AAG AAG | 4 |
| STOP | TAA | |
| AAA₆ | AAA AAA AAA AAA AAA AAA | 5 |
| AAA₉ | AAA AAA AAA AAA AAA AAA AAA AAA AAA | 6 |
| AAA₁₂ | AAA AAA AAA AAA AAA AAA AAA AAA AAA AAA AAA AAA | 7 |
| CGA₁₂ | CGA CGA CGA CGA CGA CGA CGA CGA CGA CGA CGA CGA | 8 |
| AGG₁₂ | AGG AGG AGG AGG AGG AGG AGG AGG AGG AGG AGG AGG | 9 |
| A9 | GCA GCG AAA AAA AAA TCC GTG | 10 |
| A10 | GCA AAA AAA AAA GTG | 11 |
| A11 | GCA GCA AAA AAA AAA ACC GTG | 12 |
| A12 | GCA GAA AAA AAA AAA ACC GTG | 13 |
| A13 | GCA GAA AAA AAA AAA AAC GTG | 14 |
| SLU7 | GAG AAG AAG AAG AAG AAA AAG AAG AAG AAG AAG CAT | 15 |
| MTDH | TCC AAA AAG AAA AAA AAG AAA AAG AAG AAG CAA GGT | 16 |
| Nop58 | GAG AAA AAG AAG AAA AAG AAA AAA AAG AGA GAG AGA | 17 |

TABLE 5-continued

Sequences of mCherry inserts

| Construct | Sequence inserted between 2HA tag and mCherry | SEQ ID NO: |
|---|---|---|
| ZCRB1 | CCA AAG AAG AAA GAA AAA AAG AAA AAA AAG AAA GCT | 18 |
| RASAL2 | GTG GAA AAA AAG AAA AAA AAG GAC AAG AAT AAT TAT | 19 |
| ZCRB1 | CCA AAG AAG AAA GAA AAA AAG AAA AAA AAG AAA GCT | 20 |
| ZCRB1 G>A | CCA AAG AAG AAA GAA AAA AAA AAA AAA AAG AAA GCT | 21 |
| ZCRB1 A>G | CCA AAG AAG AAA GAA AAG AAG AAA AAG AAG AAA GCT | 22 |
| RASAL2 | GTG GAA AAA AAG AAA AAA AAG GAC AAG AAT AAT TAT | 23 |
| RASAL2 G>A | GTG GAA AAA AAA AAA AAA AAG GAC AAG AAT AAT TAT | 24 |
| RASAL2 A>G | GTG GAA AAA AAG AAA AAG AAG GAC AAG AAT AAT TAT | 25 |
| RASAL2 A>G(3) | GTG GAA AAG AAG AAG AAG AAG GAC AAG AAT AAT TAT | 26 |

In Vitro mRNA Synthesis

Capped and polyadenylated mRNA was synthesized in vitro using m Message mMachine T7 Transcription Kit (LifeTechnologies) following manufacturers procedures. The quality of mRNA was checked by electrophoresis and sequencing of RT-PCR products.

RNA Extraction and Qrt-PCR

Total RNA was extracted from cells using the Ribozol RNA extraction reagent (Amresco) according to the manufacturer's instructions. 400 µl of Ribozol reagent was used per well of 6 or 12 well plates for RNA extraction. Precipitated nucleic acids were treated by Turbo DNAse (Ambion) and total RNA was dissolved in RNAse-free water and stored at −20° C. RNA concentration was measured by Nanodrop (0D260/280). iScript Reverse Transcription Supermix (Biorad) was used with 1 µg of total RNA following the manufacturer's protocol. iQ SYBR Green Supermix (Biorad) protocol was used for qRT-PCR on the CFX96 Real-Time system with Bio-Rad CFX Manager 3.0 software. Cycle threshold (Ct) values were normalized to the neomycin resistance gene expressed from the same plasmid.

Western Blot Analysis

Total cell lysates were prepared with passive lysis buffer (Promega). Blots were blocked with 5% milk in 1×TBS 0.1% Tween-20 (TBST) for 1 hour. HRP-conjugated or primary antibodies were diluted by manufacturer recommendations and incubated overnight with membranes. Membranes were washed 4 times for 5 minutes in TBST and prepared for imaging or secondary antibody was added for additional one hour incubation. Images were generated by Bio-Rad Molecular Imager ChemiDoc XRS System with Image Lab software by chemiluminescence detection or by the LI-COR Odyssey Infrared Imaging System. Blots imaged by the LI-COR system were first incubated for 1 hr with Pierce DyLight secondary antibodies.

Immunoprecipitation

Total cell lysates were prepared with passive lysis buffer (Promega) and incubated with Pierce anti-HA magnetic beads overnight at 4° C. Proteins were eluted by boiling the beads with 1× SDS sample buffer for 7 minutes. Loading of protein samples was normalized to total protein amounts.

Cell Imaging

HDF cells were electroporated with the same amount of DNA plasmids and plated in 6 well plates with the optically clear bottom. Prior to imaging, cells were washed with a fresh DMEM media without Phenol-Red and incubated 20 minutes with DMEM media containing 0.025% Hoechst 33342 dye for DNA staining. Cells were washed with DMEM media and imaged in Phenol-Red free media using an EVOS-FL microscope (40× objective). Images were analyzed using EVOS-FL software.

Sequence data and variation databases: Sequence data were derived from NCBI RefSeq resource (Pruitt et al. (2014) RefSeq: an update on mammalian reference sequences. Nucleic Acids Res. 42, D756-763), on February 2014. Two variations databases were used: dbSNP (Sherry et al. (2001) Nucleic Acids Res. 29, 308-311), build 139 and COSMIC, build v70 (Forbes et al. (2014) Nucleic Acids Res.).

mRNA Mapping

As some inconsistences between transcripts and proteins were observed in some of the sequence databases, before starting the analyses protein sequences were mapped to mRNA sequences using exonerate tool (Slater & Birney (2005) BMC Bioinformatics 6, 31), using protein2genome model and requiring a single best match. In case of multiple best matches (when several transcripts had given identical results), a first one was chosen, as the choice of corresponding isoform (as this was the most common reason for multiple matches) did not influence downstream analyses.

Ribosome Profiling Data

Three independent studies of ribosome profiling data from human cells were analyzed. These were: GSE51424 prepared by Gonzales and coworkers (Gonzalez et al. (2014) J. Neurosci. Off. J. Soc. Neurosci. 34, 10924-10936) from which samples: SRR1562539, SRR1562540 and SRR1562541 were used; GSE48933 prepared by Rooijers and coworkers (Rooijers et al. (2013) Nat. Commun. 4) from which samples: SRR935448, SRR935449, SRR935452, SRR935453, SRR935454 and SRR935455 were used; GSE42509 prepared by Loayza-Puch and coworkers (Loayza-Puch et al. (2013) Genome Biol. 14, R32) from which samples SRR627620-SRR627627 were used. The data were analyzed similarly to the original protocol created by Ingolia and coworkers (Ingolia et al. (2012) Nat. Protoc. 7, 1534-1550), with modifications reflecting the fact that reads were mapped to RNA data, instead of genome.

Raw data were downloaded and adapters specific for each experiments were trimmed. Then the reads were mapped to human noncoding RNAs with bowtie 1.0.1 (Langmead et al. (2009) Genome Biol. 10, R25) (bowtie-p 12-t-un) and unaligned reads were mapped to human RNAs (bowtie-p 12-v 0-a-m 25-best-strata-suppress 1,6,7,8). The analysis of occupancy was originally done in a similar way to Charneski and Hurst ((2013) PLoS Biol. 11, e100150817), however, given that genes with polyA were not highly expressed and the data were sparse (several positions with no occupancy), instead of mean of 30 codons prior to polyA position, it was decided to normalize only against occupancy of codon at the position 0 multiplied by the average occupancy along the gene. Occupancy data were visualized with R and Ggplot2 library using geom_boxplot aesthetics. On all occupancy graphs, the upper and lower "hinges" correspond to the first and third quartiles (the 25th and 75th percentiles). The upper and lower whiskers extend from hinges at 1.5*IQR of the respective hinge.

Variation Analysis

To assess the differences in SNPs in polyA regions vs random region of the same length in other genes, the same distribution of lengths in both cases needed to be used. The distribution of lengths for polyA regions identified as mentioned above (12 As allowing for one mismatch) up to length 19 (longer are rare) is presented in FIG. 27. Using the same distribution of lengths, one random region of length drawn from the distribution randomly placed along each gene from all human protein coding RNAs was selected. Distributions of number of SNPs per segment for all polyA segments and for one random segment for each mRNA were compared using Welch Two Sample t-test, Wilcoxon rank sum test with continuity correction and two sample permutation test with 100000 permutations.

Abundance of Polytracks in Protein Sequences

Abundance was expressed by a following equation:

$$\text{Abundance} = \frac{1}{-\log_{10}\frac{N_P}{N_R}}$$

where NP is number of proteins with K+ polytrack (at least 2, at least 3, etc.) and NR is the total number of occurrences of a particular amino acid. It is to normalize against variable amino acid presence in different organisms. All isoforms of proteins were taken into account.

Other Analyses

List of human essential genes was obtained from the work of Georgi and coworkers (PLoS Genet 9, e1003484 (2013)). Gene Ontology analyses were done using Term Enrichment Service at amigo.geneontology.org/rte. Most of graphs were prepared using the R and GGPLOT2 library. For FIG. 14A, the values of the Y-axis were computed by 1D gaussian kernel density estimates implemented in R software. Custom Perl scripts were used to analyze and merge the data.

EXAMPLE 2: PolyA Tracks can be Used to Regulate Gene Expression in *Escherichia Coli*

We have recently identified polyA tracks as a regulator of gene expression. This mechanism is used endogenously in most eukaryotic genomes and regulates approximately 2% of human genes (Arthur, et al., 2015; Habich, et al., 2016). The polyA track causes ribosomal stalling and frameshifting during translation elongation, leading to mRNA instability and degradation of nascent protein products (Arthur, et al., 2015; Koutmou, et al., 2015). The translation elongation cycle is an ideal target for a universal method of gene regulation because it is the most highly conserved step in protein biosynthesis between prokaryotes and eukaryotes (Melnikov, et al., 2012). We have thus reasoned that polyA tracks, due to their versatility in lengths and sequence composition, can be used as a system to create programmable hypomorphic mutants and regulate gene expression in wide variety of model organisms (FIG. 29).

Figure 29A:
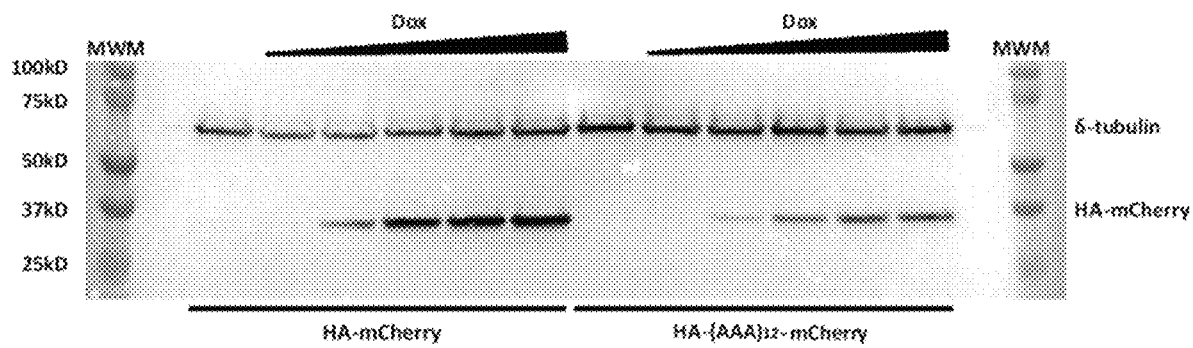
FIG. 29A, FIG. 29B, and FIG. 29C show PolyA tracks regulate mCherry reporter expression independently of the promoter strength.
Figure 29B:
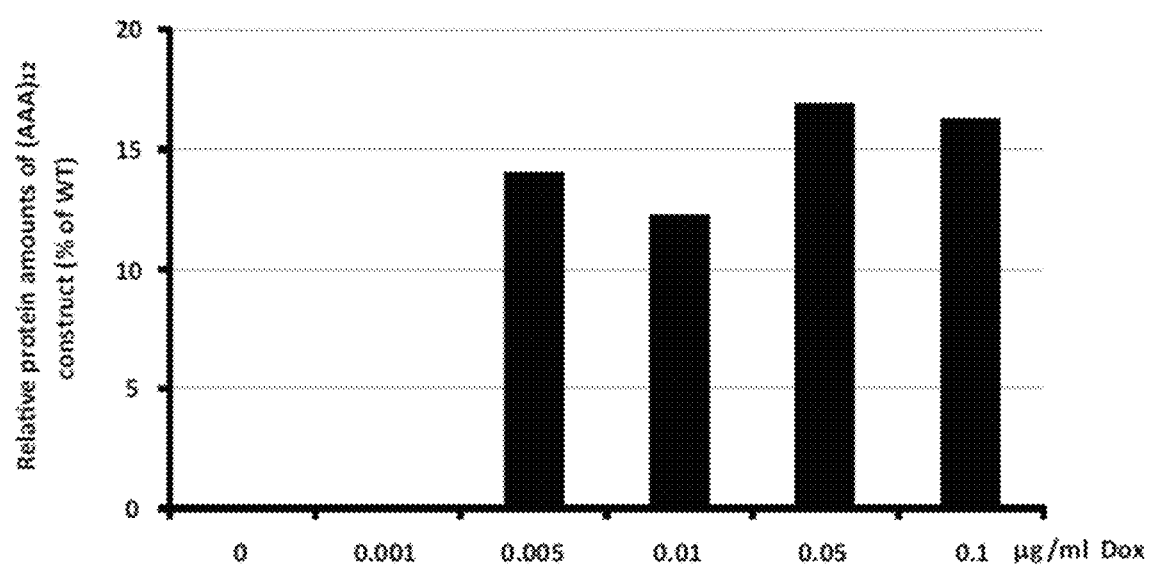
Figure 29C:
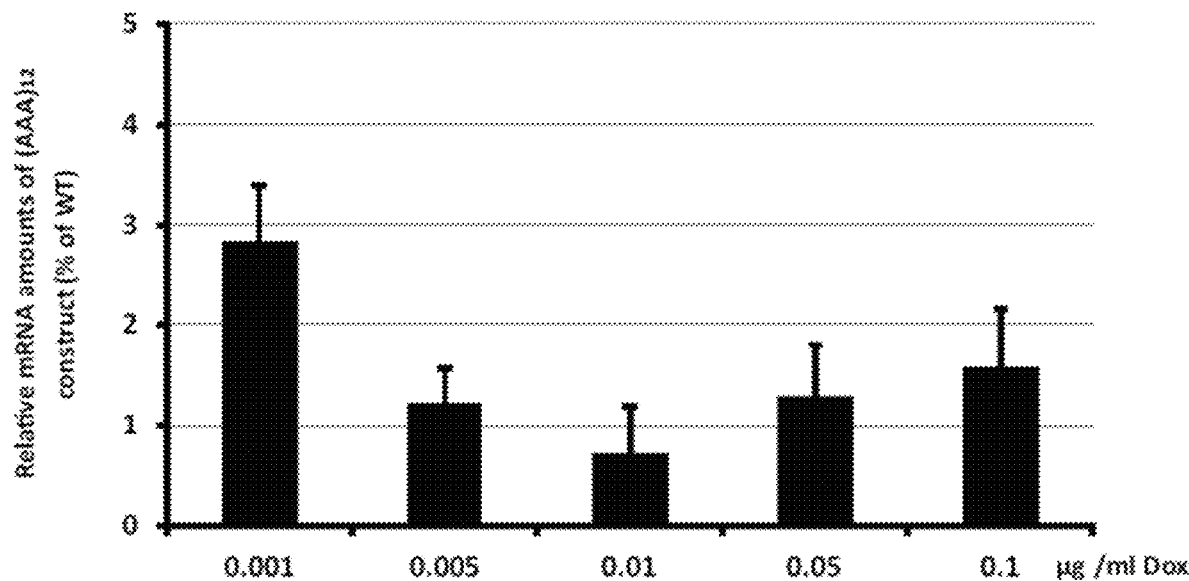

We have generated a fluorescent reporter gene that has an insertion of defined polyA tracks in order to control the amount of expression (FIG. 29A). The reporter consists of either a constitutive or inducible promoter driving expression of the mCherry fluorescence and other reporter proteins. A double HA-tag was added at the beginning of the coding sequence for detection on western blot analysis. The polyA track is inserted directly after the HA-tag. The length of the polyA track varies from 9 to 36 consecutive adenine nucleotides, adding 3 to 12 lysine residues to the protein sequence (FIG. 29A). To control for the effects of polybasic peptide arising from sequential lysine residues (Kuroha, et al., 2010; Brandman, et al., 2012), we generated control reporters with consecutive lysine AAG codons. We hypothesized that as the length of the polyA track is increased, expression of the reporter gene products will decrease (FIGS. 29B and 29C). These reporters can be transiently transfected, recombined or inserted into the genome of cell cultures or whole organisms. Likewise, endogenous genes can be edited to include a polyA tracks in their open reading frames (ORF's) using genome editing methodology.

Figure 26A:
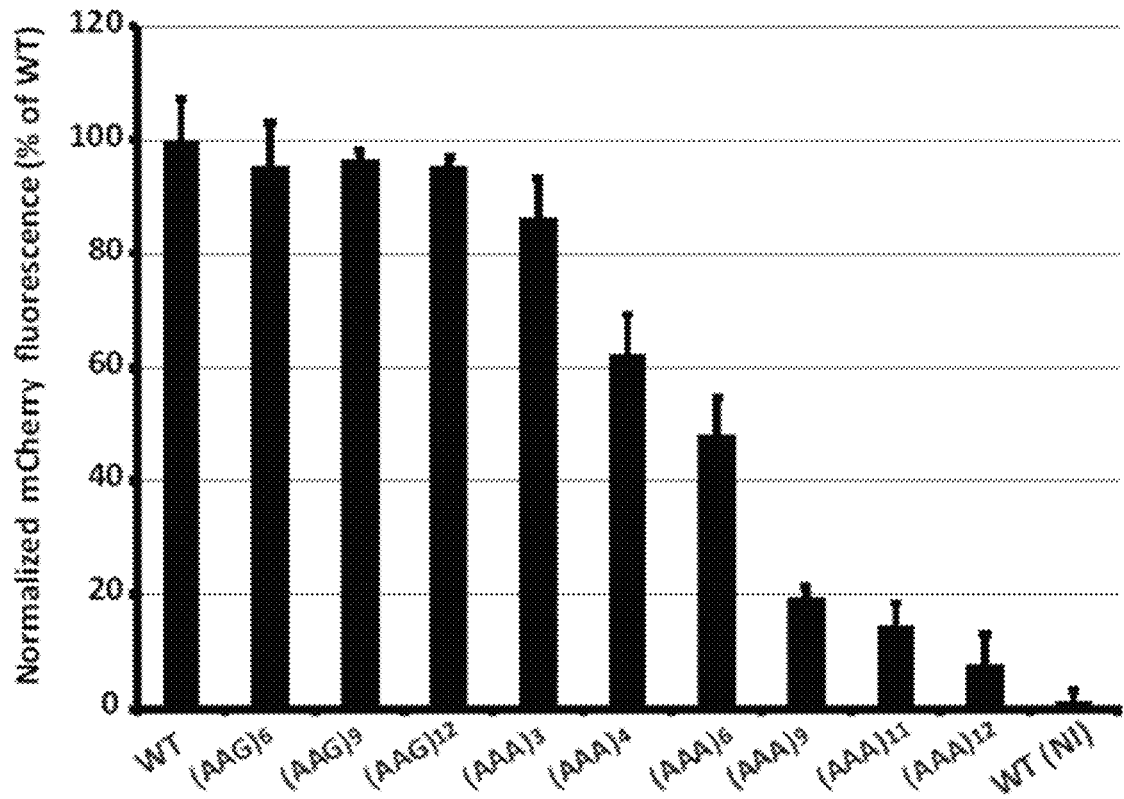
FIG. 26A, FIG. 26B, FIG. 26C, FIG. 26D, FIG. 26E, and FIG. 26F show regulation of reporter gene by polyA tracks in the single cell prokaryotic and eukaryotic organisms.
Figure 26B:
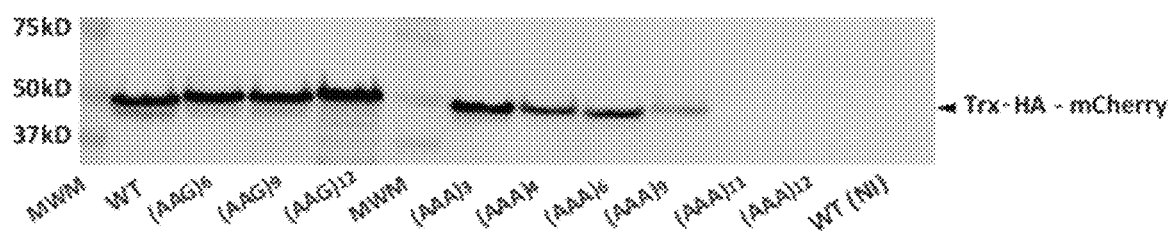
Figure 31:
FIG. 31 shows a diagram of a mCherry expression construct used in E. coli. Position of the inducible arabinose promoter (pBAD), Thioredoxin (Trx), double HA-tag (HA), insertion sequence (X) and fluorescent reporter (mCherry) are indicated. Examples of WT, LysAAG and LysAAA insertions and the resulting protein and DNA sequences of reporter constructs are shown.

We first tested whether polyA tracks can be used in single cell model organisms to attenuate gene expression from a defined reporter gene. To show that polyA tracks can be used to control gene expression in *E. coli* cells we created a set of reporters with increasing length of polyA tracks under the arabinose-inducible promoter pBAD (FIG. 31). We transformed the chemically competent *E. coli* cells (Top10 strain) with plasmids expressing HA-mCherry, HA-(AAG)n-mCherry or HA-polyA-mCherry. All *E. coli* cell cultures were induced at the same optical density and monitored for both cell growth and fluorescence of the mCherry constructs during induction. While *E. coli* containing wild type and LysAAG controls (6×, 9× and 12× lysine AAG codons) show no significant differences in the amount of mCherry fluorescence, cell cultures containing constructs with polyA tracks show progressively less fluorescence with increasing length of the polyA track (FIG. 26A). Addition of 9 and 12A's in a row (3 or 4 LysAAA codons) consistently reduced fluorescence of mCherry reporter by 15-35%. Further additions in the length of the polyA track resulted in constant decrease of mCherry reporter fluorescence where 36 consecutive adenine nucleotides resulted in a barely visible expression of the reporter (<5% of wild type). Western blot analyses of equal amounts of *E. coli* cell lysates expressing different polyA track and control reporters confirmed mCherry fluorescence data and indicated again that protein abundances of polyA track reporters strongly depend on the length of polyA track (FIG. 26B). Reporters with 9 and 12As in the row (3 and 4LysAAA codons, respectively) show reduction in protein abundances in the range of 20-40% of the wild type mCherry and constructs with more than 27As in the row (9 and more LysAAA codons) were hardly detectable by western blot analyses.

EXAMPLE 3: PolyA Tracks can be Used to Regulate Gene Expression in Protozoan *Tetrahymena thermophile*

We previously showed that polyA tracks can influence expression of the reporter genes in *S. cerevisiae* (Koutmou, et al., 2015) cells. To test whether polyA tracks can regulate gene expression in another model single cell eukaryotic organism, we monitored the effect of various length tracks on YFP expression in the protozoan *T. thermophila*. The genome of *T. thermophila* has extremely high AT content (>75%) and has been extensively used as microbial animal model [Collins, K. and M. A. Gorovsky (2005). "*Tetrahymena thermophila*." Curr Biol 15(9): R317-318.] (Eisen, et al., 2006). Our *T. thermophila* reporter contained the coding sequence of a Macronucleus-Localized Protein of unknown function (MLP1, TTHERM_00384860) fused to eYFP protein (FIG. 45A-D). The fusion with MLP1 directed YFP to

Figure 26C:
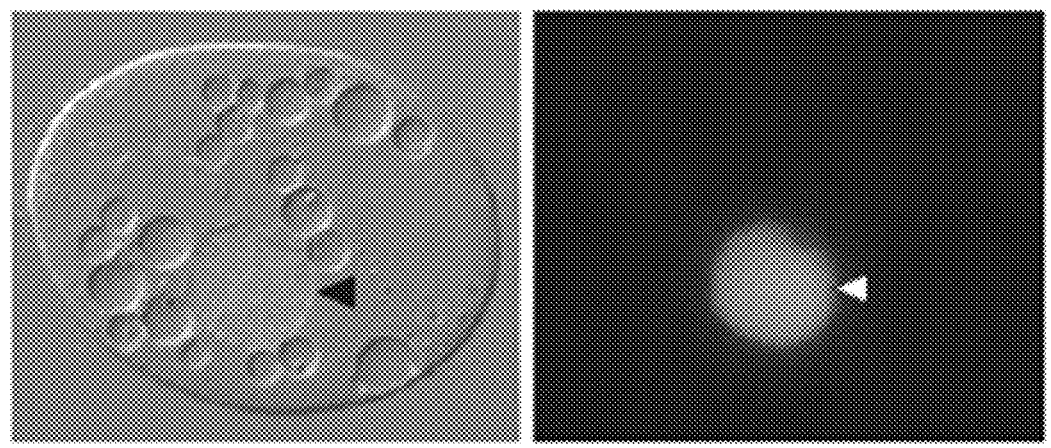
Figure 26D:
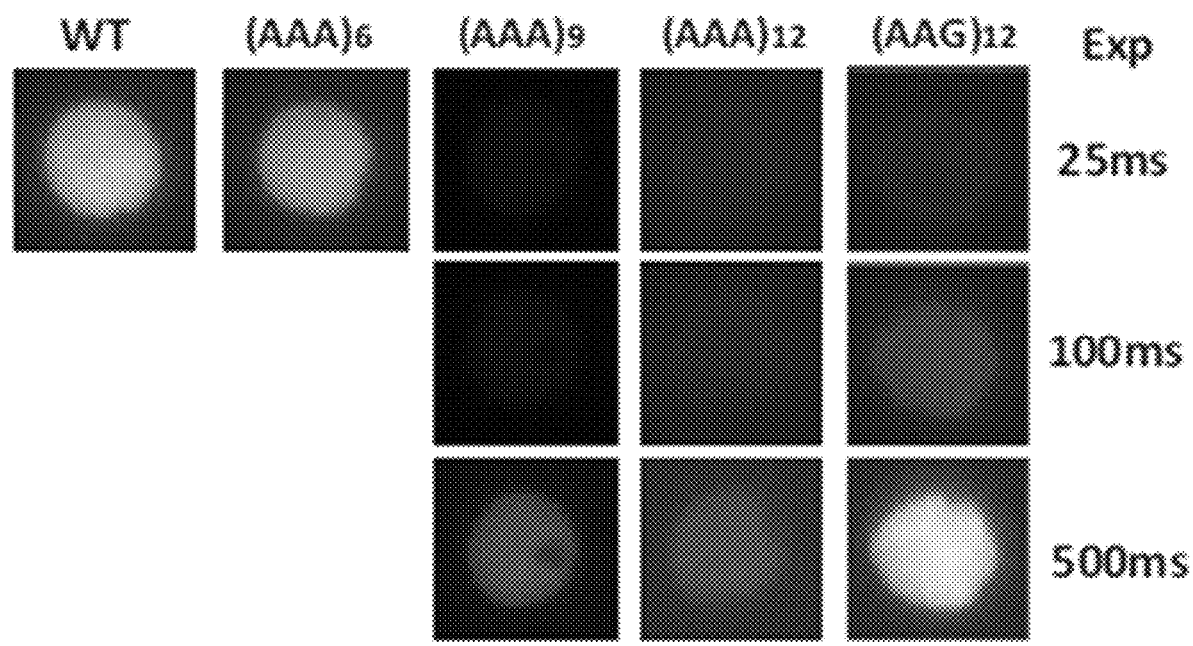
Figure 26E:
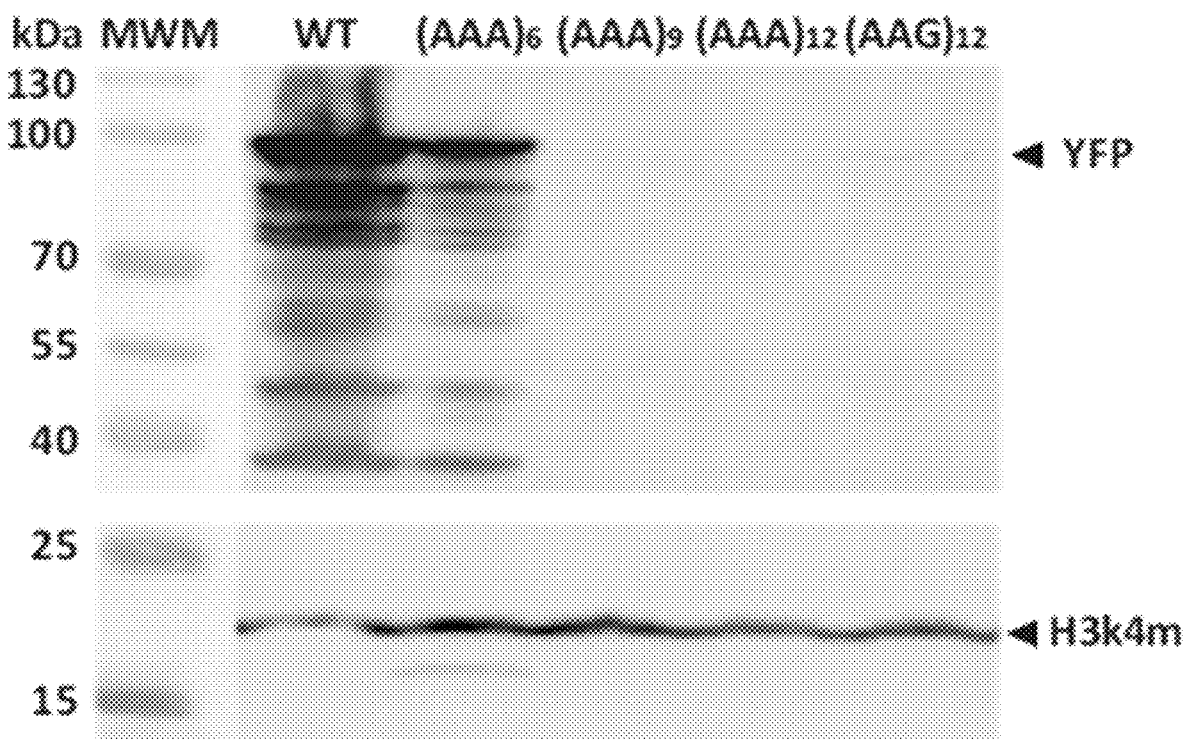
Figure 26F:
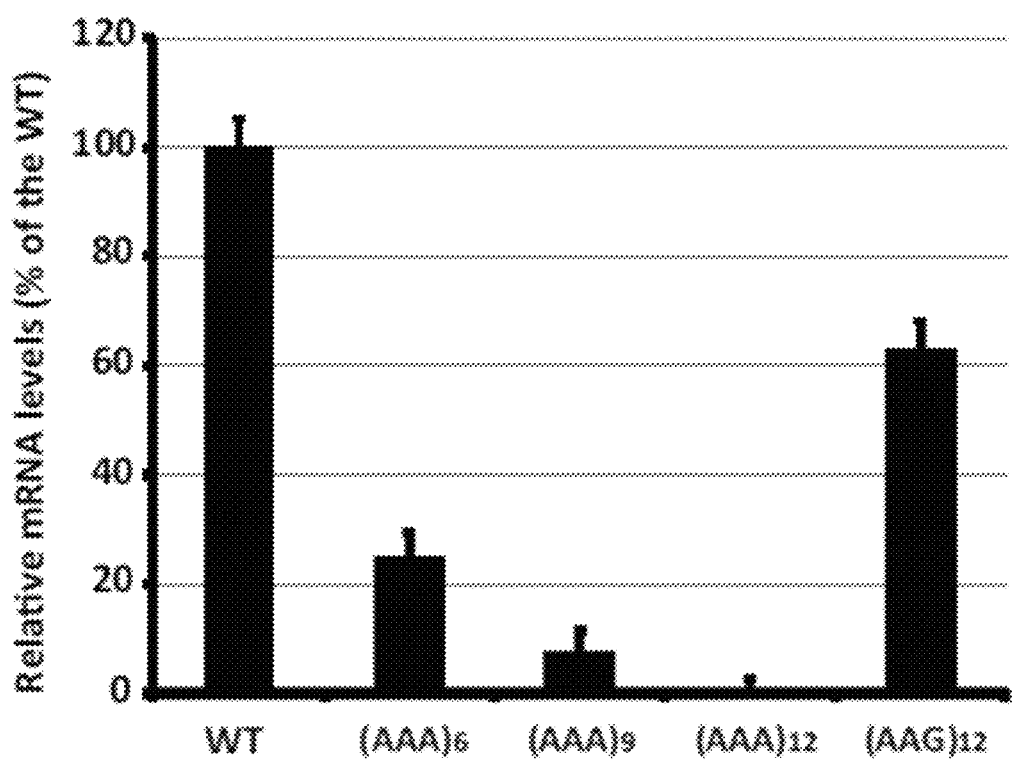

*Tetrahymena* macronuclei to allow easier quantification of YFP levels (FIG. 26C). These two proteins were fused, separated by linkers containing an HA-tag (MLP1-HA-YFP (WT)) and polyA tracks of 18, 27, or 36As, (AAA)6, (AAA)9, or (AAA)12, respectively, or 12 LysAAG (AAG) 12 codons inserted as a control. All constructs were expressed upon cadmium-induction of the upstream MTT1 promoter. Just as in our *E. coli* experiments with mCherry reporter, the YFP gene containing increasing lengths of polyA tracks exhibited a progressive decrease in total protein accumulation, measured by fluorescence, relative to the HA-linker fusion or LysAAG insertion controls (FIG. 26D). The construct with 18As in a row (6LysAAA) showed approximately 50% reduction in protein fluorescence, while constructs with 27 and 36As required 20 times longer exposure for detection of YFP by microscopy. The construct with 12LysAAG codons showed fluorescence that was readily 4-5 fold lower then WT construct. This effect could be attributed to polybasic peptide stalling that was observed earlier in *S. cerevisiae* cells (Koutmou, et al., 2015; Kuroha, et al., 2010; Brandman, et al., 2012). We further confirmed our fluorescence results by Western blot analyses (FIG. 26E). The MLP1-HA-YFP-fusion (WT) was readily visible whereas the polyA track-YFP fusions showed attenuation of expression. Insertion of 18A's (6LysAAA) showed expression levels that were approximately 35% of the HA-YFP control, while 27 and 36A's (9 and 12LysAAA) constructs were at the limit of detection (FIG. 26E). Insertion of 12LysAAG codons in the fusion protein, showed 6- to 8-fold reduction in expression of fusion protein. Since the different fusion proteins were all transcribed from the MTT1 promoter under identical induction conditions, we reasoned that amount of mRNA produced for each construct should be equivalent. We used qRT-PCR to quantify the steady state level of YFP mRNA of each fusion (FIG. 26F). The steady-state mRNA levels of polyA track-YFP constructs strongly reflected the decreasing YFP protein accumulation relative to the WT. Insertion of 18As (6LysAAA codons) reduced mRNA levels to approximately 30-35% of WT levels, while insertion of 27 and 36As (9 and 12LysAAA codons, respectively) reduced mRNA levels to less than 5% of the HA-YFP construct (FIG. 26D). Interestingly, while the attenuation at the protein level was stronger for the insertion of 12LysAAG codons than for 6LysAAA codons the trend was lost at mRNA levels. This can be due to the different pathways that resolve polybasic peptide stalling and polyA track-induced stalling and frameshifting in eukaryotic cells (Arthur, et al., 2015; Koutmou, et al., 2015). Nonetheless, we were able to control expression of reporter genes using polyA tracks in a similar manner in *T. thermophila*, a single cell AT-rich protozoan, as we did previously in *S. cerevisiae* and above mentioned *E. coli* cells (Koutmou, et al., 2015).

Figure 27A:
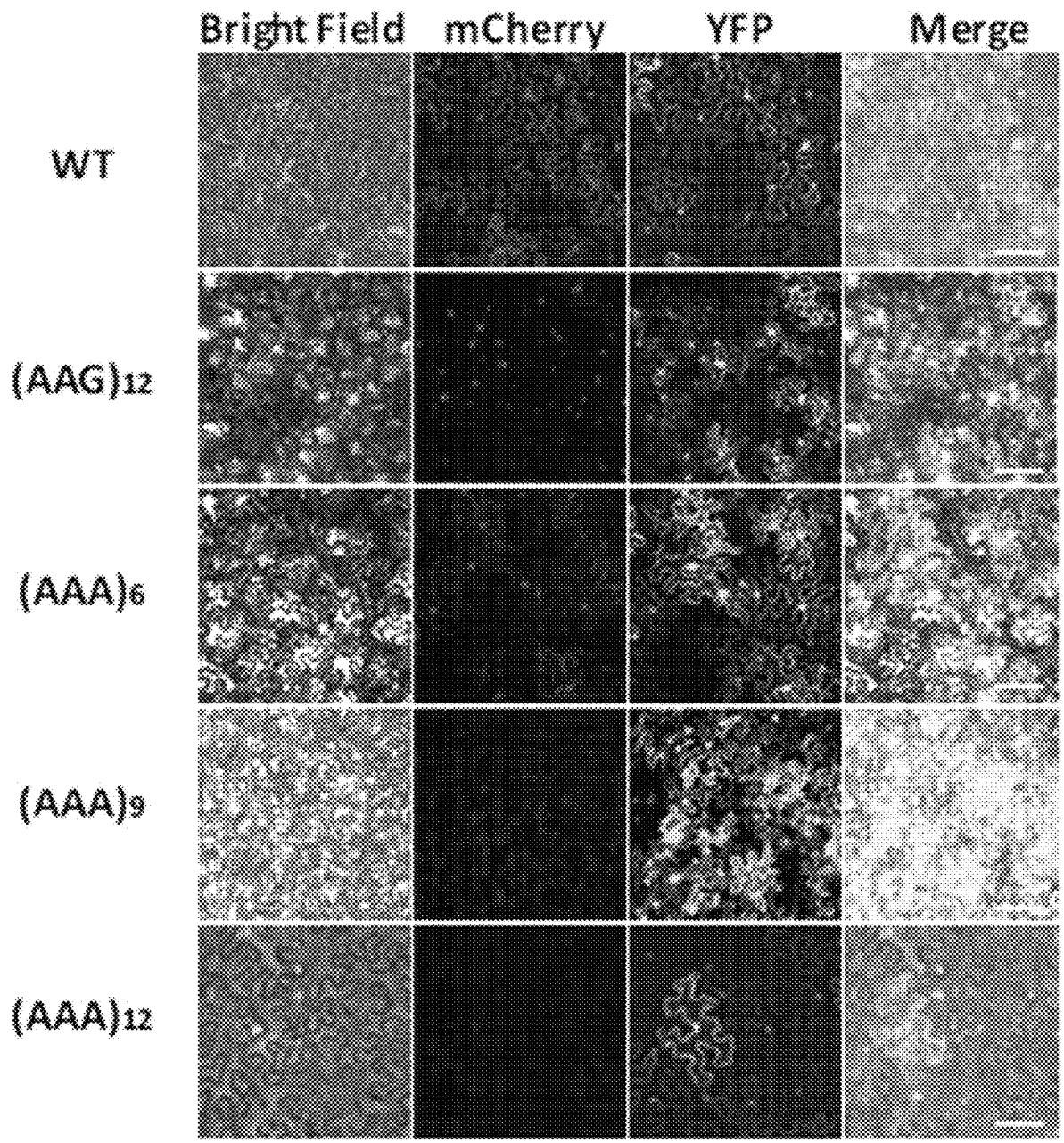
FIG. 27A, FIG. 27B, FIG. 27C, FIG. 27D, FIG. 27E, and FIG. 27F show regulation of reporter gene by polyA tracks in the eukaryotic tissue cultures.
Figure 27B:
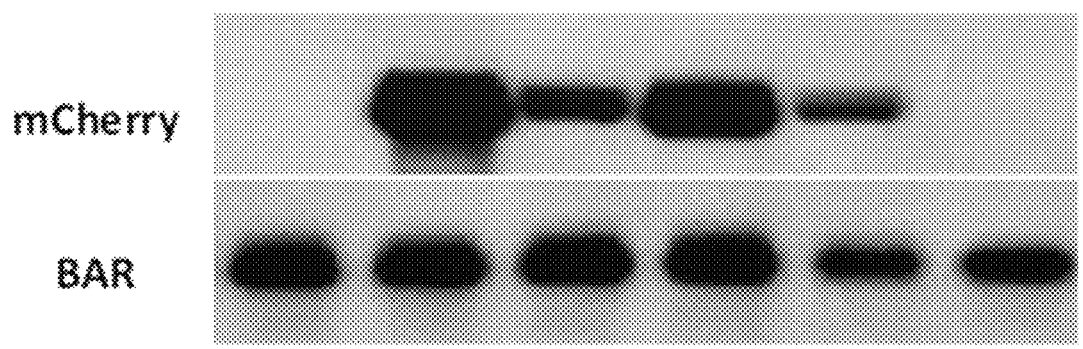
Figure 27C:
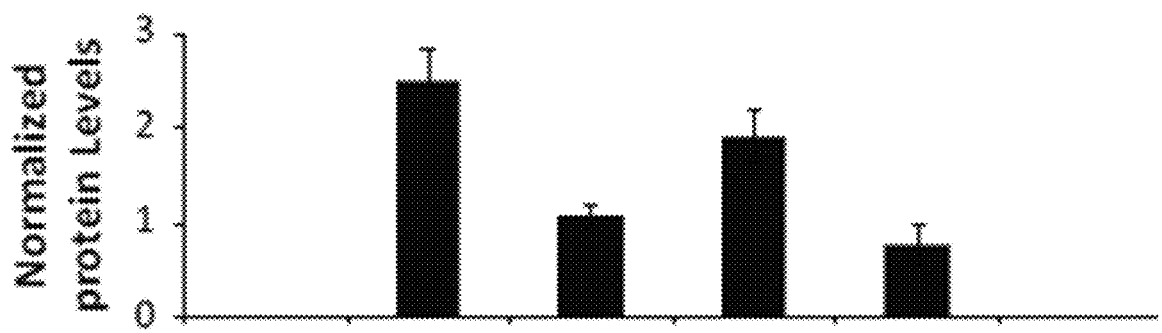
Figure 27D:
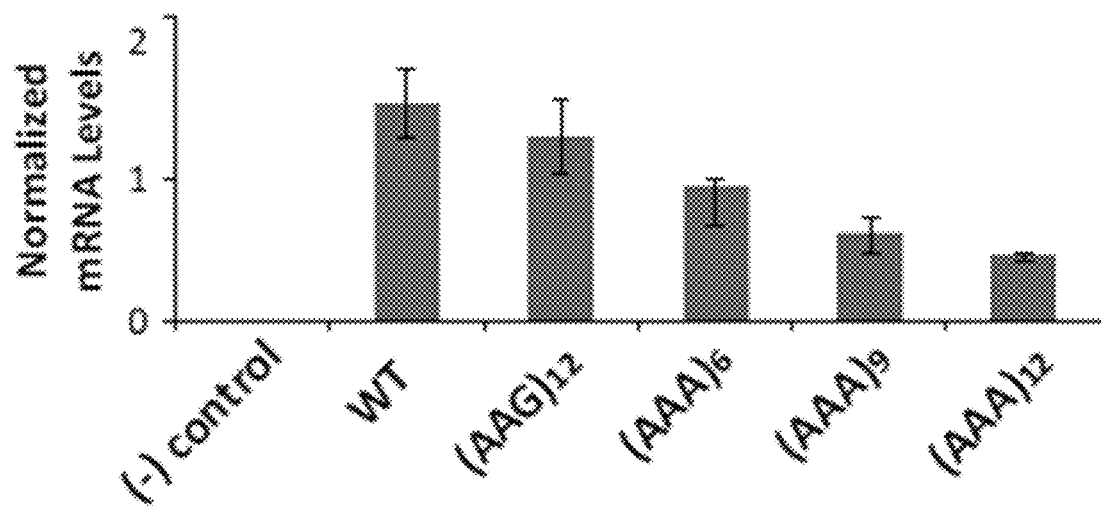
Figure 33:
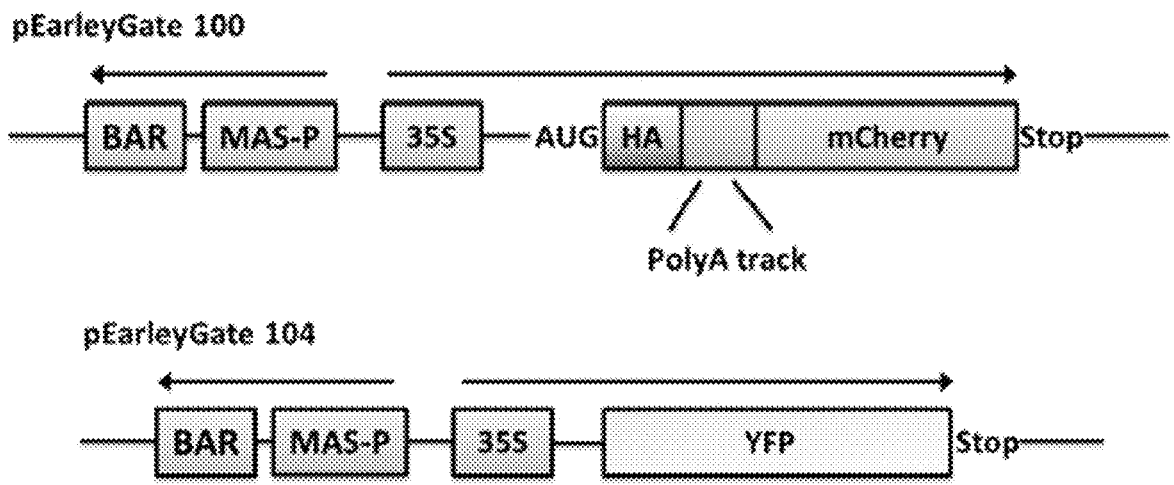
FIG. 33 shows diagram of mCherry and YFP expression constructs used in N. benthamiana. Position of the mannopine synthase promoter (MAS-P), the cauliflower mosaic virus 35S promoter and its upstream enhancer (35S), phosphinotricin acetyl transferase (BAR, herbicide resistance gene for selection of transgenic plants), double HA-tag (HA) and fluorescent reporters, mCherry and YFP, are indicated. Red box designates the position of in frame inserted polyA tracks and 12 LysAAG sequences. WT construct contains no insertions at this position.

EXAMPLE 4: PolyA Tracks can be Used for Gene Expression Regulation in Plant Tissues To test whether polyA tracks can attenuate gene expression in plants, we transiently co-expressed HA-polyA-mCherry with an YFP construct as internal control in the model plant *Nicotiana benthamiana* (FIG. 33). The expression of mCherry and YFP was assessed by fluorescence imaging (FIG. 27A). Like single cell cultures, *N. benthamiana* epidermal cells showed attenuated mCherry fluorescence proportional to the length of the polyA tracks (6,9 and 12 LysAAA codons) compared to the HA-mCherry and 12 LysAAG control constructs (FIG. 27A). The fluorescence data for each construct revealed the same trend of gene expression regulation as in *T. thermophila* cells (FIG. 26D). As fluorescence in this assay was not quantifiable, protein abundance was determined by semi-quantitative Western blot analysis of *N. benthamiana* leaves infiltrated with the HA-polyA-mCherry. The levels of HA-mCherry proteins were normalized to levels of the cis-linked selectable marker phosphinotricin acetyl transferase (BAR) in the same sample (FIG. 27B and FIG. 27C). The addition of a polyA track with 18As (6 LysAAA) decreased protein accumulation to approximately 70% of HA-mCherry levels. Further reduction of mCherry protein accumulation, to 30% and below detection limit was observed in 9 LysAAA and 12 LysAAA constructs, respectively (FIG. 27C). Parallel analyses of steady state mRNA levels of transcripts with increasing lengths of polyA tracks showed progressively reduced levels of polyA track mRNAs when compared to transcript levels of the HA-mCherry and AAG-containing control constructs (FIG. 27D). mRNA levels were reduced to approximately 50-55% of WT expression for 6LysAAA transcripts, while 9 and 12LysAAA constructs had reduced mRNA levels to approximately 30 and 20% of controls, respectively (FIG. 27D). These results indicate that polyA tracks affect both mRNA and protein levels and can be used to regulate the gene expression in plants.

Figure 27E:
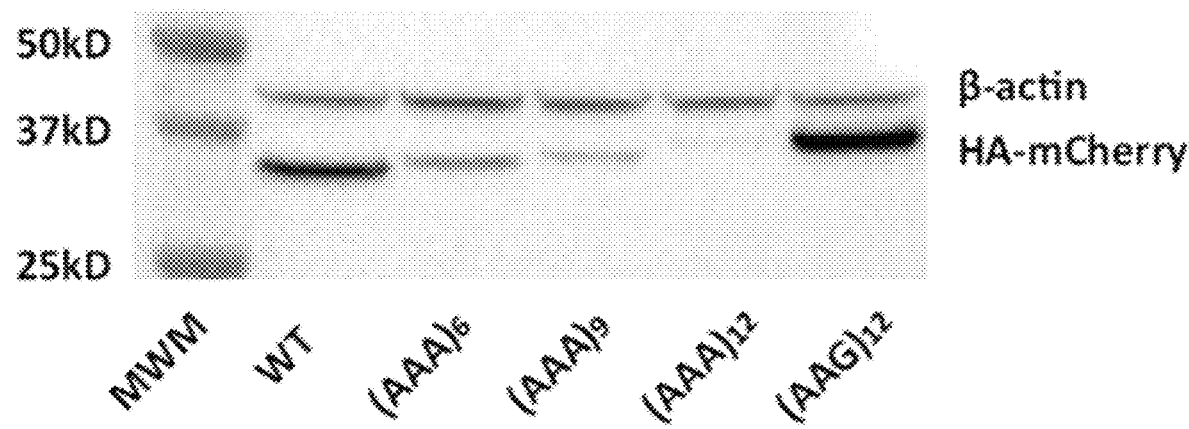
Figure 27F:
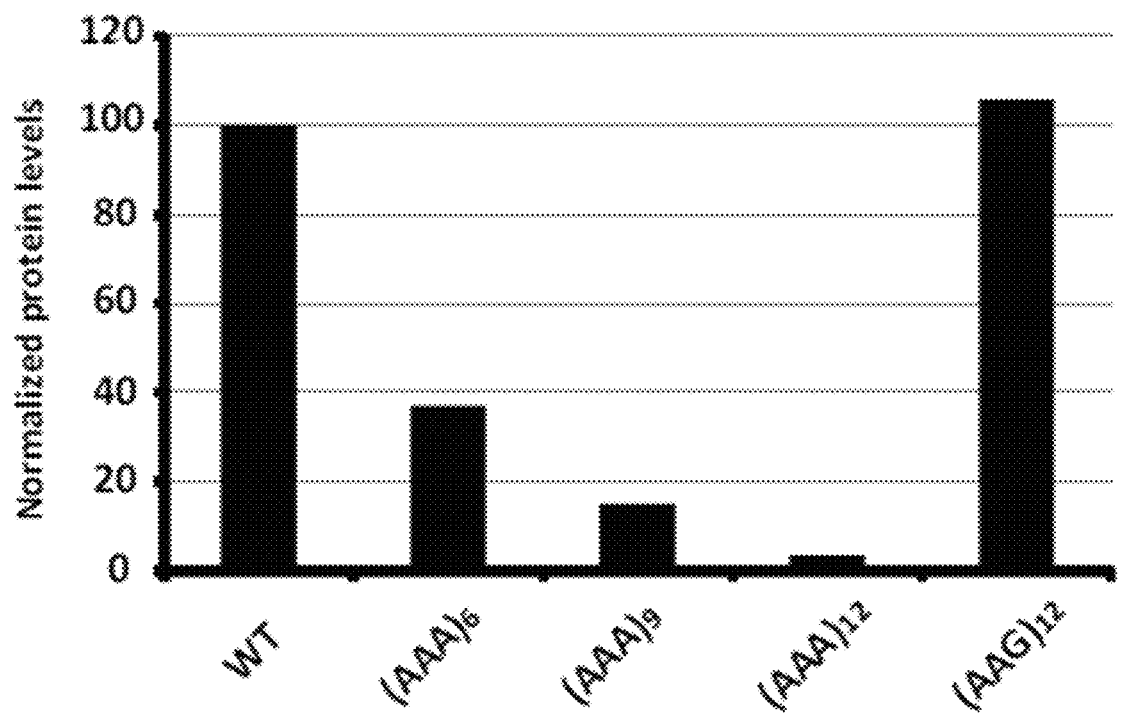
Figure 28A:
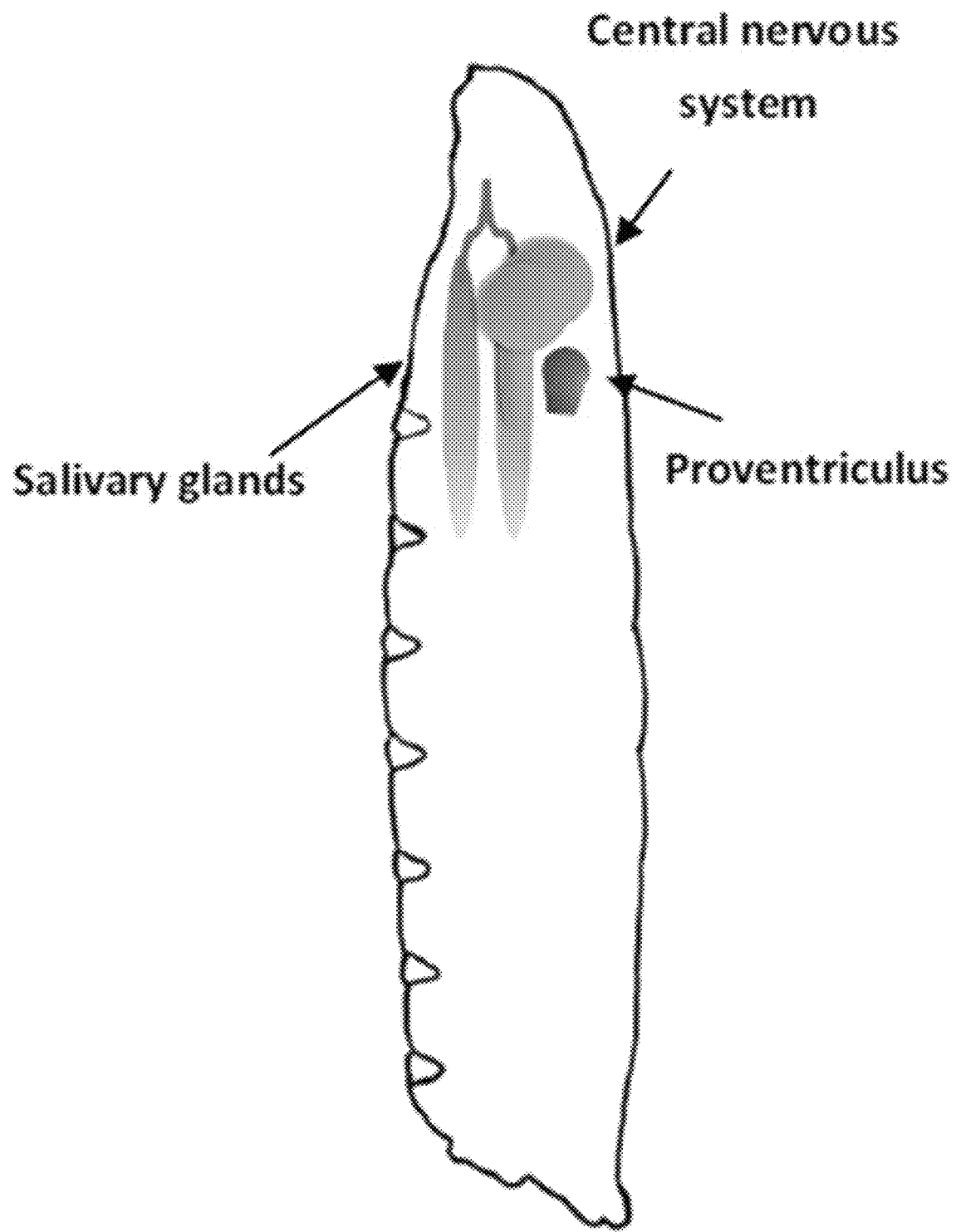
FIG. 28A, FIG. 28B, FIG. 28C, and FIG. 28D show PolyA tracks regulate mCherry reporter gene expression in different organs of D. melanogaster.
Figure 28B:
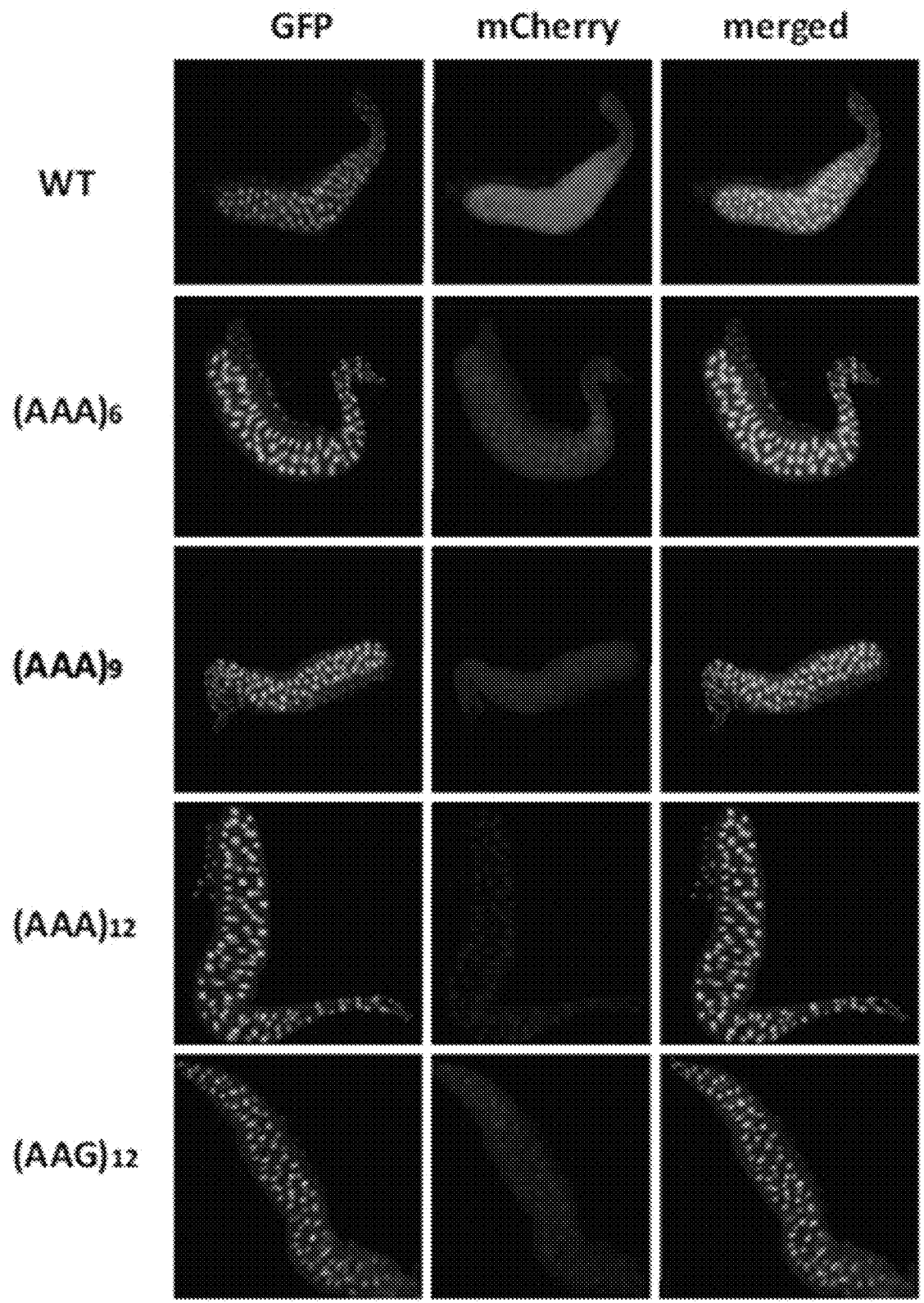
Figure 28C:
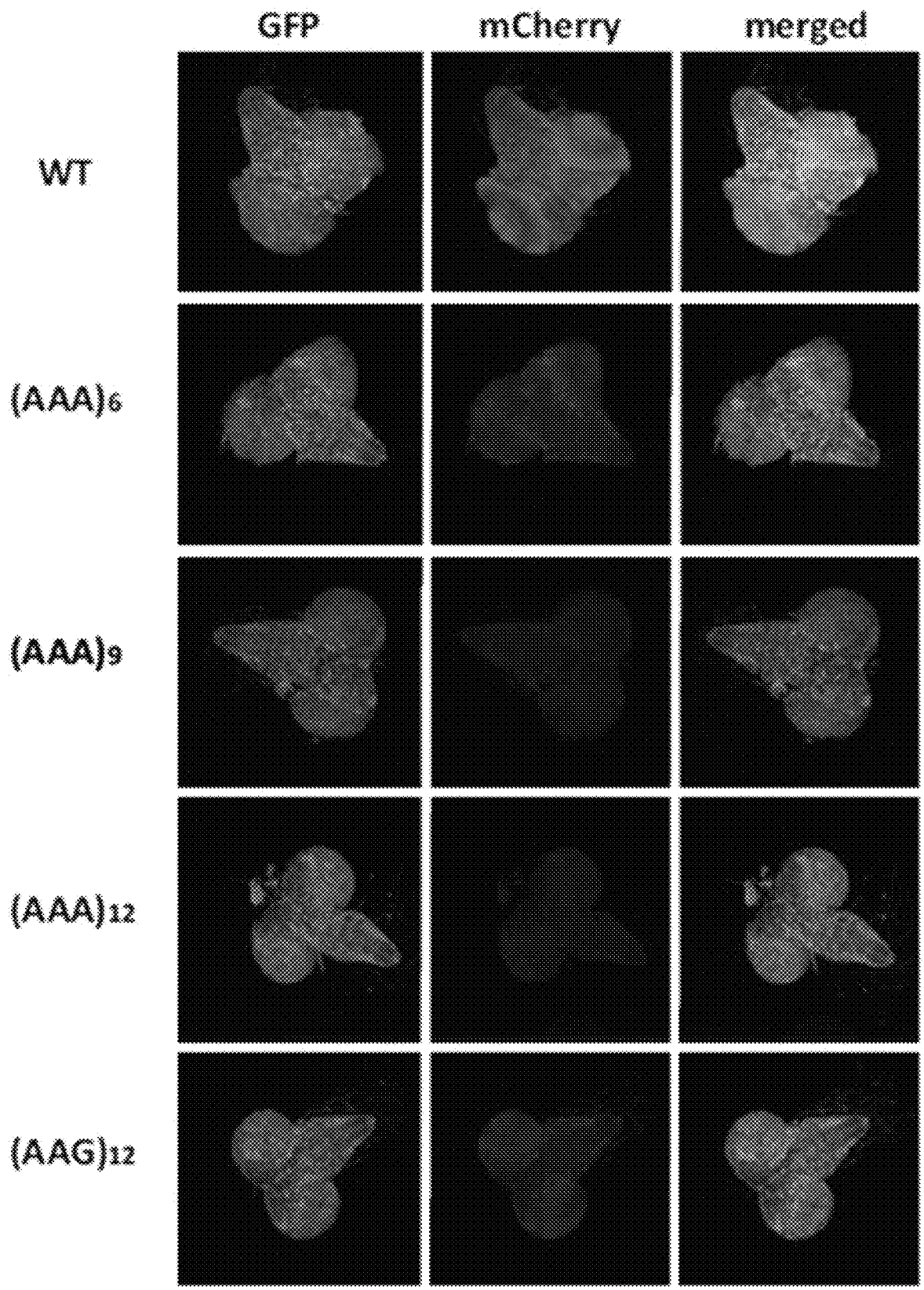
Figure 28D:
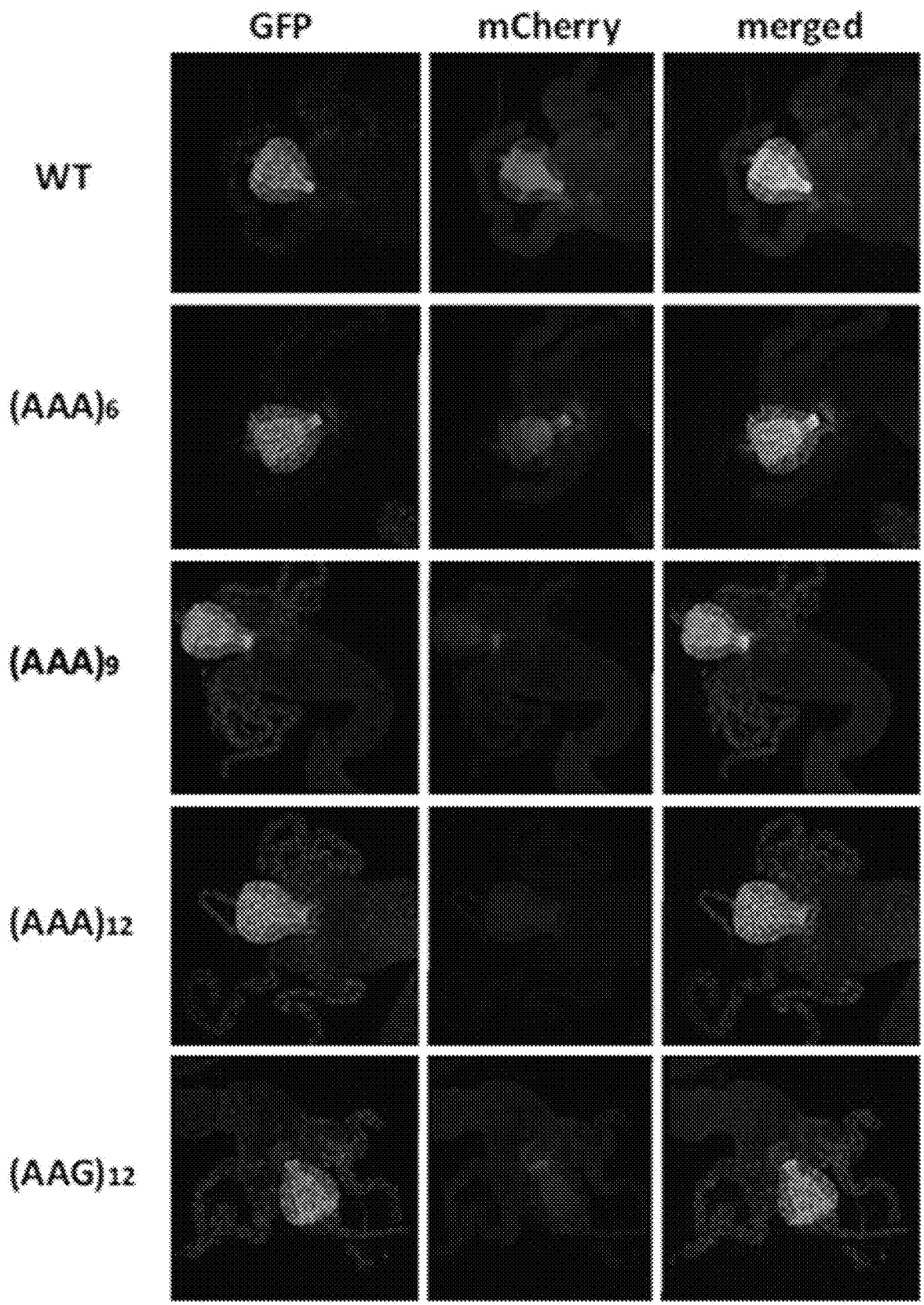

EXAMPLE 5: PolyA Tracks can be Used to Regulate Gene Expression in Human Tissue Cultures To further assess the universality of polyA tracks on protein expression, we tested our reporter series in human tissue cultures using HeLa cells. Plasmids with HA-mCherry, HA-12LysAAG-mCherry and HA-polyA-mCherry reporters, driven by the constitutively active CMV promoter, were electroporated into HeLa cells for transient expression. Protein abundances were assessed by Western blot analyses 24 hours after electroporation (FIG. 27E). As in our previous study on expression of endogenous and synthetic polyA tracks in various human tissue cultures (Arthur, et al., 2015), constructs with increasing length of polyA tracks (6, 9 and 12 LysAAA) were expressed less than control constructs and reduction in protein expression was proportional with the length of polyA track. Construct with 18As (6LysAAA) displayed approximately 3-fold reduction in expression compared to WT construct. Insertion of 27 and 36As (9 and 12LysAAA, respectively), exhibited 6 and 25-fold reduction of HA-mCherry expression compared to WT (FIG. 27F). Our control construct with 12LysAAG codons did not show any reduction in protein levels compared to WT construct (FIG. 27E and FIG. 27F). This again indicates differences between translational stalling induced by polybasic peptides (Arthur, et al., 2015; Koutmou, et al., 2015; Kuroha, et al., 2010; Brandman, et al., 2012), which seems to be cell or organism specific and unpredictable, and polyA track-induced ribosomal stalling and frameshifting (Arthur, et al., 2015; Koutmou, et al., 2015) which is clearly dependent on the length of polyA tracks and conserved between multiple organisms and tissue cultures. mRNA stability of the reporters corresponded to protein expression as it was seen in our previous report (data not shown) (Arthur, et al., 2015). Together with our previous study (Arthur, et al., 2015), our results indicate that polyA tracks can easily be used to regulate expression of reporters or genes transiently transfected in diverse eukaryotic tissues and cultured cell systems, such as *N. benthamiana* and human cell cultures, as well as other mammalian or insect tissue culture systems (Arthur, et al., 2015).

Figure 34:
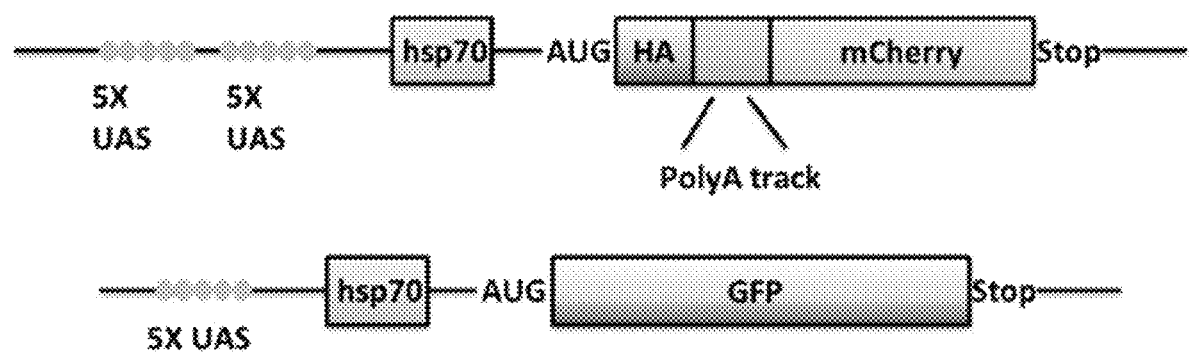
FIG. 34 shows diagram of mCherry and GFP expression constructs used in D. melanogaster. Position of the heat shock protein 70 promoter (hsp70), upstream activating sequences (UAS, GAL4 DNA binding sequence), double HA-tag (HA) and fluorescent reporters, mCherry and GFP, are indicated. Red box designates the position of in frame inserted polyA tracks and 12 LysAAG sequences. WT construct contains no insertions at this position. Tub-GAL4 driver line used for the expression of mCherry and GFP was derived from BSC42734.
Figure 35A:
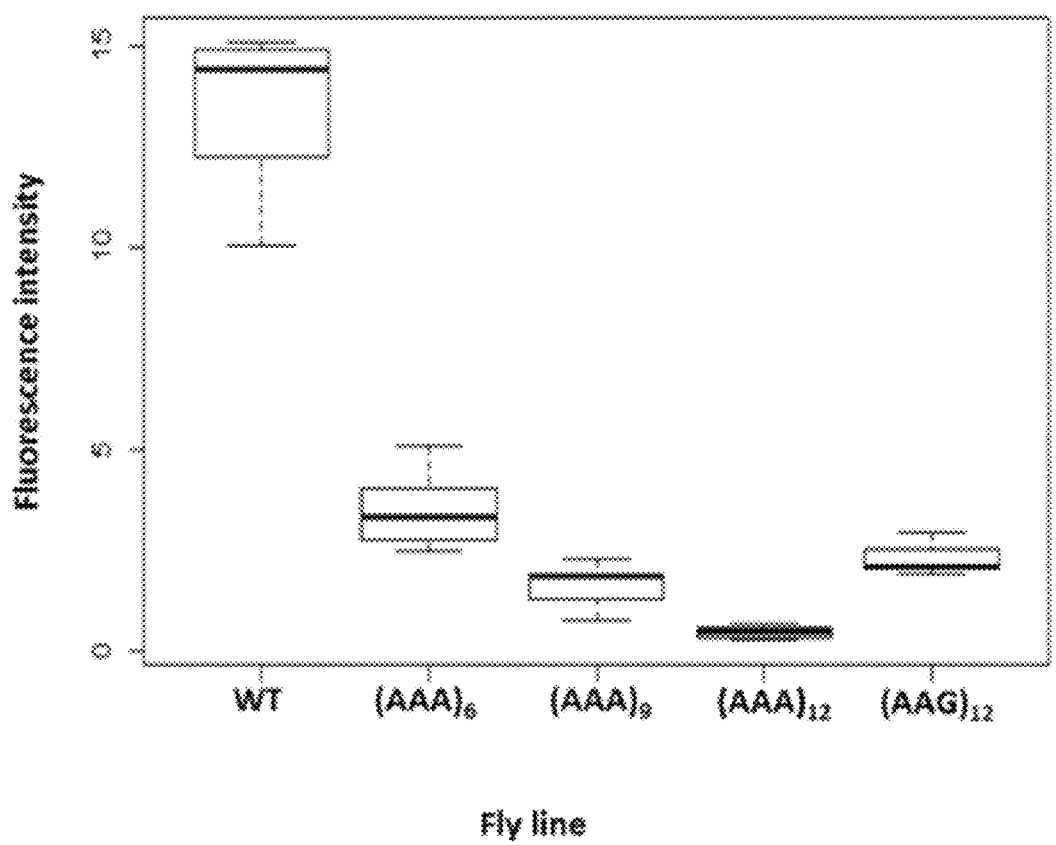
FIG. 35A, FIG. 35B, and FIG. 35C show quantification of mCherry fluorescence in D. melanogaster Salivary Glands (SG), Central Nervous System (CNS), and Proventriculus (PV). Normalized mCherry fluorescence intensity of WT, 12 LysAAG and 6-12 LysAAA in D. melanogaster SG (FIG. 35A), CNS (FIG. 35B) and PV (FIG. 35C). GFP fluorescence was excited by a 488 nm laser and mCherry by a 561 nm laser. All microscopy parameters were constant between tissues, except master gain which was set as follows: SG—488 nm laser master gain was 509, 561 nm laser was 560, CNS—488 nm laser master gain was 625, 561 nm laser was 720, and PV—488 nm laser master gain was 618, 561 nm laser was 616. Fluorescence intensity was measured as an average intensity from each tissue image (Zen 9 software) and plotted as a ratio of mCherry to GFP intensity. Box plots indicate median intensity ratio per construct (n≥5).
Figure 35B:
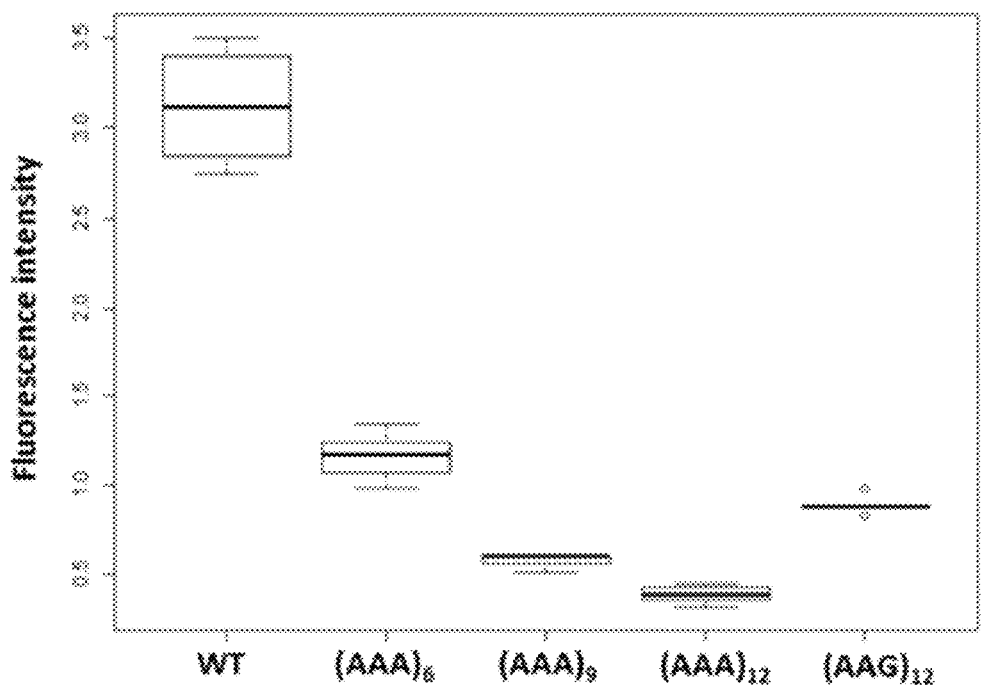
Figure 35C:
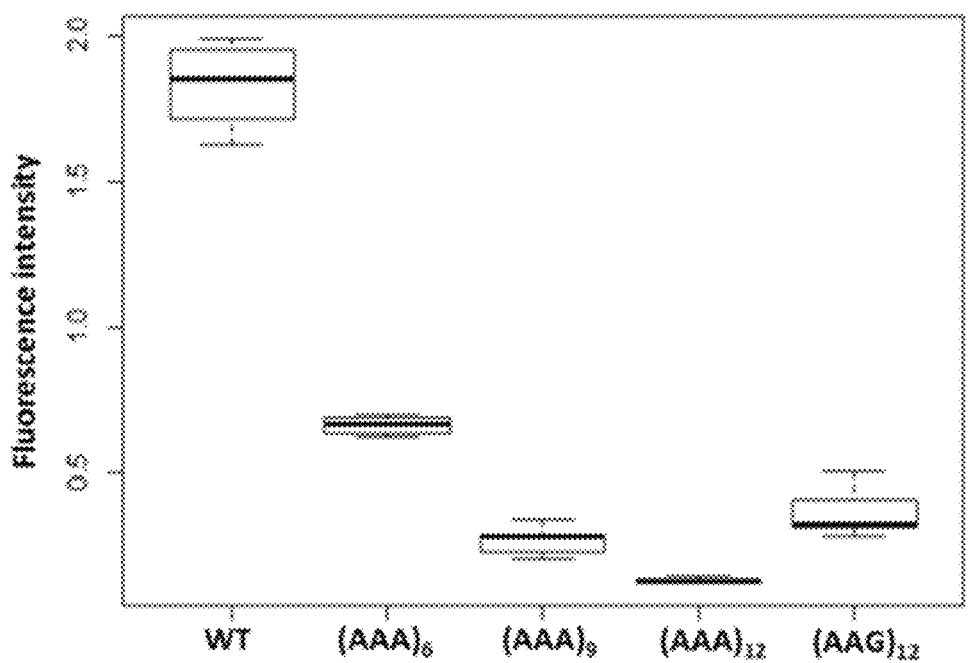

EXAMPLE 6: PolyA Tracks can be Used for Gene Expression Regulation in all Tissues of Model Organism We next sought to test whether polyA tracks can be used to regulate reporter gene expression in complex, multicellular organisms. We chose fruit fly, *D. melanogaster*, due to the well-developed tools in the manipulation of endogenous genetic loci, as well as for the easier assessment of our mCherry reporter screen. Using the PhiC31-integrase approach (Groth, et al., 2004), we generated single transgene insertions of the HA-mCherry and HA-12LysAAG-mCherry controls, and HA-polyA-mCherry (6, 9 and 12LysAAA) constructs in the identical genomic location in the third chromosome (FIG. 34). All constructs contained Upstream Activation Sequence (UAS) followed by HSP70 promoter which actively transcribes mCherry reporter mRNAs in response to expression of GAL4 protein (Duffy, 2002). To drive expression of mCherry in all tissues, each transgenic line was crossed to a line that carried the Tub-GAL4 driver line that expresses GAL4 protein in all tissues and a UAS-linked GFP transgene, which allowed us to use GFP expression for normalization of the mCherry reporter genes (FIG. 34).

Figure 36A:
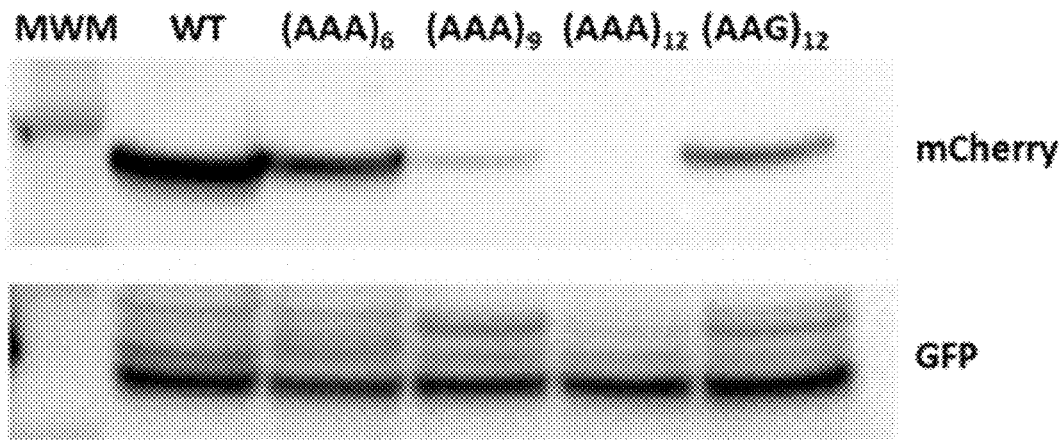
FIG. 36 shows western blot analysis and quantification of mCherry protein from third instar *D. melanogaster* larvae. Five third instar fruit fly larvae expressing either WT, 12 LysAAG or 6-12LysAAA constructs were frozen, homogenized, sonicated and lysed in SDS sample buffer. Equal amounts of lysate were analyzed by SDS-PAGE followed by western blot transfer. mCherry protein was detected using HA-tag antibody (Santa Cruz Biotechlogy Inc) and relative amounts were calculated based on the GFP expression control. GFP protein was detected using GFP specific antibody (Clontech). Relative amounts of mCherry expression are shown as percentage of WT-mCherry expression.
Figure 36B:
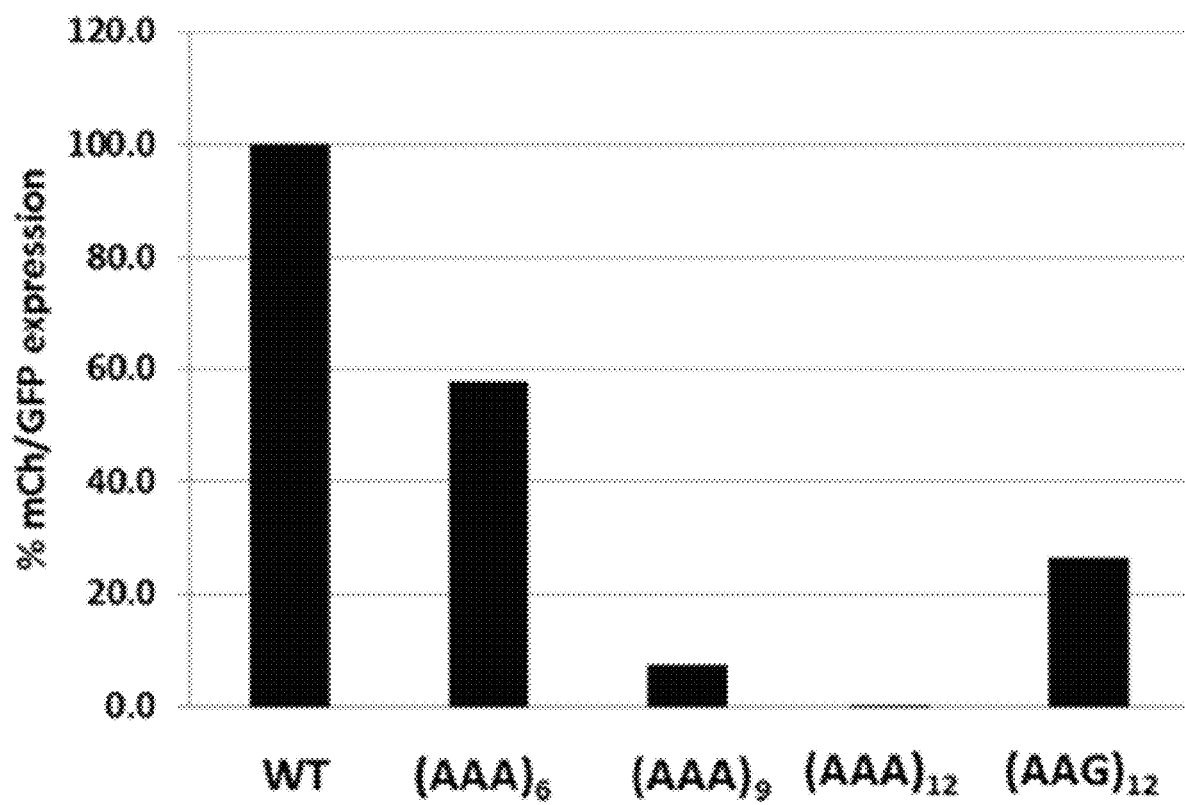
Figure 37:
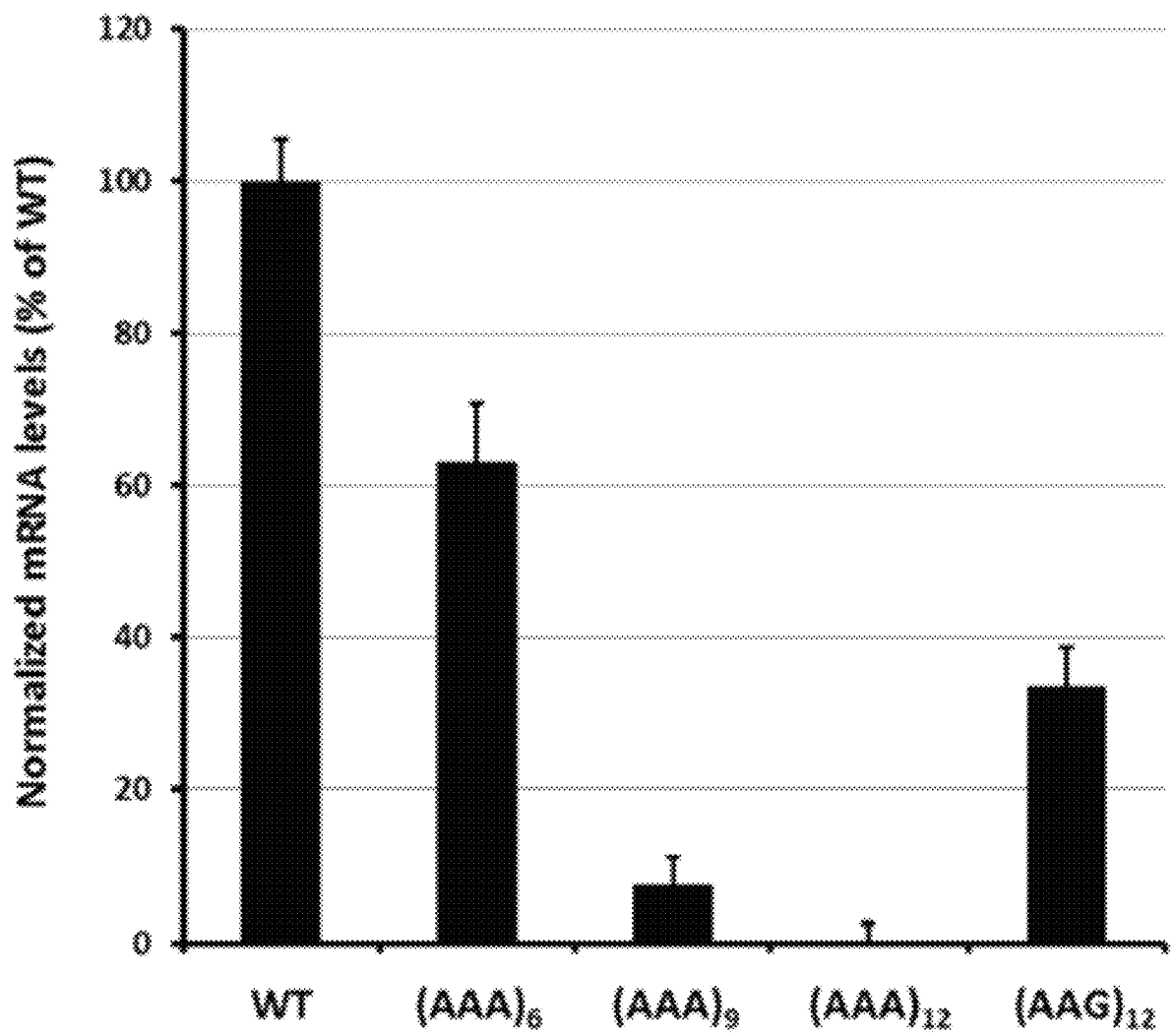
FIG. 37 shows mCherry mRNA abundance in whole third instar *D. melanogaster* larvae measured by RT-qPCR. Five third instar fruit fly larvae expressing either WT, 12 LysAAG or 6-12LysAAA constructs were frozen, homogenized, and lysed in RiboZol (Ambion). mCherry RNA abundance was measured by RT-qPCR. Relative amounts of mCherry mRNA were normalized to levels of Elongation Factor 1 alpha-100 (EF1) and shown as percentage of WT-mCherry levels. Error bars indicate mean±standard.
Figure 40:
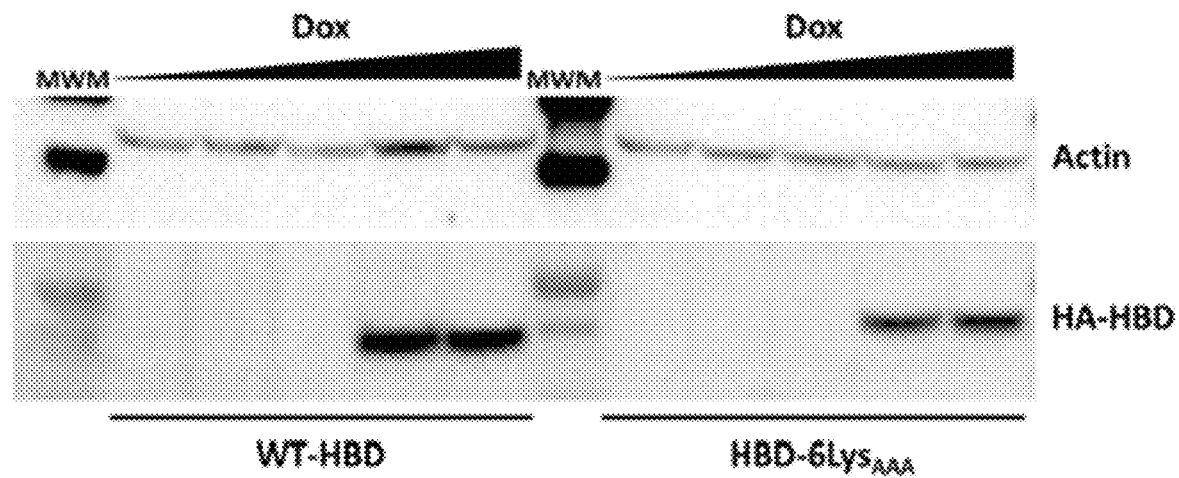
FIG. 40 shows western blot analysis of HBD protein abundance during Dox induction. Western blot analysis of the cell lysates from Flp-InTM T-RExTM 293 stable cell lines expressing doxycycline (Dox) inducible wild type (WT-HBD) and 6 LysAAA insertion construct (HBD-6LysAAA) from a single locus. Dox concentration in the media was varied from 0.0 to 1 µg/ml. Constitutively expressed β-actin (Actin) was used as a loading control and was detected using specific antibody. Positions of the HA-tagged HBD protein (HA-HBD), normalization control (β-actin) and molecular weight marker (MWM) are indicated.

Expression of mCherry was assessed by fluorescence imaging of formaldehyde fixed salivary glands (SG), central nervous system (CNS), and proventriculus (PV) dissected from otherwise wild-type third instar larvae (FIG. 32A). Wild type HA-mCherry expressed well in all imaged tissues. Addition of a polyA track with 18A's (6LysAAA) reduced mCherry expression to approximately 30% of the wild type construct in all three tissues (FIG. 28B, FIG. 28C, FIG. 28D, and FIG. 35). Constructs with 27As and 36As (9 and 12LysAAA codons, respectively) reduced expression of mCherry in all assayed tissues to approximately 20% and 10% of wild type levels, respectively (FIG. 28B, FIG. 28C, FIG. 28D, and FIG. 35). Western blot analysis on cell lysates produced from five fruit fly larvae for each independent construct confirmed our quantification of fluorescence imaging data (FIG. 40). As in the previous experiments with *T. Thermophila* and tissue cultures (FIG. 30 and FIG. 31), mRNA stability of polyA track constructs in fruit fly larvae showed inverse correlation with the length of polyA track (FIG. 36) and concordance with protein abundances measured by Western blot analyses. Insertion of 12LysAAG codons had moderate effect on levels of mCherry mRNA and protein and was in the range of 18As (6LysAAA) insertion construct (FIG. 28B, FIG. 28C, FIG. 28D, FIG. 36, and FIG. 36). Our data indicate that individual tissues of a complex multicellular organism, such as fruit fly, are equally sensitive to gene expression attenuation mediated by polyA tracks. Therefore, one can use polyA track constructs to create hypomorphic alleles and allelic series, in complex multicellular organisms with similar relative gene expression attenuation efficiency in the different tissues.

EXAMPLE 7: PolyA Tracks Control Gene Expression Independently of the Promoter Strength Our data from fruit fly experiment indicated that the ratio between reporters with polyA track insertion and control is maintained in all tissues (FIG. 27B, FIG. 27C, FIG. 27D, FIG. 35, FIG. 36, FIG. 37). This suggests that inserted polyA tracks maintain their capacity of gene regulation independently of the strength of mRNA transcription, which is known to have a large dynamic range across genes and cell types (Li, et al., 2014).

Figure 38A:
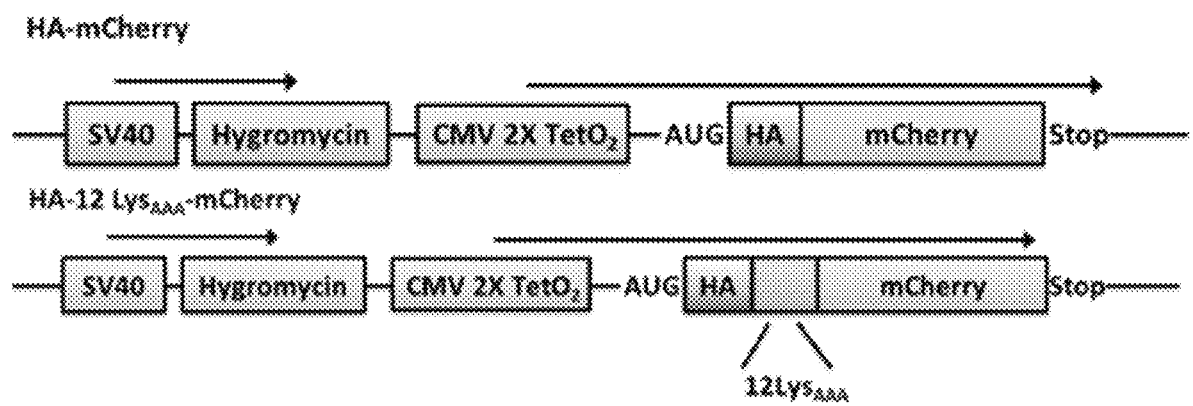
FIG. 38A and FIG. 38B show a diagram of mCherry expression constructs and their transcriptional activation in Flp-InTM T-RExTM 293 stable cell lines.
Figure 38B:
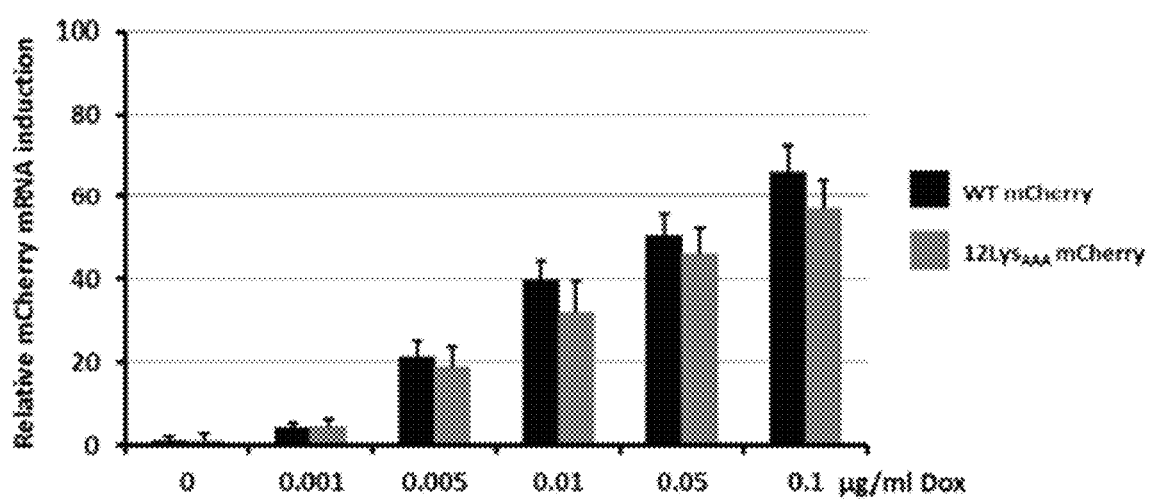
Figure 39:
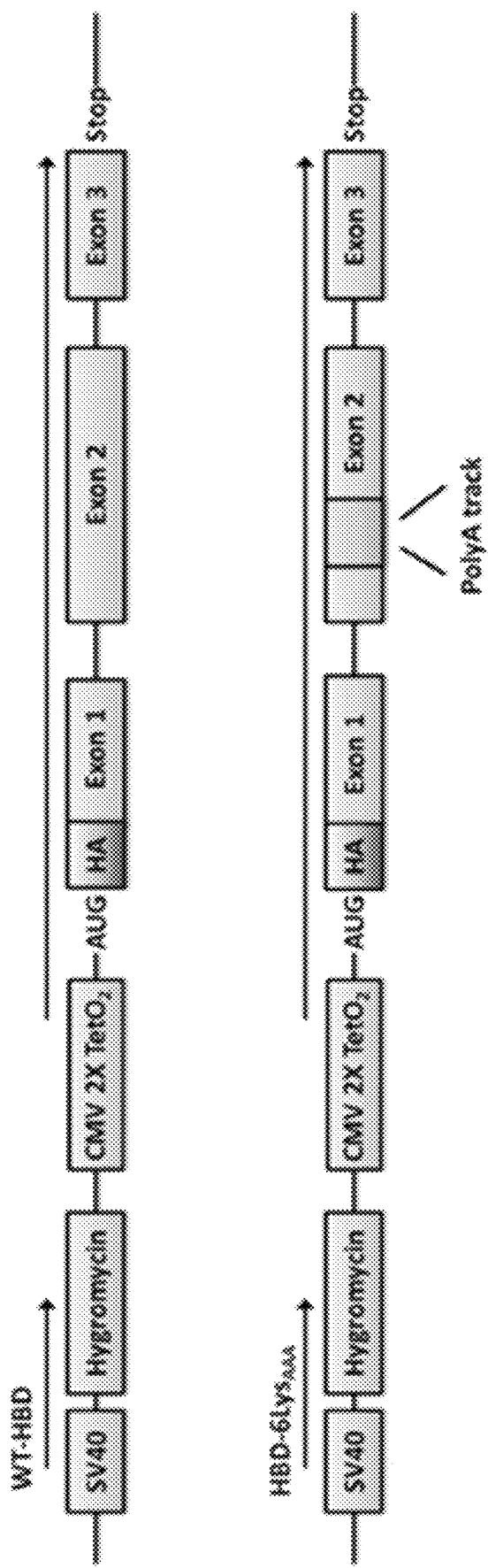
FIG. 39 shows diagram of human beta globin delta chain (HBD) expression constructs in Flp-InTM T-RExTM 293 stable cell lines. Scheme of genetic loci expressing WT-HBD and HBD-6LysAAA constructs in stable Flp-InTM T-RExTM 293 cell lines. Position of the SV40 promoter (SV40), hygromycin B phosphotransferase (Hygromycin), antibiotic resistance gene for selection of single insertion constructs), doxycyclin-inducible CMV promoter (CMV 2× TetO2), double HA-tag (HA) and HBD reporter (mCherry) are indicated. Red box designates the position of in frame inserted 6 LysAAA sequence. WT construct contains no insertions at this position.
Figure 41:
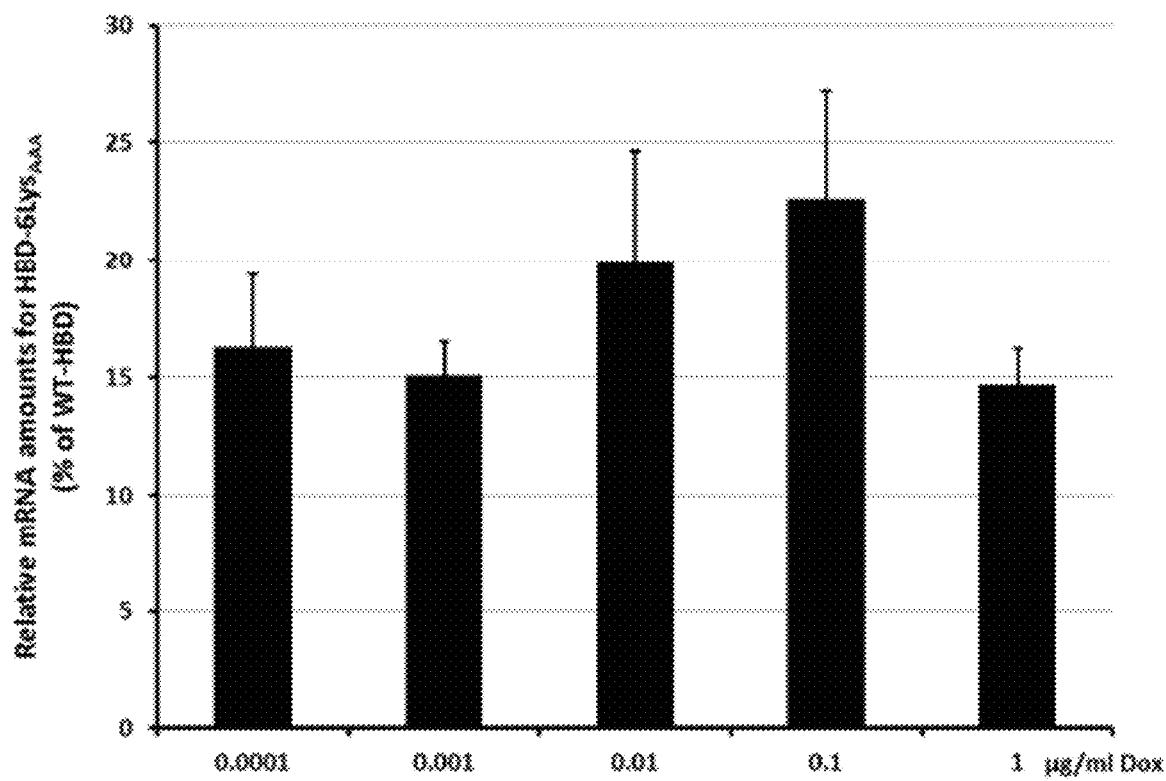
FIG. 41 shows ratio of WT-HBD and HBD-6LysAAA mRNA abundance from Flp-InTM T-RExTM 293 stable cell lines. Steady state mRNA levels of the 6LysAAA insertion construct (HBD-6LysAAA) measured by qRT-PCR. Relative levels of the mRNA for HBD-6LysAAA are presented as percentage of the wild type HBD (WT-HBD) construct mRNA levels. Error bars represent mean±standard deviation values (n=3). Numbers indicate final concentration of Dox in the media.

To systematically evaluate how differences in the strength of transcription would affect gene regulation and hypomorphic expression of reporters with polyA track insertion, we used human Flp-InTM T-RexTM 293 cell lines. Using a protocol for generation of stable and inducible expression cell lines, we have generated cells with a single insertion of our mCherry control and 36A polyA track construct in the defined chromosomal locus (FIG. 38). The strength of transcription in these cell lines was varied by use of increasing amounts of doxycycline (0.001 to 0.1 mg/ml of Dox) present in the growth media and levels of transcription was assayed in relation to constitutively expressed hygromycin B phosphotransferase. Dose-dependence response of doxycycline-inducible CMV promoter for both polyA track and control mCherry transcript ranged over two orders of magnitude. At the same time, relative expression of polyA track construct was kept constant at 5-8% of expression of control construct based on the Western blot analysis (FIG. 29A and FIG. 29B). Moreover, relative mRNA levels of control and polyA track constructs measured by the normalized ratios did not change under different transcriptional strengths (FIG. 29C). The steady state amount of 36As polyA track construct was constantly in the range between 1-3% of the normalized control construct. The same results are obtained using stable cell lines that express HA-tagged human hemoglobin (delta chain, WT-HBD) and an 18As HBD construct (HBD-6LysAAA) with polyA track inserted in the second exon of the HBD coding sequence (FIG. 39). Expression of the HBD-6LysAAA protein was 3-fold reduced compared to WT-HBD construct, based on Western blot analysis (FIG. 40), and mRNA levels were approximately 20% of the HBD-WT mRNA levels, measured by qRT-PCR (FIG. 41). The relative ratios of WT-HBD and HBD-6LysAAA protein and mRNA levels were constant for different doxycycline induction levels. Together with previous data, showing regulated expression of mCherry reporter in different tissues of the transgenic fruit fly, these data demonstrate that polyA tracks can control gene expression independently of the promoter strength associated with assayed gene, keeping relative ratio of the protein levels between wild type and polyA track-attenuated product constant.

EXAMPLE 8: PolyA-Tracks can be Used to Create Sets of Hypomorphic Mutants in Functional Genes The polyA tracks are mainly composed of lysine residues, AAA or AAG codons, which can be problematic when expressed as tags due to their charge and specific modifications (ubiquitination, acetylation, SUMOylition and hydroxylation). These features of poly-lys chains can further influence protein function as well as cell homeostasis (Brandman, et al., 2012; Dimitrova, et al., 2009; Choe, et al., 2016; Yonashiro, et al., 2016).

Figure 30A:
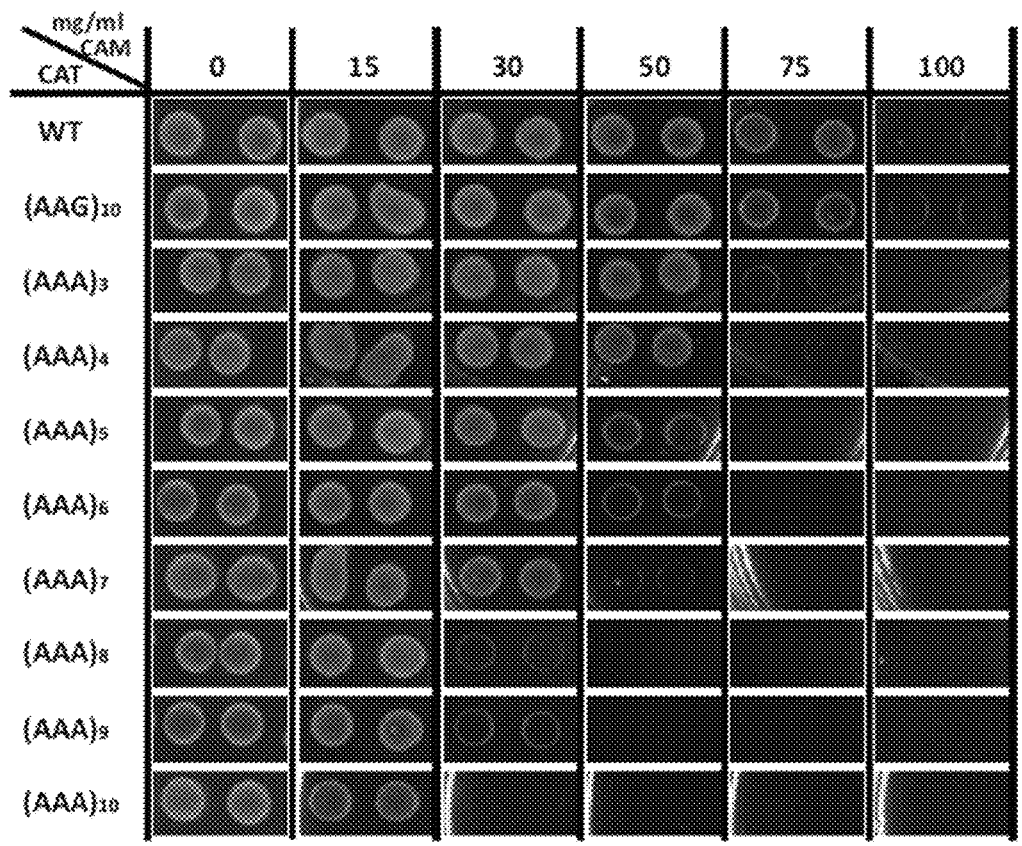
FIG. 30A and FIG. 30B show regulation of drug resistance and metabolic survival by insertion of polyA track tags in genes from E. coli and S. cerviseae.
Figure 42:
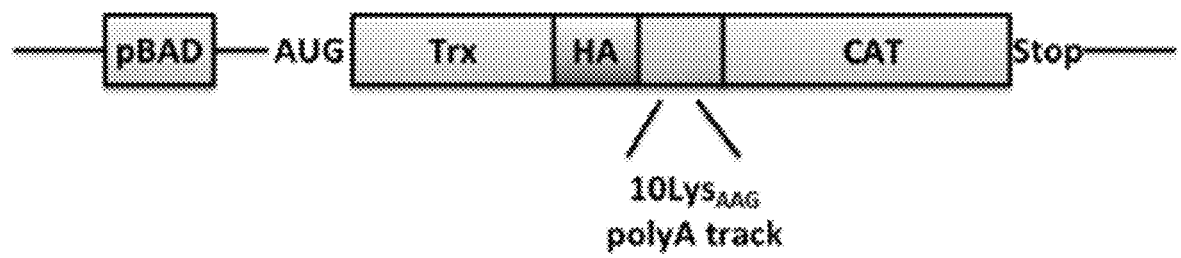
FIG. 42 shows diagram of chloramphenicol acetyltransferase (CAT) expression construct used in *E. coli*. Position of the inducible arabinose promoter (pBAD), Thioredoxin (Trx), double HA-tag (HA), insertion sequences (10 LysAAG and polyA track (3-10LysAAA) and reporter gene (CAT) are indicated.
Figure 43:
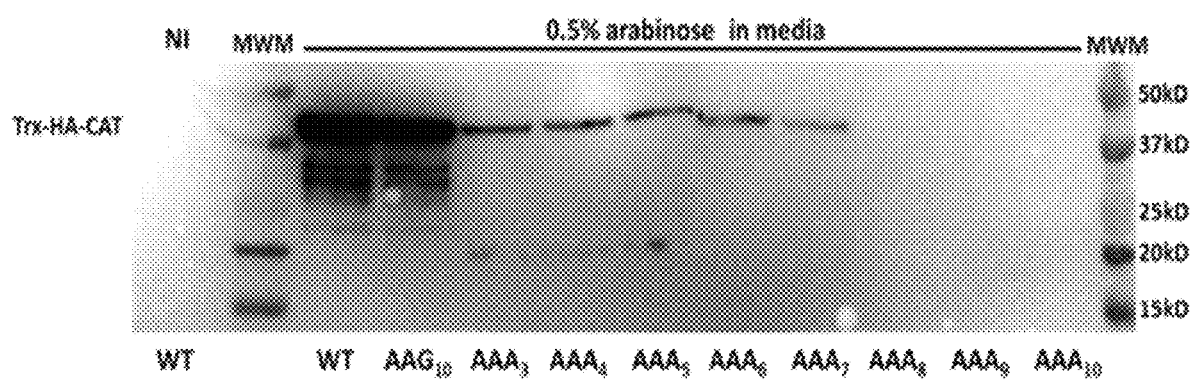
FIG. 43 shows expression of arabinose-inducible fusion Thioredoxin-HA-CAT constructs in *E. coli*. Western blot analysis of the lysates from *E. coli* cells expressing arabinose-inducible wild type Trx-HA-CAT (WT), 10 LysAAG (AAG10) and 3-10 LysAAA insertion constructs (AAA3-10). Cells were induced with 0.5% (w/v) of arabinose in the media for 30 minutes. Equal number of cells were harvested, lysed in SDS sample buffer and loaded on SDS-PAGE gel. Trx-HA-CAT fusion proteins were detected using HA-tag specific antibody. Positions of the Trx-HA-CAT proteins and molecular weight marker (MWM) are indicated. NI represents negative control; WT construct without induction.

We tested our ability to regulate gene expression of functional proteins in both prokaryotic and eukaryotic cell system. In *E. coli*, the chloramphenicol acetyltransferase (CAT) gene confers resistance to the broad spectrum antibiotic chloramphenicol (CAM) in a dose-dependent manner (Shaw, et al., 1991). To show that we can regulate expression of CAT protein by insertion of polyA tracks we assessed *E. coli* survival under increasing concentrations of CAM in comparison with wild type CAT gene. To control for the influence of additional lysine residues in the N-terminus of CAT protein we also inserted 10LysAAG codons in the N-terminus of CAT gene. Expression of WT-CAT, AAG10-CAT and polyA-CAT constructs was driven by the inducible arabinose promoter (pBAD, FIG. 42). All *E. coli* cultures were pulse induced, with addition of 0.1% arabinose, and growth was monitored on LB plates using different amounts of CAM in the media. WT-CAT and AAG10-CAT control constructs were able to survive CAM selection to the same level of CAM concentration in the media (75 mg/ml CAM, FIG. 30A). Therefore, the function of CAT protein is not affected by the addition of 10 consecutive Lys residues. PolyA tracks in constructs led to increased CAM sensitivity, of *E. coli* cells, which correlated with the length of the polyA tracks inserted in CAT gene (FIG. 30A). While majority of constructs could grow on minimal addition of CAM in the media (15 mg/ml), constructs with 24, 27 or 30As (8, 9 and 10LysAAA) were unable to grow on LB-plates with CAM concentration of 30 mg/ml. Furthermore, survivability of *E. coli* cells with CAT constructs having 15, 18 and 21As (5, 6 and 7LysAAA) on one hand, and 9 and 12As (3 and 4LysAAA) on the other hand, was impaired when cells were grown on LB-plates with final CAM concentrations of 50 mg/ml or 75 mg/ml, respectively (FIG. 30A). The survivability of *E. coli* cultures with different CAT constructs was in concordance with expression levels of CAT protein assayed by Western blot analyses (FIG. 43). The insertion of 10LysAAG codons in CAT gene did not affect *E. coli* cell growth on CAM selective media or levels of CAT protein expression arguing that insertion of multiple lysine residues in the N-terminus is not detrimental for the function and stability of CAT protein. These data demonstrate that polyA tracks can regulate levels of certain enzyme expression (CAT) in *E. coli* cells proportionally with their length.

Figure 30B:
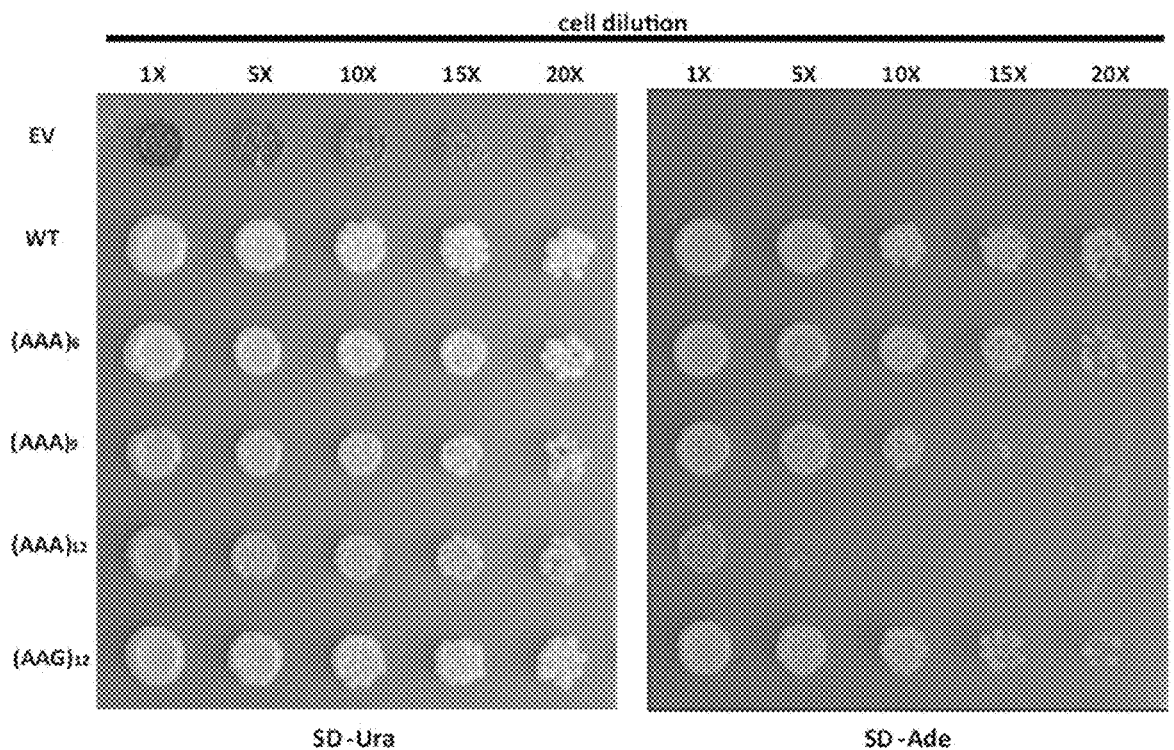

To test ability of polyA tracks to regulate expression and function of protein in a eukaryotic cell we monitored how polyA tracts affect expression of N-succinyl-5-aminoimidazole-4-carboxamide ribotide synthetase (Ade1) in *Saccharomyces cerevisiae* (FIG. 30B). Disruption of the ADE1 gene results in the storage of a red pigment due to the buildup of a metabolic byproduct of the adenine biosynthesis pathway. Yeast cells that are ade1Δ are a dark red color; reintroduction of functional Ade1 protein restores the wild type white coloration in a dose-dependent manner. Differences in colony color and ability to grown on adenine dropout media (SD-Ade) have been utilized to differentiate strains of yeast prions (Liebman, et al., 2012), assess mitotic stability (Hieter, et al., 1985), and monitor gene expression (Mano, et al., 2013).

Figure 44A:
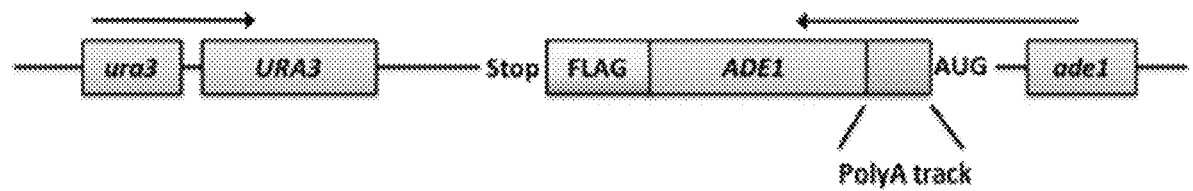
FIG. 44A and FIG. 44B shows a diagram of N-succinyl-5-aminoimidazole-4-carboxamide ribotide synthetase (ADE1) construct and expression of ADE1 constructs in *S. cerevisiae*.
Figure 44B:
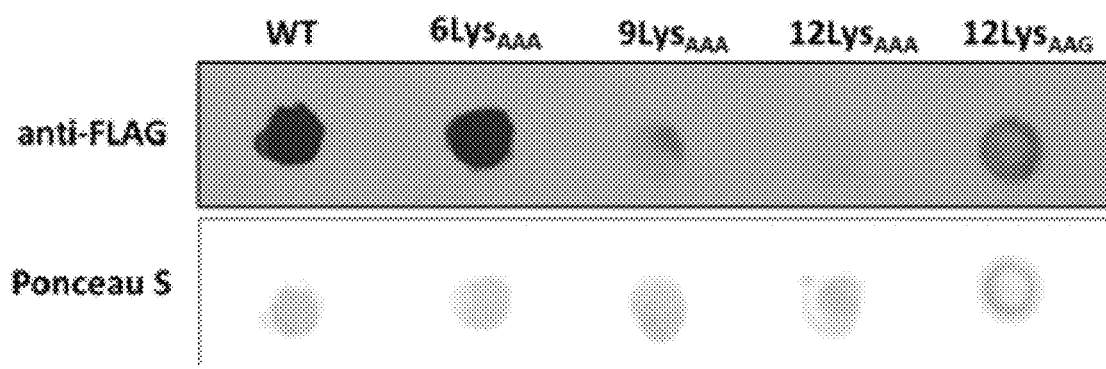
Figures 45B, 45C:
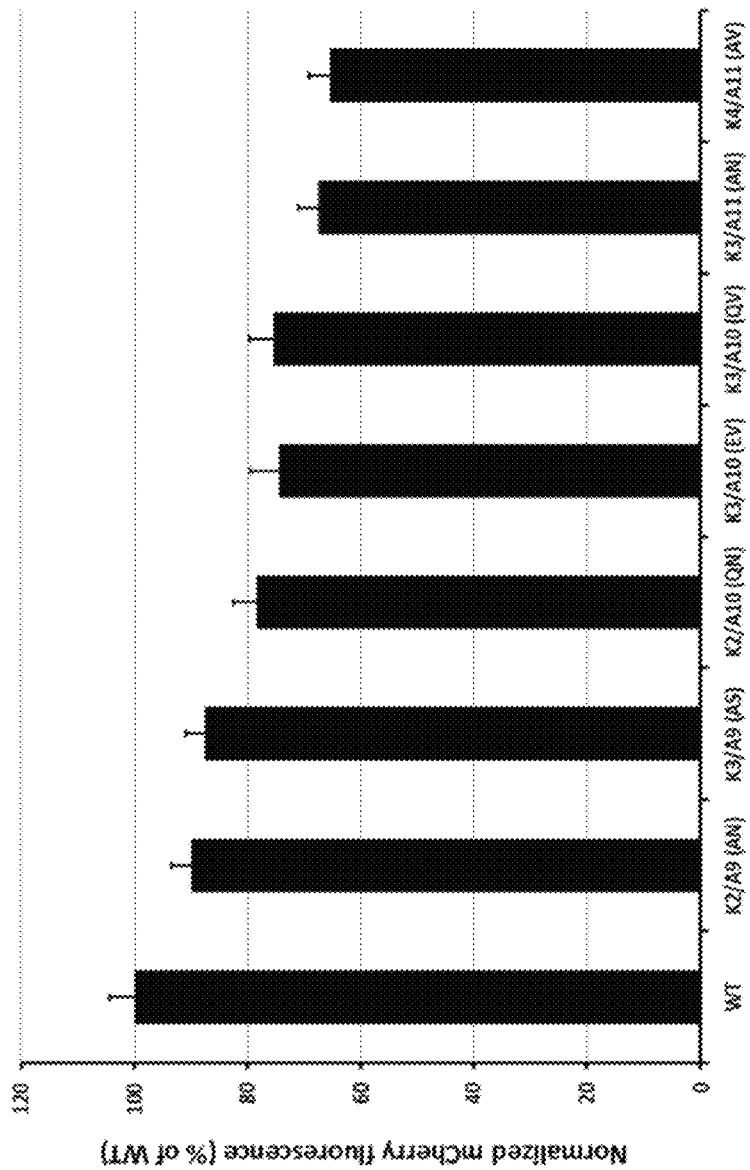
Figure 45D:
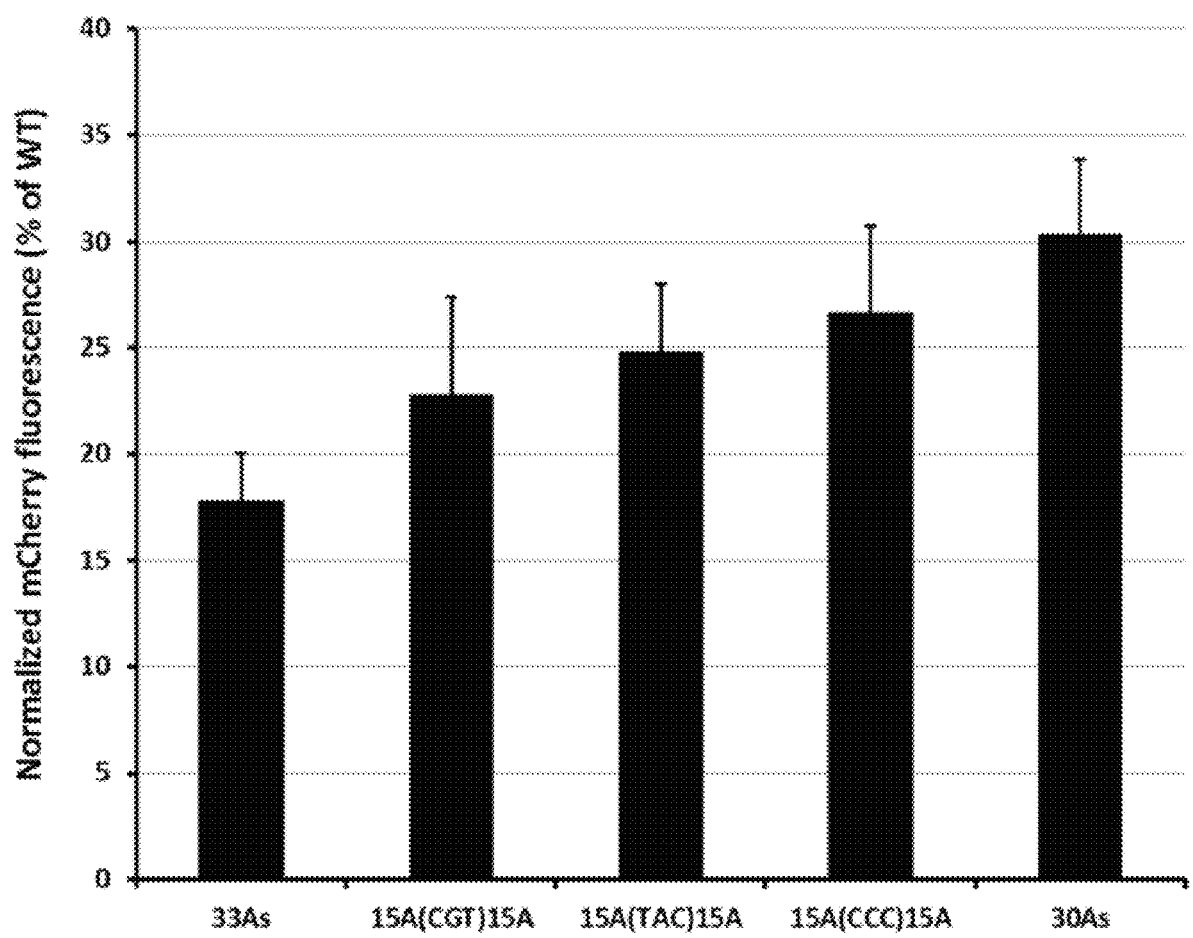
Figures 46A, 46B:
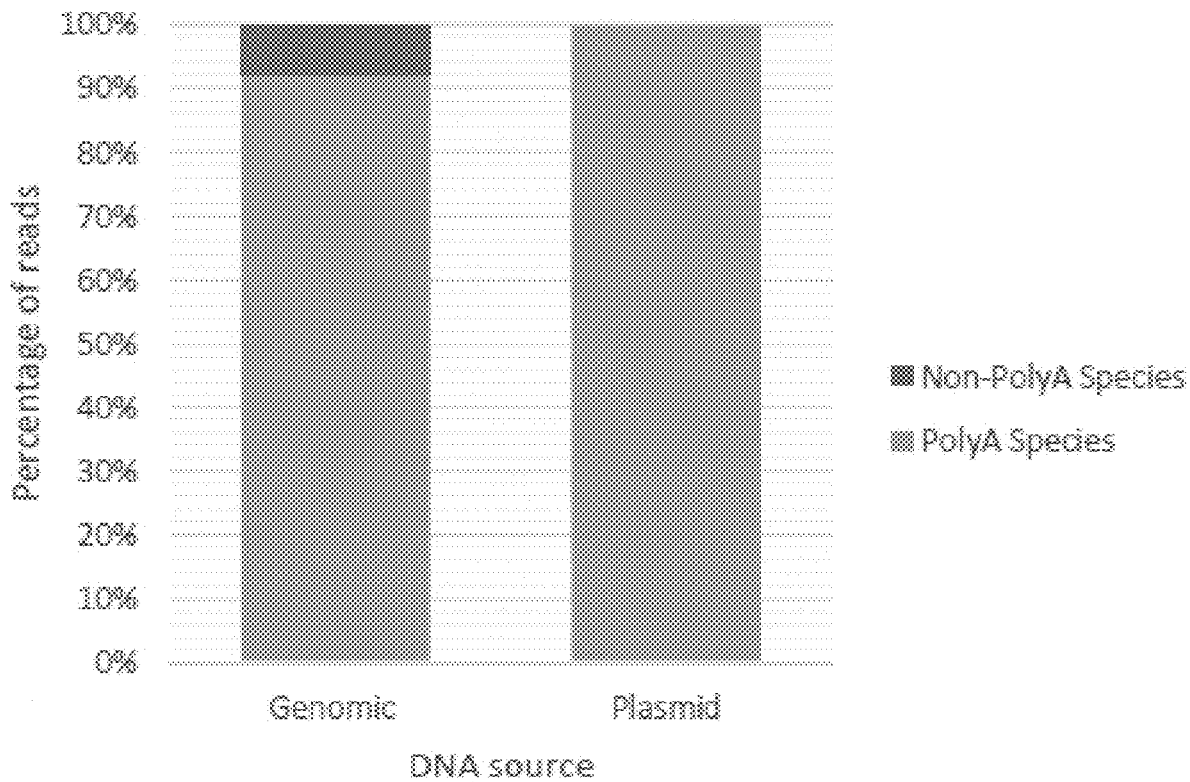
FIG. 46A and FIG. 46B. Illumina sequencing of polyA track genomic insertion. Approximately 30 generations after insertion of HA-(AAA)12-mCherry, genomic DNA was sequenced to examine mutation rate of long PolyA tracks. The fraction of sequencing reads which contain a polyA track vs reads that do not are shown for both genomic DNA and plasmid DNA (FIG. 46A). The non-polyA species of reads from genomic DNA are shown. The nucleic acid sequence shown is SEQ ID NO: 110 (FIG. 46B).
Figure 47:
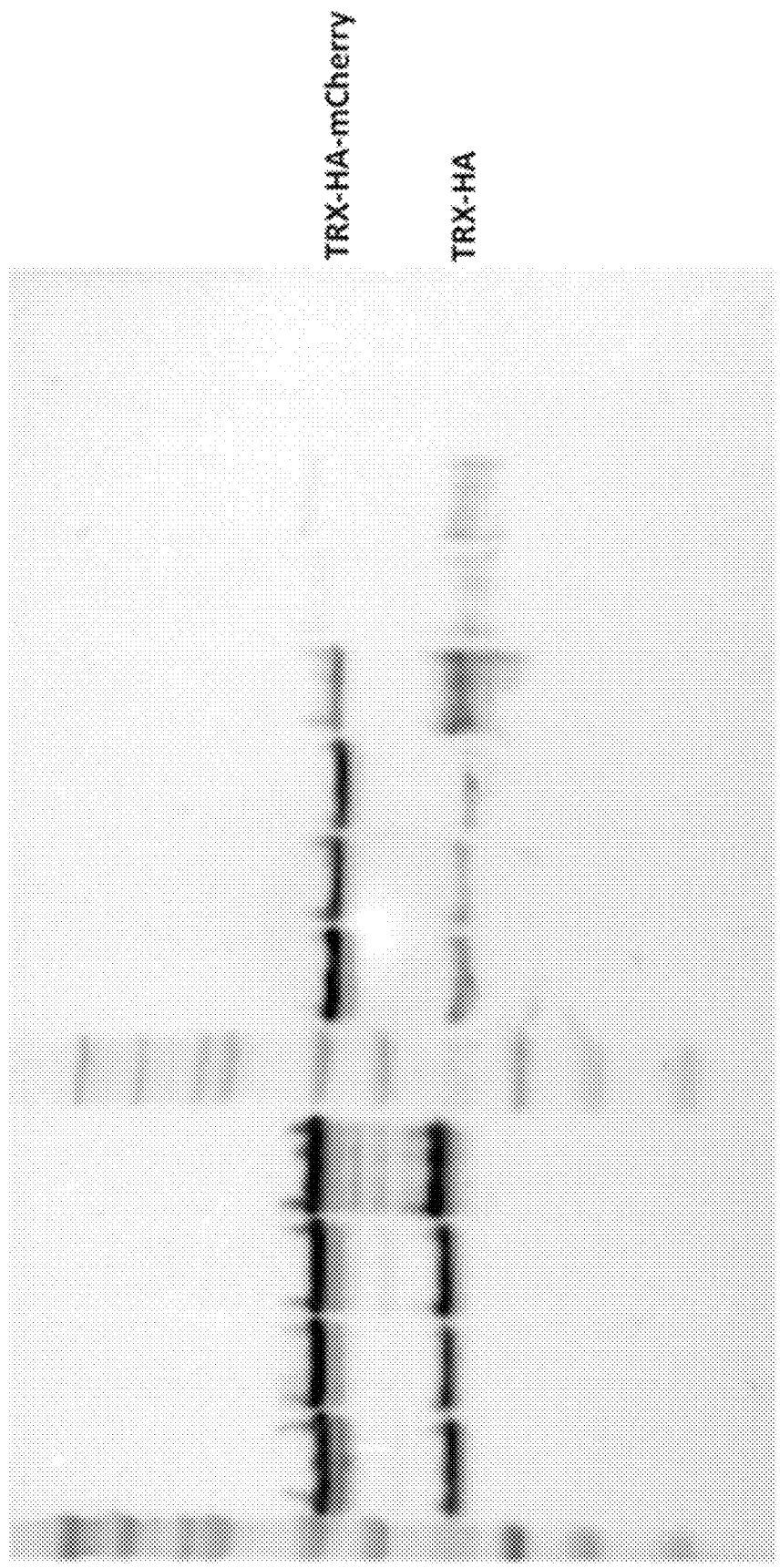
FIG. 47. Image of the full western blot used in FIG. 26B. Degradation of frameshifted product TRX-HA is indicated. Orientation of the gel is as in the original figure.
Figure 48A:
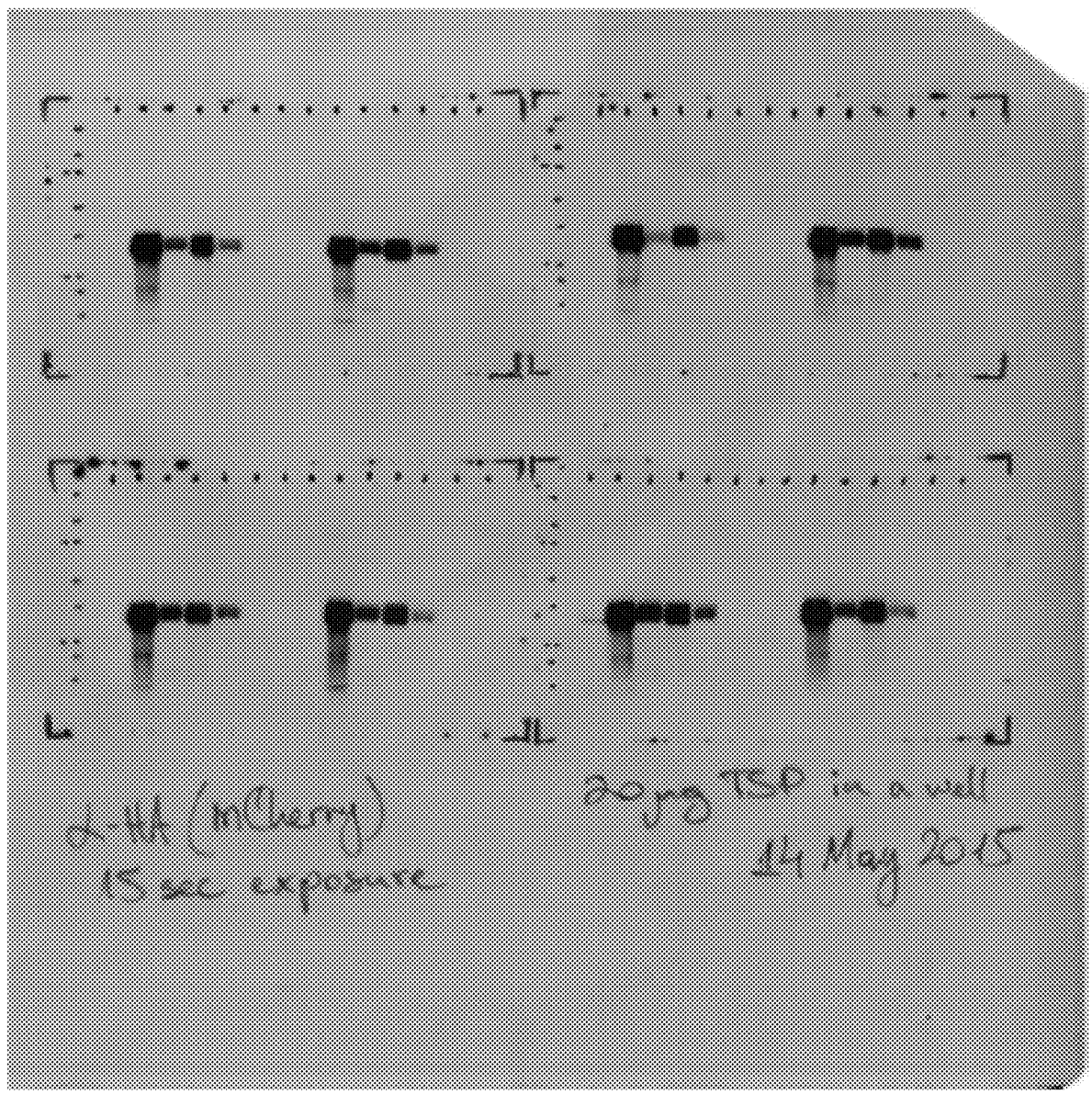
FIG. 48A and FIG. 48B Eight biological replicas for experiment represented in FIG. 27B. Loading of samples is in the same order as in the original figure for both mCherry and BAR (BASTA) western blots.
Figure 48B:
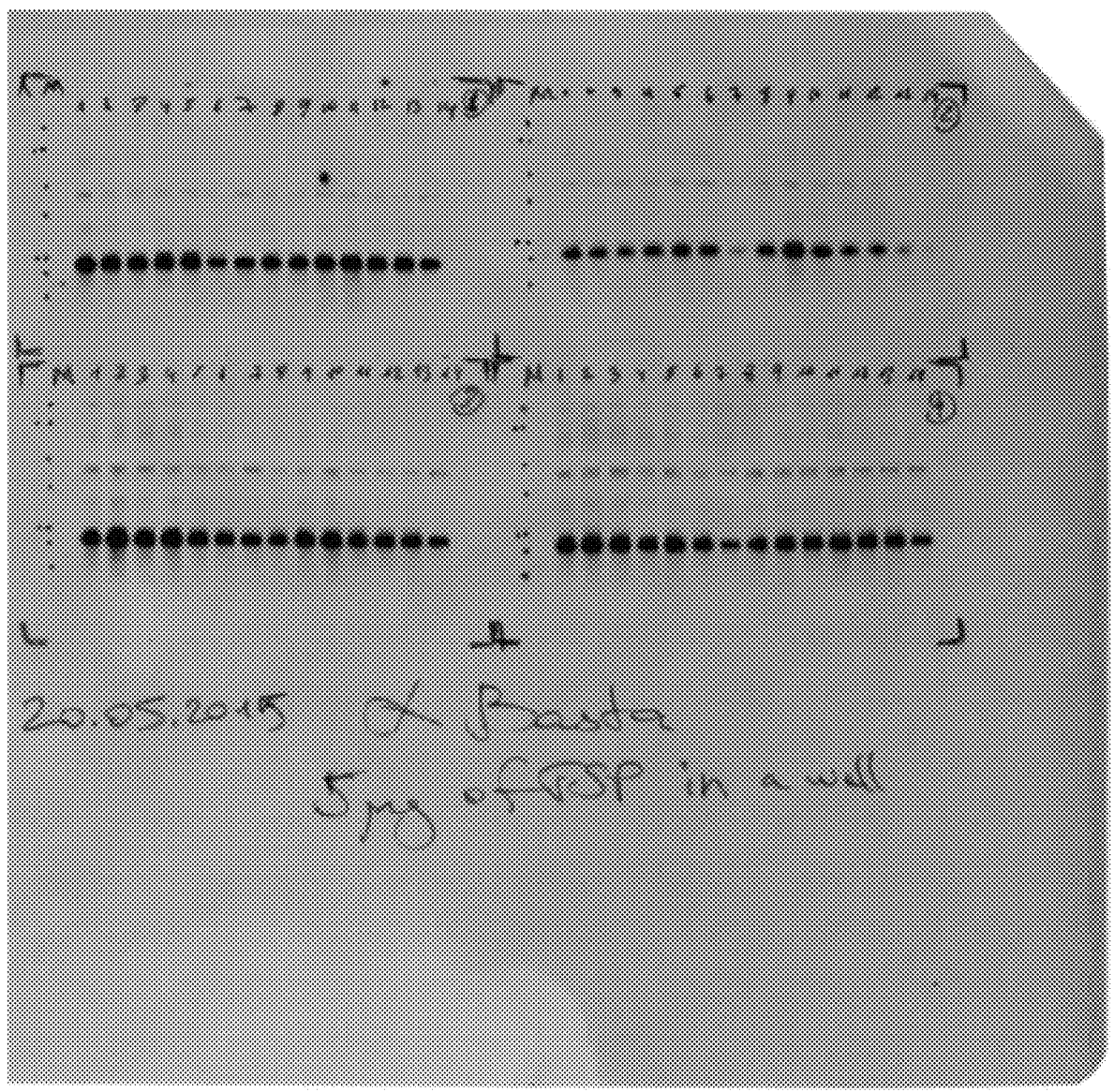
Figure 49:
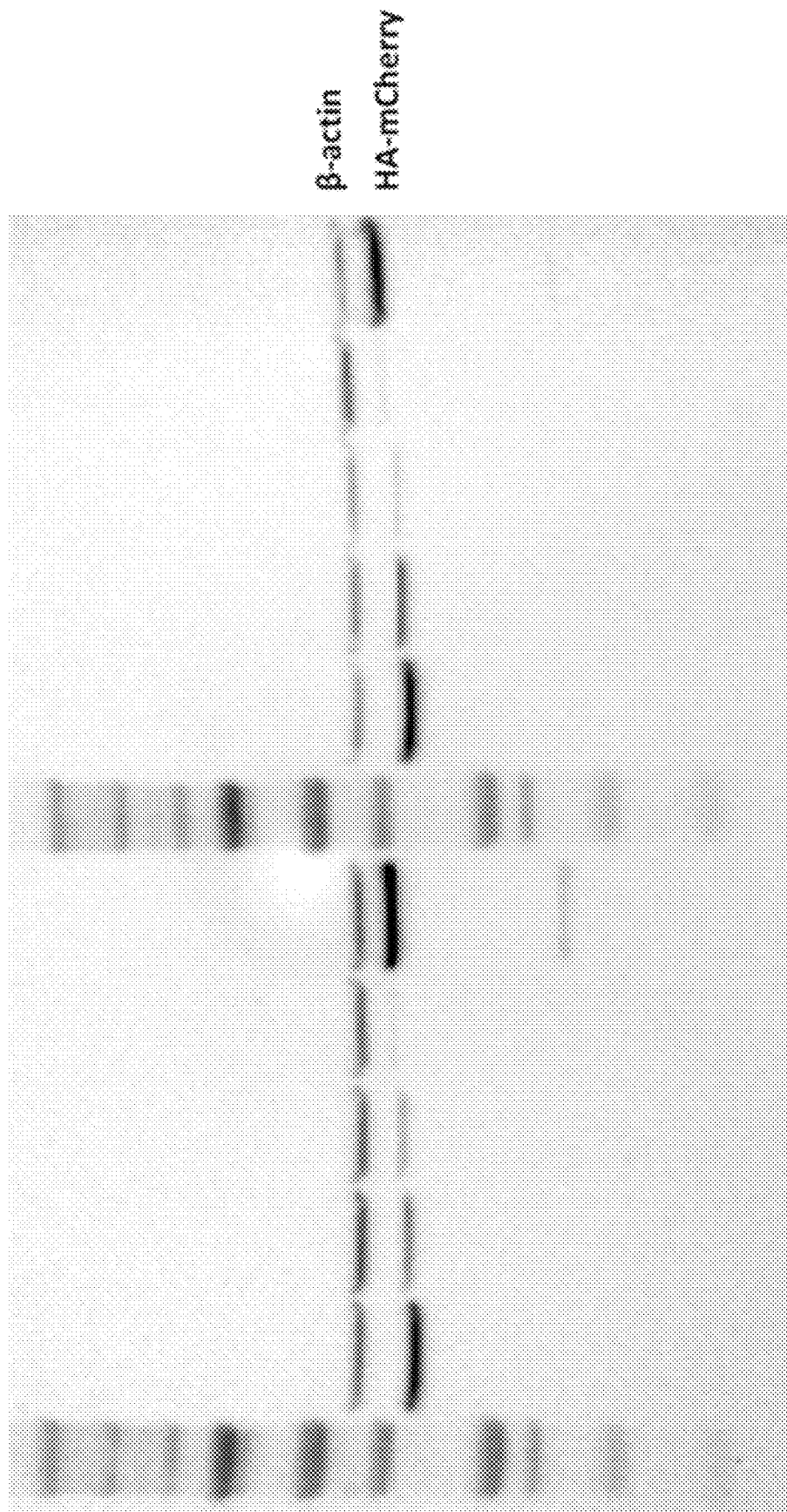
FIG. 49. Complete image of the western blot used in FIG. 27E. Loading and orientation of the western blot is the same as in the original figure. Samples from two biological replicas (left side and right side) are shown on this image.
Figure 50:
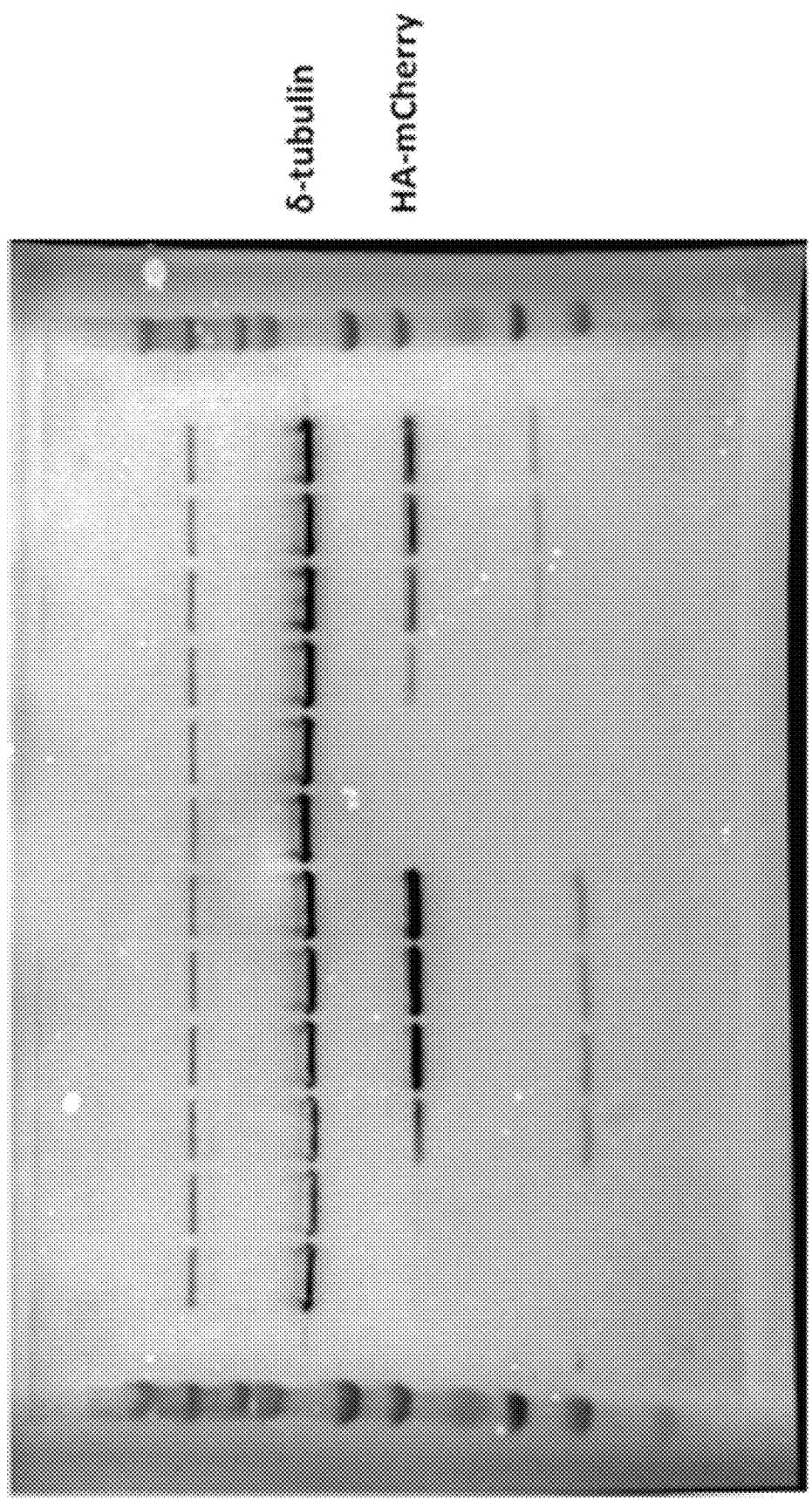
FIG. 50. Image of the full western blot represented FIG. 29A. Low molecular weight band for degradation product (reacting with HA-antibody) and unspecific high molecular band (reacting with δ-tubulin antibody) are visible on the image. Orientation of the gel is the same as in the original figure.
Figure 51:
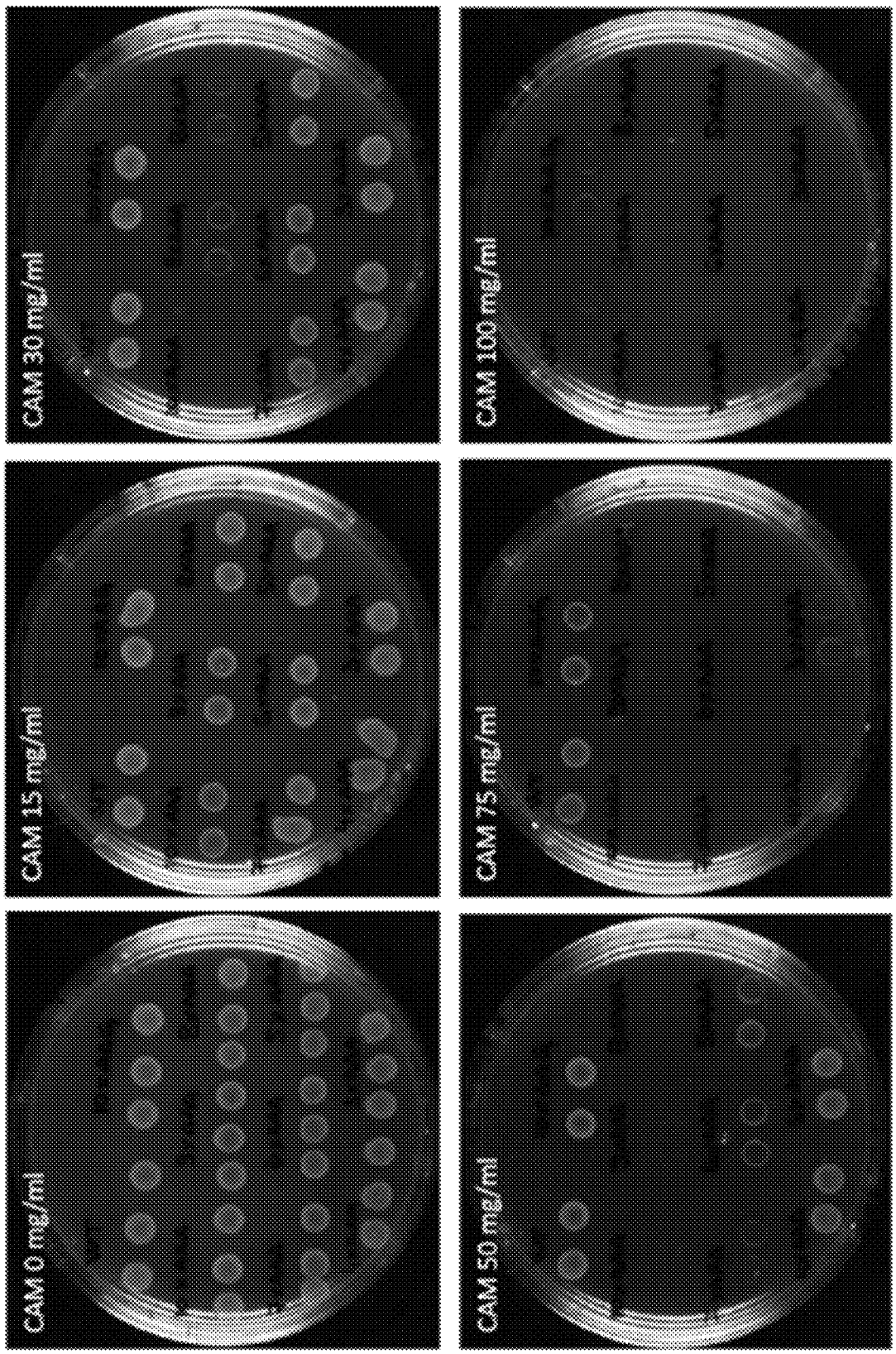
FIG. 51. Original plates for the experiments described in FIG. 30A. Two colonies for each construct are excised from the plates to make the final figure.

To survey how polyA tracts affect expression of Ade1, we transformed ade1Δ strains of *S. cerevisiae* with single copy plasmids (p416) encoding polyA-ADE1-FLAG, with the polyA tracks containing 18, 27 or 36As (6, 9, or 12 LysAAA, FIG. 44). Control plasmids contained no insertions (WT) or 12 LysAAG codons. Transformants were spotted onto plates to monitor color phenotype and growth on media lacking adenine (SD-Ade, FIG. 30B). The empty vector control exhibited a dark red coloration and inability to grow on SD-Ade, consistent with disruption of the ADE1 locus, while the wild type Ade1-FLAG restored both the white phenotype and growth on SD-Ade. Yeasts containing constructs with polyA track length of 18, 27 and 36A showed progressively pinker coloration and poorer growth on SD-Ade; however, the control 12LysAAG construct conferred a nearly-WT white color and strong growth on SD-Ade (FIG. 30B). Dot blot analysis of Ade1 protein expression, normalized to total protein, was in accordance with our phenotypic results and revealed visibly reduced amounts of expression for constructs with insertion of 9 and 12LysAAA codons (FIG. 44). Expression of Ade1 protein with 12 lysine residues at the N-terminus, as in the case of 12LysAAG, did not impair function of the assayed protein (Ade1) and show similar results as insertion of 6LysAAA codons. Therefore, addition of polyA tracks to functional genes in both *E. coli* and *S. cerevisiae* preserved protein function but regulated protein abundance and as such polyA tracks could potentially be used in creation of hypomorphic gene mutants with fixed levels of protein expression.

Methods for Examples 2-8

*E. Coli* Experiments mCherry reporter constructs used for expression in *E. coli* cells were subcloned using LR clonase recombination (Thermo Fisher Scientific) from pENTR/D-Topo constructs used in this study or in previous studies (Arthur, et al., 2015; Koutmou, et al., 2015). The resulting pBAD-DEST49 vector constructs express Thioredoxin (Thrdx) fusion protein as Thrdx-HA tag-insert-mCherry. For assaying expression of mCherry reporter all constructs were expressed in 2 ml *E. coli* Top10 strain grown in LB-Carbencilin (LB-Carb; final concentration 100 ug/ml). The cells were grown to optical optical density at 600 nm (OD600) of 0.4 at 37° C. and induced with addition of arabinose (0.5% w/v). Fluorescence of mCherry reporter for each construct was measured in triplicates 2 to 4 hours after induction using Biotek Synergy H4 plate reader (Excitation 475±9, Emission 620±9). The amount of fluorescence was normalized to number of cells measured by OD600. To additionally check for expression of fusion proteins, 200 ul of the cells was harvested 2 hr post-induction, resuspended in 100 ul of 2×SDS sample buffer and analyzed by SDS-PAGE followed by western blot analysis using HA-tag specific probe. Images of western blot analyses were generated by Bio-Rad Molecular Imager ChemiDoc XRS System with Image Lab software for chemiluminescence detection.

The chloramphenicol acetyltransferase (CAT) constructs used for functional protein studies were created by amplification of the CAT gene from pENTR/D-Topo vector (Thermo Fisher Scientific) using primers listed in Table 6. Constructs were subcloned into pBAD-DEST49 vector for use in functional assays. *E. coli* Top10 cells freshly transformed with pBAD-DEST49 plasmids expressing CAT reporters with different polyA tracks as well as CAT control reporters were grown in liquid LB-Carb media (100 ug/ml). For the chloramphenicol (CAM) survivability assay *E. coli* cells were grown to OD600=0.4 and non-induced (NI) fractions were spotted on LB-Carb plates (Carb 100 ug/ml) without chloramphenicol or to LB-Carb/CAM plates with raising amount of chloramphenicol in the media (CAM 15-100 ug/ml). The residual amount of the cells was induced for 1 hour with arabinose (final concentration 0.1% (w/v)). Cells were washed twice in M9 minimal media, resuspended in the staring volume of LB-Carb media and 5 ul of cells was spotted as induced (I) fraction on LB-Carb and LB-Carb-CAM plates. Plates were incubated overnight at 37° C. and imaged 24 hours post induction using Bio-Rad Molecular Imager ChemiDoc XRS System.

TABLE 6

Oligos used for generation of *E. coli* expressing CAT constructs

| SEQ ID NO: | Construct/ Oligo Name | Primer Sequence |
|---|---|---|
| 27 | CAT WT For | CACCATGCACCATCACCATCACCATGAAA AAAAAATCACTGGATATACCACCGTTGATA TATCCC |

TABLE 6-continued

Oligos used for generation of E. coli expressing CAT constructs

| SEQ ID NO: | Construct/ Oligo Name | Primer Sequence |
|---|---|---|
| 28 | CAT 10xAAG | CACCATGCACCATCACCATCACCATGAG AAGAAGAAGAAGAAGAAGAAGAAGA AGATCACTGGATATACCACCGTTGATATA TCCC |
| 29 | CAT 3xAAA | CACCATGCACCATCACCATCACCATGAAA AAAAAAAATCACTGGATATACCACCGTT GATATATCCC |
| 30 | CAT 4xAAA | CACCATGCACCATCACCATCACCATGAAA AAAAAAAAAATCACTGGATATACCACC GTTGATATATCCC |
| 31 | CAT 5xAAA | CACCATGCACCATCACCATCACCATGAAA AAAAAAAAAAAATCACTGGATATACC ACCGTTGATATATCCC |
| 32 | CAT 6xAAA | CACCATGCACCATCACCATCACCATGAAA AAAAAAAAAAAAAATCACTGGATAT ACCACCGTTGATATATCCC |
| 33 | CAT 7xAAA | CACCATGCACCATCACCATCACCATGAAA AAAAAAAAAAAAAAAAATCACTGGA TATACCACCGTTGATATATCCC |
| 34 | CAT 8xAAA | CACCATGCACCATCACCATCACCATGAAA AAAAAAAAAAAAAAAAAAAATCACT GGATATACCACCGTTGATATATCCC |
| 35 | CAT 9xAAA | CACCATGCACCATCACCATCACCATGAAA AAAAAAAAAAAAAAAAAAAAAAATCA CTGGATATACCACCGTTGATATATCCC |
| 36 | CAT 10xAAA | CACCATGCACCATCACCATCACCATGAAA AAAAAAAAAAAAAAAAAAAAAAAAAA TCACTGGATATACCACCGTTGATATATCCC |
| 37 | CAT Rev | CATTACAGATCTTCTTCAGAAATAAGTTTT TGTTCCGCCCCGCCCTGCCACTCATCGC AG |

*Saccharomyces cerevisiae* Experiments

In order to conduct functional studies with polyA track hypomorphic attenuation in *S. cerevisiae* cells the ADE1 locus was deleted from 74D-964 yeast strein via homologous recombination. Resultant ade1Δ strains were transformed with an empty vector or a plasmid-based ADE1 containing variable length of polyA tracks as well as WT and 12AAG insertion constructs. Constructs were generated by performing PCR on ADE1 isolated from the yeast genomic tiling library (Open Biosystems) with primers listed in Table 6. PCR products were digested and ligated into a p416 vector backbone containing the ADE1 endogenous promotor. Clones were verified via sequencing and correct constructs were transformed into ade1Δ deletions strains via the PEG-LiOAc method (Table 6). To generate dilution spottings, three colonies were picked from each transformation plate and grown overnight in selective media. In the morning, cultures were normalized to OD600=1.0 and 10 ul of cells spotted onto rich media, SD-Ura, and SD-Ade for phenotypic analysis.

Relative protein abundance was determined via Western dot blotting. Briefly, yeast transformants were picked from selection plates to inoculate 10 mL of SD-Ura and grown overnight to ~OD=0.6. In the morning, cells were harvested and lysed in buffer (25 mM Tris-HCl pH 7.5, 50 mM KCl, 1 mM EDTA, Roche protease inhibitor cocktail) via mechanical disruption with acid-washed glass beads (Sigma). Total protein was normalized to 1 mg/ml via Bradford assay, and 20 μg of total protein was spotted onto a nitrocellulose membrane. Western blotting was performed by overnight incubation with anti-Flag (Sigma M2, 1:1000 in 5% milk) and goat anti-rabbit (Sigma, 1:10,000 in 5% milk) antibodies followed by detection with chemiluminescence (Amersham ECL).

TABLE 7

Primers used for generation of ADE1 constructs

| SEQ ID No: | Name | Sequence |
|---|---|---|
| 38 | FwdAde1-SpeIWT | 5'GGactagtATGTCAATTACGAAGACTGAA CTGG |
| 39 | FwdAde1-SpeI6AAA | 5'GGactagtATGAAAAAAAAAAAAAAAAA TCAATTACGAAGACTGAACTGG |
| 40 | FwdAde1-SpeI9AAA | 5'GGactagtATGAAAAAAAAAAAAAAAAA AAAAAAAAATCAATTACGAAGACTGAACT GG |
| 41 | FwdAde1-SpeI12AAA | 5'GGactagtATGAAAAAAAAAAAAAAAAA AAAAAAAAAAAAAAAATCAATTACGAA GACTGAACTGG |
| 42 | FwdAde1-SpeI12AAG | 5'GGactagtATGAAGAAGAAGAAGAAGAA GAAGAAGAAGAAGAAGTCAATTACG AAGACTGAACTGG |
| 43 | RevAde1-ClaIFLAG | 5'GGatcgatTTACTTGTCGTCATCGTCCTT GTAGTCGTGAGACCATTTAGACCC |
| 44 | FwdAde1-PromSacI | 5'GGgagctcACACGATAGCAAAGCAG |
| 45 | RevAde1-PromXbaI | 5' GGtctagaTATCGTTAATATTTCG |

TABLE 8

S. Cerevisiae strains used in this study

| Name | Strain Background | Genotype |
|---|---|---|
| HT 971 | 74D-694 | Mat A, ade1::KANMX4, trp1-289(UAG), his3Δ-200, ura3-52, leu2-3, 112 |
| HT 972 | 74D-694 | Mat A, ade1::KANMX4, trp1-289(UAG), his3Δ-200, ura3-52, leu2-3, 112 |

*Tetrahymena thermophila* Experiments

*T. thermophila* strain B2086 (II) was used for all experiments reported. Similar results were obtained with strain CU428 [(VII) mpr1-1/mpr1-1]. To assess the effect of polyA-tracks on protein accumulation, we modified a fluorescent protein tagging vector, pBSICY-gtw (Mott, et al., 2011) so as to fuse YFP to the carboxyl-terminus of a macronucleus-localized protein of unknown function (MLP, TTHERM_00384860), separated by a Gateway recombination cassette (Invitrogen/Life Technologies, Inc), and expressed from the cadmium inducible MTT1 promoter (Shang, et al., 2002). The MLP gene coding region was amplified with oligonucleotides 5' ALM Bsi' 5'-CAC CCG TAC GAA TAA AAT GAG CAT TAA TAA AGA AGA AGT-3' (SEQ ID. No: 46) and 3' ALM RV 5'-GAT ATC TTC AAT TTT AAT TTT TCT TCG AAG TTG C 3' (SEQ ID NO: 47) and cloned into pENTR-D in a topoisomerase mediated reaction prior to digesting with BsiWI and EcoRV and inserting into BsiWI/PmeI digested pBSICY-gtw. Subsequently, LR Clonase II was used to insert a linker containing the sequence coding for an HA epitope tag alone (WT) or the tag plus different length of polyA tracks or AAG insertions in place of the Gateway cassette.

The expression cassette is located within the 5' flanking region of a cycloheximide resistant allele of the rpL29 gene to direct its integration into this genomic locus. These constructs were linearized with PvuI and SacI in the region flanking the *Tetrahymena* rpl29 sequences and introduced into starved *Tetrahymena* cells by biolistic transformation (Cassidy-Hanley, et al., 1997; Bruns, et al., 2000). Transformants were selected in 1× SPP medium containing 12.5 µg/ml cycloheximide. To control for copy number, PCR assays with primers MTT2386 5'-TCTTAGCTACGTGAT-TCACG-3' (SEQ ID NO: 48) and Chx-117, 5'-ATGTGTT-ATTAATCGATTGAT-3' (SEQ ID NO: 49) and Chx85r, 5'-TCTCTTTCATGCATGCTAGC-3' (SEQ ID NO: 50) verified that all rpL29 loci contained the integrated expression construct.

Transgene expression was induced by addition of 0.4 µg/ml CdCl2 and cells were grown 12-16 hours before monitoring protein accumulation. YFP accumulation was visualized by epifluorescence microscopy as previously described (Matsuda, et al., 2010). Whole cells extracts were generated by boiling concentrated cell pellets in 1× Laemmli sample buffer, followed by were fractionation on 10% SDS polyacrylamide gels and transfer to nitrocellulose. YFP accumulation was a monitored with mouse anti-GFP antisera (G28R anti-GFP (OAEA00007) antibody, Aviva Systems Biology) and normalized to acetylated alpha Tubulin (6-11B-1 monoclonal Anti-Acetylated Tubulin antibody (T7451) Sigma-Aldrich). qPCR analysis was done using 5'-AGGCCTACAAGACCAAGGGT-3' (SEQ ID NO: 51) and 5'-AGAGCGGTTTTGACGTTGGA-3' (SEQ ID NO: 52) primers for T. *Thermophila* ribosomal protein L21 (rpl21) which was used for normalization. Primers 5'-CCCGTATGACGTACCGGATTATG-3' (SEQ ID NO: 53) and 5'-ACTTCAGGGTCAGCTTGCC-3' (SEQ ID NO: 54) were used for detection and estimation of fusion protein transcript levels using SybrGreen master mix and CFX96 Touch™ Real time PCR Detection System (BioRad). Normalized ΔCt values were used to calculate fold ratio between WT, 12LysAAG and polyA track constructs.

Nicotiano *Benthamiana* Experiments

Constructs for expression of HA-tagged mCherry reporters that were already cloned in pEntryD-TOPO vector were sub-cloned to pEarleyGate 100 (ABRC stock number CD3-724) through LR reaction using LR clonase (Invitrogen™) The mCherry reporter constructs, pEARLY100 and pBIN61 plasmids were individually electroporated into *Agrobacterium tumefaciens* strains GV3101 (Koncz, et al., 1986). The strain carrying pBIN61 construct expressing p19 protein from tomato bushy stunt virus was co-infiltrated with the reporter constructs to suppress post-transcriptional gene silencing (Voinnet, et al., 2003). The *Agrobacterium* suspensions carrying the reporter constructs were infiltrated into the leaves of 5- to 6-week-old *N. benthamiana* plants as described in Joensuu, J. J. et al. Briefly, saturated over-night cultures were spun-down and resuspended in the infiltration solution (3.2 g/L Gamborg's B5 plus vitamins, 20 g/L sucrose, 10 mM MES pH 5.6, 200 µM 4'-Hydroxy-3',5'-dimethoxyacetophenone) to a final OD600=1.0; *Agrobacterium* suspensions carrying the reporter constructs were individually mixed with suspensions carrying the pBIN61 construct in 1:1 ratio prior to infiltrations. These suspensions were infiltrated into separate segments of two young leaves on each of eight different *N. benthamiana* plants, which served as biological replicates. For control, 1:1 suspension of *A. tumefaciens* carrying pEARLY 100 with no insert along with pBIN61 was used. The infiltrated plants were maintained in a controlled growth chamber conditions at 22° C., with a 16h photoperiod.

Samples of the abaxial epidermis of *N. benthamiana* leaves infiltrated with different mCherry reporter constructs were collected 6 days post-infiltration. Infiltration was performed as described in the previous section, with the addition of an YFP-expressing construct pEARLY104 (ABRC stock number CD3-686), which served as infiltration control. The samples were visualized for fluorescence by confocal laser-scanning microscopy using a Leica TCS SP2 confocal microscope.Samples for RNA and total soluble protein (TSP) extraction were separately collected from the infiltrated plants 6 days post-infiltration using a cork borer (7.1 mm in diameter); each sample contained equal amounts of leaf tissue (2 leaf discs) collected from each of the segments on the two leaves infiltrated with the same construct.

Analysis of mCherry protein accumulation was carried out by Western blot as described in Gutiérrez et al., 2013 and Conley et al., 2009. Briefly, phosphate-buffered saline (PBS: 8 g/L NaCl, 1.16 g/L Na2HPO4, 0.2 g/L KH2PO4, 0.2 g/L KCl, pH 7.4), supplemented with 1 mM EDTA, 1 mM phenylmethanesulfonylfluoride (PMSF), 1 µg/ml leupeptin 0.1% Tween-20 and 100 mM sodium L-ascorbate was used for total soluble protein (TSP) extractions. Bradford assay (Biorad) was used to quantify TSP in the extracts using a standard curve (r2=0.99) of known concentrations of Bovine Serum Albumin (BSA). Sample extracts (25 µg TSP for mCherry and 5 µg TSP for phosphinotricin acetyl transferase [BAR] protein detection) were separated by SDS-PAGE, blotted onto nitrocellulose membrane and probed with a primary anti-HA tag antibody (Genscript) for mCherry, or anti-Phosphinotricin acetyl transferase antibody (Abcam) for BAR, both at 1:2000 dilution, followed by HRP-conjugated secondary antibody (Biorad) at 1:5000 dilution. The blots were washed (3 times×10 min) in 1×Tris-buffered Saline (TBS, 50 mM Tris, 150 mM NaCl, pH 7.5) containing 0.1% Tween (Sigma) and images were obtained after 1 min incubation with the enhanced chemiluminescence (ECL) detection system (GE Healthcare). Numerical values for protein accumulation were derived from the detected band intensities on the analyzed images using TotalLab TL 100 software (Nonlinear Dynamics, Durham, USA). The mCherry accumulation values were normalized for Basta accumulation detected in the same sample. Normalized values of the mCherry protein accumulation for each reporter construct were presented as the mean of eight biological replicates±SE; Tukey's honest significance test (JMP software, SAS Institute Inc.) was used to identify significantly different means (α=0.05).

For quantitative RT-PCR (qPCR), total RNA was extracted using an RNeasy plant mini kit coupled with DNase treatment (Qiagen). The purified RNA (500 ng) was reverse-transcribed using the Maxima first-strand cDNA synthesis kit (Thermo Fisher Scientific). The resulting cDNA (2 ng/µl) was quantified by qPCR using the Maxima SYBR Green/ROX qPCR master mix (Thermo Fisher Scientific) and CFX384 Touch™ Real-Time PCR Detection System (Biorad). Cycle threshold (Ct) values were normalized to phosphinotricin N-acetyltransferase (BAR) gene expressed in the same plasmid used for transient expression. Primer sequences used: For mCherry-mCherryFWD: 5'-GGCTACCCATACGATGTTCC-3'(SEQ ID NO: 55);

mCherryREV: 5'-CCTCCATGTGCACCTTGAAG-3' (SEQ ID NO: 56); for BASTA-BAR-F3: 5'-TCAAGAGCGTGGTCGCTG-3' (SEQ ID NO: 57) and BAR-R3: 5'-CAAATCTCGGTGACGGGCAG-3' (SEQ ID NO: 58).

*Drosophila melanogaster* Experiments

Reporter gene expression was achieved with the GAL4/UAS system. The UAS-mCherry transgene plasmids were constructed from the phiC31 integrase plasmid, pJFRC28-10XUAS-IVS-GFP-p10 (Addgene plasmid #36431) (Pfeiffer, et al., 2012). GFP was removed by digestion with Kpnl and Xbal and replaced with HA-mCherry and HA-polyA-mCherry. Transgenic fly lines were obtained by injecting P{CaryP}attP2 embryos with each pJFRC28 mCherry construct to achieve site-specific, single insertion on the third chromosome at the attP2 landing site (Rainbow Transgenic Flies, Inc.). Injected GO adult flies were backcrossed to w1118 flies. Red-eyed progeny indicated successful germline integration of the UAS-mCherry expression cassette. Male red-eye progeny were crossed to female w;TM3 Sb/TM6 Tb flies followed by sib-crosses of the F1 progeny to generate homozygous UAS-mCherry transgenic lines. Insertion was confirmed by Sanger sequencing of PCR amplified mCherry from genomic DNA of individual flies. Each mCherry transgenic fly line was crossed to a TubGal4 UAS-GFP driver line (derived from BSC42734) to achieve mCherry expression in all tissues. GFP expression was used for normalization. All flies were maintained at 25° C.

Third instar larvae from each cross were fixed in formaldehyde and dissected to recover the salivary glands (SG), intact central nervous system (CNS), and proventriculus (PV). The tissues were mounted on glass cover slips and confocal images were taken on a Zeiss Imager 2 upright microscope using identical parameters for all images of each tissue type. Fluorescence intensity of the mCherry and GFP were quantified with Zen 9 software.

Total RNA was extracted from each cross by pooling 5 third instar larvae in 1.5 ml RNase-free Eppendorf tubes which were then frozen in dry ice. Frozen samples were homogenized using 1.5 ml pestles (Fisherbrand, RNase- and DNase-free). After homogenization, 1 ml RiboZol reagent (Amresco) was added and extraction was completed according to manufacturer's instructions. Total RNA samples were treated with TURBO DNA-free kit (Ambion) to remove potential genomic DNA. cDNA synthesis was performed with iScript Reverse Transcription Supermix (Bio-Rad) with 1 µg of total RNA in a 20 µl reaction. RT-qPCR was performed in the Bio-Rad CFX96 Real-Time System with iQ SYBR Green Supermix (Bio-Rad). The mCherry transcript was detected with the following primers: 5'-TGACGTACCGGATTATGCAA-3' (SEQ ID NO: 59) and 5'-ATATGAACTGAGGGGACAGG-3' (SEQ ID NO: 60). Cycle threshold (Ct) values were normalized to EF1 with the following primers: 5'-GCGTGGGTTTGT-GATCAGTT-3' (SEQ ID NO: 61) and 5'-GATCTTCTCCTTGCCCATCC-3' (SEQ ID NO: 62)) (Ponton, et al., 2011).

For western blot analysis, five third instar larvae from each cross were collected and frozen in dry ice. Frozen samples were homogenized using 1.5 ml pestles (Fisherbrand, RNase- and DNase-free). After homogenization, SDS sample buffer was added and the samples were boiled for 10 minutes. Anti-HA was used to detect mCherry expression. Samples were normalized with anti-GFP.

*H. sapiens* Cell Culture Experiments mCherry reporter constructs used for transient expression in human cells were subcloned using LR clonase recombination (Thermo Fisher Scientific) from pEntryD-Topo constructs used in other experiments or in previous studies (Arthur, et al., 2015). DNA fragments for constructs used for creation of inducible and stable cell lines were PCR amplified, purified and ligated into pcDNA 5/FRT/TO vector (Thermo Fisher Scientific).

HeLa cells were cultured in Dulbecco's modified Eagle's medium (DMEM) (Gibco) and supplemented with 10% fetal bovine serum, 5% minimum essential medium nonessential amino acids (100×, Gibco), 5% penicillin and streptomycin (Gibco), and L-glutamine (Gibco). Flp-In T-REx Hek-293 cells were grown in the same media with addition of 5 ug/ml of blastocidin and 100 ug/ml of Zeocin for non-recombined cells, or 5 ug/ml of blastocidin and 100 ug/ml of hygromycin for growth of stable cell lines expressing mCherry or HBD constructs.

Plasmids were introduced to the tissue culture cells by the Neon Transfection System (Thermo Fisher Scientific) using 100-µl tips according to cell-specific protocols (www.lifetechnologies.com/us/en/home/life-science/cell-culture/transfection/transfection-selection-misc/neon-transfection-system/neon-protocols-cell-line-data.html). Hela cells, used for transient expression, were electroporated with 1.5 ug of DNA plasmids and were harvested 24 hours after the electroporation. Flp-In T-REx Hek-293 cells were electroporated with plasmids, selected for positive clones as described by protocol (https://tools.thermofishercom/content/sfs/manuals/flpinsystem_man.pdf). Expression of polyA track and control constructs was induced by addition of various amounts of doxycycline from a common stock (1 µg/ml) and harvested 24 or 48 hours after induction, if not indicated differently.

Total RNA was extracted from cells using the RiboZol RNA extraction reagent (Amresco) according to the manufacturer's instructions or using GenElute™ Direct. RiboZol reagent (500 µl) was used in each well of 6- or 12-well plates for RNA extraction. Precipitated nucleic acids were treated with Turbo deoxyribonuclease (Ambion), and total RNA was dissolved in ribonuclease-free water and stored at −20° C. RNA concentration was measured by NanoDrop (0D260/280). iScript Reverse Transcription Supermix (Bio-Rad) was used with 1 µg of total RNA following the manufacturer's protocol. RT-qPCR was performed in the Bio-Rad CFX96 Real-Time System with iQ SYBR Green Supermix (Bio-Rad). For both transient expression samples and stable cell line samples, the mCherry transcript was detected with the following primers: 5'-TGACGTACCGGATTATGCAA-3' (SEQ ID NO: 63) and 5'-ATATGAACTGAGGGGACAGG-3' (SEQ ID NO: 64). Cycle threshold (Ct) values were normalized to the neomycin resistance gene expressed from the same plasmid for transient expression (5'-CTGAAT-GAACTGCAGGACGA-3' (SEQ ID NO: 65) and 5'-ATACTTTCTCGGCAGGAGCA-3' (SEQ ID NO: 66)) or hygromycin (5'-GATGTAGGAGGGCGTGGATA-3' (SEQ ID NO: 67) and 5'-ATAGGTCAGGCTCTCGCTGA-3' (SEQ ID NO: 68) or actin gene for stable cell lines (5'-AGAAAATCTGGCACCACACC-3' (SEQ ID NO: 69) and 5'-AGAGGCGTACAGGGATAGCA-3' (SEQ ID NO: 70).

Total cell lysates were prepared with passive lysis buffer (Promega). Blots were blocked with 5% milk in 1× tris-buffered saline-0.1% Tween 20 (TBST) for 1 hour. Horseradish peroxidase-conjugated or primary antibodies were diluted according to the manufacturer's recommendations and incubated overnight with membranes. The membranes were washed four times for 5 min in TBST and prepared for imaging, or secondary antibody was added for additional 1 hour of incubation. Images were generated by Bio-Rad Molecular Imager ChemiDoc XRS System with Image Lab software by chemiluminescence detection or by the LI-COR Odyssey Infrared Imaging System. Blots imaged by the LI-COR system were first incubated for 1 hour with Pierce DyLight secondary antibodies.

Discussion for EXAMPLES 2-8

We have presented a rapid method of generating hypomorphic mutations in a reporter or gene of interest. Insertion of a polyA track into a coding sequence shows predictable and robust attenuation of gene expression in all tested cell culture and model organism systems. The length of the polyA track can be manipulated to achieve full-range of expression levels, allowing for the generation of an allelic series from complete knockout to wild-type expression for the study of gene function. This method can also be used in synthetic biology applications that require precise gene control and modeling of metabolic and signaling networks (Chuang, et al., 2010).

The use of polyA tracks overcomes many of the challenges present in current methods of generating hypomorphic mutations and controllable gene expression. For instance, a recent approach to attenuate gene expression in *E. coli* is mutagenesis of the Shine-Dalgarno sequence in the gene of interest. The expression levels from all possible six-mer Shine-Dalgarno sequences were experimentally determined and the information is available in the EMOPEC database (Bonde, et al., 2016). However, this valuable resource would have to be generated anew to use this approach in other prokaryotes and it could not be used in eukaryotic systems. Additionally, many orthogonal translation systems rely on modified Shine-Dalgarno sequences (Hui, et al., 1987; Hui, et al., Methods Enzymol., 1987; Lee, et al., 1996; Rackham, et al., 2005). Use of an orthogonal translation system would prohibit use of the Shine-Dalgarno sequence for expression regulation. The polyA track system of gene regulation and creation of hypomorphic mutations overcomes this issue due to its dependency on regulation of translation elongation cycle which is conserved between prokaryotes and eukaryotes (Melnikov, et al., 2012).

Hypomorphic mutations have been generated in eukaryotic cell systems by insertion of an antibiotic resistance gene into introns (Meyers, et al., 1998) or the 3'-untranslated region of genes (Breslow, et al., 2008). Insertion of the neomycin resistance gene (neo) into an intron introduces a cryptic splice site that causes aberrant splicing of transcripts, effectively reducing gene expression (Meyers, et al., 1998). The reliance on stochastic cryptic splicing events leads to unpredictable changes in transcript expression and is rather gene dependent. Insertion of neo in various genes have resulted in expression of a functionally null allele (Nagy, et al., 1998), hypomorphic expression(Meyers, et al., 1998; Hirotsune, et al., 1998), or no change in expression (Wolpowitz, et al., 2000). Our system of polyA tracks gives predictable gene expression attenuation in variety of different eukaryotic systems and, furthermore, shows relative gene expression attenuation efficiency in the different tissues of the same organism.

Figure 32:
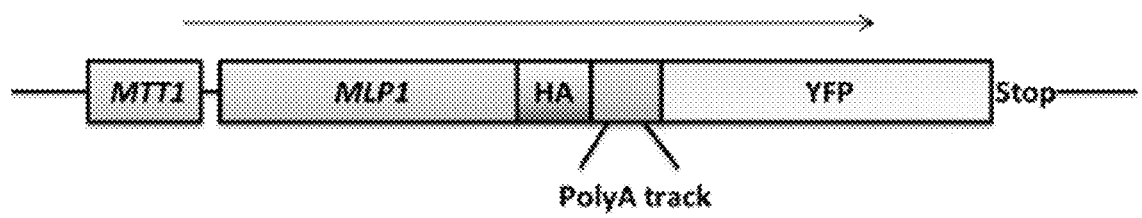
FIG. 32 shows a diagram of a mCherry expression construct used in T. thermophila. Position of the inducible metallothionein promoter (MTT1), Macronucleus-Localized Protein 1 (MLP1), double HA-tag (HA) and fluorescent reporter (eYFP) are indicated. Red box designates the position of in frame inserted polyA tracks and 12 LysAAG sequences. WT construct contains no insertions at this position.

We have primarily introduced polyA tracks at the N-terminal regions of reporter genes due to the uniformity of the construct design and to reduce potential frameshifting effects (Arthur, et al., 2015; Koutmou, et al., 2015). We do not anticipate this to be a major limitation of this method. Our *Tetrahymena* reporters place the polyA tracts at the N-terminus of YFP, but at the C-terminus of the linked *Tetrahymena* gene (FIG. 32). Furthermore, insertion of polyA track in the second exon of the human beta globin gene (HBD) gene, an unstructured loop of the protein, argue that polyA tracks can be introduced at various positions in the gene (FIG. 39, FIG. 40, and FIG. 41). Additionally, we have shown previously that naturally occurring polyA track sequences exist in the human genome and that potential frameshifted products are efficiently degraded by non-sense mediated decay mechanisms (Arthur, et al., 2015).

PolyA tracks that are used endogenously in eukaryotic genomes are typically interrupted by other nucleotides at various positions within the A-rich sequence. We have observed that the position of the interrupting nucleotide, in combination with the length of the A-rich sequence, modulate gene expression (Arthur, et al., 2015). This characteristic indicates that polyA mediated regulation can be further developed for even more precise control of gene expression. Lastly, approximately 2% of human genes are endogenously regulated by polyA tracks, including many well-studied, disease-associated genes, such as BRCA1, TCOF1 and MTDH among others (Arthur, et al., 2015; Habich, et al., 2016). As we showed in our previous study, synonymous mutations of the internal polyA track of such genes can allow investigators to dramatically change expression levels of these genes without manipulation of protein sequence or the gene regulatory elements such as promoters and enhancers (Arthur, et al., 2015).

The addition of a polyA track to the target gene will result in additional lysine residues in the protein product. Like any protein tag, it is important to consider the effects of the additional residues when studying the functionality of the protein. We have shown that the function and stability of two structurally diverse proteins, CAT and Ade1, are not affected by up to 12 additional lysine residues. To control for possible effects of the poly-lysine tracks, investigators can create an allele with the same number of lysine residues encoded by AAG codons. The AAG codons will have minimal effect on expression levels while encoding a synonymous protein. Furthermore, the flexibility in polyA track placement within the coding sequence allows investigators to choose the most suitable insertion site for the protein of interest.

The conservation of the polyA track sequences in the multiple genes across vertebrates as well as our analysis of mutation rates of polyA tracks (36As) inserted in the defined locus of *D. melanogaster* genome argue that polyA tracks can be used to create stable hypomorphic gene alleles. Our results are in the range of already described hypermutability (approximately 8%) of the short tandem repeats (STRs) and BAT-40 microsatellite (40As) located in the second intron of the 3-beta-hydroxysteroid dehydrogenase gene. The distinction is that our data show general mutation rates for the whole fruitfly after more than 30 generations while in the case of the mentioned study28 the mutation rate is dependent on the cell type. An additional study found that the mutation rate in polyA region, 10As in this case, is in the range of 10-4 per cell per generation. As such, the authors argue that approximately 1% of cells will be affected by a polyA region mutation in 100 generations. Similar rates were observed in the other studies with approximately $10^{-6}$-$10^{-2}$ mutation rate for the different lengths of homopolymeric regions or STRs. PolyA tracks used in our study tend to operate on the shorter side of the length distribution of STRs and as such should have similar if not even lower rates of mutations.

PolyA tracks that are used endogenously in eukaryotic genomes are typically interrupted by other nucleotides at various positions within the A-rich sequence, which further reduces potential hypermutability effects. We have observed that the position of the interrupting nucleotide or codon, in combination with the length of the A-rich sequence, modulates gene expression (FIG. 45A-D). These observations suggest that polyA-mediated regulation can be further developed for even more precise control of gene expression. Lastly, approximately 2% of human genes are endogenously regulated by polyA tracks, including many well-studied, disease-associated genes, such as BRCA1, TCOF1 and MTDH among others. As we showed in our previous study, synonymous mutations of the internal polyA track of such genes can allow investigators to dramatically change expression levels of these genes without manipulation of protein sequence or gene regulatory elements such as promoters and enhancers. The use of our method is not restricted only to these genes, and we feel that the synthetic biology field will benefit from this application. Control of biosynthetic pathways for production of useful secondary metabolites, antibiotics, or recombinant antibodies, as well as introduction of controllable retrosynthetic and fully engineered pathways or ultimate control of metabolic pathways in the modeling of diseases are just a few among the multiple possible applications of this method in the future.

REFERENCE FOR EXAMPLES

Arthur, L. L. et al. Translational control by lysine-encoding A-rich sequences. Sci. Adv. (2015).

Bonde, M. T. et al. Predictable tuning of protein expression in bacteria. Nat. Methods 13, (2016).

Brandman, O. et al. A ribosome-bound quality control complex triggers degradation of nascent peptides and signals translation stress. Cell 151, 1042-1054 (2012).

Breslow, D. K. et al. A comprehensive strategy enabling high-resolution functional analysis of the yeast genome. Nat. Methods 5, 711-718 (2008).

Bruns, P. J. & Cassidy-Hanley, D. Biolistic transformation of macro- and micrnuclei. Methods cell biolgy 62, 303-305 (2000).

Cassidy-Hanley, D. et al. Germline and somatic transformation of mating Tetrahymena thermophila by particle bombardment. Genetics 146, 135-47 (1997).

Chappell, J., Watters, K. E., Takahashi, M. K. & Lucks, J. B. A renaissance in RNA synthetic biology: New mechanisms, applications and tools for the future. Curr. Opin. Chem. Biol. 28, 47-56 (2015).

Choe, Y.-J. et al. Failure of RQC machinery causes protein aggregation and proteotoxic stress. Nature 531, 191-195 (2016).

Chuang, H.-Y., Hofree, M. & Ideker, T. A decade of systems biology. Annu. Rev. Cell Dev. Biol. 26, 721-44 (2010).

Dawlaty, M. M. & van Deursen, J. M. Gene targeting methods for studying nuclear transport factors in mice. Methods 39, 370-378 (2006).

Dimitrova, L. N., Kuroha, K., Tatematsu, T. & Inada, T. Nascent peptide-dependent translation arrest leads to Not4p-mediated protein degradation by the proteasome. J. Biol. Chem. 284, 10343-52 (2009).

Doudna, J. A. & Charpentier, E. The new frontier of genome engineering with CRISPR-Cas9. Science (80-). 346, 1258096-1258096 (2014).

Duffy, J. B. GAL4 system in Drosophila: a fly geneticist's Swiss army knife. Genesis 34, 1-15 (2002).

Eisen, J. A. et al. Macronuclear genome sequence of the ciliate Tetrahymena thermophila, a model eukaryote. PLoS Biol. 4, 1620-1642 (2006).

Ferri, A. L. et al. Sox2 deficiency causes neurodegeneration and impaired neurogenesis in the adult mouse brain. Development 131, 3805-3819 (2004).

Gari, E., Piedrafita, L., Aldea, M. & Herrero, E. A set of vectors with a tetracycline-regulatable promoter system for modulated gene expression in Saccharomyces cervisiae. Yeast 13, 837-848 (1997).

Goto, T., Hara, H., Nakauchi, H., Hochi, S. & Hirabayashi, M. Hypomorphic phenotype of Foxn1 gene-modified rats by CRISPR/Cas9 system. Transgenic Res. (2016). doi: 10.1007/s11248-016-9941-9

Groth, A. C., Fish, M., Nusse, R. & Calos, M. P. Construction of Transgenic Drosophila by Using the Site-Specific Integrase from Phage phiC31. Genetics 166, 1775-1782 (2004).

Hieter, P., Mann, C., Snyder, M. & Davis, R. W. Mitotic stability of yeast chromosomes: A colony color assay that measures nondisjunction and chromosome loss. Cell 40,381-392 (1985).

Habich, M., Djuranovic, S. & Szczesny, P. PATACSDB—the database of polyA translational attenuators in coding sequences. PeerJ Comput. Sci. 2, e45 (2016).

Hirotsune, S. et al. Graded reduction of Pafah1b1 (Lis1) activity results in neuronal migration defects and early embryonic lethality. Nat. Genet. 19,333-339 (1998).

Hui, A. & de Boer, H. a. Specialized ribosome system: preferential translation of a single mRNA species by a subpopulation of mutated ribosomes in Escherichia coli. Proc. Natl. Acad. Sci. U.S.A 84,4762-6 (1987).

Hui, A. et al. Directing Ribosomes to a Single mRNA Species: A Method to Study Ribosomal RNA Mutations and Their Effects on Translation of a Single MEssenger in Escherichia coli. Methods Enzymol. 153,432-452 (1987).

Joung, J. K. & Sander, J. D. TALENs: a widely applicable technology for targeted genome editing. Nat Rev Mol Cell Biol 14,49-55 (2013).

Kuroha, K. et al. Receptor for activated C kinase 1 stimulates nascent polypeptide-dependent translation arrest. EMBO Rep. 11,956-61 (2010).

Koncz, C. & Schell, J. The promoter of TL-DNA gene 5 controls the tissue-specific expression of chimaeric genes carried by a novel type of Agrobacterium binary vector. MGG Mol. Gen. Genet. 204,383-396 (1986).

Koutmou, K. S. et al. Ribosomes slide on lysine-encoding homopolymeric A stretches. Elife 4,1-18 (2015).

LaFave, M. C. & Sekelsky, J. Transcription initiation from within P elements generates hypomorphic mutations in Drosophila melanogaster. Genetics 188,749-752 (2011).

Lee, K., Holland-Staley, C. A. & Cunningham, P. R. Genetic analysis of the Shine-Dalgarno interaction: Selection of alternative functional mRNA-rRNA combination. RNA 2,1270-1285 (1996).

Li, J. & Zhang, Y. Relationship between promoter sequence and its strength in gene expression. Eur. Phys. J. E 37,1-6 (2014).

Liebman, S. W. & Chernoff, Y. O. Prions in yeast. Genetics 191,1041-1072 (2012).

Mano, Y., Kobayashi, T. J., Nakayama, J. ichi, Uchida, H. & Oki, M. Single Cell Visualization of Yeast Gene Expression Shows Correlation of Epigenetic Switching between Multiple Heterochromatic Regions through Multiple Generations. PLoS Biol. 11, (2013).

Matsuda, A., Shieh, A. W. Y., Chalker, D. L. & Forney, J. D. The conjugation-specific Die5 protein is required for development of the somatic nucleus in both Paramecium and Tetrahymena. Eukaryot. Cell 9,1087-1099 (2010).

Melnikov, S. et al. One core, two shells: bacterial and eukaryotic ribosomes. Nat. Struct. Mol. Biol. 19,560-567 (2012).

Meyers, E. N., Lewandoski, M. & Martin, G. R. An Fgf8 mutant allelic series generated by Cre- and Flp-mediated recombination. Nat. Genet. 18,136-41 (1998).

Motl, J. A. & Chalker, D. L. Zygotic expression of the double-stranded RNA binding motif protein Drb2p is required for DNA elimination in the ciliate *Tetrahymena thermophila*. Eukaryot. Cell 10,1648-1659 (2011).

Muller, H. J. Further Studies on the Nature and Causes of Gene Mutations. Proc. 6th Int. Congr. Genet. 1,213-255 (1932).

Nagy, a et al. Dissecting the role of N-myc in development using a single targeting vector to generate a series of alleles. Curr. Biol. 8,661-664 (1998).

Pfeiffer, B. D., Truman, J. W. & Rubin, G. M. Using translational enhancers to increase transgene expression in *Drosophila*. Proc. Natl. Acad. Sci. U.S.A 109,6626-31 (2012).

Ponton, F., Chapuis, M. P., Pernice, M., Sword, G. A. & Simpson, S. J. Evaluation of potential reference genes for reverse transcription-qPCR studies of physiological responses in *Drosophila melanogaster*. J. Insect Physiol. 57,840-850 (2011).

Rackham, O. & Chin, J. W. A network of orthogonal ribosome-mRNA pairs. Nat. Chem. Biol. 1,159-166 (2005).

Redden, H., Morse, N. & Alper, H. S. The synthetic biology toolbox for tuning gene expression in yeast. FEMS Yeast Res. 15,1-10 (2015).

Shang, Y. et al. A robust inducible-repressible promoter greatly facilitates gene knockouts, conditional expression, and overexpression of homologous and heterologous genes in *Tetrahymena thermophila*. Proc. Natl. Acad. Sci. U.S.A 99, 3734-9 (2002).

Shaw, W. V. & Leslie, A. G. W. Chloramphenicol acetyl transferase w. Annu. Rev. Chem. Biomol. Eng. Vol 3 20,363-386 (1991).

Voinnet, O., Rivas, S., Mestre, P. & Baulcombe, D. Bushy Stunt Virus Et Ra C Et Ra C. Plant J. 949-956 (2003).

Wolpowitz, D. et al. Cysteine-rich domain isoforms of the neuregulin-1 gene are required for maintenance of peripheral synapses. Neuron 25,79-91 (2000).

Yonashiro, R. et al. The Rqc2/Tae2 subunit of the Ribosome-Associated Quality Control (RQC) complex marks ribosome-stalled nascent polypeptide chains for aggregation. Elife 5, (2016).

---

What is claimed is:

1. A method for modulating the level of expression of a polypeptide in a cell, the method comprising: introducing into the cell an expression vector comprising a polynucleotide sequence encoding a polypeptide to be expressed, comprising:
   (a) introducing into an open reading frame of the polynucleotide sequence a polynucleotide tag sequence comprising at least three consecutive AAA lysine codons, wherein the AAA lysine codons decrease expression of the polynucleotide sequence when the expression vector is introduced into a cell relative to a reference vector without the at least three consecutive AAA lysine codons; or
   (b) introducing into an open reading frame of the polynucleotide sequence: a polynucleotide tag sequence comprising at least one AAG lysine codon, wherein the at least one AAG lysine codon increases expression of the at least one polynucleotide sequence when the expression vector is introduced into a cell relative to a reference vector without the at least one AAG lysine codon, thereby modulating the level of expression of the polypeptide in the cell; and
wherein the expression vector comprises a cloning site having at least two endonuclease recognition sequences for inserting the at least one polynucleotide sequence and at least one polynucleotide tag sequence in the open reading frame of the polynucleotide sequence encoding a polypeptide to be expressed between a start codon and the cloning site.

2. The method of claim 1, wherein modulating the level of expression comprises: increasing the amount of consecutive A nucleotides by inserting a polynucloetide tag comprising at least three AAA lysine codons into the open reading frame of the polynucleotide sequence encoding the polypeptide.

3. The method of claim 2, wherein the polynucleotide tag sequence comprising at least three consecutive AAA lysine codons is inserted into an open reading frame at a position selected from the group consisting of in a 5' untranslated region (UTR), in an exon, at an exon/intron boundary, and in a 3' UTR.

4. The method of claim 1, wherein modulating the level of expression comprises: decreasing the amount of consecutive A nucleotides by inserting a polynucleotide tag comprising at least one AAG lysine codon into the open reading frame of the polynucleotide sequence encoding the polypeptide in the cell.

5. The method of claim 4, wherein the at least one AAG lysine codon is inserted into polynucleotide sequence for expression at the N-terminus or C-terminus of the polypeptide in the cell.

6. The method of claim 1, wherein the polynucleotide tag sequence in (b) comprises at least one polylysine track comprising at least two consecutive AAG lysine codons.

7. A method for modulating the level of expression of a polypeptide in a cell, the method comprising: introducing into the cell an expression vector comprising a polynucleotide sequence encoding a polypeptide to be expressed comprising:
   introducing into an open reading frame of the polynucleotide sequence at least one synonymous G to A nucleotide mutation into at least one AAG lysine codon, wherein the at least synonymous mutation decreases expression of the polynucleotide sequence when the expression vector is introduced into a cell relative to a reference vector without the a synonymous mutation in lysine codon.

8. The method of claim 7, wherein at least one polylysine track comprises the at least one lysine codon, and wherein the at least one polylysine track comprises a combination of AAG and AAA lysine codons or a plurality of AAG lysine codons.

* * * * *